United States Patent
Levine et al.

(10) Patent No.: US 12,344,846 B2
(45) Date of Patent: Jul. 1, 2025

(54) COMPOSITIONS AND METHODS USING CpG OLIGONUCLEOTIDES

(71) Applicant: Six Therapeutics Inc., Flanders, NJ (US)

(72) Inventors: Howard Levine, Killington, VT (US); Nyron Khan, Flanders, NJ (US); Prashant Girinath, Arlington, MA (US); Simon Talbot, Boston, MA (US)

( * ) Notice: Subject to any disclaimer, the term of this patent is extended or adjusted under 35 U.S.C. 154(b) by 0 days.

(21) Appl. No.: 18/885,005

(22) Filed: Sep. 13, 2024

(65) Prior Publication Data

US 2025/0002922 A1 Jan. 2, 2025

Related U.S. Application Data

(63) Continuation of application No. PCT/US2023/084608, filed on Dec. 18, 2023.

(60) Provisional application No. 63/433,623, filed on Dec. 19, 2022.

(51) Int. Cl.
| | |
|---|---|
| C07H 21/02 | (2006.01) |
| A61K 9/00 | (2006.01) |
| A61P 17/02 | (2006.01) |
| C07H 21/04 | (2006.01) |
| C12N 15/117 | (2010.01) |

(52) U.S. Cl.
CPC .......... C12N 15/117 (2013.01); A61K 9/0014 (2013.01); A61P 17/02 (2018.01); C12N 2310/17 (2013.01); C12N 2310/315 (2013.01); C12N 2320/35 (2013.01)

(58) Field of Classification Search
CPC .................................................. C12N 15/117
See application file for complete search history.

(56) References Cited

U.S. PATENT DOCUMENTS

| | | |
|---|---|---|
| 7,615,227 B2 | 11/2009 | Klinman |
| 7,935,351 B2 | 5/2011 | Klinman |
| 8,466,116 B2 | 6/2013 | Klinman |
| 8,470,342 B2 | 6/2013 | Klinman |
| 9,453,228 B2 | 9/2016 | Kandimalla |
| 10,076,535 B2 | 9/2018 | Klinman |

FOREIGN PATENT DOCUMENTS

| | | | |
|---|---|---|---|
| AU | 2013252785 B2 | 5/2017 | |
| CA | 2871490 C | 10/2022 | |
| WO | WO-9956755 A1 * | 11/1999 | ......... A61K 31/7088 |
| WO | WO-0061151 A2 * | 10/2000 | ......... A61K 31/7088 |
| WO | 2013162828 A1 | 10/2013 | |
| WO | 2018237300 A1 | 12/2018 | |

OTHER PUBLICATIONS

Wang et al. (Nucleic Acid Therapeutics, Apr. 23, 2013, 253-263).*
Anonymous: "Human TLR9 Agonist Kit I Stimulatory CpG ODNs", InvivoGen, May 13, 2015 (May 13, 2015), downloaded from the Internet Jun. 3, 2024.
Branski et al., A porcine model of full-thickness burn, excision and skin autografting, Burns, 2008, vol. 34, No. 8, p. 1119-1127.
Chen et al., Imiquimod regulating Th1 and Th2 cell-related chemokines to inhibit scar hyperplasia, Int Wound J, 2019, vol. 16, p. 1281-1288.
International Search Report and Written Opinion for PCT/US2023/084608, mailed May 16, 2024.
Ito et al., Characteristic of K3 (CpG-ODN) as a Transcutaneous Vaccine Formulation Adjuvant, Pharmaceutics, 2020, vol. 12, No. 267, p. 1-17.
Khalifa et al., Modulation of immune response in canine chronic wound stimulated with Class C CpG oligonucleotide, Benha Journal of Applied Sciences, 2022, vol. 7, No. 4, p. 79-84.
Kinsley et al., A Yorkshire swine (Sus scrofa domesticus) model for nerveregeneration and ischemia based on the sciatic nerve and femoralartery, Annals of Anatomy, 2021, vol. 233, p. 1-7.
Kuo et al., Skin wound healing assessment via an optimized wound array model in miniature pigs, Scientific Reports, 2022, vol. 12, No. 445, p. 1-15.
Otsuka et al., CpG ODN (K3)—toll-like receptor 9 agonist—induces Th1-type immune response and enhances cytotoxic activity in advanced lung cancer patients: a phase I study, BMC Cancer, 2022, vol. 22, No. 744, p. 1-15.
Sato et al: "Accelerated wound healing mediated by activation of Toll-like receptor 9", Wound Repair and Regeneration, Wiley-Blackwell Publishing Inc., 2010, vol. 18, No. 6, p. 586-593.
Seaton et al., Porcine Models of Cutaneous Wound Healing, ILAR Journal, 2015, vol. 56, No. 1, p. 127-138.
Yamamoto et al: "The acceleration of wound healing in primates by the local administration of immunostimulatory CpG oligonucleotides", Biomaterials, Elsevier, Amsterdam, NL, vol. 32, No. 18, Feb. 18, 2011 (Feb. 18, 2011), pp. 4238-4242.

* cited by examiner

Primary Examiner — Amy Rose Hudson
(74) Attorney, Agent, or Firm — Greenberg Traurig, LLP

(57) ABSTRACT

Compositions and pharmaceutical compositions are provided herein which can comprise oligonucleotides, such as synthetic CpG oligonucleotides, related to immune responses, and/or other ingredient(s). Compositions and pharmaceutical compositions described herein include those that result in a TLR9 activation. Also described are methods, among other things, for accelerating wound healing, for cell expansion, and improved methods of activated cell expansion by compositions and pharmaceutical compositions herein.

20 Claims, 114 Drawing Sheets
Specification includes a Sequence Listing.

Sections were cut at every 30μM into the incision; at first level wound healing/ remodelling can be seen in both control but with the test item (D, 0.3) closure of the stratum corneum.

CpG oligonucleotide D Cytokine Data

CpG oligonucleotide C Cytokine Data

Haematoxylin and Eosin (H&E) stained sections

Time 0 untreated/before any treatment

Time 144 E

Time 144 PBS

Time 144 D

Time 144 F

Time 144 C

BMP 6 stained sections

144Hr PBS

144Hr D

144Hr F

144Hr C

144Hr E

MMP1 stained sections

144Hr PBS

144Hr D

144Hr E

144Hr C

144Hr F

Vimentin stained sections

144Hr PBS

144Hr D

144Hr F

144Hr C

144Hr E

CpG oligonucleotide 'D'; 144hrs, R2 resectioned deeper
BMP6

Area of remodelled incision

MMP1

Vimentin

CpG oligonucleotide 'E' 144Hrs

COMPOSITIONS AND METHODS USING CpG OLIGONUCLEOTIDES

CROSS-REFERENCE

This application is a continuation of PCT Application No. PCT/US2023/084608, filed Dec. 18, 2023, which claims the benefit of U.S. Provisional Application No. 63/433,623, filed on Dec. 19, 2022, which applications are incorporated herein by reference in their entirety.

TECHNICAL FIELD

The disclosure generally relates, among other things, to systems, compositions, methods and the administration of compositions, and compositions for use, related to, among other things, wound healing, accelerated wound healing, treatments for skin-related medical conditions, prevention or treatment of infections and methods for facilitating improved cell expansion.

SEQUENCE LISTING

The instant application contains a Sequence Listing which has been submitted electronically in ST.26 (xml) format and is hereby incorporated by reference in its entirety. Said ST.26 (xml) copy, created on Jan. 4, 2024, is named 209830-701601_SL.xml and is 64,213 bytes in size.

INCORPORATION BY REFERENCE

All publications, patents, and patent applications mentioned in this specification are herein incorporated by reference to the same extent as if each individual publication, patent, or patent application was specifically and individually indicated to be incorporated by reference.

SUMMARY

Provided herein are compositions and pharmaceutical compositions comprising a synthetic CpG oligonucleotide that comprises a sequence of: ATCACGTAGCAT-CACGTAGC (SEQ ID NO: 5); ATCACGGAGCATCACG-GAGC (SEQ ID NO: 6); ATCTCGTAGCATCTCGTAGC (SEQ ID NO: 7); ATCTCGGAGCATCTCGGAGC (SEQ ID NO: 8); ATCGCGTAGCATCGCGTAGC (SEQ ID NO: 9); ATCGCGGAGCATCGCGGAGC (SEQ ID NO: 10); ATTCGTCGGCGTCGACGGTC (SEQ ID NO: 11); ATGCGACGTCGACGTCGGTC (SEQ ID NO: 12); ATACGACGTCGTCGTCGATC (SEQ ID NO: 13); ATGCGTCGGCGACGTCGTGC (SEQ ID NO: 14); GTACGACGTCGTCGACGTGA (SEQ ID NO: 15); or TAGCGTCGACGACGTCGATG (SEQ ID NO: 16), where each nucleic acid residue comprised in the CpG oligonucleotide is independently linked to adjacent nucleic acid residue by a phosphodiester group or a phosphorothioate group and each of SEQ ID NOs: 5-16 can have 0, 1, 2, 3, or 4 nucleobase modifications; and an excipient, diluent, carrier, or any combination of these. Also provided herein are compositions comprising a synthetic CpG oligonucleotide having the following sequence:
A*T*C*T*C*G*T*A*G*C*A*T*C*T*C*G*T*A*G*C (SEQ ID NO: 17);
A*T*C*T*C*T*C*G*T*A*G*C*A*T*C*T*C*G*T*A*G*C (SEQ ID NO: 18);
A*T*C*T*C*T*C*G*G*A*G*C*A*T*C*T*C*G*G*A*G*C (SEQ ID NO: 19);
A*T*C*T*C*G*G*A*G*C*A*T*C*T*C*G*G*A*G*C (SEQ ID NO: 20);
A*T*G*C*G*T*C*G*G*C*G*A*C*G*T*C*G*T*G*C (SEQ ID NO: 21);
T*A*G*C*G*T*C*G*A*C*G*A*C*G*T*C*G*A*T*G (SEQ ID NO: 22);
A*T*G*C*A*C*T*C*T*G*C*A*G*G*C*T*T*C*T*C (SEQ ID NO: 23); or
A*T*A*T*A*C*T*C*T*A*T*A*G*A*T*T*T*C*T*C (SEQ ID NO: 24), where * indicates a phosphorothioate group, and where at least one phosphorothioate group between a C and a G is replaced by a phosphodiester group; and an excipient, diluent, carrier, or any combination of these. Also provided herein are compositions comprising: a synthetic CpG oligonucleotide, having the following sequence:
A*T*C*T*C^G*T*A*G*C*A*T*C*T*C*G*T*A*G*C (SEQ ID NO: 25);
A*T*C*T*C^G*T*A*G*C*A*T*C*T*C*G*T*A*G*C (SEQ ID NO: 26);
A*T*C*T*C^G*G*A*G*C*A*T*C*T*C*G*G*A*G*C (SEQ ID NO: 27);
A*T*C*T*C^G*G*A*G*C*A*T*C*T*C*G*G*A*G*C (SEQ ID NO: 28);
A*T*G*C^G*T*C*G*G*C*G*A*C*G*T*C*G*T*G*C (SEQ ID NO: 29); or
T*A*G*C^G*T*C*G*A*C*G*A*C*G*T*C*G*A*T*G (SEQ ID NO: 30), where * indicates a phosphorothioate group and ^ indicates a phosphodiester group between a C and a G; an excipient, diluent, carrier, or any combination of these. Also disclosed herein are compositions comprising a synthetic CpG oligonucleotide that comprises 5'$(N_1)_a(N_2)_a$ $(W)_a$-CpG-$(X)_a$-CpG-$(Y)_a$-CpG-$(Z)_a$-CpG-$(B)_a$-CpG-$(D)_a$ $(N_3)_a(N_4)_a$ 3' (SEQ ID NO: 1), where: $N_1$ is A or T, $N_2$ is A or T, W is G, X is T, Y is A, Z is A, B is T, D is A or T, $N_3$ is G or T, and $N_4$ is C or G, where each nucleic acid residue comprised in the synthetic CpG oligonucleotide is independently linked to an adjacent nucleic acid residue by a phosphodiester group or a phosphorothioate group; a is independently in each case 0, 1, 2, or 3; and an excipient, diluent, carrier, or combination of any of these. Provided herein are compositions comprising a synthetic CpG oligonucleotide that comprises: 5'$(N_1)_a(N_2)_a(W)_a$-CpG-$(X)_a$-CpG-$(Y)_a$-CpG-$(Z)_a$-CpG-$(B)_a$-CpG-$(D)^a(N_3)^a(N_4)^a$ 3' (SEQ ID NO: 2) where each: $N_1$, $N_2$, W, X, Y, Z, B, D, $N_3$ and $N_4$ is independently A, T, G, C, or U, each nucleic acid residue comprised in the synthetic CpG oligonucleotide is independently linked to an adjacent nucleic acid residue by a phosphodiester or a phosphorothioate group; a is independently in each case 0, 1, 2, or 3; and an excipient, diluent, carrier, or combination of any of these. Also provided herein are compositions comprising: synthetic CpG oligonucleotide that comprises: 5'$(E)_b(F)_b(H)_b(J_1)_b$-CpG-$(N_1)_b(P)_b$ $(J_2)_b$ $(K)_b(L)_b(M)_b(O)_b(Q)_b$-CpG-$(N_2)_b(R)_b(S)_b(V)_b$ 3' (SEQ ID NO: 3) where: E is A, F is T, H is C, $J_1$ is T, $N_1$ is T or G, P is A, $J_2$ is G, K is C, L is A, M is T, O is C, Q is T, $N_2$ is T or A, R is A, S is G, and V is C, where each nucleic acid residue comprised in the synthetic CpG oligonucleotide is independently linked to an adjacent nucleic acid residue by a phosphodiester group or a phosphorothioate group, b is independently in each case 0, 1, 2, or 3; an excipient, diluent, carrier, or combination of any of these. Also provided herein are compositions comprising a synthetic CpG oligonucleotide that comprises 5'$(E)_b(F)_b(H)_b(J_1)_b$-CpG-$(N_1)_b(P)_b(J_2)_b$ $(K)_b(L)_b(M)_b(O)_b(Q)_b$-CpG-$(N_2)_b(R)_b(S)_b(V)_b$ 3' (SEQ ID No: 4) where each: E, F, H, $J_1$, $N_1$, P, $J_2$, K, L, M, O, Q, $N_2$, R, S, and V is independently A, T, C, G, or U, where each nucleic acid residue comprised in the synthetic CpG oligonucleotide is independently linked to an adjacent nucleic acid residue by a phosphodiester group or a phosphorothioate group; b is independently in each case 0, 1, 2, or 3; and an excipient, diluent, carrier, or combination of any of these. Provided herein are compositions comprising a synthetic CpG oligonucleotide comprising a sequence of A*T*C*T*C*G*T*A*G*C*A*T*C*T*C*G*T*A*G*C (SEQ ID NO: 17) and an excipient, diluent, carrier, or any combination of these, where * indicates a phosphorothioate group. Also provided herein are compositions comprising a synthetic CpG oligonucleotide comprising a sequence of A*T*C*T*C^G*T*A*G*C*A*T*C*T*C*G*T*A*G*C (SEQ ID NO: 25) and an excipient, diluent, carrier, or any combination of these, where * indicates a phosphorothioate group and ^ indicates a phosphodiester group between a C and a G. In some embodiments, the synthetic CpG oligonucleotide in the composition is a TLR agonist. In some embodiments, the composition when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition, in an in vitro assay. In some embodiments, the synthetic CpG oligonucleotide has a sequence length of from about 15 to about 40 nucleic acid residues. In some embodiments, the synthetic CpG oligonucleotide does not contain an epigenetic modification. In some embodiments, each CpG in the synthetic CpG oligonucleotide is unmethylated. In some embodiments, a nucleobase present in the synthetic CpG oligonucleotide contains an epigenetic mark that is a: methyl, hydroxymethyl, formyl, or carboxylic acid. In some embodiments, the synthetic CpG oligonucleotide comprises a chemical modification to a sugar of a nucleobase. In some embodiments, a is 1 in each case. In some embodiments, each nucleic acid residue comprised in the synthetic CpG oligonucleotide is independently linked to an adjacent nucleic acid residue by a phosphorothioate group. In some embodiments, b is 1 in each case. In some embodiments, a C nucleic acid residue and a G nucleic acid residue in a CpG are linked by a phosphodiester group. In some embodiments, other than the C nucleic acid resided and the G nucleic acid residue in the CpG that are linked by a phosphodiester group, each remaining nucleic acid residue comprised in the synthetic CpG oligonucleotide is linked to an adjacent remaining nucleic acid residue by a phosphorothioate group. In some embodiments, the synthetic CpG nucleotide consists of the SEQ ID NO: 17. In some embodiments, the synthetic CpG nucleotide consists of the SEQ ID NO: 25. In some embodiments, the composition is a pharmaceutical composition. In some embodiments, the pharmaceutical composition is in unit dose form. In some embodiments, the pharmaceutical composition further comprises a further therapeutic. In some embodiments, the further therapeutic comprises an antibiotic, an antiviral, an antifungal, an antiparasitic agent, or a pharmaceutically acceptable salt of any of these. In some embodiments, the synthetic CpG oligonucleotide is independently present in the composition or the pharmaceutical composition in an amount of from about 1 ng to about 100 ng, about 100 ng to about 500 ng, about 500 ng to about 1 mg, or about 1 mg to about 100 mg, or about 1 ng to about 25,000 mg. In some embodiments, the composition or the pharmaceutical composition is formulated for systemic administration. In some embodiments, the composition or pharmaceutical composition formulated for systemic administration is in the form of a liquid, an emulsion, a suspension, a suppository, a pill, or a capsule. In some embodiments, the composition or the pharmaceutical composition is formulated for topical administration. In some embodiments, the composition or pharmaceutical composition formulated for topical administration is in the form of a spray, a cream, a lotion, a powder, a gel, or is comprised on or in a pad, a bandage, or a dressing. In some embodiments, synthetic CpG oligonucleotide in the composition or pharmaceutical composition is comprised in a vesicle. In some embodiments, synthetic CpG oligonucleotide in the composition or pharmaceutical composition is comprised in a liposome, a micelle, or a particle. In some embodiments, the vesicle, the liposome, or the micelle is a nanovesicle, a nanoliposome, a nano-micelle or a nanoparticle. In some embodiments, the composition or pharmaceutical when stored in a sealed container in an environment having a temperature of 68° F. and an atmosphere 50 percent relative humidity, retains intact at least about 80% by weight of the synthetic CpG oligonucleotide initially present after 6 months as measured by high-performance liquid chromatography (HPLC), sequencing, or both. Also provided herein is a kit containing the composition or the pharmaceutical composition as disclosed herein, and a container.

Disclosed herein are compositions for use in treating a disease in a subject in need thereof, the composition comprising a synthetic CpG oligonucleotide that comprises a sequence A*T*C*T*C*G*T*A*G*C*A*T*C*T*C*G*T*A*G*C (SEQ ID NO: 17) and an excipient, diluent, carrier, or any combination of these, where * indicates a phosphorothioate group. Also disclosed herein are compositions for use in treating a disease in a subject in need thereof, the composition comprising a synthetic CpG oligonucleotide that comprises a sequence A*T*C*T*C^G*T*A*G*C*A*T*C*T*C*G*T*A*G*C (SEQ ID NO: 25) and an excipient, diluent, carrier, or any combination of these, where * indicates a phosphorothioate group and ^ indicates a phosphodiester group between a C and a G. In some embodiments are compositions for use in accelerating a healing of a wound in a subject, the composition comprises a therapeutically effective amount of the composition or the pharmaceutical composition as disclosed herein, where the composition is administered by contacting the wound of the subject with the composition, thereby accelerating the healing of the wound as compared to an otherwise comparable wound not contacted with the composition or the pharmaceutical composition. In some embodiments are compositions for use in regenerating skin or a tissue of a subject, the composition comprising a therapeutically effective amount of the composition or the pharmaceutical composition as disclosed herein, where the composition is administered by contacting the skin or the tissue of the subject with the composition, thereby regenerating the skin or the tissue of the subject. In some embodiments, the subject in need thereof is a mammal. In some embodiments, the mammal is a human. In some embodiments, the disease or condition is a wound. In some embodiments, the skin or the tissue comprises a wound. In some embodiments, the wound is a surgical wound, a scar, an unclean wound, a clean wound, a deep incisional wound, a superficial incisional wound, an ulcer, a diabetic ulcer, a diabetic foot ulcer, a radiation dermatitis, an acute radiation dermatitis, a burn, acne, a cancer, a skin cancer, a psoriasis, a combat wound, an infection, a viral infection, a bacterial infection, a fungal infection, a parasitic infection, a cutaneous infection, a subcutaneous infection, or any combination thereof. In some embodiments, the surgical wound is associated with scar revision, donor site skin grafts, panniculectomies, biopsies, or plastic surgery. In some embodiments, the skin or the tissue comprises an infection. In some embodiments, the infection is a cutaneous infection. In some embodiments, the cutaneous infection is a bacterial infection, a viral infection, a fungal infection, a parasitic infection, or any combination thereof. In some embodiments, the composition or the pharmaceutical composition is formulated for systemic administration. In some embodiments, the composition or pharmaceutical composition is formulated for systemic administration and is in the form of a liquid, an emulsion, a suspension, a suppository, a pill, or a capsule. In some embodiments, the composition or the pharmaceutical composition is formulated for topical administration. In some embodiments, the composition or pharmaceutical composition is formulated for topical administration and is in the form of a spray, a cream, a lotion, a powder, a gel, or is comprised on or in a pad, a bandage, or a dressing. In some embodiments, an antibiotic, an antiviral, an antifungal, an antiparasitic agent, or a pharmaceutically acceptable salt thereof is administered concurrently or consecutively with the contacting. In some embodiments, the synthetic CpG oligonucleotide is independently present in the composition or the pharmaceutical composition in an amount ranging from about 1 ng to about 100 ng, about 100 ng to about 500 ng, about 500 ng to about 1 mg, or about 1 mg to about 100 mg, or about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed. In some embodiments, the composition is localized to the skin of the human.

Provided herein are methods of treating a disease or condition in a subject, the method comprising administering the composition or the pharmaceutical composition as disclosed herein to the subject in a therapeutically effective amount, thereby treating the disease or condition. Also provided herein are methods of accelerating a healing of a wound in a subject, the method comprising contacting the wound of the subject with the composition or the pharmaceutical composition of as disclosed herein, in an amount effective to accelerate the healing of the wound in the subject, thereby accelerating the healing of the wound as compared to an otherwise comparable wound not contacted with the composition or the pharmaceutical composition. Also provided herein are methods of inducing an inflammatory response in a tissue of a subject without introducing a bacterial infection, a fungal infection, or a viral infection into the tissue, the method comprising contacting the tissue of the subject with the composition or the pharmaceutical composition as disclosed herein, thereby inducing the inflammatory response in the tissue of the subject. Also provided herein are methods of regenerating skin or a tissue of a subject, the method comprising contacting the skin or the tissue of the subject with the composition or pharmaceutical composition as disclosed herein, in an amount effective to regenerate the skin or the tissue of the subject, thereby regenerating the skin or the tissue of the subject. In some embodiments, the subject is a subject in need thereof. In some embodiments, the subject or the subject in need thereof is a mammal. In some embodiments, the mammal is a human. In some embodiments, the disease or condition is a wound. In some embodiments, the wound is a surgical wound, a scar, an unclean wound, a clean wound, a deep incisional wound, a superficial incisional wound, an ulcer, a diabetic ulcer, a diabetic foot ulcer, a radiation dermatitis, a burn, acne, a cancer, a skin cancer, a psoriasis, a combat wound, an infection, a viral infection, a bacterial infection, a fungal infection, a parasitic infection, a cutaneous infection, a subcutaneous infection, or any combination of these. In some embodiments, the composition or the pharmaceutical composition is formulated for systemic administration. In some embodiments, the composition or pharmaceutical composition formulated for systemic administration is in the form of a liquid, an emulsion, a suspension, a suppository, a pill, or a capsule. In some embodiments, the composition or the pharmaceutical composition is formulated for topical administration. In some embodiments, the composition or pharmaceutical composition formulated for topical administration is in the form of a spray, a cream, a lotion, a powder, a gel, or is comprised on or in a pad, a bandage, or a dressing. In some embodiments, an antibiotic, an antiviral, an antifungal, an antiparasitic agent, or a pharmaceutically acceptable salt of any of these is administered concurrently or consecutively with the contacting. In some embodiments, the antibiotic, the antiviral, the antifungal, the anti-parasitic agent, or the pharmaceutically acceptable salt of any of these is administered consecutively. In some embodiments, the skin or the tissue comprises an infection. In some embodiments, the infection is a bacterial infection, a viral infection, a fungal infection, a parasitic infection, or any combination thereof. In some embodiments, the synthetic CpG oligonucleotide is independently present in the composition or the pharmaceutical composition in an amount ranging from about 1 ng to about 100 ng, about 100 ng to about 500 ng, about 500 ng to about 1 mg, or about 1 mg to about 100 mg, or about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed.

Also provided herein are methods of expanding a plurality of cells ex vivo, the method comprising, contacting the plurality of cells with the composition or pharmaceutical composition as disclosed here, in an amount effective to expand the plurality of cells ex vivo, thereby expanding the plurality of cells ex vivo. In some embodiments, the plurality of cells comprises mammalian cells. In some embodiments, the mammalian cells comprise human cells. In some embodiments, an antibiotic or a pharmaceutically acceptable salt thereof is administered concurrently or consecutively with the contacting. In some embodiments, the expanding is conducted in a cell culture medium. In some embodiments, the cell culture medium is a liquid cell culture medium. In some embodiments, the expanding is conducted at a temperature ranging from about 25 degrees Celsius to about 37 degrees Celsius. In some embodiments, the expanding is conducted for a period of time ranging from about 24 hours to about 168 hours. In some embodiments, the plurality of cells comprises stem cells, T-cells, or natural killer (NK) cells. In some embodiments, the plurality of cells comprises T-cells that comprise cluster of differentiation 8 (CD8) glycoproteins. In some embodiments, the plurality of cells comprises T-cells that comprise cluster of differentiation 4 (CD4) glycoproteins. In some embodiments, the contacting further comprises contacting the plurality of cells with at least one of interleukin 15 (IL-15), interleukin 7 (IL-7), interleukin 2 (IL-2), or any combination of these. In some embodiments, the synthetic CpG oligonucleotide is independently present in the composition or the pharmaceutical composition in an amount ranging from about 1 ng to about 100 ng, about 100 ng to about 500 ng, about 500 ng to about 1 mg, or about 1 mg to about 100 mg, or about 1 ng to about 25,000 mg.

Also provided herein are methods of activating a pattern recognition receptor in a cell, the method comprising contacting the cell with the composition or pharmaceutical composition as disclosed herein in an amount effective to activate the pattern recognition receptor, thereby activating the pattern recognition receptor in the cell. In some embodiments, the pattern recognition receptor comprises a toll-like receptor, a C-type lectin receptor, a NOD-like receptor, or a RIG-I like receptor. In some embodiments, the pattern recognition receptor comprises the toll-like receptor (TLR). In some embodiments, the TLR is located on or within the cell. In some embodiments, the TLR is TLR3, TLR7, TLR8, or TLR9. In some embodiments, the TLR is TLR9. In some embodiments, the cell is a mammalian cell. In some embodiments, the mammalian cell is a human cell. In some embodiments, the cell is isolated; comprised within a tissue, substantially proximal to a wound comprised within the mammal or any combination of these. In some embodiments, the synthetic CpG oligonucleotide is present in the composition in an amount ranging from about 1 ng to about 100 ng, 1 ng to about 500 mg, about 100 ng to about 500 ng, about 500 ng to about 1 mg, or about 1 mg to about 100 mg, or about 1 ng to about 25,000 mg. In some embodiments, the activation of the pattern recognition receptor in the cell modulates the expression of one or more chemokines, cytokines, growth factors, antibodies, or any combination thereof. In some embodiments, the one or more chemokine, cytokines, growth factors, antibodies comprises Brain-derived neurotrophic factor (BDNF), Epidermal growth factor (EGF), Eotaxin (C-C motif chemokine 11 (CCL11)), Fibroblast growth factor 2 (FGF-2), granulocyte-macrophage colony-stimulating factor (GM-CSF), GRO alpha (chemokine (C-X-C motif) ligand 1 (CXCL1)), Hepatocyte growth factor (HGF), type-1 interferon (IFN) alpha, IFN gamma, Immunoglobulin M (IgM), interleukin 1 (IL-1) alpha, IL-1 beta, IL-1RA, IL-2, IL-5, IL-6, IL-7, IL-8 (CXCL8), IL-9, IL-10, IL-12p70, IL-13, IL-15, IL-17A (Cytotoxic T-lymphocyte associated protein 8 (CTLA-8)), IL-18, IL-21, IL-22, IL-23, IL-27, IL-31, IP-10 (CXCL10), Leukemia inhibitory factor (LIF), monocyte chemoattractant protein (MCP) 1 (CCL2), macrophage inflammatory protein 1 (MIP-1) alpha (CCL3), MIP-1 beta (CCL4), Platelet-derived growth factor subunit B beta (PDGF-BB), Placenta growth factor 1 (PlGF-1), Regulated on activation, normal T cell expressed and secreted (RANTES), stromal cell-derived factor 1 (SDF-1) alpha, Transforming growth factor beta (TGF beta), Tumor necrosis factor (TNF) alpha, TNF beta, Vascular endothelial growth factor (VEGF)-A, and VEGF-D. In some embodiments, the activation of the pattern recognition receptor in the cell results in a dose-dependent increase in expression of one or more chemokines, cytokines, growth factors, antibodies, or any combination thereof. In some embodiments, the one or more chemokines, cytokines, growth factors, antibodies comprises BDNF, HGF, IFN gamma, IgM, IL-1 alpha, IL-1 beta, IL-1RA, IL-2, IL-5, IL-6, IL-7, IL-10, IL-12p70, IL-18, IL-22, IL-23, IL-31, IP-10 (CXCL10), LIF, MCP-1 (CCL2), MIP-1 alpha (CCL3), MIP-1 beta (CCL4), PDGF-BB, RANTES, SDF-1 alpha, TNF alpha, TNF beta, and VEGF-A. In some embodiments, the activation of the pattern recognition receptor in the cell results in a dose-dependent decrease in expression of one or more chemokines, cytokines, growth factors, antibodies, or any combination thereof. In some embodiments, the one or more chemokine, cytokines, growth factors, antibodies comprises FGF-2, IL-9, and TGF beta.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 3A shows how a tissue section is visualized for imaging assays. FIG. 3B shows levels of sections where incisions were made using a scalpel into Labskin. Sections were cut at every 30 μm into the incisions.

FIG. 9A shows hematoxylin and eosin (H&E) staining of the razorblade full-thickness wound mimics in Labskin samples. FIG. 9B shows BMP6 staining of the razorblade full-thickness wound mimics in Labskin samples. FIG. 9C shows MMP1 staining of the razorblade full-thickness wound mimics in Labskin samples. FIG. 9D shows Vimentin staining of the razorblade full-thickness wound mimics in Labskin samples.

FIG. 10A shows absorbance intensity for Labskin samples treated with CpG oligonucleotides. FIG. 10B shows percent cell viability normalized to the PBS control. FIG. 10C shows a measure of IL-la release for the SDS control and the CpG oligonucleotides tested, after the 24-hour incubation period.

FIG. 11A shows tissue imaging of MMP1 staining. FIG. 11B shows corresponding cytokine production data.

FIG. 13A shows staining for CpG oligonucleotide 'F'.

FIG. 13B shows staining for CpG oligonucleotide 'E'. FIG. 13C shows staining for CpG oligonucleotide 'D'. FIG. 13D shows staining for CpG oligonucleotide 'C.'

FIG. 14A depicts the protein target human B cell-activating factor (BAFF). FIG. 14AA depicts the protein target IL-23. FIG. 14AB depicts the protein target IL-25 also known as IL-17E. FIG. 14AC depicts the protein target IL-27. FIG. 14AD depicts the protein target IL-31. FIG. 14AE depicts the protein target IL-33. FIG. 14AF depicts the protein target Interleukin 1 receptor-like 1 (IL1RL1) also known as IL-33R and ST2. FIG. 14AG depicts the protein target Interferon gamma-induced protein 10 (IP-10) also known as CXCL10. FIG. 14AH depicts the protein target Leptin. FIG. 14AI depicts the protein target Leukemia inhibitory factor (LIF). FIG. 14AJ depicts the protein target monocyte chemoattractant protein 1 (MCP-1) also known as CCL2. FIG. 14AK depicts the protein target MCP-3 also known as CCL7. FIG. 14AL depicts the protein target macrophage colony-stimulating factor (M-CSF). FIG. 14AM depicts the protein target macrophage inflammatory protein 1 (MIP-1) alpha also known as CCL3. FIG. 14AN depicts the protein target MIP-1 beta also known as CCL4. FIG. 14AO depicts the protein target MIP-2 alpha also known as CXCL2. FIG. 14AP depicts the protein target Receptor activator of nuclear factor kappa-B ligand (RANKL). FIG. 14AQ depicts the protein target Regulated on activation. normal T cell expressed and secreted (RANTES) also known as CCL5. FIG. 14AR depicts the protein target Transforming growth factor (TGF) beta. FIG. 14AS depicts the protein target Tumor necrosis factor (TNF) alpha. FIG. 14AT depicts the protein target and Vascular endothelial growth factor A (VEGF-A).

FIG. 15A depicts the protein target Brain-derived neurotrophic factor (BDNF).

FIG. 15AA depicts the protein target IL-22. FIG. 15AB depicts the protein target IL-23. FIG. 15AC depicts the protein target IL-27. FIG. 15AC depicts the protein target IL-31. FIG. 15AE depicts the protein target IP-10 (CXCL10). FIG. 15AF depicts the protein target LIF. FIG. 15AG depicts the protein target MCP-1 (CCL2). FIG. 15AH depicts the protein target MIP-1 alpha (CCL3). FIG. 15AI depicts the protein target MIP-1 beta (CCL4). FIG. 15AJ depicts the protein target Platelet-derived growth factor subunit B beta (PDGF-BB). FIG. 15AK depicts the protein target Placenta growth factor 1 (PlGF-1). FIG. 15AL depicts the protein target RANTES (CCL5). FIG. 15AM depicts the protein target stromal cell-derived factor 1 (SDF-1) alpha. FIG. 15AN depicts the protein target TGF beta. FIG. 15AO depicts the protein target TNF alpha. FIG. 15AP depicts the protein target TNF beta. FIG. 15AQ depicts the protein target VEGF-A.

DETAILED DESCRIPTION OF THE INVENTION

Figure 1:
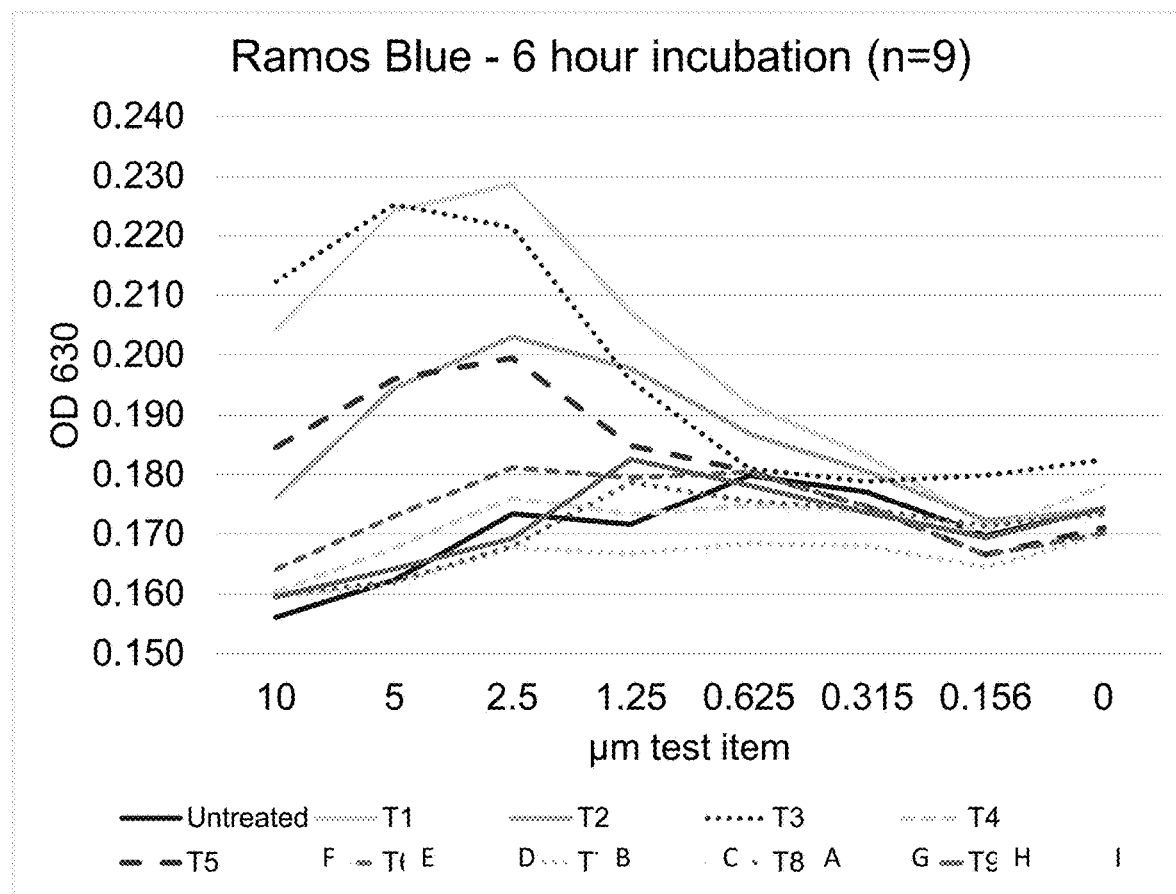
FIG. 1 shows a graphical representation of an optical density graph for TLR9 activation of Ramos Blue B lymphocytes exposed to synthetic CpG oligonucleotides at different synthetic CpG oligonucleotide concentrations.

The following discussion of the present disclosure has been presented for purposes of illustration and description. The following is not intended to limit the invention to the form or forms disclosed herein. Although the description of the present disclosure has included description of one or more embodiments and certain variations and modifications, other variations and modifications are within the scope of the present disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges, or steps to those claimed, whether or not such alternate, interchangeable and/or equivalent structures, functions, ranges or steps are disclosed herein, and without intending to publicly dedicate any patentable subject matter.

The section headings used herein are for organizational purposes only and are not to be construed as limiting the subject matter described.

Although various features of the disclosure may be described in the context of a single embodiment, the features can also be provided separately or in any suitable combination. Conversely, although the disclosure may be described herein in the context of separate embodiments for clarity, various aspects and embodiments can be implemented in a single embodiment.

The practice of some embodiments disclosed herein employ, unless otherwise indicated, techniques of immunology, biochemistry, chemistry, molecular biology, microbiology, cell biology, genomics, and recombinant DNA, which are within the skill of the art.

Definitions

Any methods and materials similar or equivalent to those described herein can be used in the practice for testing of the present disclosure. Accordingly, the terminology used herein is for the purpose of describing particular embodiments only, and is not intended to be limiting.

Herein, use of the singular includes the plural unless specifically stated otherwise. As used herein, the singular forms "a," "an" and "the" include plural referents unless the context clearly dictates otherwise. Furthermore, use of the term "including" as well as other forms, such as "include", "includes," and "included," is not limiting and is equivalent to the term "comprising."

As used herein, a synthetic CpG oligonucleotide means an engineered CpG oligonucleotide. Synthetic CpG oligonucleotides can be made by any method, including but not limited to synthesis on a DNA or RNA synthesizer, or in a biological system such as a bacterium, or in a bioreactor.

The terms "and/or" and "any combination thereof" and their grammatical equivalents as used herein, can be used interchangeably. These terms can convey that any combination is specifically contemplated. Solely for illustrative purposes, the following phrases "A, B, and/or C" or "A, B, C, or any combination thereof" can mean "A individually; B individually; C individually; A and B; B and C; A and C; and A, B, and C."

The term "or" is used disjunctively unless the context specifically refers to a conjunctive use.

The term "SSRI" as used herein means a selective serotonin reuptake inhibitor. Examples of SSRIs include but are not limited to: citalopram, escitalopram, fluoxetine, fluvoxamine, verteporfin, paroxetine, sertraline, and vilazodone.

Any composition or pharmaceutical composition herein can comprise, consist of, or consist essentially of any engineered oligonucleotide or synthetic CPG oligonucleotide sequence comprising any SEQ ID NO. herein. Embodiments herein can comprise an engineered oligonucleotide or synthetic CPG oligonucleotide sequence having a sequence having at least about 70, 75, 80, 85, 90, 95, 96, 97, 98, or 99 percent identity to the sequence of any SEQ ID NO. herein and/or at least about 80, 85, 90, 95, 96, 97, 98, or 99 percent length to the sequence of any SEQ ID NO. herein.

The term "about" or "approximately" means within an acceptable error range for the particular value as determined by one of ordinary skill in the art, which can depend in part on how the value is measured or determined, e.g., the limitations of the measurement system. For example, "about" can mean within 1 or more than 1 standard deviation, per the practice in the art. Alternatively, "about" can mean a range of up to 20%, up to 10%, up to 5%, or up to 1% of a given value. Alternatively, particularly with respect to biological systems or processes, the term can mean within an order of magnitude, within 5-fold, and/or within 2-fold, of a value. Where particular values are described in the application and claims, unless otherwise stated the term "about" meaning within an acceptable error range for the particular value should be assumed.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps. It is contemplated that any embodiment discussed in this specification can be implemented with respect to any method or composition of the invention, and vice versa. Furthermore, compositions and pharmaceutical compositions herein can be used to achieve methods herein.

Reference to "some embodiments," "an embodiment," "one embodiment" or "other embodiments" means that a particular feature, structure, or characteristic described in connection with the embodiments is included in at least some embodiments, but not necessarily all embodiments.

As used herein, an "excipient" includes functional and/or non-functional ingredients in a composition or a pharmaceutical composition. In some cases, an excipient or a pharmaceutically acceptable excipient can comprise acacia, acesulfame potassium, acetic acid, glacial, acetone, acetyl tributyl citrate, acetyl triethyl citrate, agar, albumin, alcohol, alginic acid, aliphatic polyesters, alitame, almond oil, alpha tocopherol, aluminum hydroxide adjuvant, aluminum oxide, aluminum phosphate adjuvant, aluminum stearate, ammonia solution, ammonium alginate, ascorbic acid, ascorbyl palmitate, aspartame, attapulgite, bentonite, benzalkonium chloride, benzethonium chloride, benzoic acid, benzyl alcohol, benzyl benzoate, boric acid, bronopol, butylated hydroxyanisole, butylated hydroxytoluene, butylparaben, calcium alginate, calcium carbonate, calcium phosphate, dibasic anhydrous, calcium phosphate, dibasic dihydrate, calcium phosphate, tribasic, calcium stearate, calcium sulfate, canola oil, carbomer, carbon dioxide, carboxymethylcellulose calcium, carboxymethylcellulose sodium, carrageenan, castor oil, castor oil, hydrogenated, cellulose (e.g. microcrystalline, powdered, silicified microcrystalline, acetate, acetate phthalate) ceratonia, cetostearyl alcohol, cetrimide, cetyl alcohol, cetylpyridinium chloride, chitosan, chlorhexidine, chlorobutanol, chlorocresol, chlorodifluoroethane, chlorofluorocarbons, chloroxylenol, cholesterol, citric acid monohydrate, colloidal silicon dioxide, coloring agents, copovidone, corn oil, cottonseed oil, cresol, croscarmellose sodium, crospovidone, cyclodextrins, cyclomethicone, denatonium benzoate, dextrates, dextrin, dextrose, dibutyl phthalate, dibutyl sebacate, diethanolamine, diethyl phthalate, difluoroethane, dimethicone, dimethyl ether, dimethyl phthalate, dimethyl sulfoxide, dimethylacetamide, disodium edetate, docusate sodium, edetic acid, erythorbic acid, erythritol, ethyl acetate, ethyl lactate, ethyl maltol, ethyl oleate, ethyl vanillin, ethylcellulose, ethylene glycol palmitostearate, ethylene vinyl acetate, ethylparaben, fructose, fumaric acid, gelatin, glucose, glycerin, glyceryl behenate, glyceryl monooleate, glyceryl monostearate, glyceryl palmitostearate, glycofurol, guar gum, hectorite, heptafluoropropane, hexetidine, hydrocarbons, hydrochloric acid, hydroxyethyl cellulose, hydroxyethylmethyl cellulose, hydroxypropyl cellulose, hydroxypropyl cellulose, low-substituted, hydroxypropyl starch, hypromellose, hypromellose acetate succinate, hypromellose phthalate, honey, imidurea, inulin, iron oxides, isomalt, isopropyl alcohol, isopropyl myristate, isopropyl palmitate, kaolin, lactic acid, lactitol, lactose, anhydrous, lactose, monohydrate, lactose, spray-dried, lanolin, lanolin alcohols, lanolin, hydrous, lauric acid, lecithin, leucine, linoleic acid, macrogol hydroxystearate, magnesium aluminum silicate, magnesium carbonate, magnesium oxide, magnesium silicate, magnesium stearate, magnesium trisilicate, malic acid, maltitol, maltitol solution, maltodextrin, maltol, maltose, mannitol, medium-chain triglycerides, meglumine, menthol, methylcellulose, methylparaben, mineral oil, mineral oil, light, mineral oil and lanolin alcohols, monoethanolamine, monosodium glutamate, monothioglycerol, myristic acid, neohesperidin dihydrochalcone, nitrogen, nitrous oxide, octyldodecanol, oleic acid, oleyl alcohol, olive oil, palmitic acid, paraffin, peanut oil, pectin, petrolatum, petrolatum and lanolin alcohols, phenol, phenoxyethanol, phenylethyl alcohol, phenylmercuric acetate, phenylmercuric borate, phenylmercuric nitrate, phosphoric acid, polacrilin potassium, poloxamer, polycarbophil, polydextrose, polyethylene glycol, polyethylene oxide, polymethacrylates, poly(methyl vinyl ether/maleic anhydride), polyoxyethylene alkyl ethers, polyoxyethylene castor oil derivatives, polyoxyethylene sorbitan fatty acid esters, polyoxyethylene stearates, polyvinyl acetate phthalate, polyvinyl alcohol, potassium alginate, potassium benzoate, potassium bicarbonate, potassium chloride, potassium citrate, potassium hydroxide, potassium metabisulfite, potassium sorbate, povidone, propionic acid, propyl gallate, propylene carbonate, propylene glycol, propylene glycol alginate, propylparaben, 2-pyrrolidone, raffinose, saccharin, saccharin sodium, saponite, sesame oil, shellac, simethicone, sodium acetate, sodium alginate, sodium ascorbate, sodium benzoate, sodium bicarbonate, sodium borate, sodium chloride, sodium citrate dihydrate, sodium cyclamate, sodium hyaluronate, sodium hydroxide, sodium lactate, sodium lauryl sulfate, sodium metabisulfite, sodium phosphate, dibasic, sodium phosphate, monobasic, sodium propionate, sodium starch glycolate, sodium stearyl fumarate, sodium sulfite, sorbic acid, sorbitan esters (sorbitan fatty acid esters), sorbitol, soybean oil, starch, starch (e.g. pregelatinized, sterilizable maize), stearic acid, stearyl alcohol, sucralose, sucrose, sugar, compressible, sugar, confectioner's, sugar spheres, sulfobutylether b-cyclodextrin, sulfuric acid, sunflower oil, suppository bases, hard fat, talc, tartaric acid, tetrafluoroethane, thaumatin, thimerosal, thymol, titanium dioxide, tragacanth, trehalose, triacetin, tributyl citrate, triethanolamine, triethyl citrate, vanillin, vegetable oil, hydrogenated, water, wax, anionic emulsifying, wax (e.g., carnauba, cetyl esters, microcrystalline, nonionic emulsifying, white, yellow), xanthan gum, xylitol, zein, zinc acetate, zinc stearate, or any combination thereof.

As used herein, the term "immunoresponsive cell" refers to a cell that functions in an immune response or a progenitor, or progeny thereof. The term, "mammal" used herein refers to human and non-human mammals.

As used herein, the term "modulate" refers positively or negatively alter. Exemplary modulations include an about 1%, about 2%, about 5%, about 10%, about 25%, about 5000, about 75%, or about 100% change. As used herein "dose-dependent increase" refers to a positive modulation. Also as used herein in "dose-dependent decrease" refers to a negative modulation.

The term "nucleotide," as used herein, can refer to a base-sugar-phosphate or a base-sugar-phosphorothioate combination. The nucleotide can be composed of three subunit molecules: a nucleobase, a five-carbon sugar (ribose or deoxyribose), and a phosphate or a phosphorothioate group. The four nucleobases in DNA can include guanine, adenine, cytosine, and thymine; in RNA, uracil can be used in place of thymine. Where DNA sequences are included herein, the corresponding RNA sequences, wherein at least one, two, three, four, five, or all T are replaced with U, are contemplated. A nucleotide can comprise a synthetic nucleotide. A nucleotide can comprise a synthetic nucleotide analog. Nucleotides can be monomeric units of a nucleic acid sequence (e.g., deoxyribonucleic acid (DNA) or ribonucleic acid (RNA)).

The term, "oligonucleotide" as used herein can refer to a linear nucleotide sequence of up to about 200 nucleotide bases in length.

As used herein, the terms "protein", "peptide" and "polypeptide" are used interchangeably to designate a series of amino acid residues connected to each other by peptide bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

The term "subject" as used herein is interchangeable with the term "patient" and includes human and non-human mammals, including for example: a primate, cow, horse, pig, sheep, goat, dog, cat, or rodent, capable of being colonized by other organisms. A mammal can be any age or at any stage of development (e.g., an adult, teen, child, infant, or a mammal in utero). A mammal can be male or female. A mammal can be a pregnant female. In some embodiments a subject can be a human. In some cases, a human can be more than about: 1 day to about 10 months old, from about 9 months to about 24 months old, from about 1 year to about 8 years old, from about 5 years to about 25 years old, from about 20 years to about 50 years old, from about 1 year old to about 130 years old or from about 30 years to about 100 years old. Humans can be more than about: 1, 2, 5, 10, 20, 30, 40, 50, 60, 70, 80, 90, 100, 110, or 120 years of age. Humans can be less than about: 1, 2, 5, 10, 20, 30, 40, 50, 60, 70, 80, 90, 100, 110, 120 or 130 years of age. A subject can be a subject in need thereof.

As used herein, "substantially pure"—when applied to a molecule, can mean sufficiently homogeneous to appear free of readily detectable impurities by weight of as determined by standard methods of analysis, such as thin layer chromatography (TLC), gel electrophoresis and high performance liquid chromatography (HPLC), used by those of skill in the art to assess such purity, or sufficiently pure such that further purification would not detectably alter the physical and chemical properties, such as enzymatic and biological activities, of the substance. A substantially chemically pure compound may, however, be a mixture of stereoisomers such as a mixture of enantiomers or diastereomers. In some embodiments, the compositions of the present disclosure are substantially pure or contain one or more substantially pure active ingredients, such as synthetic CpG oligonucleotide(s) and/or second therapeutics or pharmaceutically acceptable salts thereof.

As used herein, the term "treating" or "treatment" refers to clinical intervention in an attempt to alter the disease course of the individual or subject or subject in need thereof or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, decreasing the rate of the progression of a disease or health condition, amelioration or palliation of the disease state. By preventing progression of a disease or disorder, a treatment can prevent deterioration due to a disorder in an affected or diagnosed subject or subject in need thereof or a subject or subject suspected of having the disorder, but also a treatment may prevent the onset of the disorder or a symptom of the disorder in a subject at risk for the disorder or suspected of having the disorder.

As used herein, the term "concurrently" refers to the administration of (1) the composition, adjuvant composition, or pharmaceutical composition according to the present invention and (2) of the at least one secondary therapeutic, wherein at least a portion of the administration of the two occurs at the same time. As used herein, the term "consecutively" refers to the administration of (1) the composition, or pharmaceutical composition according to the present invention and (2) of the at least one secondary therapeutic, wherein the administration of one occurs within about an 1 hour, 2 hours, 3 hours, 4 hours, 5 hours, 6 hours, 7 hours, 8 hours, 9 hours, 10 hours, 11 hours, 12 hours, or a day of conclusion of administration of the other.

Unless otherwise stated, structures depicted herein are also meant to include all isomeric (e.g., enantiomeric, diastereomeric, geometric (or conformational) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the disclosure.

Although various features of the disclosure may be described in the context of a single embodiment, the features can also be provided separately or in any suitable combination. Conversely, although the disclosure may be described herein in the context of separate embodiments for clarity, various aspects and embodiments can be implemented in a single embodiment.

Sequences

The nucleic and amino acid sequences listed are shown using standard letter abbreviations for nucleotide bases, and one or three letter code for amino acids.

I. Cell Regeneration and Repair Uses

Described herein are compositions, pharmaceutical compositions, systems, and methods for skin regeneration, wound repair, and scar reduction. In some embodiments, the disclosure relates to administering or contacting compositions and pharmaceutical compositions with immunomodulating properties including, but not limited to, toll-like receptor agonists and/or other classes of immunosuppressants and/or immunomodulators.

The tissue subject to administration or contacting with compositions or pharmaceutical compositions described herein can be an organ, a tissue, or a cell. The tissue can be a stem cell or stem cells, the tissue can be grown de novo, the tissue can comprise a skin graft, or the tissue can be isolated from a mammal.

Immune Responses

Also described herein are methods of detecting and measuring immune responses. In some embodiments a composition described herein results in an immune response. In some embodiments, the immune response is a T cell mediated immune response. In some embodiments, the immune response is a B cell mediated immune response. In some embodiments, the immune response is a combination of a T cell mediated immune response and a B cell mediated immune response. Immune responses described herein can be at least one of: cytokine production, cellular toxicity, immune responses indirectly effected by T cell activation including antibody production, or humoral responses, activation of cytokine responsive cells including macrophages. In some embodiments the cells involved in an immune response are lymphocytes. In some embodiments, the lymphocyte is a B cell. In some embodiments, the lymphocyte is a T cell. In some embodiments the cell involved in an immune response is one of: a CD4+, CD8+, TH1 and TH2 cells.

In some embodiments, measuring immune cells includes methods of identifying expression of surface marker proteins. In some embodiments, flow cytometry is used. In some embodiments, the surface marker proteins include but is not limited to CD3, CD4, CD5, CD8a, CD8b, CD9, CD11, CD14, CD44, CD21, CD23, CD41, and VEGFR-1/FLT-1.

TLR9 Agonists

In some embodiments, a pattern recognition receptor involved in immune response comprises a toll-like receptor, a C-type lectin receptor, a NOD-like receptor, or a RIG-I like receptor. In some embodiments, the pattern recognition receptor comprises the toll-like receptor (TLR). In some embodiments, the TLR is located within the cell. In some embodiments, the TLR is TLR3, TLR7, TLR8, or TLR9. In some embodiments, the TLR is TLR9. In some embodiments, the cell is a mammalian cell. In some embodiments the cell is isolated. In some embodiments the cell is comprised within a tissue. In some embodiments the cell is substantially proximal to a wound. In some embodiments the cell is comprised within the mammal. In some embodiments, the mammal is a human. In humans, at least ten known TLRs are known to recognize different pathogenic molecular markers, such as viral double-stranded RNA (TLR3), flagellin (TLR5) and components of bacterial cell wall including lipopolysaccharide (LPS; TLR4) 25 or lipopeptide (TLR2). Ligand-stimulated TLRs interact with various Toll/interleukin-I receptor (TIR) domain. Thirteen TLRs (TLR1 to TLR13) have been identified in humans and mice together, and equivalent forms of many of these have been found in other mammalian species. TLRs recognize conserved motifs found in various pathogens and mediate defense responses. Triggering of the TLR pathway can lead to the activation of NF-κB and subsequent regulation of immune and inflammatory genes. The TLRs and members of the interleukin (IL)-1 receptor family share a conserved stretch of about 200 amino acids known as the TIR domain. Upon activation, TLRs associate with a number of cytoplasmic adaptor proteins containing TIR domains including MyD88 (myeloid differentiation factor), MAL/TIRAP (MyD88-adaptor-like/TIR-associated protein), TRIP (Toll-receptor-associated activator of interferon) and TRAM (Toll-receptor associated molecule). Cells in vivo, express TLRs as 4- and 6-kb transcripts that are most abundant in placenta and pancreas. TLR activity includes activation of NF-KB. Activation of TLRs can result in increased production of tumor necrosis factor a (TNF alpha), interleukin (IL)-1, IL-6, IL-8, IL-12, RANTES, MIP-la, and MIP-lb. In some embodiments, the synthetic CpG oligonucleotide can increase the production of human B cell-activating factor (BAFF), betacellulin (BTC), Brain-derived neurotrophic factor (BDNF), Epithelial Neutrophil-Activating Protein 78 Mouse (ENA-78) also known as C-X-C motif chemokine 5 (CXCL5), Epidermal growth factor (EGF), Eotaxin also known as C-C motif chemokine 11 (CCL11), Fibroblast growth factor 2 (FGF2), granulocyte colony-stimulating factor (G-CSF) also known as colony-stimulating factor 3 (CSF-3), granulocyte-macrophage colony-stimulating factor (GM-CSF), GRO alpha also known as chemokine (C-X-C motif) ligand 1 (CXCL1), Hepatocyte growth factor (HGF), type-1 interferon (IFN) alpha, IFN gamma, Immunoglobulin M (IgM), interleukin 1 (IL-1) alpha, IL-1 beta, IL-2, IL-2 receptor (IL-2R), IL-4, IL-5, IL-6, IL-7R alpha, IL-9, IL-10, IL-12p70, IL-13, IL-15, IL-17A also known as cytotoxic T-lymphocyte associated protein 8 (CTLA8), IL-18, IL-19, IL-23, IL-25 also known as IL-17E, IL-27, IL-31, IL-33, Interleukin 1 receptor-like 1 (IL1RL1), also known as IL-33R and ST2, Interferon gamma-induced protein 10 (IP-10) also known as CXCL10, Leptin, Leukemia inhibitory factor (LIF), monocyte chemoattractant protein 1 (MCP-1) also known as CCL2, MCP-3 also known as CCL7, macrophage colony-stimulating factor (M-CSF), macrophage inflammatory protein 1 (MIP-1) alpha also known as CCL3, MIP-1 beta also known as CCL4, MIP-2 alpha also known as CXCL2, Platelet-derived growth factor subunit B beta (PDGF-BB), Placenta growth factor 1 (PlGF-1), Receptor activator of nuclear factor kappa-B ligand (RANKL), Regulated on activation, normal T cell expressed and secreted (RANTES) also known as CCL5, stromal cell-derived factor 1 (SDF-1) alpha, Transforming growth factor (TGF) beta, Tumor necrosis factor (TNF) alpha, and Vascular endothelial growth factor A (VEGF-A). In some embodiments are TLR8 antagonists. In some embodiments, a TLR8 antagonist is a negative control in TLR assays.

In some embodiments, a synthetic CpG oligonucleotide is present in a composition or pharmaceutical composition in an amount ranging from about 1 ng to about 25,000 mg. In some embodiments, the synthetic CpG oligonucleotide is present, for example in a composition or a pharmaceutical composition, in an amount from: about 1 ng to about 100 ng, about 100 ng to about 500 ng, about 500 ng to about 1 mg, about 1 mg to about 500 mg, about 500 mg to about 1000 mg, about 1000 mg to about 5000 mg, about 5000 mg to about 10000 mg, about 10000 to 25000 mg, or about 25000 to 50000 mg. In some embodiments, the synthetic CpG oligonucleotide is present in the composition or the pharmaceutical composition is about 1 ng, about 10 ng, about 100 ng, about 200 ng, about 300 ng, about 400 ng, about 500 ng, about 600 ng, about 700 ng, about 800 ng, about 900 ng, about 1 ug, about 10 ug, about 50 ug, about 100 ug, about 200 ug, about 300 ug, about 400 ug, about 500 ug, about 600 ug, about 700 ug, about 800 ug, about 900 ug, about 1 mg, about 10 mg, about 100 mg, about 200 mg, about 300 mg, about 400 mg, about 500 mg, about 600 mg, about 700 mg, about 800 mg, about 900 mg, 1000 mg, about 2000 mg, about 5000 mg, about 10,000 mg, about 15,000 mg, about 20,000 mg, about 25,000 mg.

CpG Oligonucleotides

Also disclosed herein are compositions and pharmaceutical compositions comprising synthetic CpG oligonucleotides (CpG ODN). CpG ODNs can be short, single stranded DNA molecules that contain a can cytosine deoxynucleoside, followed by a guanine deoxynucleoside, connected by a phosphodiester linker, or a phosphorothioate (PS) linker. A synthetic CpG oligonucleotide can be unmethylated or a nucleobase or nucelobases in the synthetic CpG oligonucleotide can be unmethylated. In one embodiment, at least the C of the 5' CpG 3' is unmethylated. CpG ODNs can function as pathogen-assisted molecular patterns (PAMPs). CpG PAMPs can be recognized by Toll-like receptor (TLR9 or TLR-9) which are expressed in B cells and plasmacytoid dendritic cells (pDCs).

Wound Healing

In some embodiments are provided methods for wound healing. In some embodiments, a wound refers to a break in the skin. In some embodiments, a wound refers to the specific layer of skin being abraded. In some embodiments, wound healing, refers to the reconstruction of the outer layers of this skin, including the dermis and/or epidermis. In some embodiments, a wound is a closed wound. In some embodiments, a wound is an open wound. In some embodiments, a wound is a clean wound. In some embodiments, a wound is a dirty, or unclean wound. Wound healing, or wound repair is a complex process involving multiple biological interactions and processes. Three phases of wound healing can include: acute inflammatory phase, extracellular matrix and collagen synthesis, and remodeling. Keratinocytes, fibroblasts and/or inflammatory cells can interact at the wound site. Keratinocytes can interact with structure protein matrices and receptors. The receptors can include matrix metalloproteinases (MMP). MMP levels can be activated and expressed during wound healing, or more generally, during tissue remodeling. Bone morphogenetic protein (BMP6) can play a role in the control of skin development and remodeling by regulating keratinocyte proliferation and differentiation. BMP6 synthesis and development is associated of the multilayer structure of the skin which declines in adult. However, BMP6 can be strongly elevated and expressed during wound healing, fibrosis but not during inflammation. Vimentin is a cytoskeletal protein which can contribute to the normal function of repair modulating cells in tissue regeneration and wound closure at the wound edge. Vimentin can be a regulator for leader cell to modulate wound repair and direct invasion of epithelial cells intermediated filaments to development of fibrosis.

Scar Occurrence and Immunosuppressants

Some embodiments described herein involve skin healing which includes cell regeneration and tissue remodeling applications. Scar formation involves immune factors and increased collagen deposition. In certain embodiments, described herein are the treatment of scars. The three main groups of scars are: 1) atrophic scars, wherein collagen formation is depleted, often associated with acne scarring; 2) hypertrophic scars, which are quite prevalent in and are marked by scar hyperplasia paired with an increase in collagen deposits; and 3) keloid scars which are marked by an overgrowth of granulation tissue at a healed wound site. Collagen-1 deposit can slowly replace the granulation tissue of a keloid scar.

Hypertrophic scars, identified by having observable width, raised areas of the skin, can be of interest. Recent developments investigating the inhibition of scar hyperplasia have focused on immunosuppressants, and Botox, among others. Immunosuppressive agents can regulate function of T-helper cells, specifically Th1 and Th2. In some embodiments, a scar is measured by a scar elevation index, wherein the area of the scar and the area of excision are added together and divided by the size of the cartilage wound base. In some embodiments, scar measurements are taken over time prior to, during, and after administration of a pharmaceutical composition comprising a synthetic CpG oligonucleotide comprising a sequence of: SEQ ID NOS: 1-30.

In some embodiments, compositions or pharmaceutical compositions herein can comprise a therapeutic, which can include an antibiotic or a pharmaceutically acceptable salt thereof. An antibiotic or pharmaceutically acceptable salt thereof can be: Amikacin, Gentamicin, Kanamycin, Neomycin, Netilmicin, Tobramycin, Paromomycin, Streptomycin, a Spectinomycin, an Ansamycin, Geldanamycin, Herbimycin, Rifaximin, Carbacephem, Loracarbef, a Carbapenem, Ertapenem, Doripenem, Imipenem/Cilastatin, Meropenem, a Cephalosporin, Cefadroxil, Cefazolin, Cephradine, Cephapirin, Cephalothin, Cefalexin, Cefaclor, Cefoxitin, Cefotetan, Cefamandole, Cefmetazole, Cefonicid, Loracarbef, Cefprozil, Cefuroxime, Cefixime, Cefdinir Omnicef, Cefditoren, Cefoperazone, Cefotaxime, Cefpodoxime, Ceftazidime, Ceftibuten, Ceftizoxime, Moxalactam, Ceftriaxone, Cefepime, Ceftaroline fosamil, Ceftobiprole, a Glycopeptide, Teicoplanin, Vancomycin, Telavancin, Dalbavancin, Oritavancin, a Lincosamide, Clindamycin, Lincomycin, Lipopeptide, Daptomycin, a Macrolide(Bs), Azithromycin, Clarithromycin, Erythromycin, Roxithromycin, Telithromycin, Spiramycin, Fidaxomicin, a Monobactam, Aztreonam, Nitrofurans, Furazolidone, a Nitrofurantoin, an Oxazolidinone, Linezolid, Posizolid, Radezolid, Torezolid, a Penicillin, Amoxicillin, Ampicillin, Azlocillin, Dicloxacillin, Flucloxacillin, Mezlocillin, Methicillin, Nafcillin, Oxacillin, Penicillin G, Penicillin V, Piperacillin, Penicillin G, Temocillin, Ticarcillin, a Polypeptide, Bacitracin, Colistin Coly-Mycin-S, Polymyxin B, Quinolones/Fluoroquinolones, Ciprofloxacin, Enoxacin, Gatifloxacin, Gemifloxacin, Levofloxacin, Lomefloxacin, Moxifloxacin, Nadifloxacin, Nalidixic acid, Norfloxacin, Ofloxacin, Trovafloxacin, Grepafloxacin, Sparfloxacin, Temafloxacin, a Sulfonamide, Mafenide, Sulfacetamide, Sulfadiazine, Silver sulfadiazine, Sulfadimethoxine, Sulfamethizole, Sulfamethoxazole, Sulfanilimide, Sulfasalazine, Sulfisoxazole, Trimethoprim-Sulfamethoxazole (Co-trimoxazole) (TMP-SMX), Sulfonamidochrysoidine, a Tetracycline, Demeclocycline, Doxycycline, Metacycline, Minocycline, Oxytetracycline, Tetracycline, Clofazimine, Dapsone, Capreomycin, Cycloserine, an Ethambutol, Ethionamide, Isoniazid, Pyrazinamide, Rifampicin, Rifabutin, Rifapentine, Streptomycin, Arsphenamine, a Chloramphenicol, Fosfomycin, Fusidic acid, Metronidazole, Mupirocin, Platensimycin, Quinupristin/Dalfopristin, Thiamphenicol, a Tigecycline, Tinidazole, Trimethoprim, a pharmaceutically acceptable salt of any of the foregoing, or any combination of the foregoing.

In some instances, compositions or pharmaceutical compositions herein can comprise a therapeutic, which can include a corticosteroid or a pharmaceutically acceptable salt thereof. A corticosteroid or pharmaceutically acceptable salt thereof can be: Amcinonide, Budesonide, Ciclesonide, Deflazacort, Desonide, Formocortal (fluoroformylone), Fluclorolone, Fludroxycortide, Flunisolide, Fluocinolone acetonide, Fluocinonide, Halcinonide, Triamcinolone acetonide, Alclometasone, Beclometasone, Betamethasone, Clobetasol, Clobetasone, Clocortolone, Desoximetasone, Dexamethasone, Diflorasone, Difluocortolone, Fluclorolone, Flumetasone, Fluocortin, Fluocortolone, Fluprednidene, Fluticasone, Fluticasone furoate, Halometasone, Meprednisone, Mometasone, Mometasone furoate, Paramethasone, Prednylidene, Rimexolone, Ulobetasol (halobetasol), Alclometasone, Beclometasone, Betamethasone, Clobetasol, Clobetasone, Clocortolone, Desoximetasone, Dexamethasone, Diflorasone, Difluocortolone, Fluclorolone, Flumetasone, Fluocortin, Fluocortolone, Fluprednidene, Fluticasone, Fluticasone furoate, Halometasone, Meprednisone, Mometasone, Mometasone furoate, Paramethasone, Prednylidene, Rimexolone, Chloroprednisone, Cloprednol, Difluprednate, Fludrocortisone, Fluocinolone, Fluperolone, Fluprednisolone, Loteprednol, Methylprednisolone, Prednicarbate, Prednisolone, Prednisone, Tixocortol, Triamcinolone, Flugestone (flurogestone), Fluorometholone, Medrysone (hydroxymethylprogesterone), Prebediolone acetate (21-acetoxypregnenolone), Cortisol (hydrocortisone), 11-Dehydrocorticosterone, 11-Deoxycorticosterone (deoxycortone, desoxycortone; 21-hydroxyprogesterone), 11-Deoxycortisol (cortodoxone, cortexolone), 11-Ketoprogesterone (11-oxoprogesterone; Ketogestin), 11β-Hydroxypregnenolone, 11β-Hydroxyprogesterone (21-deoxycorticosterone), 11β,17α,21-Trihydroxypregnenolone, 17α,21-Dihydroxypregnenolone, 17α-Hydroxypregnenolone, 17α-Hydroxyprogesterone, 18-Hydroxy-11-deoxycorticosterone, 18-Hydroxycorticosterone, 18-Hydroxyprogesterone, 21-Deoxycortisol, 21-Deoxycortisone, 21-Hydroxypregnenolone (prebediolone), Aldosterone, Corticosterone (17-deoxycortisol), Cortisol (hydrocortisone), Cortisone, Pregnenolone, Progesterone, a pharmaceutically acceptable salt of any of the foregoing, or any combination of any of the foregoing.

Cell Expansion

T-cell expansion can relate to the antigen-specific lymphocytes undergoing cell proliferation in response to an immune reaction. Deliberate T-cell expansion can be facilitated using interleukin type cells. In some embodiments, compositions and/or pharmaceutical compositions described herein facilitate cell expansion. In some embodiments, lymphocytes are proliferated. In some embodiments, young lymphocytes are proliferated. In some embodiments, the term "young lymphocyte(s)" is interchangeable with immature lymphocytes. In some embodiments, cytokine release is propagated using a composition or pharmaceutical composition described herein. In some embodiments, compositions and/or pharmaceutical compositions described herein facilitate T-cell response. In some embodiments, compositions and/or pharmaceutical compositions described herein facilitate T-cell response without B-cell response. In some embodiments, compositions and/or pharmaceutical compositions described herein facilitate T-cell response and cytokine release.

Compositions

In some embodiments, compositions described herein comprise a synthetic CpG oligonucleotide.

In some embodiments, the sequence of the synthetic CpG oligonucleotide comprises, consists of, or consists essentially of any one of the sequences in TABLE 1 or TABLE 2. In some embodiments, a composition or pharmaceutical composition comprises a synthetic CpG oligonucleotide that comprises, consists of, or consists essentially of one of the sequences in TABLE 1 or TABLE 2 and an excipient, diluent, carrier, or any combination of these, any, or all of which may be pharmaceutically acceptable. Any of the sequences in TABLE 1 may have nucleic acid residues independently linked by phosphodiester or phosphorothioate groups.

TABLE 1

Synthetic CpG Oligonucleotide Sequences

| SEQ ID NO: | SEQUENCE |
|---|---|
| SEQ ID NO: 5 | ATCACGTAGCATCACGTAGC |
| SEQ ID NO: 6 | ATCACGGAGCATCACGGAGC |
| SEQ ID NO: 7 | ATCTCGTAGCATCTCGTAGC |
| SEQ ID NO: 8 | ATCTCGGAGCATCTCGGAGC |
| SEQ ID NO: 9 | ATCGCGTAGCATCGCGTAGC |
| SEQ ID NO: 10 | ATCGCGGAGCATCGCGGAGC |
| SEQ ID NO: 11 | ATTCGTCGGCGTCGACGGTC |
| SEQ ID NO: 12 | ATGCGACGTCGACGTCGGTC |
| SEQ ID NO: 13 | ATACGACGTCGTCGTCGATC |
| SEQ ID NO: 14 | ATGCGTCGGCGACGTCGTGC |
| SEQ ID NO: 15 | GTACGACGTCGTCGACGTGA |
| SEQ ID NO: 16 | TAGCGTCGACGACGTCGATG |

Any composition or pharmaceutical composition herein can comprise, consist of, or consist essentially of any engineered oligonucleotide or synthetic CpG oligonucleotide sequence comprising any SEQ ID NO. herein. Embodiments herein can comprise an engineered oligonucleotide or synthetic CpG oligonucleotide sequence having a sequence having at least about 70, 75, 80, 85, 90, 95, 96, 97, 98, or 99 percent identity to the sequence of any SEQ ID NO. herein and/or at least about 80, 85, 90, 95, 96, 97, 98, or 99 percent length to the sequence of any SEQ ID NO. herein. In some embodiments, a synthetic CpG oligonucleotide is used interchangeably with an engineered oligonucleotide or engineered CpG oligonucleotide.

In some embodiments, SEQ ID NOs: 5-16 can have 0, 1, 2, 3, or 4 nucleobase modifications. In some embodiments, a synthetic CpG oligonucleotide comprising a sequence of any one of SEQ ID NOs: 5-16, when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the synthetic CpG oligonucleotide, in an in vitro assay. In some embodiments, each nucleic acid residue comprised in a synthetic CpG oligonucleotide described in TABLE 1 is independently linked to adjacent nucleic acid residue by a phosphodiester group or a phosphorothioate group.

TABLE 2

Synthetic CpG Oligonucleotide Sequences

| SEQ ID NO: | Sequence |
|---|---|
| SEQ ID NO: 17 | A*T*C*T*C*G*T*A*G*C*A*T*C*T*C*G*T*A*G*C |
| SEQ ID NO: 18 | A*T*C*T*C*G*T*A*G*C*A*T*C*T*C*G*T*A*G*C |
| SEQ ID NO: 19 | A*T*C*T*C*G*G*A*G*C*A*T*C*T*C*G*G*A*G*C |
| SEQ ID NO: 20 | A*T*C*T*C*G*G*A*G*C*A*T*C*T*C*G*G*A*G*C |
| SEQ ID NO: 21 | A*T*G*C*G*T*C*G*G*C*G*A*C*G*T*C*G*T*G*C |
| SEQ ID NO: 22 | T*A*G*C*G*T*C*G*A*C*G*A*C*G*T*C*G*A*T*G |
| SEQ ID NO: 23 | A*T*G*C*A*C*T*C*T*G*C*A*G*G*C*T*T*C*T*C |
| SEQ ID NO: 24 | A*T*A*T*A*C*T*C*T*A*T*A*G*A*T*T*T*C*T*C |
| SEQ ID NO: 25 | A*T*C*T*C^G*T*A*G*C*A*T*C*T*C*G*T*A*G*C |
| SEQ ID NO: 26 | A*T*C*T*C^G*T*A*G*C*A*T*C*T*C*G*T*A*G*C |
| SEQ ID NO: 27 | A*T*C*T*C^G*G*A*G*C*A*T*C*T*C*G*G*A*G*C |
| SEQ ID NO: 28 | A*T*C*T*C^G*G*A*G*C*A*T*C*T*C*G*G*A*G*C |
| SEQ ID NO: 29 | A*T*G*C^G*T*C*G*G*C*G*A*C*G*T*C*G*T*G*C |
| SEQ ID NO: 30 | T*A*G*C^G*T*C*G*A*C*G*A*C*G*T*C*G*A*T*G |

*Indicates a phosphorothioate group; ^ indicates a phosphodiester group between a C and a G.

In some embodiments, at least one phosphorothioate group between a C and a G of a sequence in TABLE 2 can be replaced by a phosphodiester group.

In some embodiments, a composition or pharmaceutical composition can comprise a synthetic CpG oligonucleotide that comprises at least a portion of a sequence of TABLE 1 or TABLE 2. In some embodiments, a synthetic CpG oligonucleotide here can have about: 80, 85, 90, 95, 96, 97, 98, or 99% identity to any SEQ ID NO. herein, for example, SEQ ID NOs: 1-30. In some embodiments, a composition or pharmaceutical composition comprises a synthetic CpG oligonucleotide having from about 10 to about 20 nucleic acid residues, about 15 to about 25 nucleic acid residues, about 15 to about 30 nucleic acid residues, about 15 to about 40 nucleic acid residues, about 20 to about 30 nucleic acid residues, about 20 to about 40 nucleic acid residues, or about 30 to about 50 nucleic acid residues. In some embodiments, a composition or pharmaceutical composition herein can comprise an oligonucleotide comprising a synthetic CpG oligonucleotide wherein the oligonucleotide can have from about 10 to about 20 nucleic acid residues, about 15 to about 25 nucleic acid residues, about 20 to about 30 nucleic acid residues, about 20 to about 40 nucleic acid residues, or about 30 to about 50 nucleic acid residues. In some embodiments herein, a synthetic CpG oligonucleotide can have about: 80, 85, 90, 95, 96, 97, 98, or 99% sequence length to any SEQ ID NO. herein, for example, SEQ ID NOs: 1-30 In some embodiments, the synthetic CpG nucleotide does not contain an epigenetic modification. In some embodiments, each CpG oligonucleotide is unmethylated. In some embodiments, a nucleobase present in the synthetic CpG oligonucleotide contains an epigenetic mark. In some embodiments, the epigenetic mark can be, for example: methyl, hydroxymethyl, formyl, or a carboxylic acid. In some embodiments, the synthetic CpG oligonucleotide comprises a chemical modification to a sugar of a nucleobase.

In some embodiments, synthetic CpG oligonucleotides may be represented by formulae wherein specific nucleotides may be interchangeable at one or more linked nucleotides within the synthetic CpG oligonucleotide sequence. In some embodiments, is a synthetic CpG oligonucleotides comprising a sequence of: 5'$(N_1)_a(N_2)_a(W)_a$-CpG-$(X)_a$-CpG-$(Y)_a$-CpG-$(Z)_a$-CpG-$(B)_a$-CpG-$(D)_a(N_3)_a(N_4)_a$ 3' (SEQ ID NO: 1), wherein: $N_1$ is A or T, $N_2$ is A or T, W is G, X is T, Y is A, Z is A, B is T, D is A or T, $N_3$ is G or T, and $N_4$ is C or G; a is independently in each case 0, 1, 2, or 3. In some embodiments, is a synthetic CpG oligonucleotide comprising a sequence of: 5'$(N_1)_a(N_2)_a(W)_a$-CpG-$(X)_a$-CpG-$(Y)_a$-CpG-$(Z)_a$-CpG-$(B)_a$-CpG-$(D)_a(N_3)_a(N_4)_a$ 3' (SEQ ID NO: 2) wherein each: $N_1$, $N_2$, W, X, Y, Z, B, D, $N_3$ and $N_4$ is independently A, T, G, C, or U. In some embodiments, is a synthetic CpG oligonucleotide comprising a sequence of: 5'$(E)_b(F)_b$ $(H)_b(J)_b$-CpG $(N_1)_b(P)_b(J)_b(K)_b(L)_b$ $(M)_b(O)_b(Q)_b$-CpG-$(N_2)_b(R)_b(S)_b(V)_b$ 3' (SEQ ID NO: 3) wherein: E is A, F is T, H is C, J is T, $N_1$ is T or G, P is A, J is G, K is C, L is A, M is T, O is C, Q is T, $N_2$ is T or A, R is A, S is G, and V is C. In some embodiments, is a synthetic CpG oligonucleotide comprising a sequence of: 5'$(E)_b(F)_b$ $(H)_b(J_1)_b$-CpG-$(N_1)_b(P)_b(J_2)_b(K)_b(L)_b(M)_b(O)_b$ $(Q)_b$-CpG-$(N_2)_b(R)_b(S)_b(V)_b$ 3' (SEQ ID NO: 4) wherein each: E, F, H, $J_1$, $N_1$, P, $J_2$, K, L, M, O, Q, $N_2$, R, S, and V is independently A, T, C, G, or U. In some embodiments, a synthetic CpG oligonucleotide, when contacted with a Ramos-Blue B lymphocyte cell, results in an increased concentration of secreted embryonic alkaline phosphatase (SEAP) from the Ramos-Blue B lymphocyte cell compared to an otherwise comparable Ramos-Blue B lymphocyte cell that is not contacted with the synthetic CpG oligonucleotide, in an in vitro assay.

In some embodiments, a synthetic CpG oligonucleotide is present, for example in a composition or a pharmaceutical composition, in an amount from: about 1 ng to about 100 ng, about 100 ng to about 500 ng, about 500 ng to about 1 mg, about 1 mg to about 500 mg, about 500 mg to about 1000 mg, about 1000 mg to about 5000 mg, about 5000 mg to about 10000 mg, about 10000 to 25000 mg, or about 25000 to 50000 mg. In some embodiments, the synthetic CpG oligonucleotide is present in the composition or the pharmaceutical composition is about 1 ng, about 10 ng, about 100 ng, about 200 ng, about 300 ng, about 400 ng, about 500 ng, about 600 ng, about 700 ng, about 800 ng, about 900 ng, about 1 ug, about 10 ug, about 50 ug, about 100 ug, about 200 ug, about 300 ug, about 400 ug, about 500 ug, about 600 ug, about 700 ug, about 800 ug, about 900 ug, about 1 mg, about 10 mg, about 100 mg, about 200 mg, about 300 mg, about 400 mg, about 500 mg, about 600 mg, about 700 mg, about 800 mg, about 900 mg, 1000 mg, about 2000 mg, about 5000 mg, about 10,000 mg, about 15,000 mg, about 20,000 mg, about 25,000 mg.

In some embodiments, a composition and/or pharmaceutical composition can stimulate the immune system. In some embodiments, stimulation of the immune system results in the production of one or more growth factors. In some embodiments, a composition and/or pharmaceutical composition can further comprise a growth factor in an effective or therapeutically effective amount. In some embodiments, therapeutically effective amounts of the compositions and/or pharmaceutical compositions described herein are administered before, in conjunction with, simultaneously, concurrently, or after administration of a growth factor in an effective or therapeutically effective amount. In some embodiments, concurrent administration of a composition or pharmaceutical composition described herein, and a growth factor, such as vascular endothelial growth factor (VEGF), promote angiogenesis. In some embodiments, the growth factor is a hormone-releasing factor (GHRF). In some embodiments, the growth factor is a platelet-derived growth factor (PDGF). In some embodiments, the growth factor is a basic fibroblast growth factor (bFGF or FGF-2).

Delivery Systems

In some embodiments, compositions or pharmaceutical compositions described herein are administered or contacted for treatment of a skin or a tissue, for example of a subject or a subject in need thereof. In some embodiments, the compositions or pharmaceutical compositions are in the form of a spray, a lotion, a cream, an ointment, a gel, a bandage with an amount of a composition described herein, a lyophile for long term storage, or an ointment. In some embodiments, compositions or pharmaceutical compositions herein can be homogenous, substantially homogenous, heterogenous, or substantially heterogenous. In some embodiments, an ointment can be a semi-solid external agent. In some embodiments the ointment is of a consistency for easy application to the skin. In some embodiments an ointment comprises at least one of: a fat, a fatty oil, a lanoline, Vaseline, a paraffin, a wax, a hard ointment, a resin, a higher alcohol, a plastic, a glycol, glycerol, a water or an emulsifier and a suspending agent.

In some embodiments, the compositions and/or pharmaceutical compositions described herein are administered once, twice, three, four, five, six, seven, eight, nine, ten or multiple times. In some embodiments, compositions and/or pharmaceutical compositions described herein are administered directly to or contacted directly or indirectly to immune cells.

In some embodiments, compositions and/or pharmaceutical compositions described herein are formulated in extended-release formulations, wherein the synthetic CpG oligonucleotide(s) from the extended-release formulation(s) are exposed to a skin or a tissue over a defined duration of time. In some embodiments the duration of time is at least about: 1 hour, at least about 2 hours, at least about 3 hours, at least about 4 hours, at least about 5 hours, at least about 6 hours, at least about 7 hours, at least about 8 hours, at least about 9 hours, at least about 10 hours, at least about 15 hours, at least about 20 hours, at least about 24 hours, at least about 2 2 days, at least about 3 days, at least about 4 days, at least about 5 days, at least about 6 days, at least about 7 days wherein a day is 24 hours, at least about 2 weeks, at least about 3 weeks, at least about 4 weeks, at least about 8 weeks, at least about 12 weeks, at least about 16 weeks, at least about 20 weeks, at least about 24 weeks, or for as long as necessary or desired.

In some embodiments, the compositions and/or pharmaceutical compositions herein further comprises a booster. In some embodiments the booster is a protein. In some embodiments the protein is a boosting protein. In some embodiments the boosting protein is an interleukin protein. In some embodiments, the interleukin protein is an IL-7. In some embodiments the booster is a tumor infiltrating lymphocyte (TIL).

Pharmacological Carriers and Diluents

In some embodiments, pharmacologically acceptable carriers and pharmaceutically acceptable carriers may be referred to interchangeably herein. Exemplary pharmaceutically acceptable carriers include but are not limited to buffered solutions. In some embodiments, a buffered solution can be a solution that resists changes in pH when acid or alkali is added to it. In some embodiments, a buffered solution is or comprises phosphate buffered saline (PBS). In some embodiments, a carrier or a pharmaceutically acceptable carrier can be or include a penetrant. In some embodiments, a penetrant can aid one or more components of a composition or pharmaceutical composition herein, for example a synthetic CpG oligonucleotide, in entering into or penetrating through one or more layers of at least a portion of a skin of a subject or a subject in need thereof. In some embodiments, the penetrant can be a conventional penetrant used to topically apply agents and/or formulations for wound healing. In some embodiments, the carrier or the pharmaceutically acceptable carrier is or comprises a synthetic or natural hydrophilic polymer. In some embodiments, the carrier or the pharmaceutically acceptable carrier is or comprises a petroleum jelly, such as Vaseline. In some embodiments, the petroleum jelly comprises at least about: 1%, 2%, 3%, 4%, or 5% by weight stearyl alcohol based on the total weight of the petroleum jelly. In some embodiments, the petroleum jelly is or further comprises a liquid paraffin. In some cases, a composition and/or a pharmaceutical composition can comprise a pharmaceutically acceptable carrier and/or a diluent. In some instances, a carrier or diluent or pharmaceutically acceptable carrier or diluent can comprise a water, an alcohol, a salt solution (e.g., saline), or a mixture thereof. In some instances, a carrier or pharmaceutically acceptable carrier can comprise a carbohydrate, a buffer, a salt, a pH adjuster, or any combination thereof. In some cases, the carrier or diluent or pharmaceutically acceptable carrier or diluent can comprise at least one of: sodium phosphate, citric acid, acetic acid, tromethamine, histidine, gluconic, lactic acid, tartaric acid, aspartic acid, glutamic acid, a citric acid cycle intermediate, or any combination thereof. In some embodiments, at least one of these can be present in a buffer. In some cases, a carrier can be a substrate used in the process of drug delivery. In some cases, a carrier can contribute to a composition's or pharmaceutically acceptable composition's attributes such as stability, biopharmaceutical profile, appearance, and/or patient acceptability. In some cases, a carrier or pharmaceutically acceptable carrier can be or comprise an organic excipient. In some cases, a carrier or a diluent or pharmaceutically acceptable carrier or diluent can be or comprise a solid such as a filling agent used in the production of a pill, for example lactose or another carbohydrate.

In some embodiments, the release and/or administration of a composition or pharmaceutical composition described herein is facilitated by a delivery system. In some embodiments, the delivery system requires at least one administration or contacting. In some embodiments, the delivery system can be administered or contacted with a subject or a subject in need thereof more than once, for example 2, 3, 4, 5, 6, 7, 8, 9, or 10 times or more. In some embodiments, the delivery system requires multiple administrations.

In some embodiments, the delivery system is or can comprise a polymer-based system. In some embodiments, the polymer-based system is selected from at least one of: a poly(lactideglycolide), a copolyoxalate, a polycaprolactone, a polyesteramide, a polyorthoester, a polyhydroxybutyric acid, a polyanhydride, and any combination thereof.

Pharmaceutical Compositions

The compositions and pharmaceutical compositions herein, and/or the synthetic CpG oligonucleotides, and/or any therapeutic or further therapeutic herein, for example, and antibiotic, an antifungal, an antiviral, and/or an antiparasitic can be formulated as neutral or salt forms, including as a pharmaceutically acceptable salt. Pharmaceutically acceptable salts include those formed with free amino groups such as those derived from hydrochloric, phosphoric, acetic, oxalic, tartaric acids, etc., and those formed with free carboxyl groups such as those derived from sodium, potassium, ammonium, calcium, ferric hydroxides, isopropylamine, triethylamine, 2-ethylamino ethanol, histidine, procaine, etc. In some embodiments, a salt or a pharmaceutically acceptable salt can comprise an HCl salt, an ascorbic acid salt, a mandelic acid salt, an aspartic acid salt, a carbonic acid salt, a citric acid salt, a formic acid salt, a glutamic acid salt, a lactic acid salt, a lauric acid salt, a maleic acid salt, a palmitic acid salt, a phosphoric acid salt, or any combination thereof. In some embodiments, a salt or a pharmaceutically acceptable salt can include, but is not limited to, a metal salt such as sodium salt, potassium salt, cesium salt and the like; an alkaline earth metal salt such as calcium salt, magnesium salt and the like; an organic amine salt such as a triethylamine salt, a pyridine salt, a picoline salt, an ethanolamine salt, a triethanolamine salt, a dicyclohexylamine salt, an N,N'-dibenzylethylenediamine salt and the like; an inorganic acid salt such as hydrochloride, hydrobromide, phosphate, sulphate and the like; an organic acid salt such as citrate, lactate, tartrate, maleate, fumarate, mandelate, acetate, dichloroacetate, trifluoroacetate, oxalate, formate and the like; a sulfonate such as methanesulfonate, benzenesulfonate, p-toluenesulfonate and the like; and/or an amino acid salt such as arginate, asparginate, glutamate and the like.

The compositions and pharmaceutical compositions disclosed herein can comprise a preservative, e.g., a compound which can be added to essentially reduce bacterial and/or fungal action or presence in or on any composition or pharmaceutical composition herein. Examples of preservatives include but are not limited to octadecyldimethylbenzyl ammonium chloride, hexamethonium chloride, benzalkonium chloride (a mixture of alkylbenzyldimethylammonium chlorides in which the alkyl groups are long-chain compounds), and benzethonium chloride.

A composition or pharmaceutical composition herein can be formulated to be compatible with its intended route of administration. Examples of routes of administration include, but are not limited to, topical, systemic, parenteral, e.g., intravenous, intradermal, subcutaneous, oral, intranasal (e.g., inhalation), intratumoral, transdermal (e.g., topical), transmucosal, and rectal administration. In some embodiments, a composition or pharmaceutical composition can be formulated as a composition or pharmaceutical composition adapted for intravenous, subcutaneous, intramuscular, oral, intranasal, transdermal, or topical administration to a human being or subject or subject in need thereof. Compositions and pharmaceutical compositions for intravenous administration can be solutions in sterile isotonic aqueous buffer. Compositions and pharmaceutical compositions here can be sterile or aseptic.

Compositions and pharmaceutical compositions herein may also include a solubilizing agent and/or a local anesthetic such as lignocaine or a pharmaceutically acceptable salt of any of these, for example, to ease pain at the site of the administration, contacting, or injection. In some embodiments, the methods of the disclosure can comprise administration of a composition formulated for parenteral administration by injection (e.g., by bolus injection or continuous infusion). Formulations for injection may be presented in unit dosage form (e.g., in ampoules or in multi-dose containers) with an added preservative. The compositions may take such forms as suspensions, solutions or emulsions in oily or aqueous vehicles, and may contain agents such as suspending, stabilizing and/or dispersing agents. Alternatively, the active ingredient may be in powder form for constitution with a suitable vehicle (e.g., sterile pyrogen-free water) before use.

Accordingly, this disclosure can provide a composition or a pharmaceutical composition comprising an effective amount of a genetically modified organism, a derivative, or an extract thereof, in combination with a pharmaceutically acceptable excipient, carrier, or diluent.

In some embodiments, a composition or a pharmaceutical composition comprises a surfactant. Surfactants can lower the surface tension of a liquid, the interfacial tension between two liquids, or that between a liquid and a solid. The surfactant can be a detergent, a wetting agent, an emulsifier, a foaming agent, a dispersant, or any combination thereof. In some embodiments, the surfactant can be a polysorbate-type emulsifier. In some embodiments, the polysorbate is a PEG (polyethylene glycol)-ylated sorbitan esterified with one or more fatty acids. In some embodiments, the surfactant is selected from: Polysorbate 20 (polyoxyethylene 20 sorbitan monolaurate), Polysorbate 60, Polysorbate 80, or any combination thereof.

In other embodiments, compositions and pharmaceutical compositions provided herein can be provided in an oral form, a transdermal form, an oil formulation, an edible food, or a food substrate, an aqueous dispersion, an emulsion, an oil-in-water emulsion, a water-in-oil emulsion, a solution, a suspension, an elixir, a gel, a syrup, an aerosol, a mist, a powder, a pill, a tablet, a lozenge, a gel, a lotion, a paste, a formulated stick, a balm, a cream, an ointment, or comprised in a bandage or a dressing.

In some embodiments the emulsion is suitable for dermal application. In some embodiments, the emulsions have little to no cytotoxicity. In some instances, cytotoxicity can be measured in vivo or in vitro by determining the extent of tissue death, if any. Skin tolerability is evaluated for compositions described herein formulated in an emulsion. In some embodiments, the emulsion comprises nanocrystals. In some embodiments, the emulsion promotes skin penetration. In some embodiments, the emulsion comprises a lipid nano-mixture. In some embodiments, the emulsion is partially or in its entirety a nano-emulsion. In some embodiments, the emulsion comprises squalene, or a derivative thereof.

In some embodiments, compositions and/or pharmaceutical compositions described herein comprise a synthetic CpG oligonucleotide, for example a CpG oligonucleotide having a sequence from TABLE 1 or TABLE 2, or SEQ ID NOs: 1-4.

In some embodiments are provided methods, for example, where compositions and/or pharmaceutical compositions comprising a synthetic CpG oligonucleotide are administered to or contacted with a subject or subject in need thereof, and wherein an antibiotic, an antiviral, an antifungal, an antiparasitic agent, or a pharmaceutically acceptable salt thereof is administered to or contacted with a subject or the subject in need thereof concurrently, or consecutively with the administering or the contacting of the composition and/or the pharmaceutical composition. The methods can be methods of treating or preventing a disease or condition.

Provided herein are also kits comprising a synthetic CpG oligonucleotide, and/or compositions or pharmaceutical compositions containing a synthetic CpG oligonucleotide disclosed herein. The kits can include packaging, instructions, and/or a container. The kits can comprise a further therapeutic, which can be comprised in composition or a pharmaceutical composition, or comprised in the kit separately from the composition or the pharmaceutical composition. In some embodiments, the kits can contain additional compositions used to generate various formulation precursors.

Therapeutic Applications

In some embodiments, compositions herein are used for the treatment of a disease or condition in a subject or a subject in need thereof. In some embodiments the disease or condition is a health-related skin condition, an infection, a wound or a health condition associated with damaged cells. In some embodiments, the damaged cells are or can comprise damaged epithelial cells. In some embodiments, the damaged epithelial cells are or can comprise damaged: simple squamous epithelium, simple cuboidal epithelium, simple columnar epithelium, pseudostratified epithelium, stratified squamous (nonkeratinized) epithelium, stratified cuboidal epithelium, or transitional epithelium, or a combination thereof.

In some embodiments, compositions and/or pharmaceutical compositions described herein prevent infections. In some embodiments, compositions and/or pharmaceutical compositions have anti-infective properties. In some embodiments, compositions and/or pharmaceutical compositions prevent the progression of an infection. In some embodiments, compositions and/or pharmaceutical compositions result in cessation of an infection.

In some embodiments, compositions and/or pharmaceutical compositions herein are used for the treatment of an infection or a bacterial infection affecting a tissue. In some embodiments the tissue is a skin. In some embodiments the infection or bacterial infection is selected from: anthrax, Epstein-Barr, cellulitis, impetigo, Hansen's disease (leprosy), warts, a cellulitis, a cellulitis resulting from streptococcus or staphylococcus or a combination thereof, an erythrasma, a paronychia, syphilis or impetigo, a staphylococcus infection, a methicillin-resistant *Staphylococcus aureus* (MRSA) infection, furuncles, lymphadenitis, erysipelas, lymphangitis, a meningitis, a necrotizing skin infection, a wound infection, skin-related consequences of a disease such as scarlet fever or toxic shock syndrome. In some embodiments, the bacterial infection is caused by *Propionibacterium acnes* or *Staphylococcus* spp. In some embodiments, the Staphylococcus is selected from the group consisting of *S. aureus, S. epidermidis, S. lugdunesis, S. saprophyticus, S. haemolyticus, S. caprae,* and *S. simiae*. In some embodiments, the bacterial infection is a bacterial infection of the skin.

In some embodiments, compositions and/or pharmaceutical compositions herein are used for the treatment of a bacterial infection affecting a tissue to a patient in need thereof, wherein the patient is of particular risk of developing a skin infection. In some embodiments the patient has diabetes, poor blood flow, is hospitalized, is elderly, is immunocompromised, has human immunodeficiency virus (HIV), AIDS, hepatitis, is undergoing chemotherapy, is taking an immunosuppressant agent, or has skin that is inflamed, damaged, or has a particular propensity for skin damage or skin infection.

In some embodiments, compositions and/or pharmaceutical compositions herein are used for the treatment of a viral infection affecting a tissue. In some embodiments the tissue is a skin. In some embodiments the viral infection is: a herpes, herpes simplex virus (HSV), shingles, chickenpox, molluscum contagiosum, warts, mumps, measles, hand, food and mouth disease, roseola, a viral hepatitis, a meningitis, encephalitis, a glandular fever, a human papillomavirus, HIV/AIDS, Ebola, West Nile virus, or monkey pox. In some embodiments, the viral infection is a viral infection of the skin.

In some embodiments, compositions and/or pharmaceutical compositions herein are used for the treatment of a viral infection affecting a tissue to a patient in need thereof, wherein the patient is of a particular risk of developing a skin infection. In some embodiments the patient has a herpes, herpes simplex virus (HSV), shingles, chickenpox, molluscum contagiosum, warts, mumps, measles, hand, food and mouth disease, roseola, a viral hepatitis, a meningitis, encephalitis, a glandular fever, a human papillomavirus, HIV/AIDS, Ebola, West Nile virus, or monkey pox. In some embodiments, the viral infection is a viral infection of the skin.

In some embodiments, compositions and/or pharmaceutical compositions herein are used for the treatment of a health-related skin condition. In some embodiments, the health-related skin condition is a stress-related skin condition. In some embodiments, the health-related skin condition is an inflammatory skin condition. In some embodiments, the health-related skin condition selected from: eczema, psoriasis, acne, rosacea, ichthyosis, vitiligo, hives, seborrheic dermatitis, a precancerous condition, actinic keratosis (solar keratosis), allergic contact dermatitis, an alopecia, a cheilitis, candidiasis, an aphthous ulcer, a melasma, razor bumps, a sunburn, a cold sore, a cold sore resulting from a human papillomavirus (HPV), stretch marks, or any combination thereof.

In some embodiments, compositions and/or pharmaceutical compositions herein are used for the treatment of a fungal infection affecting a tissue to a patient in need thereof, wherein the patient is of a particular risk of developing a skin infection. In some embodiments the fungal infection is selected from: aspergillosis, a *Candida auris* infection, an invasive candidiasis, a vaginal candidiasis, a candida infection of the bloodstream, a candida infection of the mouth, throat, and esophagus, a pneumocystis pneumonia (PCP), a coccidioidomycosis (Valley Fever), a blastomycosis, ring worm, a histoplasmosis, *Tinea versicolor, Tinea pedis,* or a paracoccidioidomycosis. In some embodiments, the fungal infection is a fungal infection of the skin.

In some embodiments, compositions and/or pharmaceutical compositions herein are used for the treatment of a parasitic infection affecting a tissue to a patient in need thereof, wherein the patient is of a particular risk of developing a skin infection. In some embodiments, the patient has a protozoon, protozoa, a helminth, or an ectoparasite. In some embodiments the parasitic infection is selected from: a trichomoniasis, a giardiasis, a cryptosporidiosis, a toxoplasmosis, or both. In some embodiments, the parasitic infection is a parasitic infection of the skin.

In some embodiments, compositions and/or pharmaceutical compositions herein are used for the treatment of a wound. In some embodiments the wound is associated with an infection or health condition described herein. In some embodiments the wound is a clean wound. In some embodiments the wound is an unclean, or dirty wound. In some embodiments the wound is selected from: radiation dermatitis, a surgical wound, a combat wound, an animal bite, a dermatitis, a lesion resulting from a skin biopsy, an insect sting, a jellyfish sting, an insect bite, a blister, a diabetic ulcer, a diabetic foot ulcer, a corneal abrasion, a pre-cancerous lesion, or a wound resulting from surgical sutures.

In some embodiments, compositions and/or pharmaceutical compositions herein are used for the treatment of a pre-cancerous or cancerous tissue. In some embodiments the cancerous or pre-cancerous tissue is present in or comprises: a basal cell epithelioma, a basal cell carcinoma, sun-damaged skin, or any combination thereof.

In some embodiments, compositions and/or pharmaceutical compositions herein are used for the treatment of a thermal injury. In some embodiments, the thermal injury is a burn. The burn can be a first-degree burn, a second-degree burn, a third-degree burn, or a combination thereof. In some embodiments the burn affects: the epidermis, the derma, the fat tissue, the muscle, or a combination thereof. The burn can be a partial thickness burn. A partial thickness burn can involve the epidermis and at least a portion of the dermis. A full thickness burn extends and results in destruction of all layers of dermis. In some embodiments, the burn is a partial thickness burn. In some embodiments, the burn is a full thickness burn. In some embodiments, the burn is a laser burn. In some embodiments a composition and/or pharmaceutical composition described herein results in at least one of the following: reduces the size of a thermally-induced oedema and hyperemia, normalizes a neutrophil to lymphocyte ratio, and/or stimulates formation of fibrous components in wound-induced scar tissue.

In some embodiments, a composition and/or pharmaceutical composition herein is used in a cell therapy or cell expansion application. In some embodiments, a composition or pharmaceutical composition described herein increases cell expansion in T-cells of a subject undergoing cell therapy. In some embodiments, cell expansion is increased while the T-cells still have a young cell phenotype. In some embodiments, a cell therapy is used for treatment of a disease, health condition, or wound described herein. In some embodiments, the treatment is for acne, candida, a skin cancer, eczema, radiation dermatitis, or psoriasis.

In some embodiments, is provided a method of treatment to reduce scaring, promote skin regeneration, promote tissue regeneration, or accelerated healing of a tissue, in a subject; the method comprising administering to, or contacting the tissue of, the subject with a composition or pharmaceutical composition herein.

In some embodiments is provided a method of inducing an inflammatory response in a tissue of a subject without introducing a bacterial infection, a fungal infection, or a viral infection, or any combination of these, into the tissue. In some embodiments, the method comprises contacting the tissue of the subject with a synthetic CpG oligonucleotide herein, for example a synthetic CpG oligonucleotide comprising a sequence of any one of SEQ ID NOs: 1-30, or a composition or pharmaceutical composition comprising the synthetic CpG oligonucleotide, thereby inducing the inflammatory response in the tissue of the subject. In some embodiments, the synthetic CpG oligonucleotide is contained in a composition or a pharmaceutical composition.

In some embodiments, the inflammatory response comprises cytokine production. In some embodiments, the inflammatory response comprises T cell production. In some embodiments, the inflammatory response comprises B cell production.

In some embodiments is provided a method of treating a subject in need thereof with a therapeutic effective dose of a composition or a pharmaceutical composition described herein. In some embodiments the therapeutic effective dose is a dose sufficient to induce epithelial growth, to promote wound healing, or both. In some embodiments, the dose is sufficient to produce increased division or increased survival, or both, of epithelial cells. In some embodiments, a therapeutically effective amount is an amount sufficient to reduce, ameliorate, or prevent at least one symptom of a disease or condition.

In some embodiments, a therapeutic effective dose of a composition or pharmaceutical composition herein is administered to or contacted with a patient or portion thereof by systemic administration. In some embodiments, a therapeutic effective dose of a composition or pharmaceutical composition herein is administered to or contacted with a patient or portion thereof by topical administration. In some embodiments, topical administration of a composition or pharmaceutical composition described herein is applied or contacted only in a specific area, and not throughout the body. In some embodiments, the composition or pharmaceutical composition is applied or contacted to the skin or the eye in an area in need of re-epithelialization. The composition or pharmaceutical composition can be applied in a topical preparation to a wound, such as an epithelial wound or defect, for example a traumatic or surgical wound, such as a skin or corneal abrasion or surgical incision.

In some embodiments, a synthetic CpG oligonucleotide is independently present in an amount from: about 1 ng to about 100 ng, about 100 ng to about 500 ng, about 500 ng to about 1 mg, about 1 mg to about 500 mg, about 500 mg to about 1000 mg, about 1000 mg to about 5000 mg, about 5000 mg to about 10000 mg, about 10000 to 25000 mg, or about 25000 to 50000 mg, for example by itself or as part of a composition or pharmaceutical composition. In some embodiments, the synthetic CpG oligonucleotide is present in the composition or the pharmaceutical composition is about 1 ng, about 10 ng, about 100 ng, about 200 ng, about 300 ng, about 400 ng, about 500 ng, about 600 ng, about 700 ng, about 800 ng, about 900 ng, about 1 ug, about 10 ug, about 50 ug, about 100 ug, about 200 ug, about 300 ug, about 400 ug, about 500 ug, about 600 ug, about 700 ug, about 800 ug, about 900 ug, about 1 mg, about 10 mg, about 100 mg, about 200 mg, about 300 mg, about 400 mg, about 500 mg, about 600 mg, about 700 mg, about 800 mg, about 900 mg, 1000 mg, about 2000 mg, about 5000 mg, about 10,000 mg, about 15,000 mg, about 20,000 mg, about 25,000 mg.

In some embodiments, contacting or applying to a tissue of, or administering to a patient or a patient in need thereof, occurs daily, every other day, every third day, every fourth day, every fifth day, every sixth day, weekly, every two weeks, every three weeks, once a month, once every three months, once every six months, once a year, or as needed. In some embodiments, the contacting is once, twice, three, four, five, six, seven, eight, nine, or ten times in a 24-hour period.

In some embodiments, a composition or pharmaceutical composition comprising a synthetic CpG oligonucleotide, for example a synthetic CpG oligonucleotide comprises a sequence of: any one of SEQ ID NOs: 1-30, is contacted with, applied to, administered to, or contacts a wound or a scar once, twice, three, four, five, six, seven, eight, nine, or ten times in a 24-hour period, followed by a second composition or pharmaceutical composition independently comprising a synthetic CpG oligonucleotide, for example a synthetic CpG oligonucleotide comprising a sequence comprising any one of SEQ ID NOs: 1-30, contacting a wound or a scar once, twice, three, four, five, six, seven, eight, nine, or ten times in a 24-hour period. In some embodiments, the wound is a surgical wound, a scar, an unclean wound, a clean wound, an ulcer, a diabetic ulcer, a diabetic foot ulcer, a burn, a radiation dermatitis, an acne, a cancer, a skin cancer, a psoriasis, a combat wound, or any combination thereof.

In some embodiments is provided a method of skin regeneration or tissue regeneration, for example of a patient or a patient in need thereof, comprising contacting or applying to a skin or the tissue of the subject a portion thereof with a composition or pharmaceutical composition comprising a synthetic CpG oligonucleotide, for example a synthetic CpG oligonucleotide having a sequence of any one of SEQ ID NOs: 1-30, in an amount effective to regenerate the skin or the tissue of the subject, thereby regenerating the skin or the tissue of the patient. In some embodiments, a therapeutic effective dose is administered by topical administration. In some embodiments, topical administration of a composition described herein is applied only in a specific area, and not throughout the body. In some embodiments, the composition or pharmaceutical composition is applied to the skin or the eye in an area in need of re-epithelialization. The composition or pharmaceutical composition can be applied to or contacted, in the form of a topical preparation to a wound, such as an epithelial wound or defect, for example a traumatic or surgical wound, such as a skin or corneal abrasion or surgical incision.

In some embodiments is provided a method of ex vivo cell expansion comprising contacting a plurality of cells with a composition or pharmaceutical composition comprising a synthetic CpG oligonucleotide, for example a synthetic CpG oligonucleotide having a sequence of any one of: SEQ ID NOs: 1-30, in an amount effective to expand the plurality of cells ex vivo, thereby expanding the plurality of cells ex vivo. In some embodiments, the composition or pharmaceutical compositions further comprise ex vivo one or more antisense oligonucleotides. In some embodiments, the method of ex vivo cell expansion can result in expanded cells that, when contacted with or applied to or into a patient, improve patient survival. In some embodiments, the cells are cytotoxic T lymphocytes. In some embodiments, the cells are human hepatic cell cultures. In some embodiments, the plurality of cells comprises stem cells, T-cells, or natural killer (NK) cells. In some embodiments, the cells are hematopoietic stem cells (HSCs). In some embodiments, the plurality of cells comprises T-cells that comprise cluster of differentiation 8 (CD8) glycoproteins. In some embodiments, the plurality of cells comprises T-cells that comprise cluster of differentiation 4 (CD4) glycoproteins. In some embodiments, the cells are counted and analyzed following flow cytometry. In some embodiments, the expanding is conducted for a period of time ranging from: about 10 to about 24 hours, about 24 hours to about 96 hours, about 24 to about 168 hours, about 48 to about 168 hours, about 48 to about 240 hours, or about 72 hours to 240 hours. In some embodiments, the contacting further comprises contacting the plurality of cells with at least one of interleukin 15 (IL-15), interleukin 7 (IL-7), interleukin 2 (IL-2), or any combination of these. Contacting the cells with a T-cell growth factor such as interleukin 15 (IL-15), interleukin 7 (IL-7), interleukin 2 (IL-2) can bind to the respective receptor resulting in polyclonal expansion T cells through binding to its cell surface receptor. In some embodiments, an interleukin herein can be, for example, IL-2, IL-7, IL-15, or any combination thereof.

In some embodiments is provided a method of activating pattern recognition receptors in a cell using a composition comprising a synthetic CpG oligonucleotide, for example a synthetic CpG oligonucleotide comprising a sequence of any one of SEQ ID NOs: 1-30. In some embodiments, a pattern recognition receptor is a protein associated with the immune system. In some embodiments, a pattern recognition receptor is: a toll-like receptor (TLR), a C-type lectin receptor, a NOD-like receptor, or a RIG-I like receptor. In some embodiments, a pattern recognition receptor is a single-pass membrane spanning receptor. In some embodiments, the pattern recognition receptor is expressed on sentinel cells including macrophages and dendritic cells. In some embodiments, the TLR is TLR3, TLR7, TLR8, or TLR9.

EXEMPLARY EMBODIMENTS

Also provided herein are compositions and pharmaceutical comprising a synthetic CpG oligonucleotide that having a sequence of: ATCACGTAGCATCACGTAGC (SEQ ID NO: 5); ATCACGGAGCATCACGGAGC (SEQ ID NO: 6); ATCTCGTAGCATCTCGTAGC (SEQ ID NO: 7); ATCTCGGAGCATCTCGGAGC (SEQ ID NO: 8); ATCGCGTAGCATCGCGTAGC (SEQ ID NO: 9); ATCGCGGAGCATCGCGGAGC (SEQ ID NO: 10); ATTCGTCGGCGTCGACGGTC (SEQ ID NO: 11); ATGCGACGTCGACGTCGGTC (SEQ ID NO: 12); ATACGACGTCGTCGTCGATC (SEQ ID NO: 13); ATGCGTCGGCGACGTCGTGC (SEQ ID NO: 14); GTACGACGTCGTCGACGTGA (SEQ ID NO: 15); or TAGCGTCGACGACGTCGATG (SEQ ID NO: 16); and an excipient, diluent, carrier, a pharmaceutically acceptable salt of any of these, or any combination of these, any or all of which can be pharmaceutically acceptable. In some embodiments, each of SEQ ID NOs: 5-16 can have 0, 1, 2, 3, or 4 nucleobase modifications. In some embodiments, a composition and/or a pharmaceutical composition described herein, when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition or the pharmaceutical composition, in an in vitro assay. In some embodiments each nucleic acid residue comprised in a synthetic CpG oligonucleotide is independently linked to adjacent nucleic acid residue by a phosphodiester group or a phosphorothioate group. In some embodiments are compositions comprising a synthetic CpG oligonucleotide having a sequence of: A*T*C*T*C*G*T*A*G*C*A*T*C*T*C*G*T*A*G*C (SEQ ID NO: 17); A*T*C*T*C*T*C*G*T*A*G*C*A*T*C*T*C*G*T*A*G*C (SEQ ID NO: 18); A*T*C*T*C*G*G*A*G*C*A*T*C*T*C*G*G*A*G*C (SEQ ID NO: 19); A*T*C*T*C*G*G*A*G*C*A*T*C*T*C*G*G*A*G*C (SEQ ID NO: 20); A*T*G*C*G*T*C*G*G*C*G*A*C*G*T*C*G*T*G*C (SEQ ID NO: 21); T*A*G*C*G*T*C*G*A*C*G*A*C*G*T*C*G*A*T*G (SEQ ID NO: 22); A*T*G*C*A*C*T*C*T*G*C*A*G*G*C*T*T*C*T*C (SEQ ID NO: 23); or A*T*A*T*A*C*T*C*T*A*T*A*G*A*T*T*T*C*T*C (SEQ ID NO: 24), and an excipient, diluent, carrier, a salt of any of these, or any combination of these, any or all of which may be pharmaceutically acceptable. In some embodiments, compositions and pharmaceutical compositions described herein comprise a synthetic CpG oligonucleotide which can comprise a sequence having a phosphorothioate group wherein * indicates a phosphorothioate group and wherein, at least one phosphorothioate group between a C and a G is replaced by a phosphodiester group. In some embodiments are compositions and/or pharmaceutical compositions can comprise a synthetic CpG oligonucleotide having a sequence of: A*T*C*T*C^G*T*A*G*C*A*T*C*T*C*G*T*A*G*C (SEQ ID NO: 25); A*T*C*T*C^G*T*A*G*C*A*T*C*T*C*G*T*A*G*C (SEQ ID NO: 26); A*T*C*T*C^G*G*A*G*C*A*T*C*T*C*G*G*A*G*C (SEQ ID NO: 27); A*T*C*T*C^G*G*A*G*C*A*T*C*T*C*G*G*A*G*C (SEQ ID NO: 28); A*T*G*C^G*T*C*G*G*C*G*A*C*G*T*C*G*T*G*C (SEQ ID NO: 29); or T*A*G*C^G*T*C*G*A*C*G*A*C*G*T*C*G*A*T*G (SEQ ID NO: 30); and an excipient, diluent, carrier, a pharmaceutically acceptable salt of any of these, or any combination of these, any or all of which may be pharmaceutically acceptable. In some embodiments, compositions and pharmaceutical compositions described herein can comprise a synthetic CpG oligonucleotide that comprise a sequence having a phosphorothioate group wherein * indicates a phosphorothioate group and ^ indicates a phosphodiester group between a C and a G. In some embodiments, a synthetic CpG oligonucleotide has a sequence length of from about 20 to about 40 nucleic acid residues. In some embodiments, a synthetic CpG nucleotide does not contain an epigenetic modification. In some embodiments, each CpG oligonucleotide is unmethylated. In some embodiments, a nucleobase present in a synthetic CpG nucleotide contains an epigenetic mark that can be, for example: methyl, hydroxymethyl, formyl, or a carboxylic acid. In some embodiments, a synthetic CpG oligonucleotide comprises a chemical modification to a sugar of a nucleobase.

In some embodiments are provided compositions and pharmaceutical compositions comprising a synthetic CpG oligonucleotide that comprises a sequence: $5'(N_1)_a(N_2)_a(W)_a$-CpG-$(X)_a$-CpG-$(Y)_a$-CpG-$(Z)_a$-CpG-$(B)_a$-CpG-$(D)_a$ $(N_3)_a(N_4)_a$ 3' (SEQ ID NO: 1) wherein: $N_1$ is A or T, $N_2$ is A or T, W is G, X is T, Y is A, Z is A, B is T, D is A or T, $N_3$ is G or T, and $N_4$ is C or G; and an excipient, diluent, carrier, a salt of any of these, a combination of any of these, any or all of which may be pharmaceutically acceptable; wherein each nucleic acid residue comprised in the synthetic CpG oligonucleotide is independently linked to an adjacent nucleic acid residue by a phosphodiester group or a phosphorothioate group; a is independently in each case 0, 1, 2, or 3; and the composition, when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition, in an in vitro assay. In some embodiments, 'a' is 1 in each case. In some embodiments, each nucleic acid residue comprised in the synthetic CpG oligonucleotide is independently linked to an adjacent nucleic acid residue by a phosphorothioate group. In some embodiments, a synthetic CpG oligonucleotide has a sequence length of from about 20 to about 40 nucleic acid residues. In some embodiments, a synthetic CpG oligonucleotide does not contain an epigenetic modification. In some embodiments, a CpG oligonucleotide is unmethylated. In some embodiments, a nucleobase present in the synthetic CpG oligonucleotide contains an epigenetic mark that can be, for example, a: methyl, hydroxymethyl, formyl, or carboxylic acid.

In some embodiments, a synthetic CpG oligonucleotide comprises a chemical modification to a sugar of a nucleobase. In some embodiments are provided compositions and pharmaceutical compositions comprising a synthetic CpG oligonucleotide that comprises a sequence of: 5'$(N_1)_a(N_2)_a$ $(W)_a$-CpG-$(X)_a$-CpG-$(Y)_a$-CpG-$(Z)_a$-CpG-$(B)_a$-CpG-$(D)_a$ $(N_3)_a(N_4)_a$ 3' (SEQ ID NO: 2), wherein each: $N_1$, $N_2$, W, X, Y, Z, B, D, $N_3$ and $N_4$ is independently A, T, G, C, or U; and an excipient, diluent, carrier, a pharmaceutically acceptable salt of any of these, or any combination of the foregoing; wherein each nucleic acid residue comprised in the synthetic CpG oligonucleotide is independently linked to an adjacent nucleic acid residue by a phosphodiester or a phosphorothioate group; "a" is independently in each case 0, 1, 2, or 3; and the composition or the pharmaceutical composition, when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition of the pharmaceutical composition, in an in vitro assay.

Also disclosed herein are compositions and pharmaceutical compositions comprising: i) a synthetic CpG oligonucleotide that comprises a sequence of: 5'$(E)_b(F)_b$ $(H)_b$ $(J_1)_b$-CpG-$(N_1)_b(P)_b(J_2)_b(K)_b(L)_b(M)_b(O)_b(Q)_b$-CpG-$(N_2)_b$ $(R)_b(S)_b(V)_b$ 3' (SEQ ID NO: 3) wherein: E is A, F is T, H is C, $J_1$ is T, $N_1$ is T or G, P is A, $J_2$ is G, K is C, L is A, M is T, O is C, Q is T, $N_2$ is T or A, R is A, S is G, and V is C; and an excipient, diluent, carrier, a pharmaceutically acceptable salt of any of these, or any combination of these; wherein each nucleic acid residue comprised in the synthetic CpG oligonucleotide is independently linked to an adjacent nucleic acid residue by a phosphodiester group or a phosphorothioate group; b is independently in each case 0, 1, 2, or 3. In some embodiments, the composition, when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition, in an in vitro assay. In some embodiments, b is 1 in each case. In some embodiments are CpG oligonucleotides, wherein a C nucleic acid residue and a G nucleic acid residue in a CpG are linked by a phosphodiester group. In some embodiments are CpG oligonucleotides, wherein other than the C nucleic acid resided and the G nucleic acid residue in the CpG that are linked by a phosphodiester group, each remaining nucleic acid residue comprised in the synthetic CpG oligonucleotide is linked to an adjacent remaining nucleic acid residue by a phosphorothioate group. In some embodiments, the synthetic CpG oligonucleotide has a sequence length of from about 20 to about 40 nucleic acid residues. In some embodiments, the synthetic CpG oligonucleotide do not contain an epigenetic modification. In some embodiments, each CpG oligonucleotide is unmethylated. In some embodiments, a nucleobase present in the synthetic CpG oligonucleotide contains an epigenetic mark that can be, for example, a: methyl, hydroxymethyl, formyl, or carboxylic acid. In some embodiments, the synthetic CpG oligonucleotide comprises a chemical modification to a sugar of a nucleobase.

Also disclosed herein are compositions and pharmaceutical comprising: i) a synthetic CpG oligonucleotide that comprises a sequence of: 5'$(E)_b(F)_b$ $(H)_b(J_1)_b$-CpG-$(N_1)_b$ $(P)_b$ $(J_2)_b(K)_b(L)_b(M)_b(O)_b(Q)_b$-CpG-$(N_2)_b(R)_b(S)_b(V)_b$ 3' (SEQ ID NO: 4), wherein each: E, F, H, $J_1$, $N_1$, P, $J_2$, K, L, M, O, Q, $N_2$, R, S, and V is independently A, T, C, G, or U; and ii) an excipient, diluent, carrier, a salt of any of these, or combination of any of these, any or all of which may be pharmaceutically acceptable; wherein each nucleic acid residue comprised in the synthetic CpG oligonucleotide is independently linked to an adjacent nucleic acid residue by a phosphodiester group or a phosphorothioate group; b is independently in each case 0, 1, 2, or 3; the composition or the pharmaceutical composition, when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition or the pharmaceutical composition, in an in vitro assay.

Also disclosed are pharmaceutical compositions comprising a composition described herein. In some embodiments, the composition or the pharmaceutical composition is in unit dose form. In some embodiments, the composition or the pharmaceutical composition further comprises a further therapeutic. In some embodiments, the further therapeutic comprises an antibiotic, an antiviral, an antifungal, an antiparasitic agent, or a pharmaceutically acceptable salt thereof.

Also disclosed herein are compositions and pharmaceutical compositions wherein a synthetic CpG oligonucleotide is independently present in the composition in an amount of from about 1 ng to about 25,000 mg. In some embodiments, the composition or pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, the composition or pharmaceutical composition, when stored in a sealed container in an environment having a temperature of 68° F. and an atmosphere 50 percent relative humidity, retains intact at least about 80% by weight of the synthetic CpG oligonucleotide initially present after 6 months as measured by high-performance liquid chromatography (HPLC), sequencing, or both. In some embodiments, are kits containing the composition and pharmaceutical compositions described herein, and a container. In some embodiments are compositions pharmaceutical compositions described herein wherein a synthetic CpG oligonucleotide is independently present in the composition or the pharmaceutical composition in an amount of from about 1 ng to about 25,000 mg. In some embodiments, the composition or the pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, the composition or the pharmaceutical composition, when stored in a sealed container in an environment having a temperature of 68° F. and an atmosphere 50 percent relative humidity, retains intact at least about 80% by weight of a synthetic CpG oligonucleotide initially present after 6 months as measured by high-performance liquid chromatography (HPLC), sequencing, or both. In some embodiments, are kits containing a composition or a pharmaceutical composition described herein, and a container.

Also disclosed herein is a method of treating a disease or condition in a subject, the method comprising administering a pharmaceutical composition described herein to the subject in a therapeutically effective amount, thereby treating the disease or condition. In some embodiments, the subject is a subject in need thereof. In some embodiments, the subject or the subject in need thereof is a mammal. In some embodiments, the mammal is a primate. In some embodiments, the mammal is a non-primate. In some embodiments, the mammal is a dog, a cat, a rodent, a spiny animal, or Lagomorpha. In some embodiments, the mammal is a human. In some embodiments, the subject or the subject in need thereof is a reptile or amphibian. In some embodiments, the disease or condition is a wound. In some embodiments, the disease or condition is a surgical wound, a scar, an unclean wound, a clean wound, an ulcer, a diabetic ulcer, a diabetic foot ulcer, a radiation dermatitis, a burn, acne, a cancer, a skin cancer, a psoriasis, a combat wound, an infection, a viral infection, a bacterial infection, a fungal infection, a parasitic infection, a cutaneous infection, a subcutaneous infection, or any combination thereof.

Also disclosed herein are methods of inducing an inflammatory response in a tissue of a subject or a subject in need thereof without introducing a bacterial infection, a fungal infection, or a viral infection into the tissue, the method comprising contacting the tissue of the subject or the subject in need thereof with a composition or a pharmaceutical composition described herein, thereby inducing the inflammatory response in the tissue of the subject or the subject in need thereof. In some embodiments, the subject is a mammal. In some embodiments, the mammal is a primate. In some embodiments, the mammal is a non-primate. In some embodiments, the mammal is a dog, a cat, a rodent, a spiny animal, or Lagomorpha. In some embodiments, the mammal is a human. In some embodiments, the subject or the subject in need thereof is a reptile or amphibian. In some embodiments, the composition or the pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, an antibiotic, an antiviral, an antifungal, an antiparasitic agent, or a pharmaceutically acceptable salt thereof is administered concurrently or consecutively with the contacting. In some embodiments, the tissue comprises a wound. In some embodiments, the wound is a surgical wound, a scar, an unclean wound, a clean wound, an ulcer, a diabetic ulcer, a diabetic foot ulcer, a burn, a radiation dermatitis, an acne, a cancer, a skin cancer, a psoriasis, a combat wound, or any combination thereof. In some embodiments, the synthetic CpG oligonucleotide is independently present in the composition or the pharmaceutical composition in an amount ranging from about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed.

Also disclosed herein are methods of inducing an inflammatory response in a tissue of a subject or a subject in need thereof without introducing a bacterial infection, a fungal infection, or a viral infection into the tissue, the method comprising contacting the tissue of the subject or the subject in need thereof with a composition or a pharmaceutical composition described herein, thereby inducing the inflammatory response in the tissue of the subject or the subject in need thereof. In some embodiments, the subject or the subject in need thereof is a mammal. In some embodiments, the mammal is a primate. In some embodiments, the mammal is a non-primate. In some embodiments, the mammal is a dog, a cat, a rodent, a spiny animal, or Lagomorpha. In some embodiments, the mammal is a human. In some embodiments, the subject or the subject in need thereof is a reptile or amphibian. In some embodiments, the composition or the pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, an antibiotic, an antiviral, an antifungal, an antiparasitic agent, or a pharmaceutically acceptable salt thereof is administered concurrently or consecutively with the contacting. In some embodiments, the tissue comprises a wound. In some embodiments, the wound is a surgical wound, a scar, an unclean wound, a clean wound, an ulcer, a diabetic ulcer, a diabetic foot ulcer, a burn, a radiation dermatitis, an acne, a cancer, a skin cancer, a psoriasis, a combat wound, or any combination thereof. In some embodiments, the synthetic CpG oligonucleotide is independently present in the composition or the pharmaceutical composition in an amount ranging from about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed.

Also disclosed herein are methods of accelerating a healing of a wound in a subject or a subject in need thereof, the method comprising contacting the wound of the subject with a composition or a pharmaceutical composition described herein, in an amount effective to accelerate the healing of the wound in the subject or the subject in need thereof, thereby accelerating the healing of the wound in the subject or the subject in need thereof. In some embodiments, the subject or the subject in need thereof is a mammal. In some embodiments, the mammal is a primate. In some embodiments, the mammal is a non-primate. In some embodiments, the mammal is a dog, a cat, a rodent, a spiny animal, or Lagomorpha. In some embodiments, the mammal is a human. In some embodiments, the subject or the subject in need thereof is a reptile or amphibian. In some embodiments, the composition or the pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, an antibiotic, an antiviral, an antifungal, an antiparasitic agent, or a pharmaceutically acceptable salt of any of these is administered concurrently or consecutively with the contacting. In some embodiments, the antibiotic, the antiviral, the antifungal, the antiparasitic agent, or the pharmaceutically acceptable salt of any of these is administered consecutively. In some embodiments, the tissue comprises a wound. In some embodiments, the wound is a surgical wound, a scar, an unclean wound, a clean wound, an ulcer, a diabetic ulcer, a diabetic foot ulcer, a burn, a radiation dermatitis, an acne, a cancer, a skin cancer, a psoriasis, a combat wound, or any combination thereof. In some embodiments, the synthetic CpG oligonucleotide is independently present in the composition or the pharmaceutical composition in an amount ranging from about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed.

Also disclosed herein are methods of regenerating skin or a tissue of a subject or a subject in need thereof, the method comprising contacting the skin or tissue of the subject or the subject in need thereof with a composition or a pharmaceutical composition described herein, in an amount effective to regenerate the skin or the tissue of the subject or the subject in need thereof, thereby regenerating the skin or the tissue of the subject or the subject in need thereof. In some embodiments, the subject or subject in need thereof is a mammal. In some embodiments, the mammal is a primate. In some embodiments, the mammal is a non-primate. In some embodiments, the mammal is a dog, a cat, a rodent, a spiny animal, or Lagomorpha. In some embodiments, the mammal is a human. In some embodiments, the subject or the subject in need thereof is a reptile or amphibian. In some embodiments, the composition or the pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, an antibiotic, an antiviral, an antifungal, an antiparasitic agent, or a pharmaceutically acceptable salt thereof is administered concurrently or consecutively with the contacting. In some embodiments, the antibiotic, the antiviral, the antifungal, the antiparasitic agent, or the pharmaceutically acceptable salt of any of these is administered consecutively. In some embodiments, the tissue comprises a wound. In some embodiments, the wound is a surgical wound, a scar, an unclean wound, a clean wound, an ulcer, a diabetic ulcer, a diabetic foot ulcer, a burn, a radiation dermatitis, an acne, a cancer, a skin cancer, a psoriasis, a combat wound, or any combination thereof. In some embodiments, the synthetic CpG oligonucleotide is independently present in the composition or the pharmaceutical composition in an amount ranging from about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed. In some embodiments, the tissue comprises an infection. In some embodiments, the infection is a bacterial infection, a viral infection, a fungal infection, a parasitic infection, or any combination thereof. In some embodiments, the synthetic CpG oligonucleotide is independently present in the composition or the pharmaceutical composition in an amount ranging from about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed.

Also disclosed herein is a method of expanding a plurality of cells ex vivo, the method comprising, contacting the plurality of cells with a composition or a pharmaceutical composition described herein, in an amount effective to expand the plurality of cells ex vivo, thereby expanding the plurality of cells ex vivo. In some embodiments, the plurality of cells comprises mammalian cells. In some embodiments, the mammalian cells comprise human cells. In some embodiments, an antibiotic or pharmaceutically acceptable salt thereof is administered or contacted concurrently or consecutively with the contacting. In some embodiments, the expanding is conducted in a cell culture medium. In some embodiments, the cell culture medium is a liquid cell culture medium. In some embodiments, the expanding is conducted at a temperature ranging from about 25 degrees Celsius to about 37 degrees Celsius. In some embodiments, the expanding is conducted for a period of time ranging from about 24 hours to about 168 hours. In some embodiments, the plurality of cells comprises stem cells, T-cells, or natural killer (NK) cells. In some embodiments, the plurality of cells comprises T-cells that comprise cluster of differentiation 8 (CD8) glycoproteins. In some embodiments, the plurality of cells comprises T-cells that comprise cluster of differentiation 4 (CD4) glycoproteins. In some embodiments, the contacting further comprises contacting the plurality of cells with at least one of interleukin 15 (IL-15), interleukin 7 (IL-7), interleukin 2 (IL-2), or any combination of these. In some embodiments, a synthetic CpG oligonucleotide is independently present in the composition or the pharmaceutical composition in an amount ranging from about 1 ng to about 25,000 mg, for example, about 10 ng, about 100 ng, about 1 microgram, about 10 micrograms, about 100 micrograms, about 1 mg, about 10 mg, about 100 mg, about 1 g, about 10 g, or about 25 g. In some embodiments, an antibiotic or pharmaceutically acceptable salt thereof is independently present, optionally in the composition or the pharmaceutical composition, in an amount ranging from about 1 ng to about 25,000 mg, for example, about 10 ng, about 100 ng, about 1 microgram, about 10 micrograms, about 100 micrograms, about 1 mg, about 10 mg, about 100 mg, about 1 g, about 10 g, or about 25 g.

Also disclosed herein is a method of activating a pattern recognition receptor in a cell, the method comprising contacting the cell with a composition or a pharmaceutical composition described herein, in an amount effective to activate the pattern recognition receptor, thereby activating the pattern recognition receptor in the cell. In some embodiments, the pattern recognition receptor comprises a toll-like receptor, a C-type lectin receptor, a NOD-like receptor, or a RIG-I like receptor. In some embodiments, the pattern recognition receptor comprises the toll-like receptor (TLR). In some embodiments, the TLR is located within the cell. In some embodiments, the TLR is TLR3, TLR7, TLR8, or TLR9. In some embodiments, the TLR is TLR9. In some embodiments, the cell is a mammalian cell. In some embodiments, the mammal is a human. In some embodiments, the cell is:

a) isolated;

b) comprised within a tissue;

c) substantially proximal to a wound.
d) comprised within the mammal; or
e) any combination of b)-d).

In some embodiments, a synthetic CpG oligonucleotide is independently present in the composition or the pharmaceutical composition in an amount ranging from about 1 ng to about 25,000 mg.

In some embodiments, a synthetic CpG oligonucleotide is present in the composition or pharmaceutical composition in an amount ranging from about 1 mg to about 1,000 mg.

In some embodiments, activation of the pattern recognition receptor by the synthetic CpG oligonucleotide in the cell modulates the expression of one or more chemokines, cytokines, growth factors, antibodies, or any combination thereof. In some embodiments, the one or more chemokine, cytokines, growth factors, antibodies comprises BDNF, EGF, Eotaxin (CCL11), FGF-2, GM-CSF, GRO alpha (CXCL1), HGF, IFN alpha, IFN gamma, IgM, IL-1 alpha, IL-1 beta, IL-1RA, IL-2, IL-5, IL-6, IL-7, IL-8 (CXCL8), IL-9, IL-10, IL-12p70, IL-13, IL-15, IL-17A (CTLA-8), IL-18, IL-21, IL-22, IL-23, IL-27, IL-31, IP-10 (CXCL10), LIF, MCP-1 (CCL2), MIP-1 alpha (CCL3), MIP-1 beta (CCL4), PDGF-BB, PIGF-1, RANTES, SDF-1 alpha, TGF beta, TNF alpha, TNF beta, VEGF-A, and VEGF-D. In some embodiments, the activation of the pattern recognition receptor in the cell results in a dose-dependent increase in expression of one or more chemokines, cytokines, growth factors, antibodies, or any combination thereof. In some embodiments, the one or more chemokines, cytokines, growth factors, antibodies comprises BDNF, HGF, IFN gamma, IgM, IL-1 alpha, IL-1 beta, IL-1RA, IL-2, IL-5, IL-6, IL-7, IL-10, IL-12p70, IL-18, IL-22, IL-23, IL-31, IP-10 (CXCL10), LIF, MCP-1 (CCL2), MIP-1 alpha (CCL3), MIP-1 beta (CCL4), PDGF-BB, RANTES, SDF-1 alpha, TNF alpha, TNF beta, and VEGF-A. In some embodiments, the activation of the pattern recognition receptor in the cell results in a dose-dependent decrease in expression of one or more chemokines, cytokines, growth factors, antibodies, or any combination thereof. In some embodiments, the one or more chemokine, cytokines, growth factors, antibodies comprises FGF-2, IL-9, and TGF beta.

Also provided here in is a composition for use in treating a disease in a subject in need thereof, the composition comprising a synthetic CpG oligonucleotide that comprises a sequence A*T*C*T*C*G*T*A*G*C*A*T*C*T*C*G*T*A*G*C (SEQ ID NO: 17) and an excipient, diluent, carrier, or any combination of these, wherein * indicates a phosphorothioate group. In some embodiments, a composition for use in treating a disease in a subject in need thereof, the composition comprising a synthetic CpG oligonucleotide that comprises a sequence A*T*C*T*C^G*T*A*G*C*A*T*C*T*C*G*T*A*G*C (SEQ ID NO: 25) and an excipient, diluent, carrier, or any combination of these, wherein * indicates a phosphorothioate group and ^ indicates a phosphodiester group between a C and a G. In some embodiments, described herein is a composition for use in accelerating a healing of a wound in a subject, the composition comprises a therapeutically effective amount of the composition or the pharmaceutical composition of any one of claims 1-20, wherein the composition is administered by contacting the wound of the subject with the composition, thereby accelerating the healing of the wound in the subject. In some embodiments, a composition for use in regenerating skin or a tissue of a subject, the composition comprising a therapeutically effective amount of the composition or the pharmaceutical composition of any one of claims 1-20, wherein the composition is administered by contacting the skin or the tissue of the subject with the composition, thereby regenerating the skin or the tissue of the subject. In some embodiments, the subject in need thereof is a mammal. In some embodiments, the mammal is a human. In some embodiments, the disease or condition is a wound. In some embodiments, the disease or condition is a surgical wound, a scar, an unclean wound, a clean wound, a deep incisional wound, a superficial incisional wound, an ulcer, a diabetic ulcer, a diabetic foot ulcer, a radiation dermatitis, an acute radiation dermatitis, a burn, acne, a cancer, a skin cancer, a psoriasis, a combat wound, an infection, a viral infection, a bacterial infection, a fungal infection, a parasitic infection, a cutaneous infection, a subcutaneous infection, or any combination thereof. In some embodiments, the skin or the tissue comprises a wound. In some embodiments, the wound is a surgical wound, a scar, an unclean wound, a clean wound, a deep incisional wound, a superficial incisional wound, an ulcer, a diabetic ulcer, a diabetic foot ulcer, a burn, a radiation dermatitis, an acne, a cancer, a skin cancer, a psoriasis, a combat wound, or any combination thereof. In some embodiments, the surgical wound is associated with scar revision, donor site skin grafts, panniculectomies, biopsies, or plastic surgery. In some embodiments, the skin or the tissue comprises an infection. In some embodiments, wherein the infection is a cutaneous infection. In some embodiments, the cutaneous infection is a bacterial infection, a viral infection, a fungal infection, a parasitic infection, or any combination thereof. In some embodiments, the bacterial infection is caused by *Propionibacterium acnes*. In some embodiments, the composition or the pharmaceutical composition is in the form of a spray, a liquid, an emulsion, a suspension, a cream, a lotion, a powder, a gel, a suppository, a pill, capsule, or is comprised on or in a pad, a bandage, or a dressing. In some embodiments, an antibiotic, an antiviral, an antifungal, an antiparasitic agent, or a pharmaceutically acceptable salt thereof is administered concurrently or consecutively with the contacting. In some embodiments, the synthetic CpG oligonucleotide is independently present in the composition or the pharmaceutical composition in an amount ranging from about 1 ng to about 25,000 mg. In some embodiments, the contacting is once, twice, three, four, five, six, seven, eight, nine, or ten times in a 24-hour period. In some embodiments, the contacting occurs daily, every other day, every third day, every fourth day, every fifth day, every sixth day, weekly, every two weeks, every three weeks, once a month, once every three months, once every six months, once a year, or as needed. In some embodiments, the composition is localized to the skin of the human.

EXAMPLES

For a better understanding of the present disclosure and of its many advantages, the following examples are given by way of illustration and without limiting the scope of this disclosure.

Example 1: Gene Reporter Assay for Measuring Dose Response with Synthetic CpG Oligonucleotides SEQ ID NOs: 25-30 were exposed to Ramos Blue B lymphocytes which stably expressed using an NF-kB/API-inducible secreted embryonic alkaline phosphatase (SEAP) reporter gene, for a 6-hour incubation period at concentrations ranging from 0-10 uM. Optical density was evaluated to determine TLR-9 activation of the Ramos Blue B lymphocytes using the SEAP reporter gene assay. Measurements were collected using a spectrophotometer. Results are shown in FIG. 1. Different synthetic CpG oligonucleotides resulted in dose responses at different concentration. For example, G triggered a lower release of alkaline phosphatase, and F, E, D, and C at a concentration of 2.5 or 5 uM showed higher dose responses for F, E, D, and C.

Example 2: Cell Proliferation Assay Using a Human Monocyte Cell Line

Figure 2:
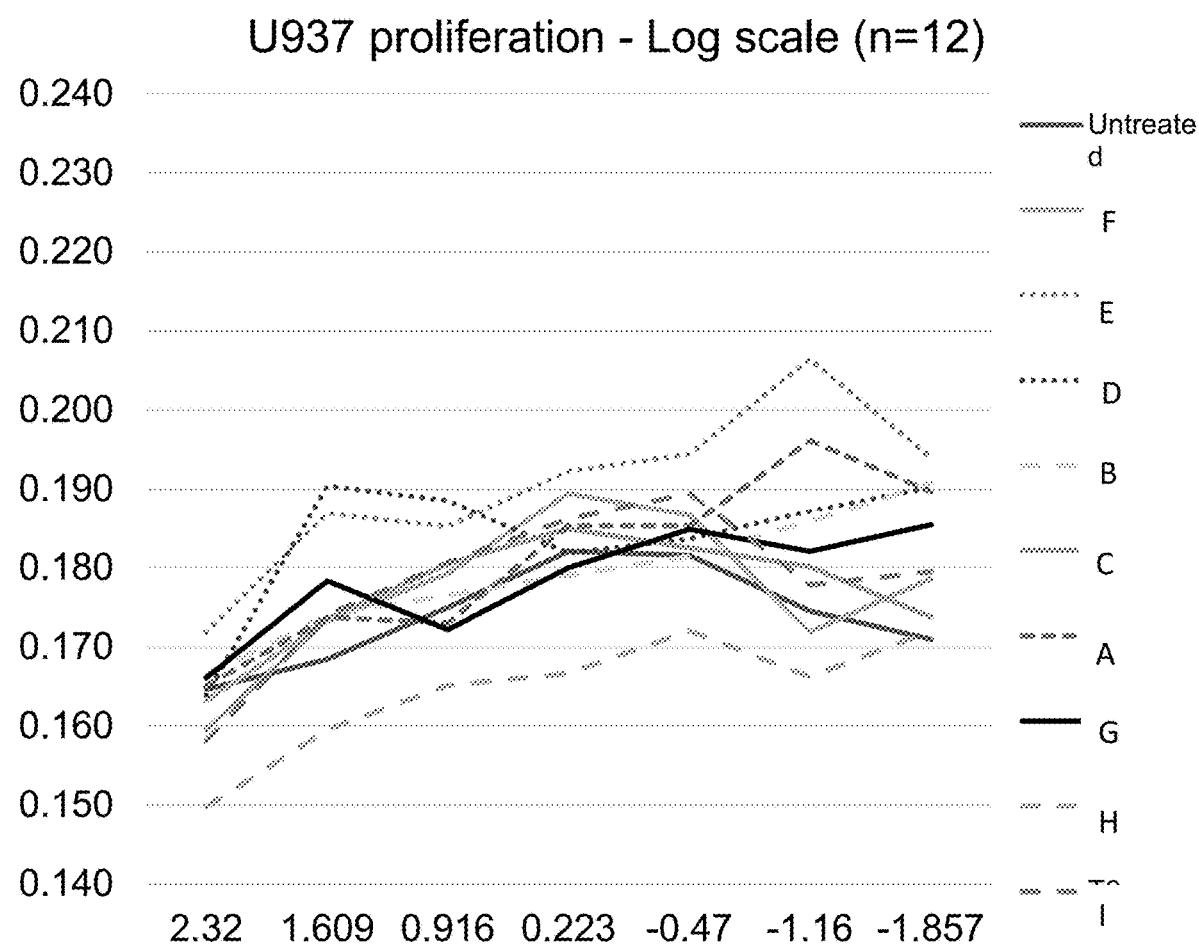
FIG. 2 shows a graphical representation of an optical density graph for TLR9 activation of U937 monocyte type cell line exposed to synthetic CpG oligonucleotides at different synthetic CpG oligonucleotide concentrations.

Synthetic CpG oligonucleotides each individually comprising a sequence of any one of SEQ ID NOs: 25-30 were exposed to U937 monocyte cell line and dose response curves were obtained for each synthetic CpG oligonucleotide against the U937 monocyte cells, which expresses TLR9, were evaluated. Activation of the TLR9 was observed upon exposure to the synthetic CpG oligonucleotides, by the increase in cell proliferation. A spectrophotometer was used to measure cell viability with a cell viability reagent. Results are depicted in FIG. 2. U937 cell proliferation at different concentrations for each synthetic CpG oligonucleotide were observed. Lymphocyte activation varied between synthetic CpG oligonucleotides. Overall, lymphocyte activation occurred at lower concentrations than observed in Example 1.

Example 3: Accelerated Wound Healing—Clean Wound Mimic

Figure 3A:
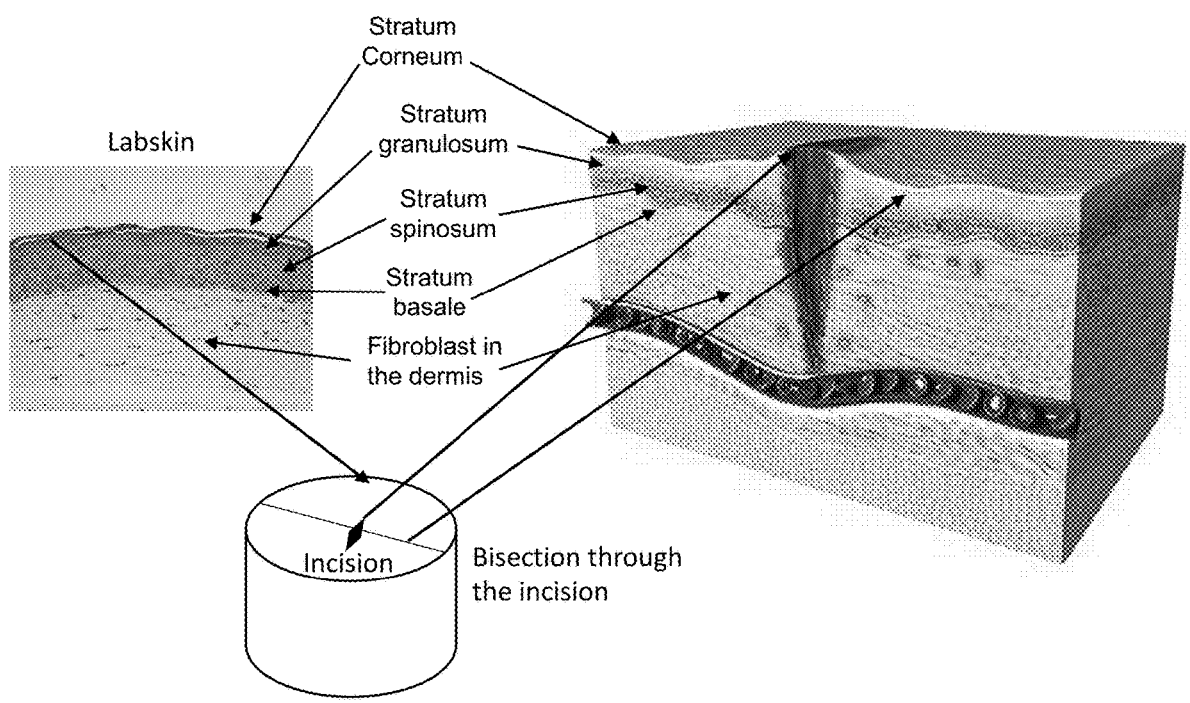
FIG. 3A-B show schematic representations of an incision is made into Labskin for experimental use.
Figure 3B:
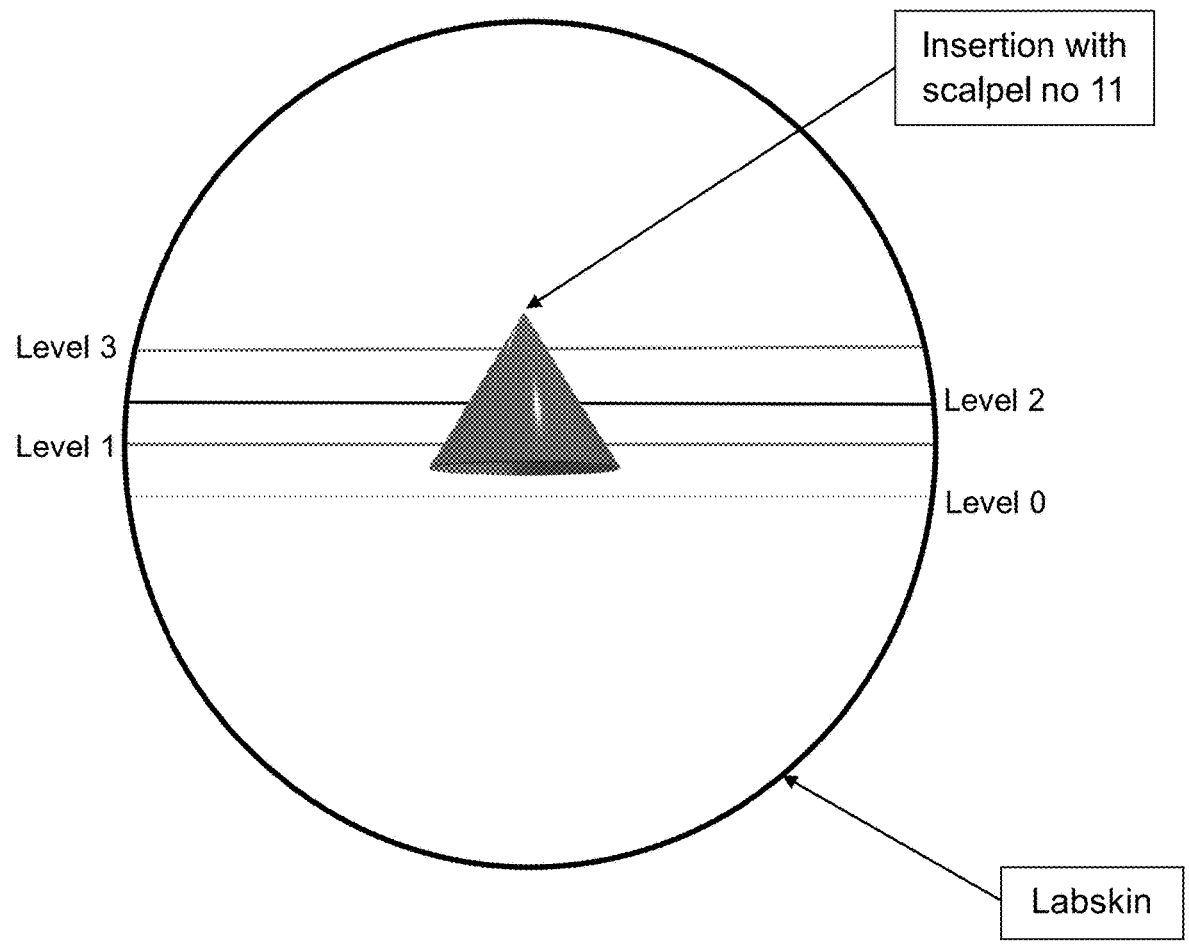
Figure 4:
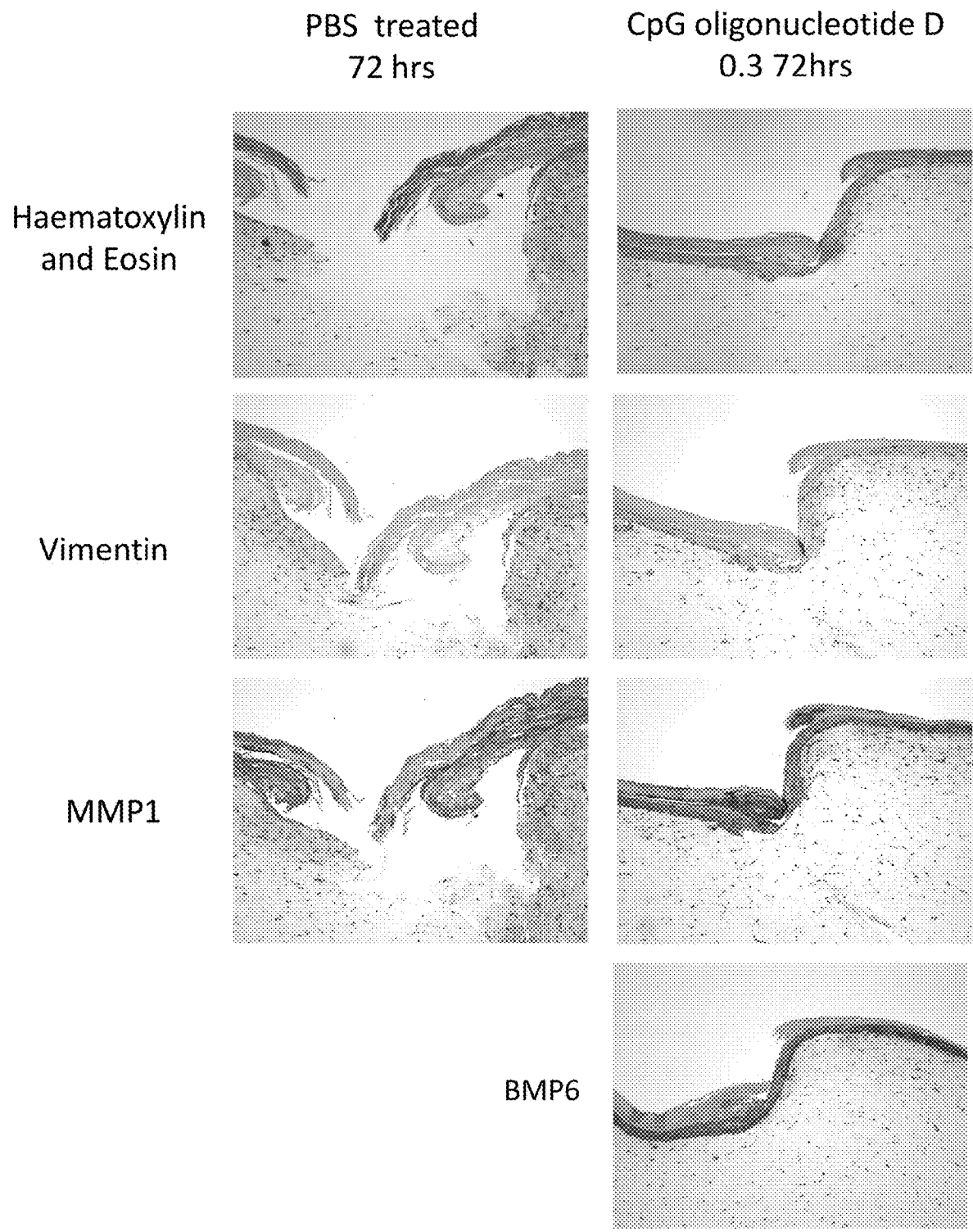
FIG. 4 shows tissue imaging of Labskin treated with synthetic CpG oligonucleotides. The top row of the tissue imaging represents a control and the corresponding imaging below represents the Labskin treated with synthetic CpG oligonucleotide 'D'. Results show that inclusion of the synthetic oligonucleotide resulted in more advanced tissue remodeling at 72 hours after initial exposure as compared to the control (PBS only).
Figure 5A:
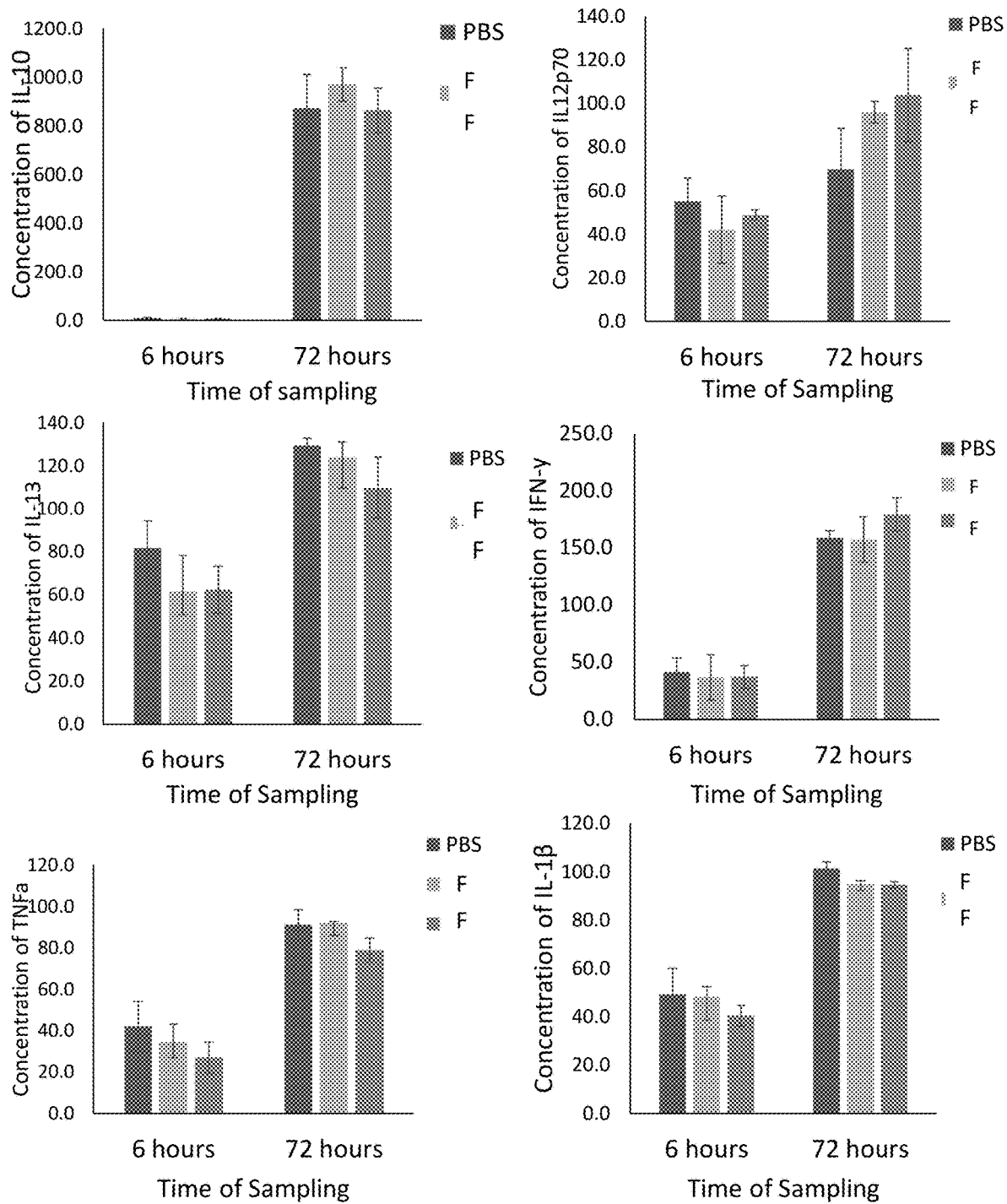
FIGS. 5A-B show graphical representations of cytokine production of wounds exposed to CpG oligonucleotide 'G' treated wound.
Figure 5B:
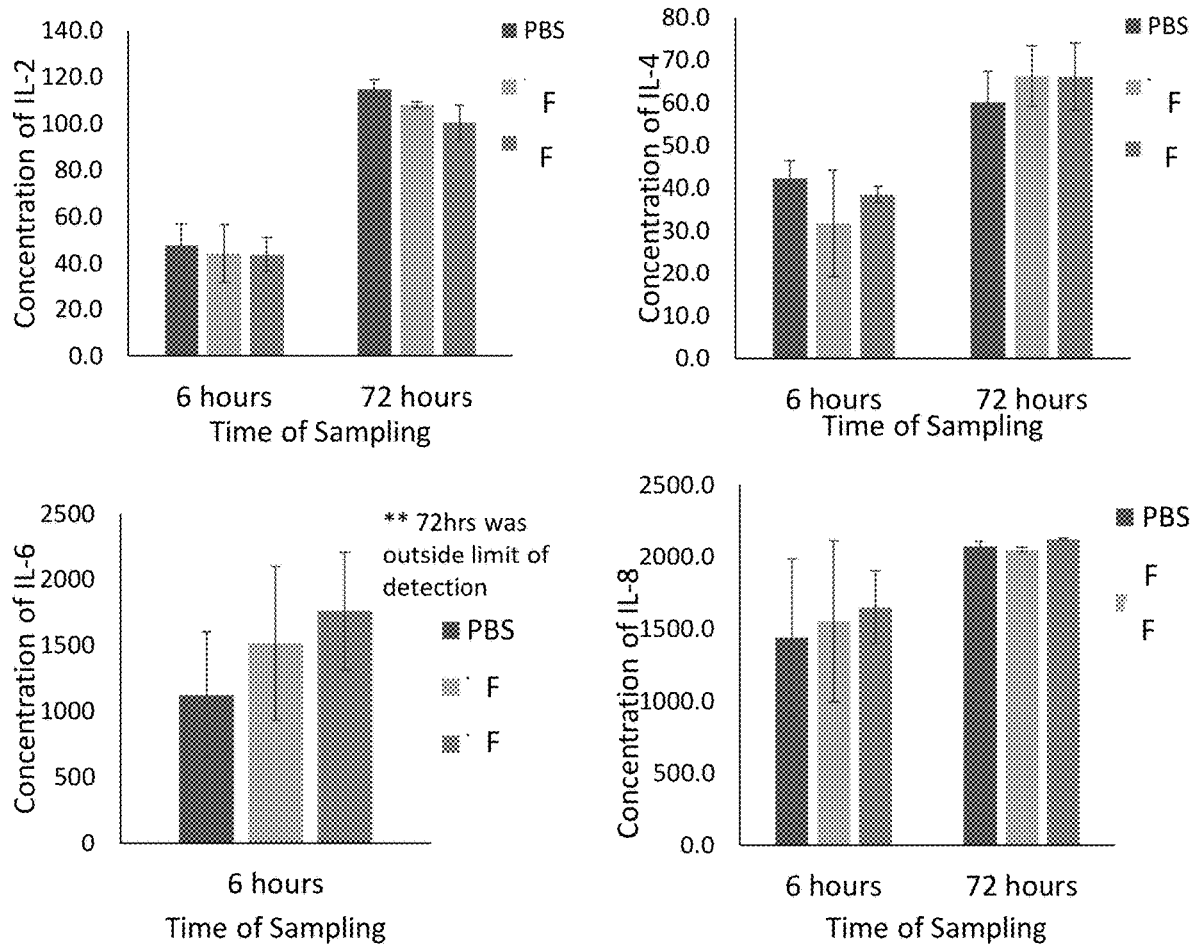
Figure 6A:
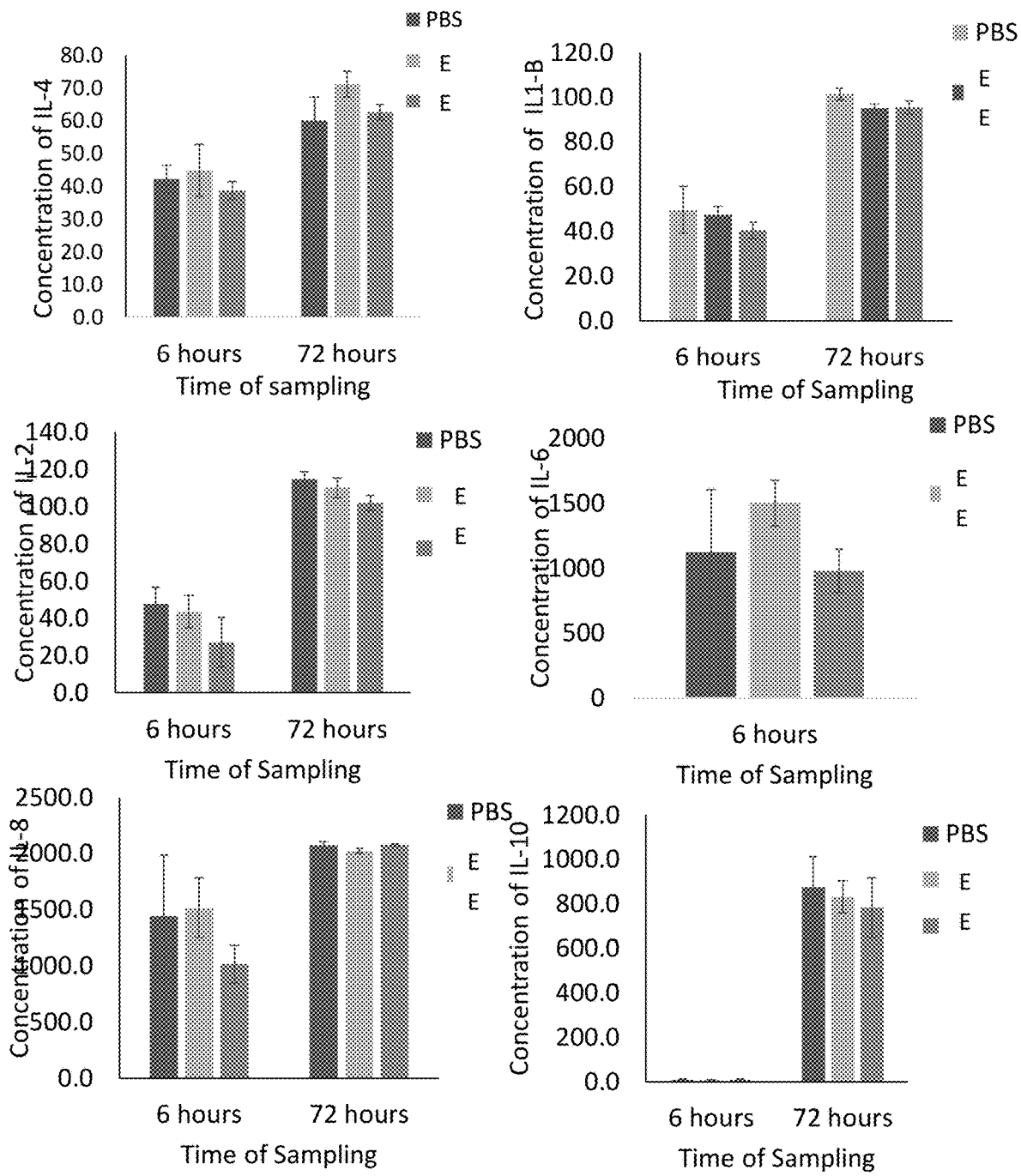
FIGS. 6A-B show graphical representations of cytokine production of wounds exposed to CpG oligonucleotide 'F' treated wound.
Figure 6B:
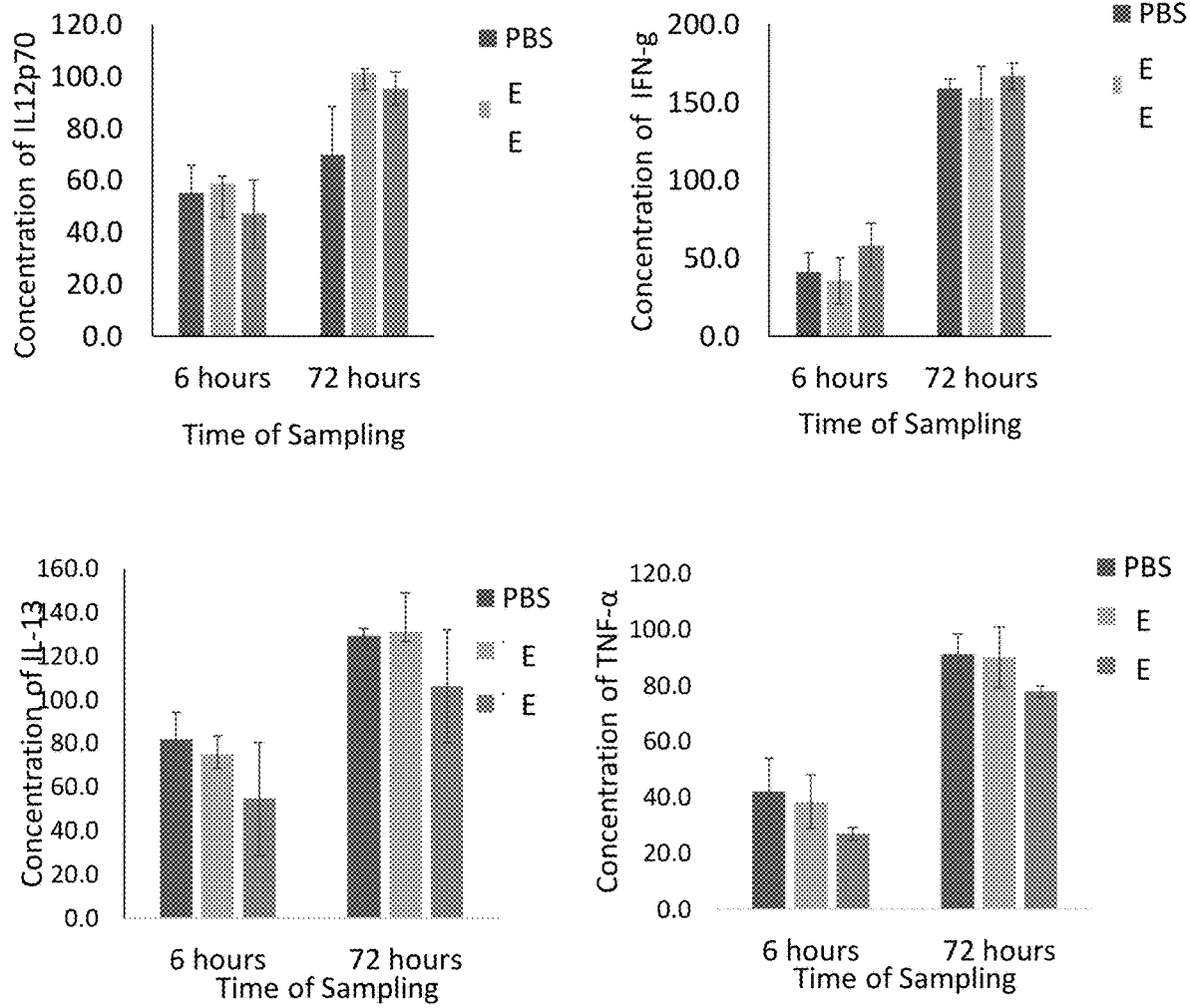
Figure 7A:
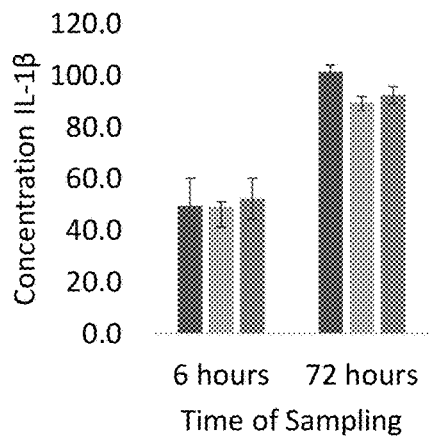
FIG. 7A-B show graphical representations of cytokine production of wounds exposed to CpG oligonucleotide 'E' treated wound.
Figure 7A:
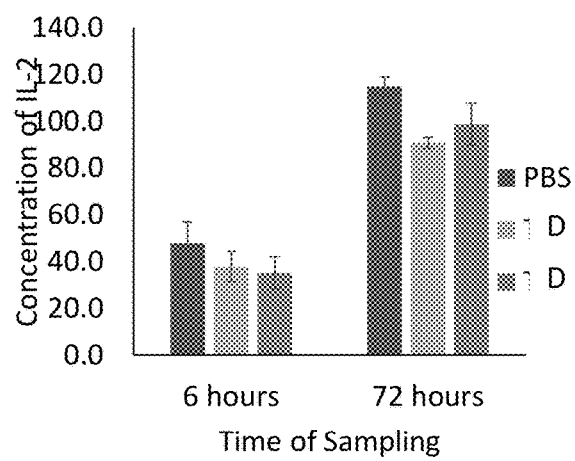
Figure 7A:
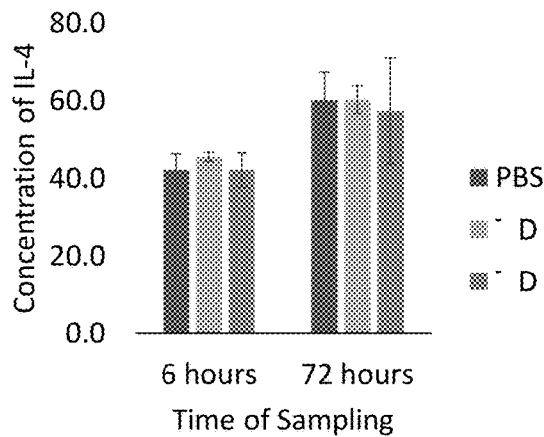
Figure 7A:
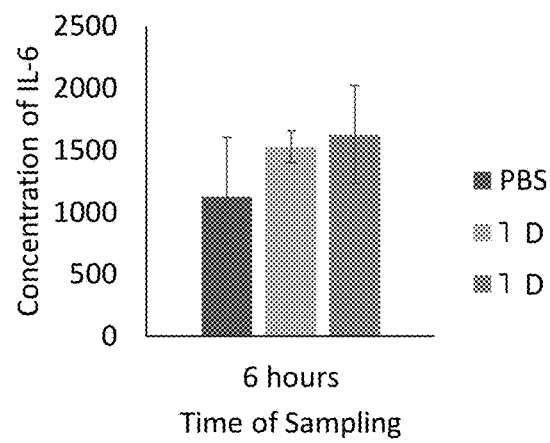
Figure 7A:
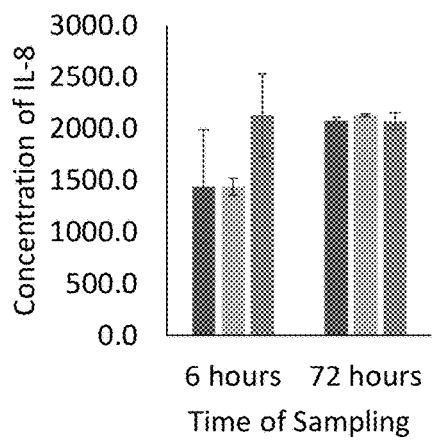
Figure 7A:
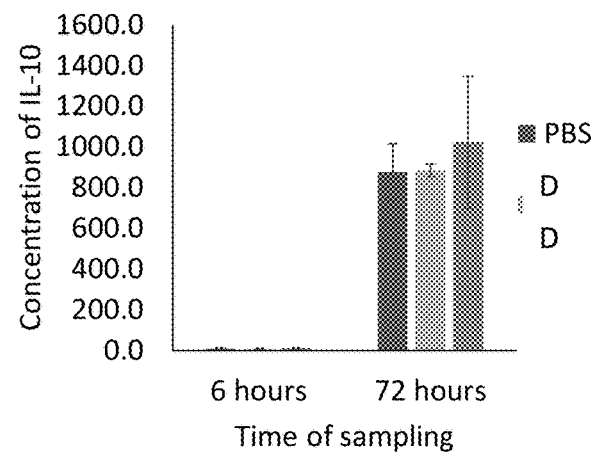
Figure 7B:
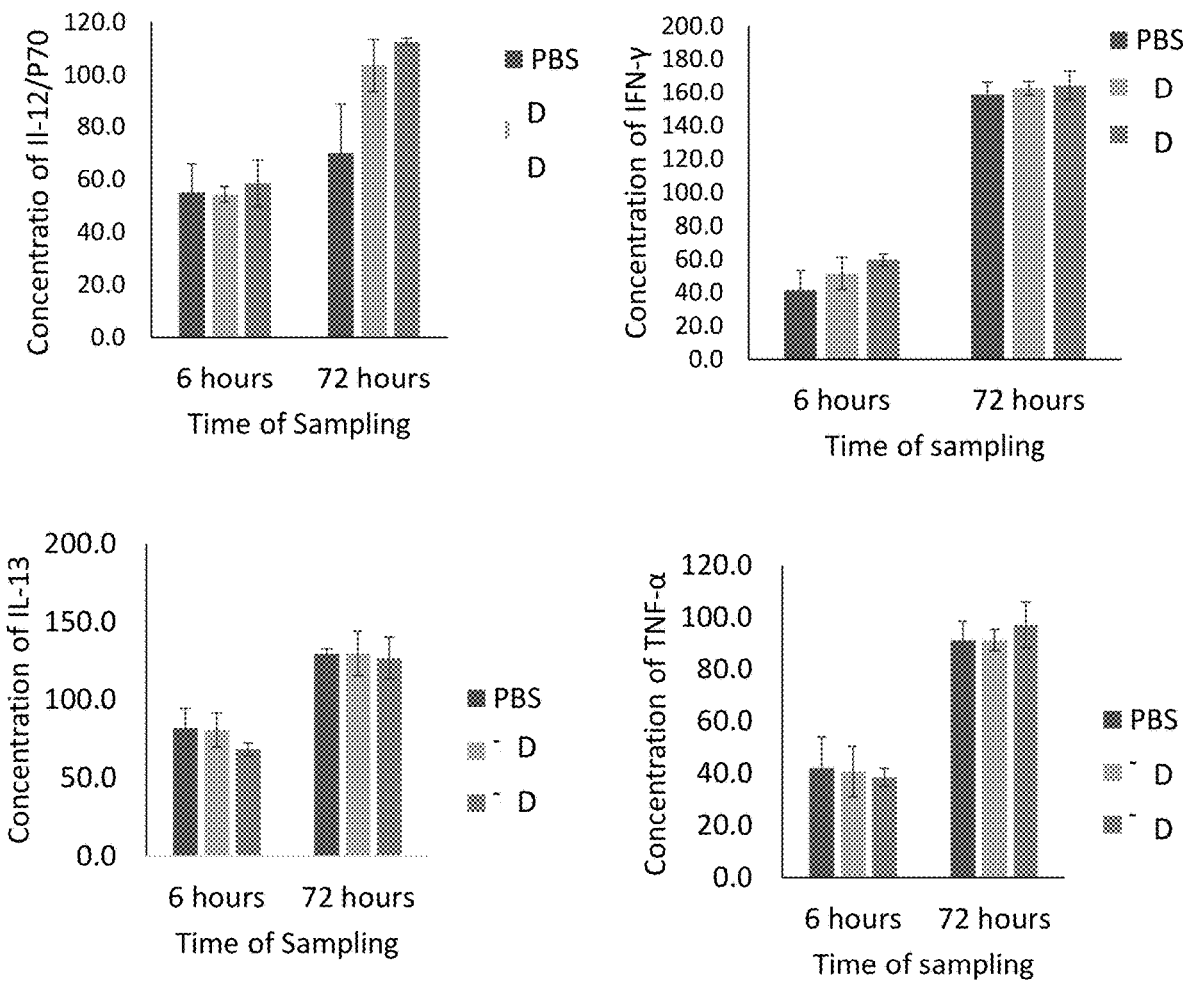
Figure 8A:
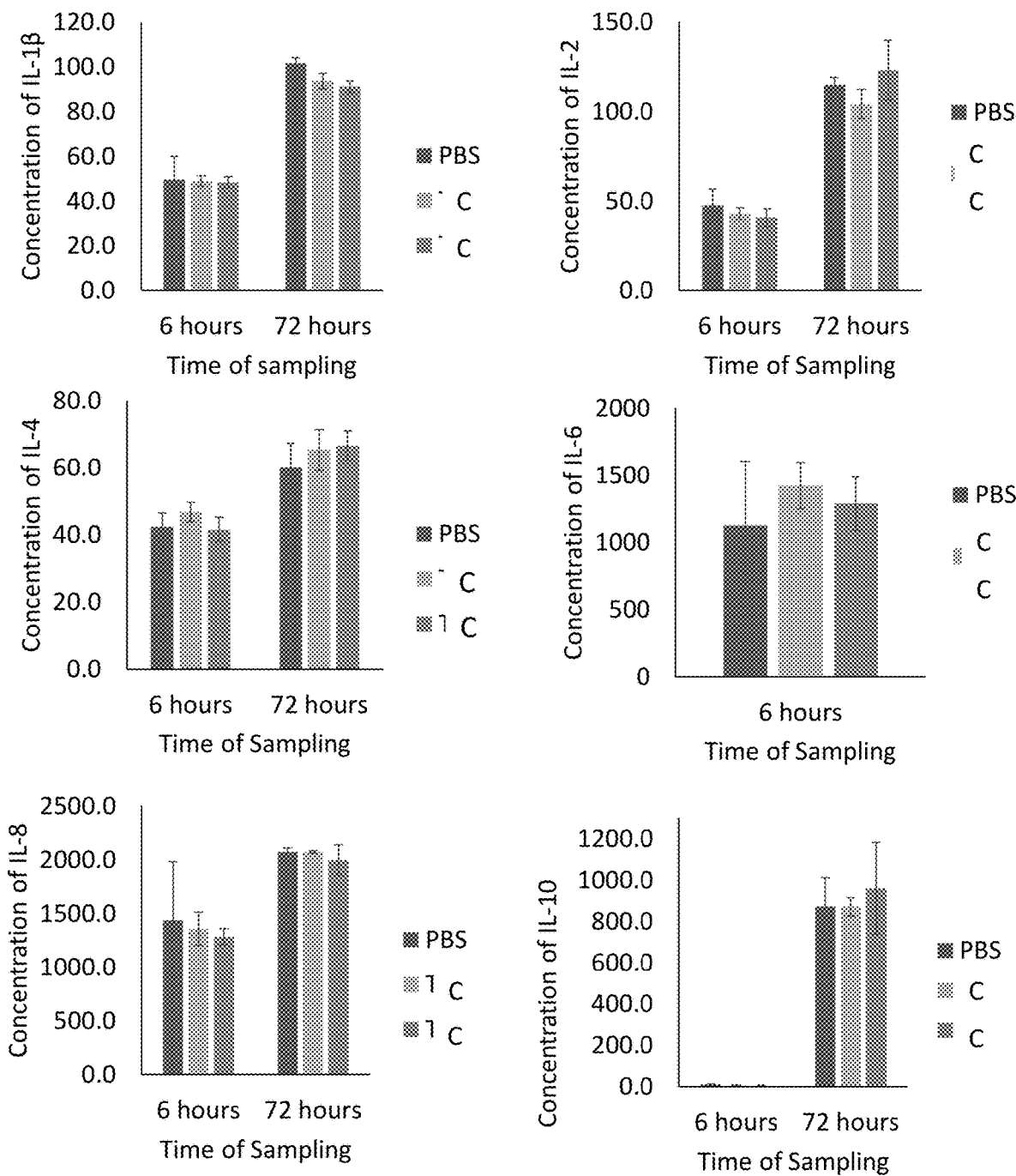
FIG. 8A-B show graphical representations of cytokine production of wounds exposed to CpG oligonucleotide 'C' treated wound.
Figure 8B:
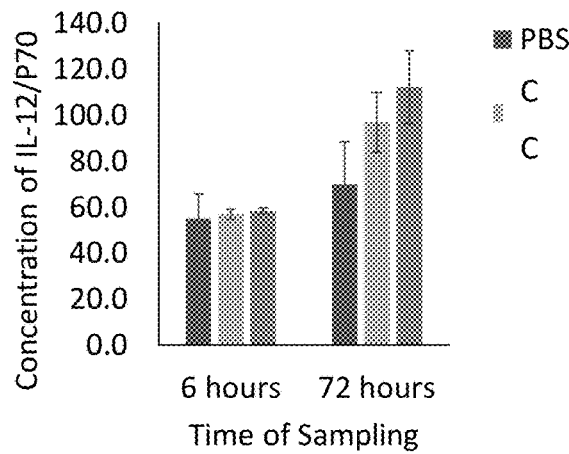
Figure 8B:
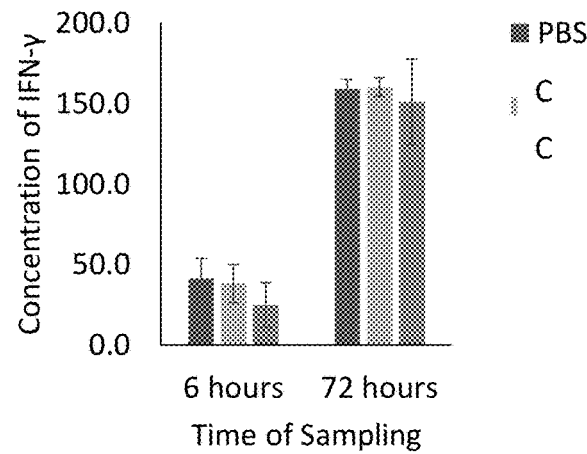
Figure 8B:
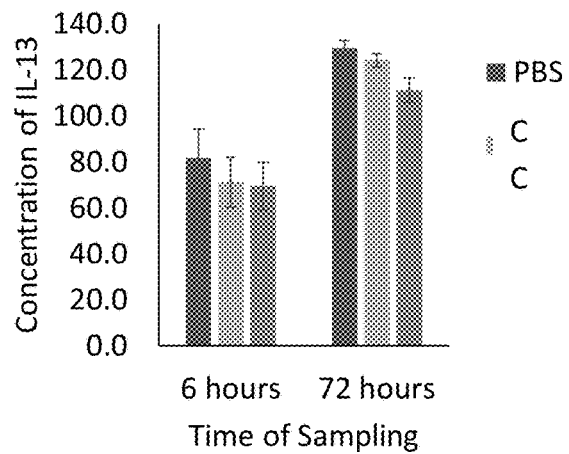
Figure 8B:
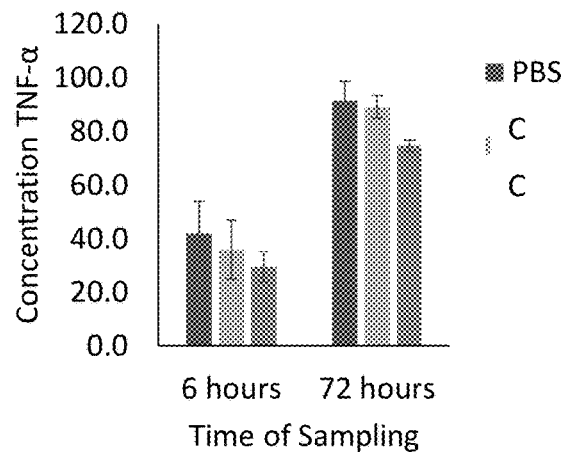

Labskin was used as a model for mammalian skin to evaluate wound healing with the synthetic CpG oligonucleotides. A sterile scalpel was used to make an incision, producing a cut using a scalpel mimicking a surgical wound as shown in FIG. 3A-3B. Each synthetic CpG oligonucleotide was then applied to each incision. Hematoxylin and eosin (H&E) staining, immunochemistry (MMP-1, vimentin, and BMP6), and Elisa (45-plex MSD) were performed to evaluate the effect of each synthetic CpG oligonucleotide as modulators of wound healing. Tissue imaging results for each immunochemistry experiment for scalpel wounds are shown in FIG. 4. The top row of the tissue imaging represents a control and the corresponding imaging below represents the Labskin treated with a synthetic CpG oligonucleotide 'D'. Results show that inclusion of the synthetic CpG oligonucleotide resulted in more advanced tissue remodeling at 72 hours after initial exposure as compared to the control (PBS only). Undernatants were subsequently collected from each condition at 6 hours and 72 hours and cytokine and growth factor analyses (Cytokine 10 plex analyses) was performed as shown in FIG. 5A-B, FIG. 6A-B, FIG. 7A-B and FIG. 8A-B for various synthetic CpG oligonucleotides by measuring specific cytokine production.

Example 4A: Accelerated Wound Healing—Infected Wound Mimic

Labskin is used as a model for mammalian skin to evaluate wound healing with synthetic CpG oligonucleotides. A sterile scalpel is used to produce a cut mimicking a surgical wound, followed by introduction of *S. aureus* bacteria to provide for infected wound conditions. Each synthetic CpG oligonucleotide is then individually applied to the cuts. Hematoxylin and eosin (H&E) staining, immunochemistry (MMP-1, vimentin, and BMP6), and Elisa (45-plex MSD) are performed to evaluate the effect of each synthetic CpG oligonucleotide as modulators of wound healing.

Example 4B: Accelerated Wound Healing—Infected Wound Mimic Bacteria Colonization Bacterial enumeration of *S. aureus* colonization is evaluated and compared between each polymer.

Figure 9A:
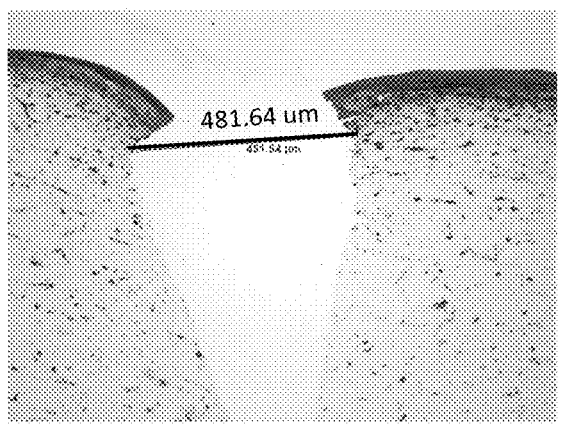
FIG. 9A-D shows tissue imaging of Labskin treated with synthetic CpG oligonucleotides.
Figure 9A:
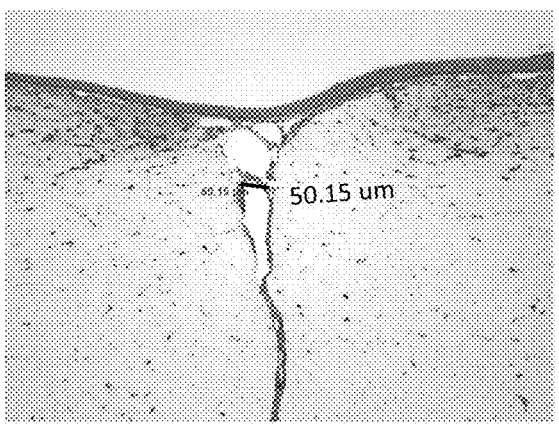
Figure 9A:
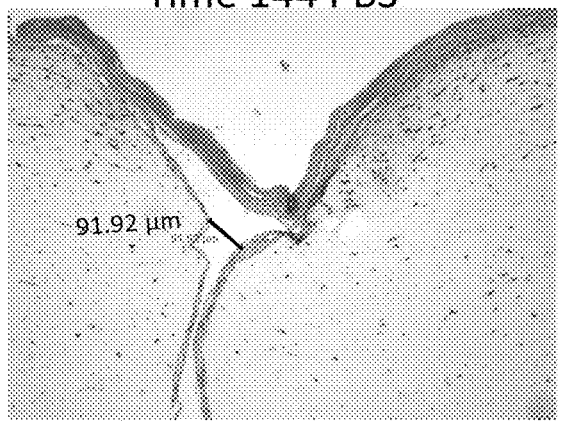
Figure 9A:
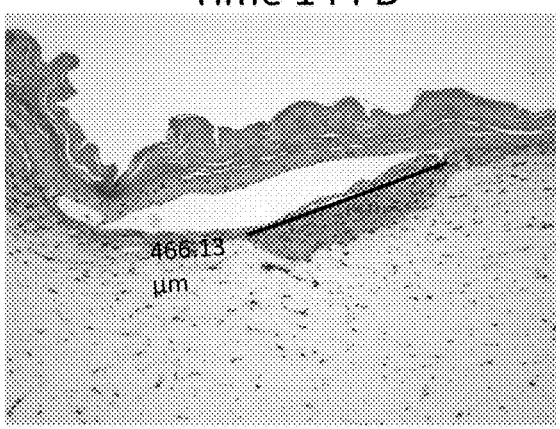
Figure 9A:
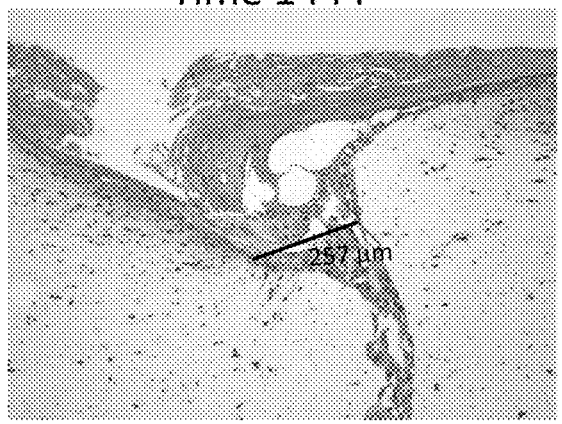
Figure 9A:
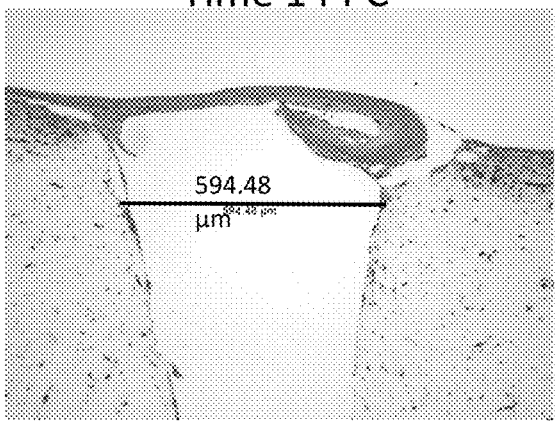
Figure 9B:
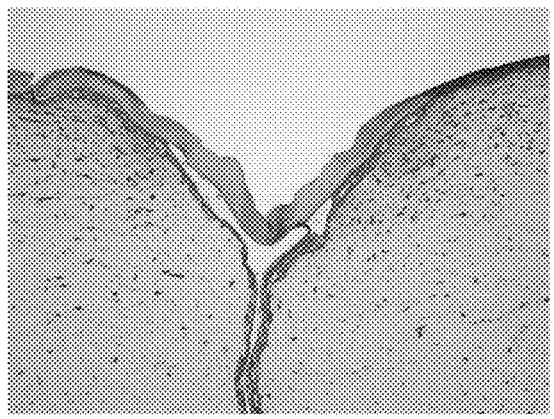
Figure 9B:
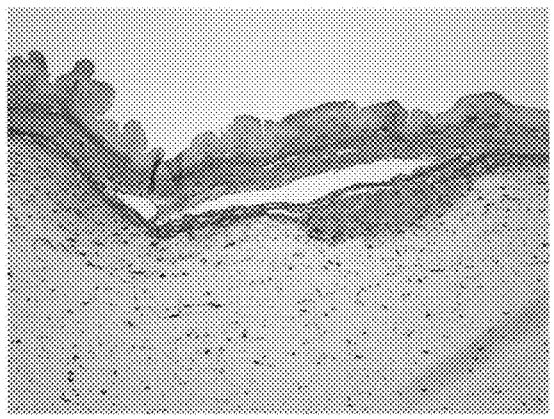
Figure 9B:
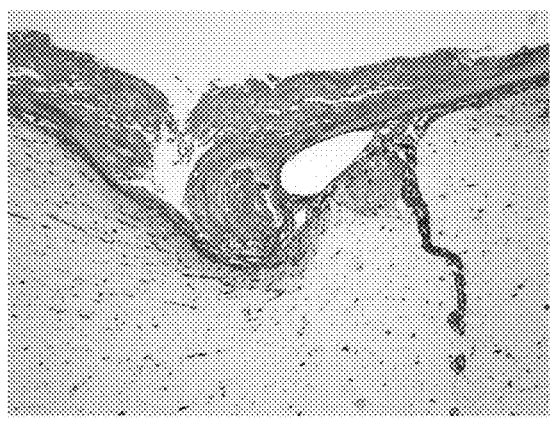
Figure 9B:
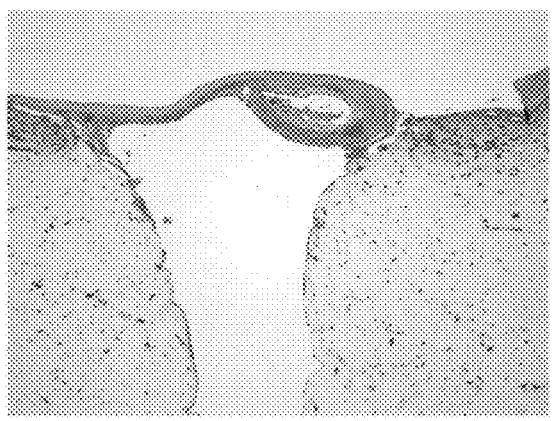
Figure 9B:
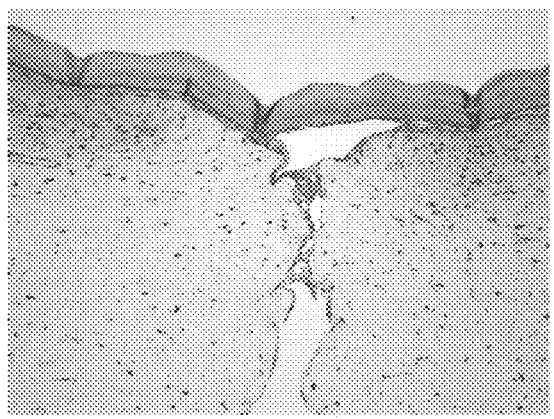
Figure 9C:
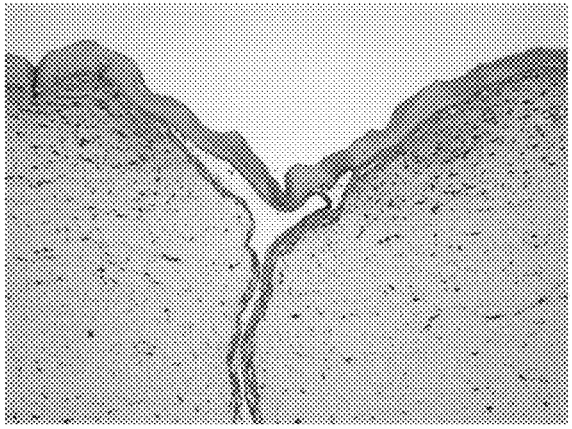
Figure 9C:
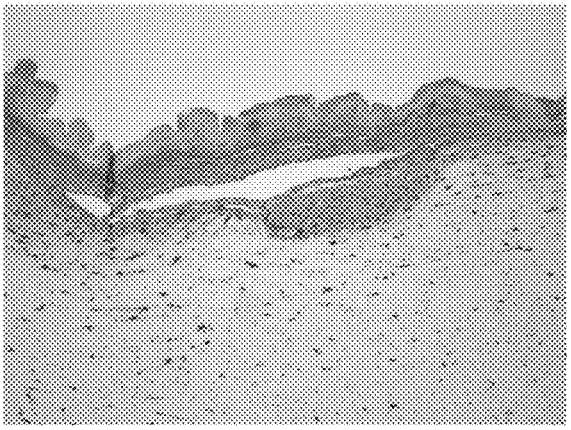
Figure 9C:
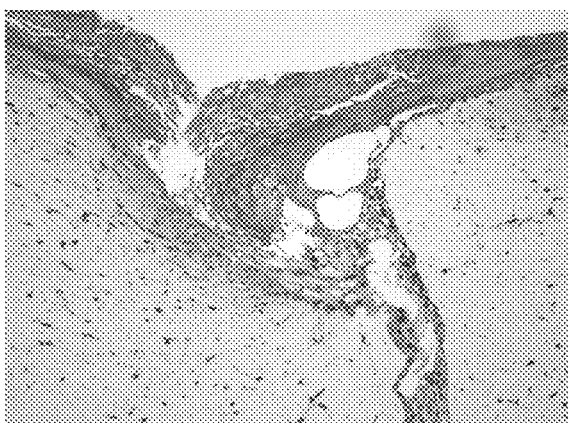
Figure 9C:
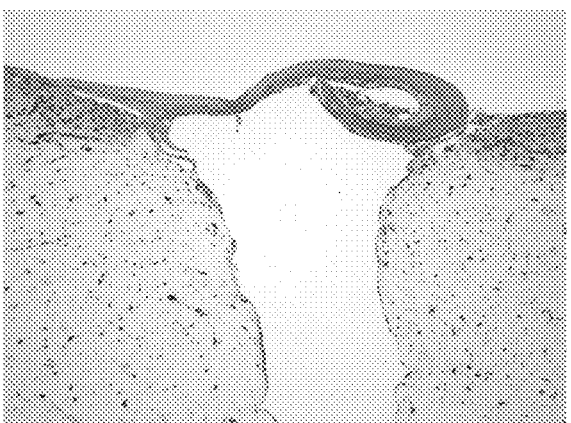
Figure 9C:
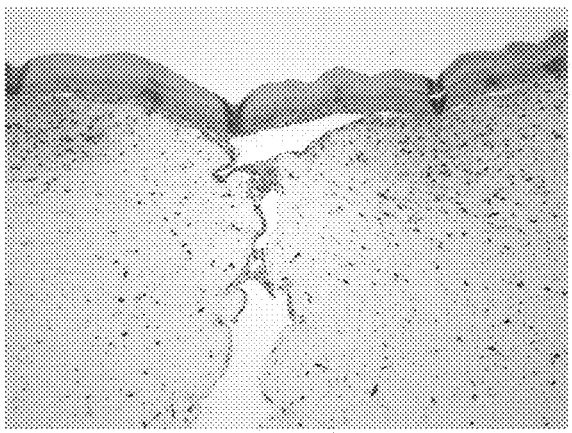
Figure 9D:
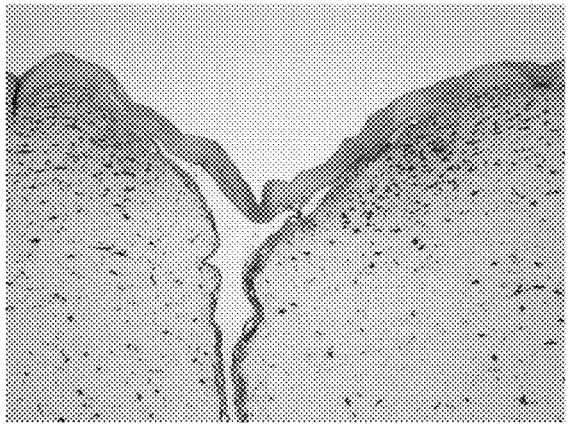
Figure 9D:
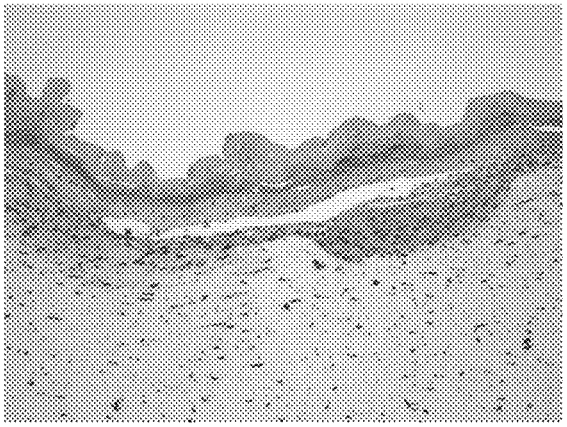
Figure 9D:
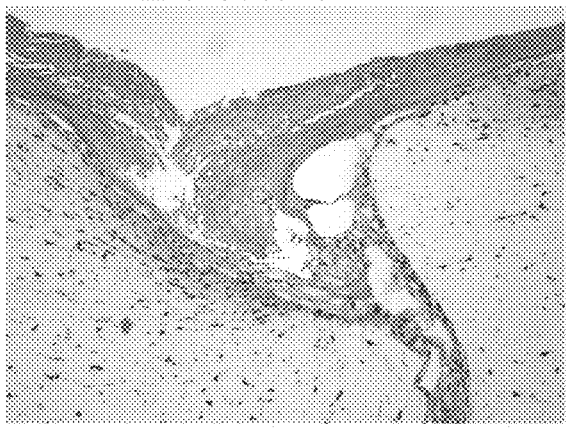
Figure 9D:
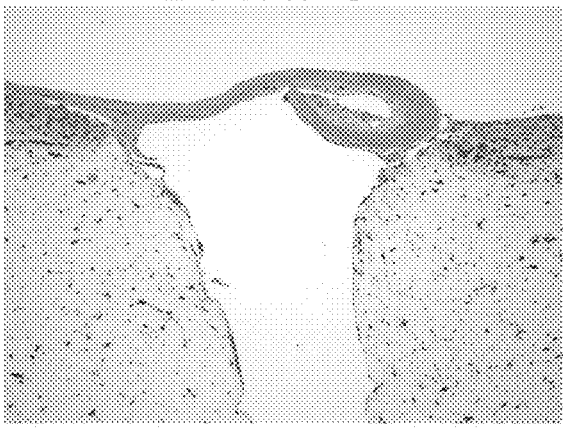
Figure 9D:
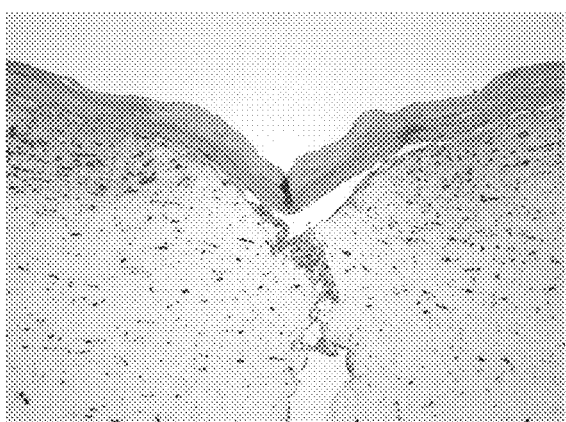

Example 5: Accelerated Wound Healing—Full-Thickness Surgical Wound Mimic with Razorblade Labskin was used as a model for mammalian skin to evaluate wound healing with the synthetic CpG oligonucleotides. A sterile razorblade was used to make an incision, producing a cut using a razorblade mimicking a full-thickness surgical wound. Each synthetic CpG oligonucleotide was then applied to each incision. Hematoxylin and eosin (H&E) staining, immunochemistry (MMP-1, vimentin, and BMP6), and Elisa (45-plex MSD) were performed to evaluate the effect of each synthetic CpG oligonucleotide as modulators of wound healing. Tissue imaging results for each immunochemistry experiment for razorblade wounds are shown in FIG. 9A-D for CpG oligonucleotides 'F', 'E', 'D', and 'C'. H&E staining, as shown in FIG. 9A, reflected almost complete wound repair when treated with CpG oligonucleotide 'F'. For the wound treated with CpG oligonucleotide 'E', the H&E staining showed complete remodeling of the wound site and migration of epithelia cells into the incision for the wound. BMP6 staining was conducted and results shown in FIG. 9B. The BMP6 staining shows that the PBS control showed BMP expression at the leading edge of the wound. The wound treated with synthetic CpG oligonucleotide 'F' showed a higher expression which indicated continuous cell recruitment and an increased extent of repair. The wound treated with synthetic CpG oligonucleotide 'E' showed a mild protein expression, however, the extent of repair was comparable to the synthetic CpG oligonucleotide 'F' wound. The wound treated with CpG oligonucleotide 'D' showed high protein expression and wound repair. The wound treated with CpG oligonucleotide 'C' showed a low protein expression with no increased expression at the leading edge of the wound as observed for the other wound conditions. MMP1 staining was conducted and results shown in FIG. 9C. The MMP1 staining demonstrates that the PBS control showed high MMP1 expression at the leading edge of the wound. The wound treated with synthetic CpG oligonucleotide 'F' showed a much higher expression which indicated continuous cell recruitment and an increased extent of repair. The wound treated with synthetic CpG oligonucleotide 'E' showed a mild protein expression, however, the extent of repair was comparable to the CpG oligonucleotide 'F' wound and does not reflect any relative slowness in repair. The wound treated with synthetic CpG oligonucleotide 'D' showed high protein expression and wound repair. The wound treated with synthetic CpG oligonucleotide 'C' showed a low protein expression with no increased expression at the leading edge of the wound as observed for the other wound conditions. Vimentin staining was conducted and results shown in FIG. 9D. The Vimentin staining shows that the PBS control showed high Vimentin expression at the leading edge of the wound and below the stratum corneum. The wound treated with synthetic CpG oligonucleotide 'F' showed a much higher expression which indicated continuous cell recruitment and an increased extent of repair. The wound treated with synthetic CpG oligonucleotide 'E' showed a mild protein expression, however, the extent of repair was comparable to the synthetic CpG oligonucleotide 'F' wound and does not reflect any relative slowness in repair. The wound treated with synthetic CpG oligonucleotide 'D' showed high protein expression and wound repair and Vimentin expression was within the migratory cells. The wound treated with synthetic CpG oligonucleotide 'C' showed a low protein expression at the leading edge, with increased expression below the stratum corneum of the wound similar to the control.

The untreated Labskin incision opening was measured at approximately 450 μm wide at the stratum spinosum at zero days after the incision. After six days post-injury microscopic assessment of H&E-stained section, the untreated Labskin had an observed opening of approximately 100 μm and showed migration of cell epithelia cells into the wound with the incision is still open. Synthetic CpG oligonucleotide 'F' showed remodeling of the incision and almost complete repair of wound. Synthetic CpG oligonucleotide 'E' also showed remodeling to a greater extent than the control. Synthetic CpG oligonucleotide 'D' showed a complete remodeling of the wound site and migration of epithelia cells into the incision. Observed remaining opening of the wounds may be attributed to a histological factor. Synthetic CpG oligonucleotide 'C' showed the least amount of remodeling including in comparison to the control wound. This is consistent with a lack of migratory cells and inhibition of wound repair.

Example 5: Scratch Assay

A two-dimensional keratinocyte scratch assay is conducted in a 48-well plate (in triplicate) and seeded with keratinocytes until confluent. A pipette tip is used to create a scratch in each test well. Synthetic CpG oligonucleotides (0.3 μM) are added and imaging is subsequently carried out. Rate of infill is calculated using ImageJ software. Cell culture shows which Synthetic CpG oligonucleotides activate keratinocyte proliferation and migration to infill a surface wound.

Example 6: Irritation Assay of CpG Oligonucleotides on Skin Mimic (Labskin)

Figure 10A:
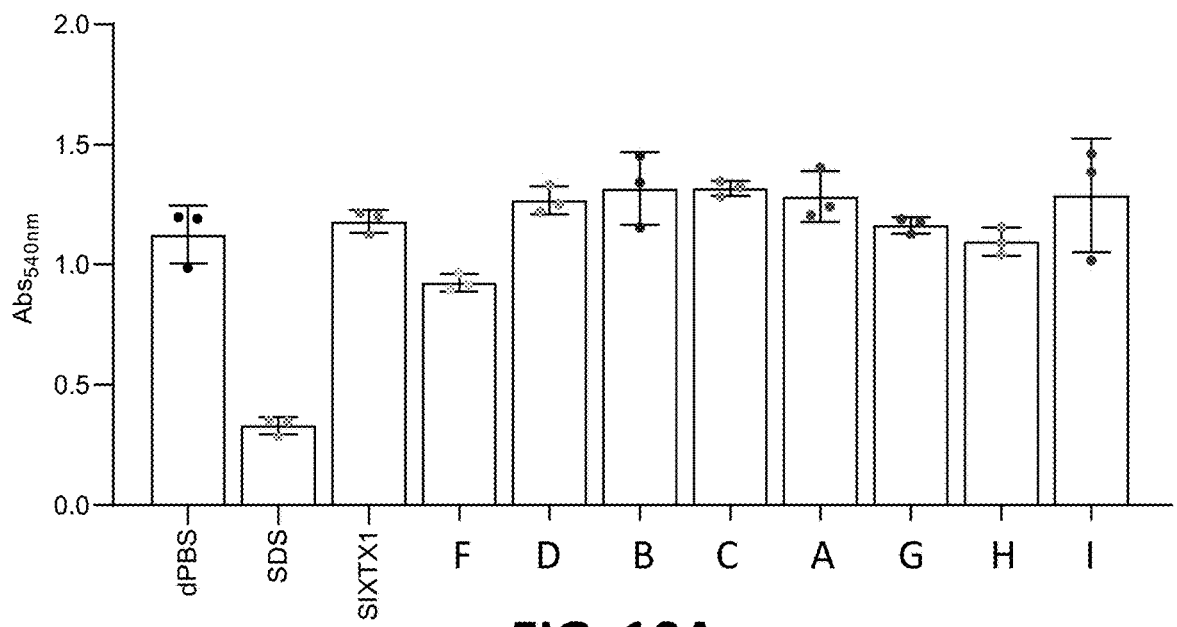
FIG. 10A-C shows graphical representations measuring cell viability using MTT conversion to formazan (absorbance near 570 nm), and inflammatory measurements.
Figure 10B:
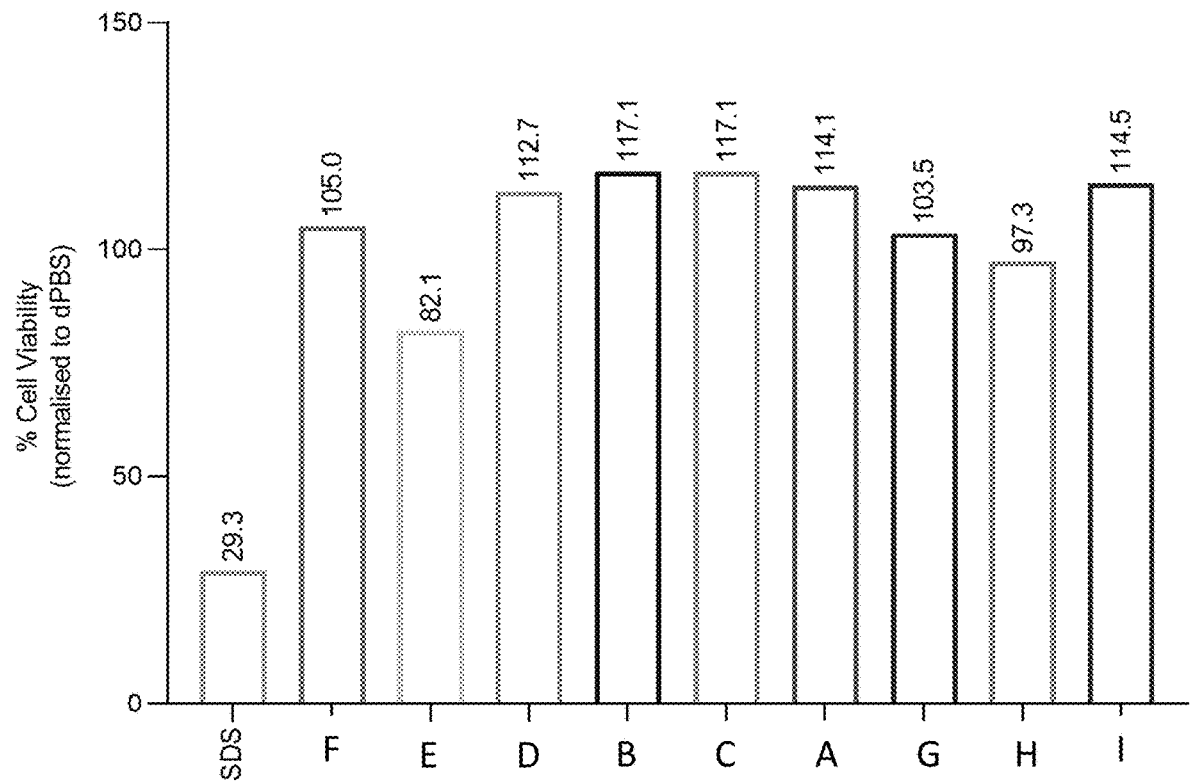
Figure 10C:
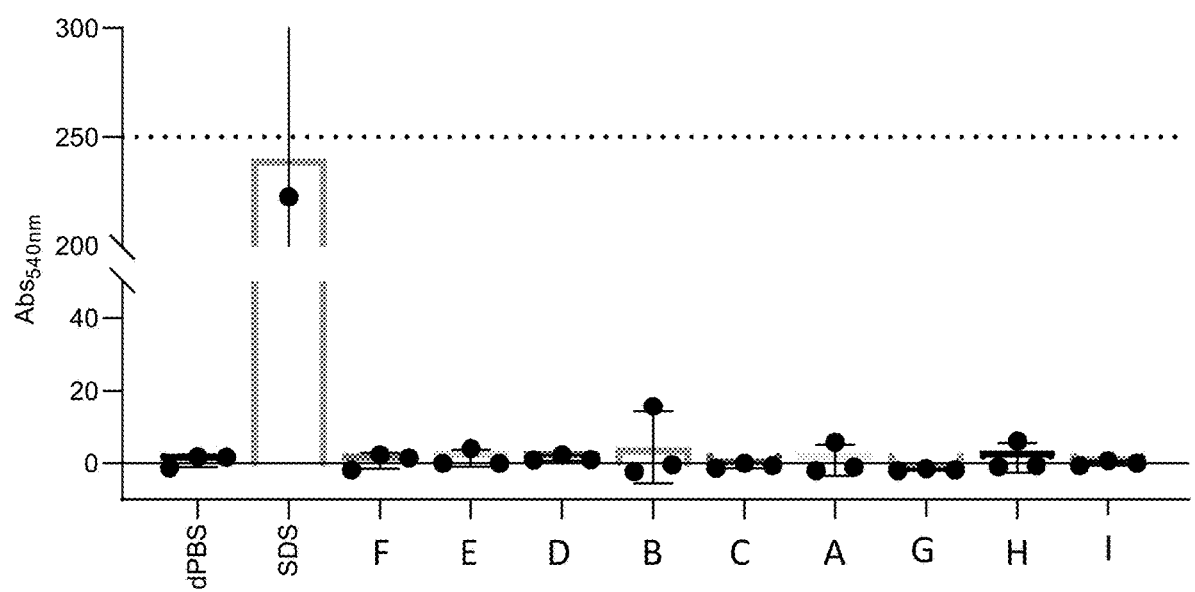

An irritation assay is performed to evaluate inflammation and irritation of synthetic CpG oligonucleotides on Labskin using the OECD TG439 method. Viable cells with active metabolism convert MTT into a purple-colored formazan product with an absorbance maximum near 570 nm. Non-viable cells cannot convert MTT to formazan so the color (absorbance measure) is a measure of cell viability as shown in FIG. 10A and FIG. 10B. As shown in FIG. 10B, the SDS control must be below 50% to be irritating. It was concluded that all CpG oligonucleotides tested were non-irritating. FIG. 10C provided a measure of IL-la release, release of an inflammatory cytokine. As shown, only the SDS control produced high levels of the IL-la after 24 hours of incubation. The CpG oligonucleotides tested did not produce high levels of absorbance, indicating they are non-inflammatory.

Example 7: Mammalian Wound Healing with CpG Oligonucleotides

Figure 11A:
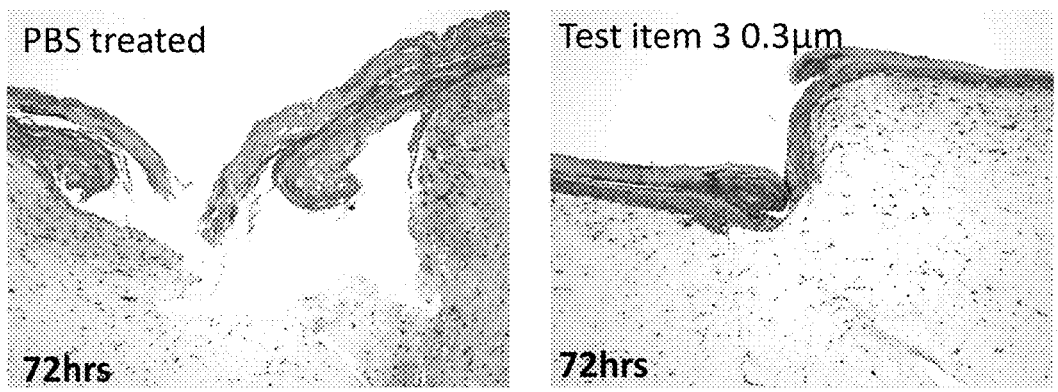
FIG. 11A-B show wound healing results for mammalian candidate tissue using CpG oligonucleotide D.
Figure 11A:
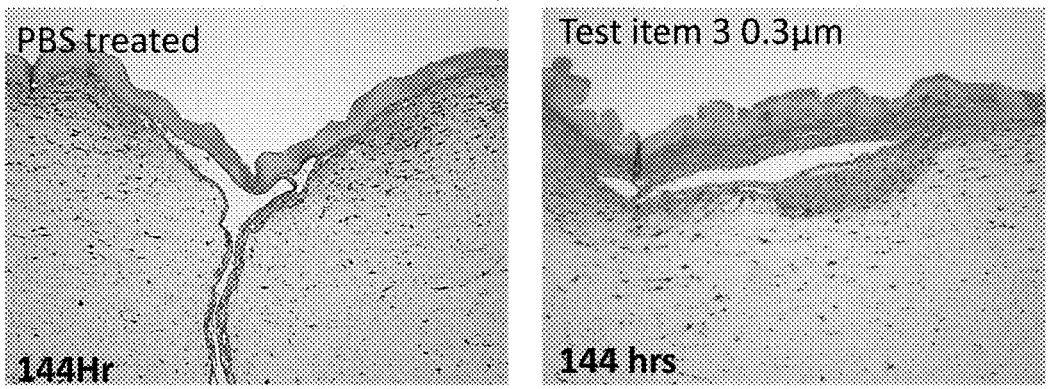
Figure 11B:
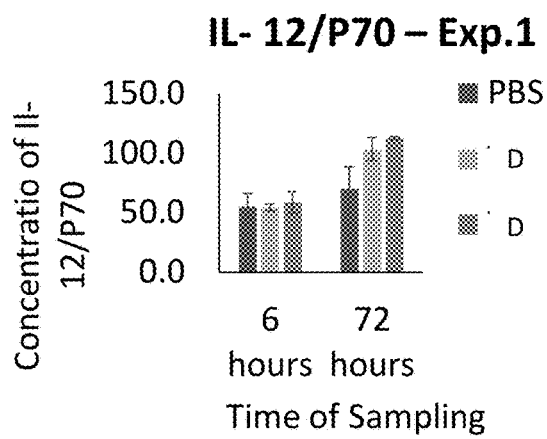
Figure 11B:
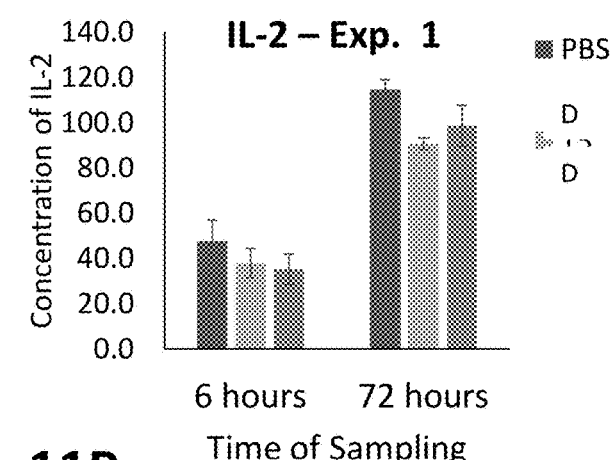
Figure 12:
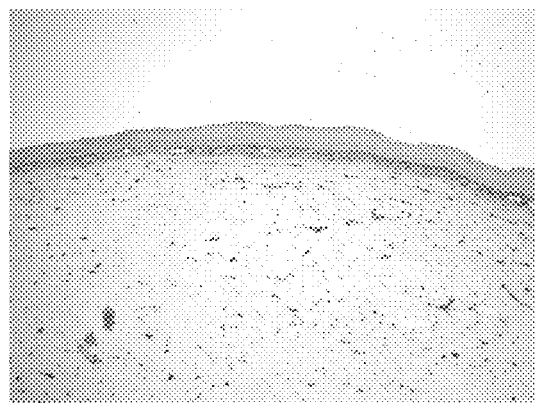
FIG. 12 shows tissue stains of resectioned, deeper tissue samples of a razorblade wounded skin, stained with BMP6, MMIP1, and Vimentin stains showing tissue remodeling of the wound area (right images) in comparison to unwounded skin (left images) after 144 hours of treatment with CpG oligonucleotide 'D'.
Figure 12:
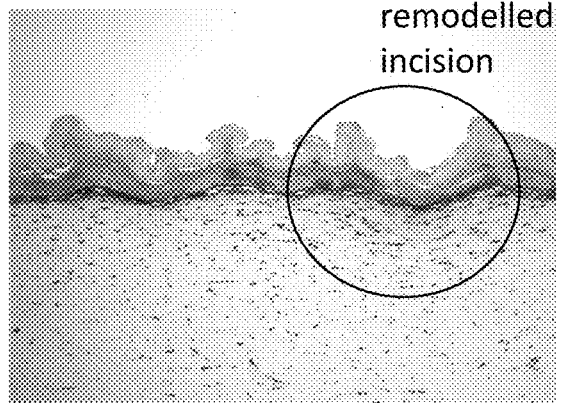
Figure 12:
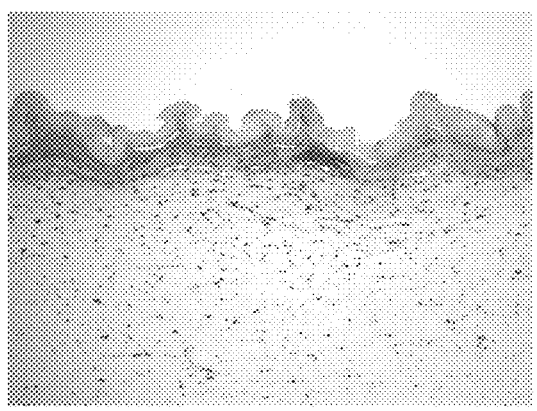
Figure 12:
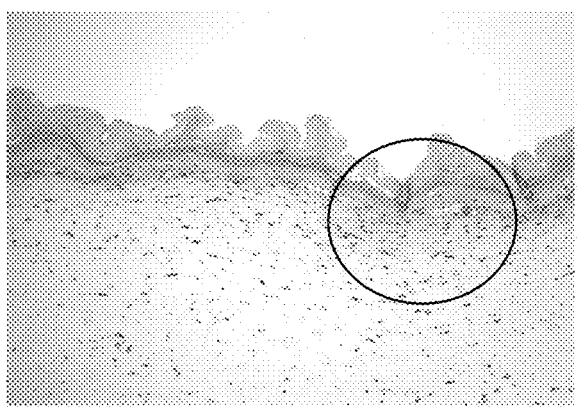
Figure 13A:
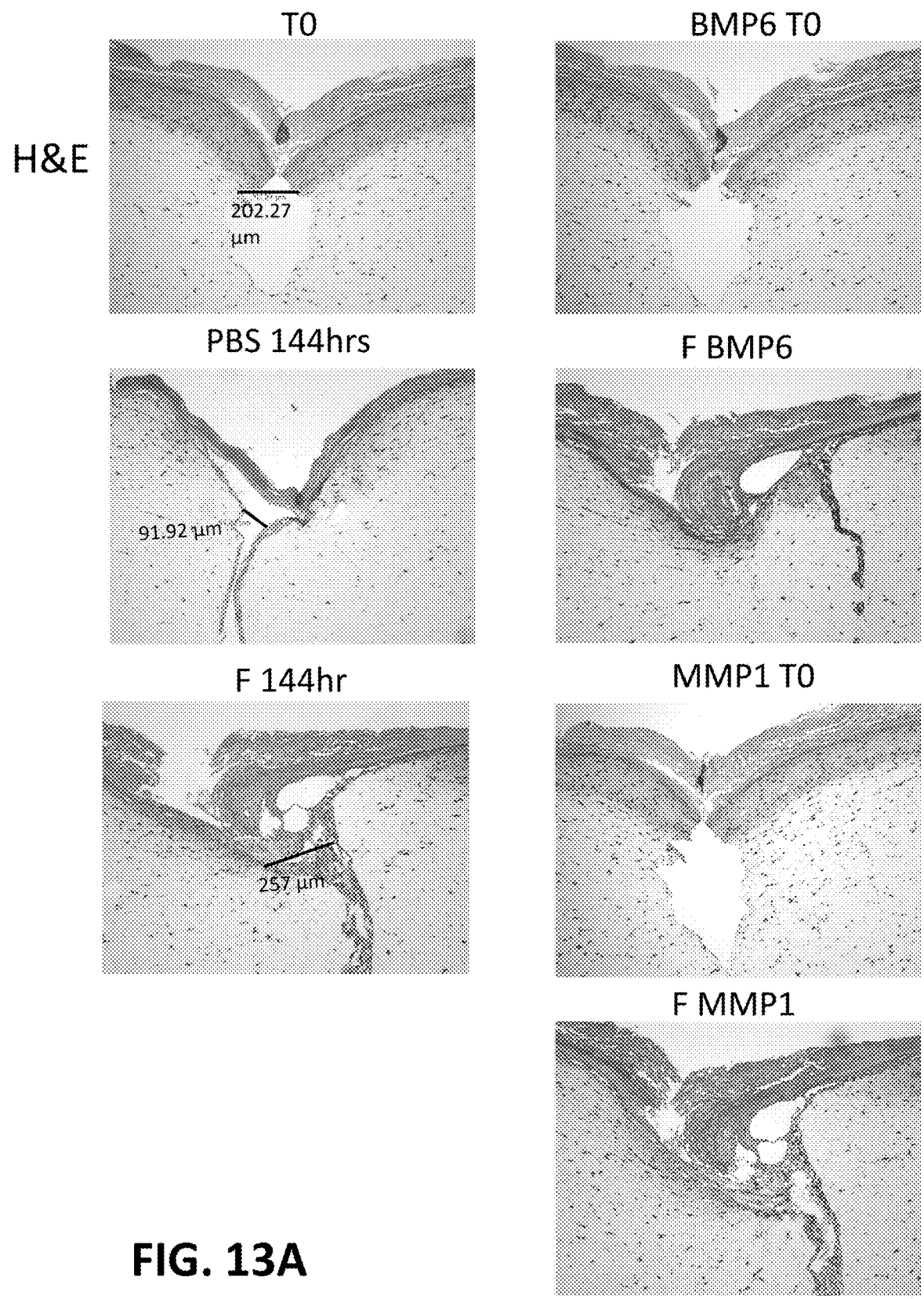
FIG. 13A-D show additional tissue stains for a control CpG oligonucleotide, a PBS control, and a CpG oligonucleotide described herein.
Figure 13B:
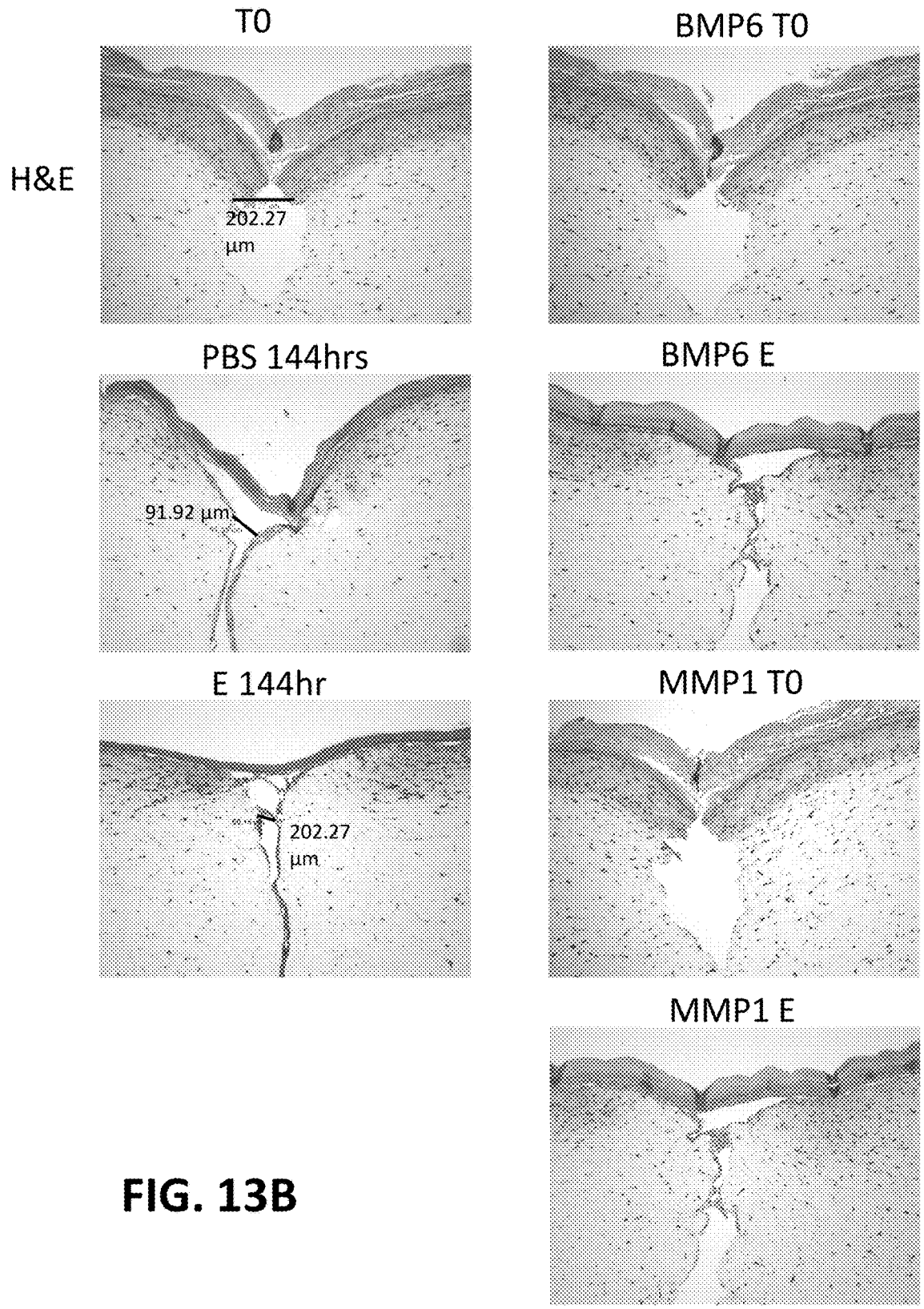
Figure 13C:
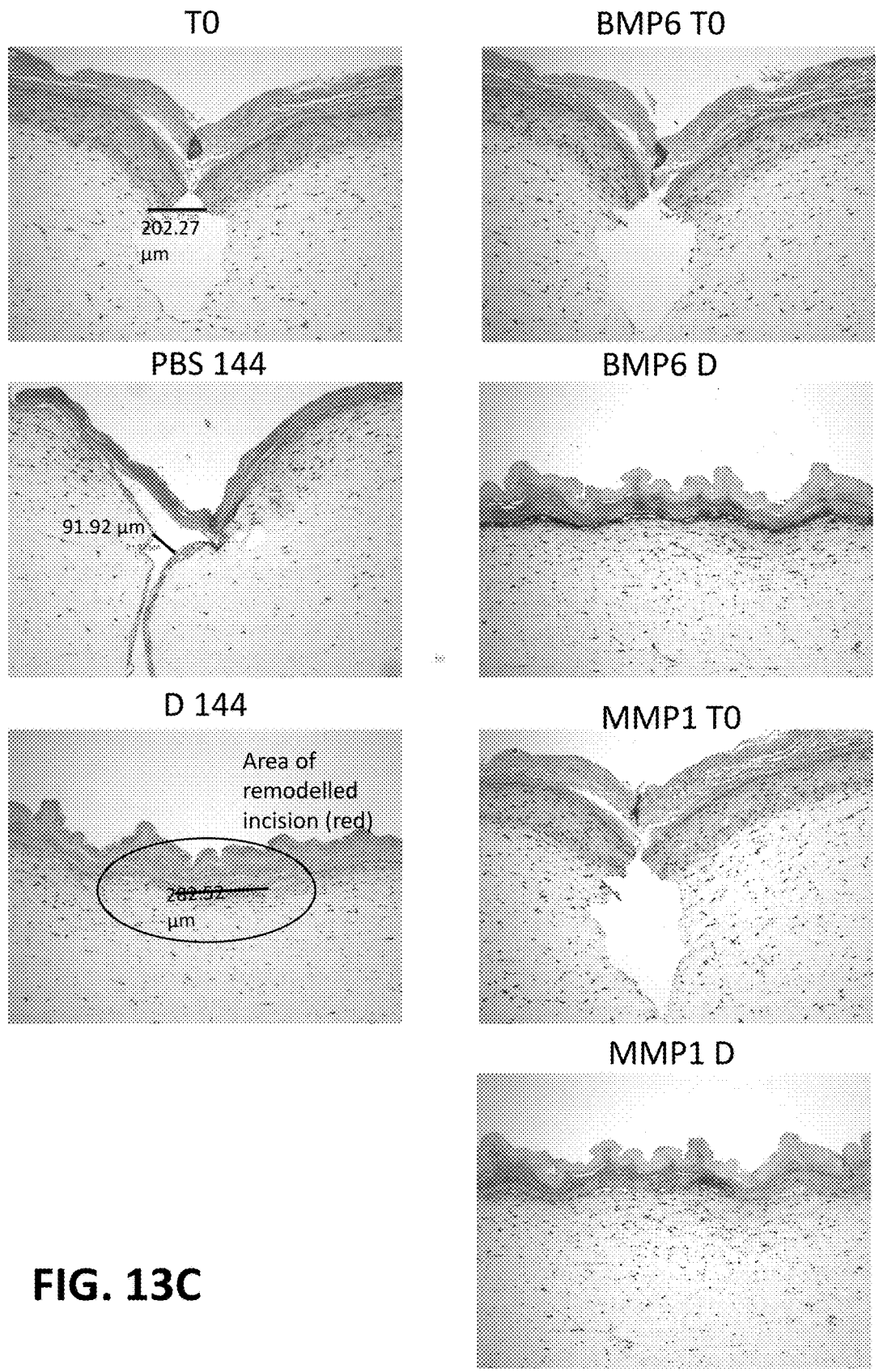
Figure 13D:
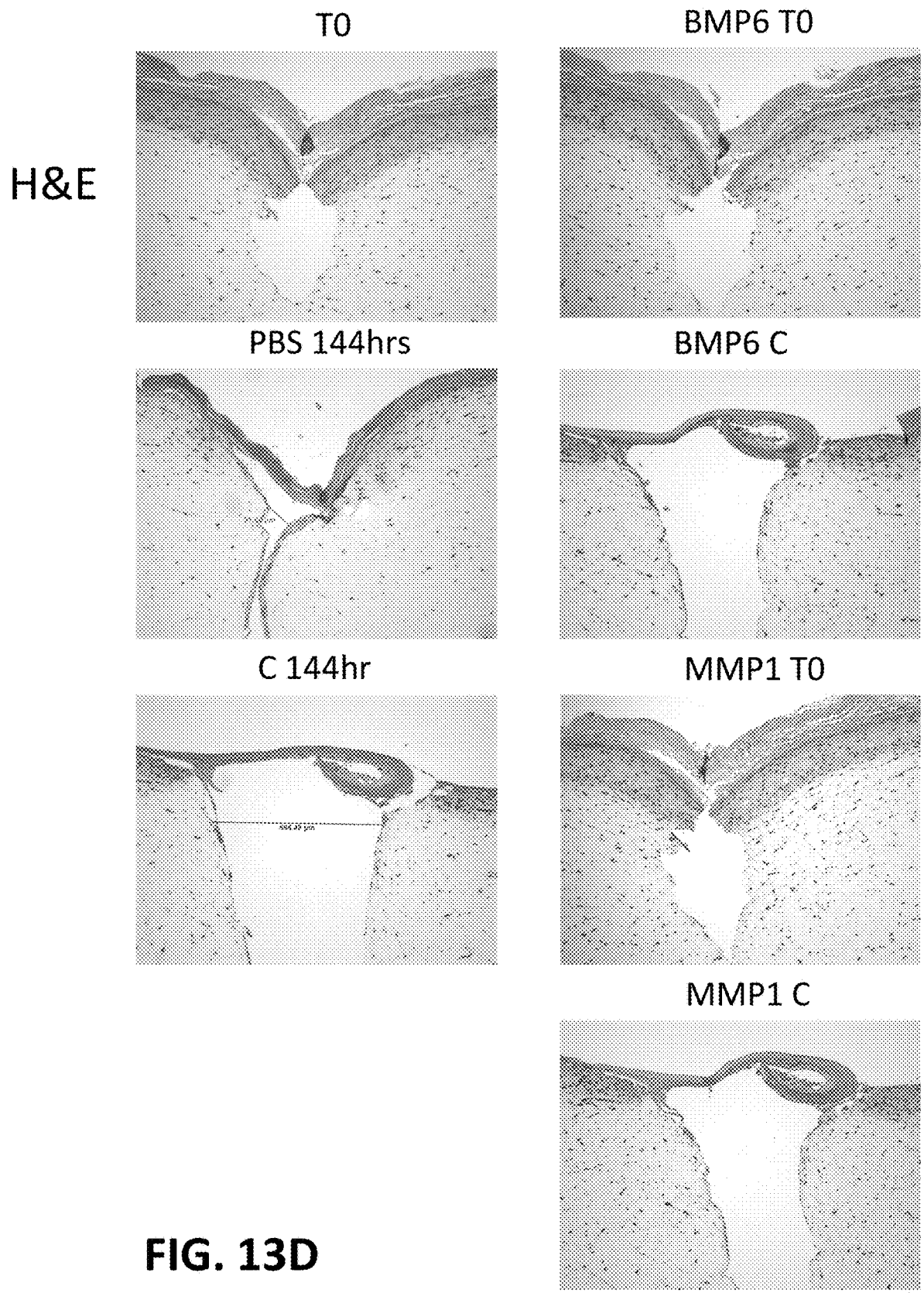

An irritation assay is performed to evaluate inflammation and irritation of the synthetic CpG oligonucleotides using the OECD TG439 method. Accelerated wound healing was observed by tissue sample staining as shown in FIG. 11A for both scalpel and razorblade wounds in comparison to the untreated, PBS control, and cytokine production was measured for IL-2 and IL-12/p70 for CpG oligonucleotide 'D' as shown in FIG. 11B. FIG. 12 Showed tissue remodeling of wounded skin re-sectioned (right images) treated with synthetic CpG oligonucleotide 'D' after 144 hours using BMP6, MMP1, and Vimentin in comparison with unwounded, control tissue (left images). FIG. 13A-C show additional tissue staining for a control synthetic CpG oligonucleotide, a PBS control, and a CpG oligonucleotide described herein. FIG. 13A shows staining for CpG oligonucleotide 'F'. FIG. 13B shows staining for synthetic CpG oligonucleotide 'E'. FIG. 13C shows staining for synthetic CpG oligonucleotide 'C'.

Example 8: Immunostimulatory Effect of CpG Oligonucleotides on Human and Mouse Peripheral Blood Mononuclear Cell (PBMC)

The effect of the synthetic CpG oligonucleotides on the production of cytokines, chemokines, growth factors and Immunoglobulin M (IgM) was assessed via in vitro testing. Human and mouse peripheral blood mononuclear cells (PBMCs) were exposed to serial dilutions of three synthetic CpG oligonucleotides (i.e., T1, T2 (SEQ ID NO: 17) and T3 (SEQ ID NO: 25)) and two controls with known stimulatory activity (i.e., CpG ODN 1826, CpG ODN 2007), and the resulting culture media was collected for protein analysis using species-specific preconfigured Luminex multiplex assays and enzyme linked immunosorbent assays (ELISAs). Results were subjected to statistical analysis (ANOVA with Tukey multiple comparisons testing) to identify treatment parameters that yielded significant changes in protein expression, tabulated in Tables 5 and 6 and in 14A-14AT and 15A-15AQ.

Figure 14A:
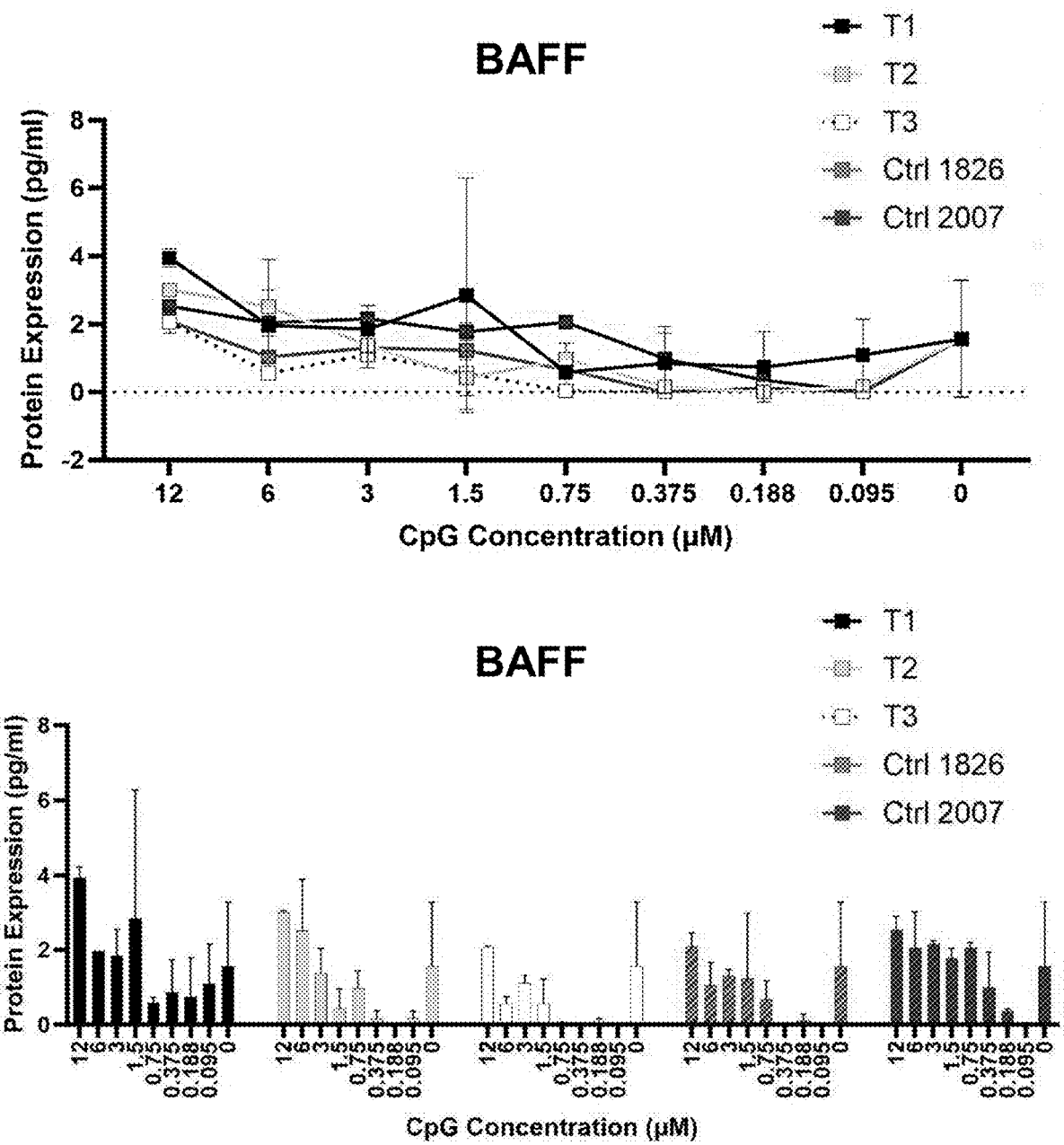
FIG. 14A-AT shows line and bar graphs for each protein target in mouse peripheral blood mononuclear cells (PBMCs) after treatment with CpG oligonucleotides as disclosed herein (i.e., T1, T2 (SEQ ID NO: 17) and T3 (SEQ ID NO: 25)) and two controls with known stimulatory activity (i.e., CpG ODN 1826, CpG ODN 2007).
Figure 14B:
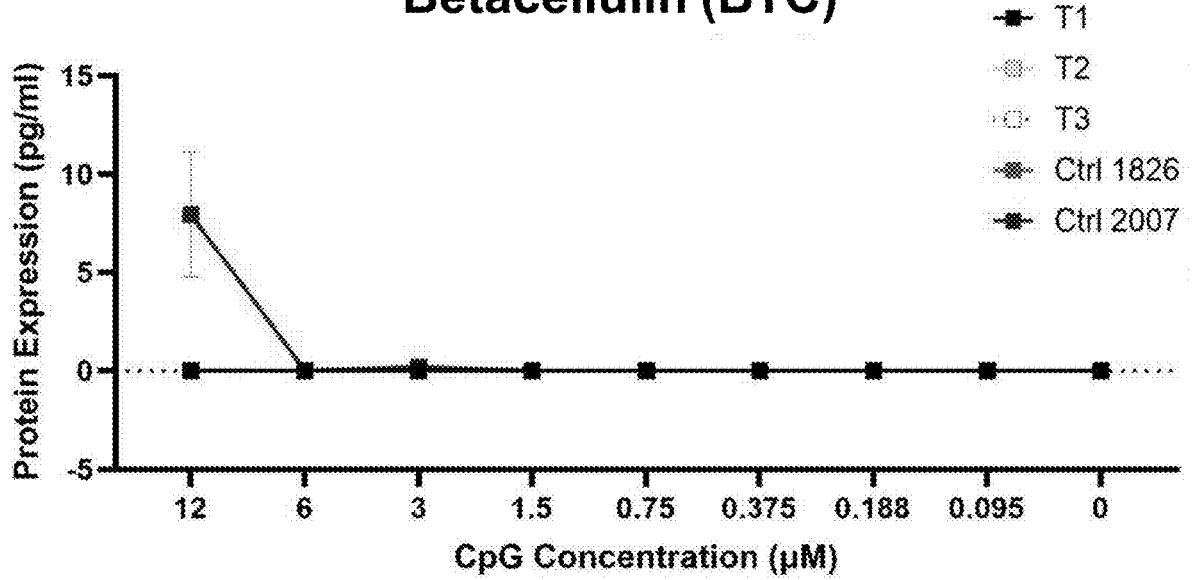
FIG. 14B depicts the protein target betacellulin (BTC).
Figure 14B:
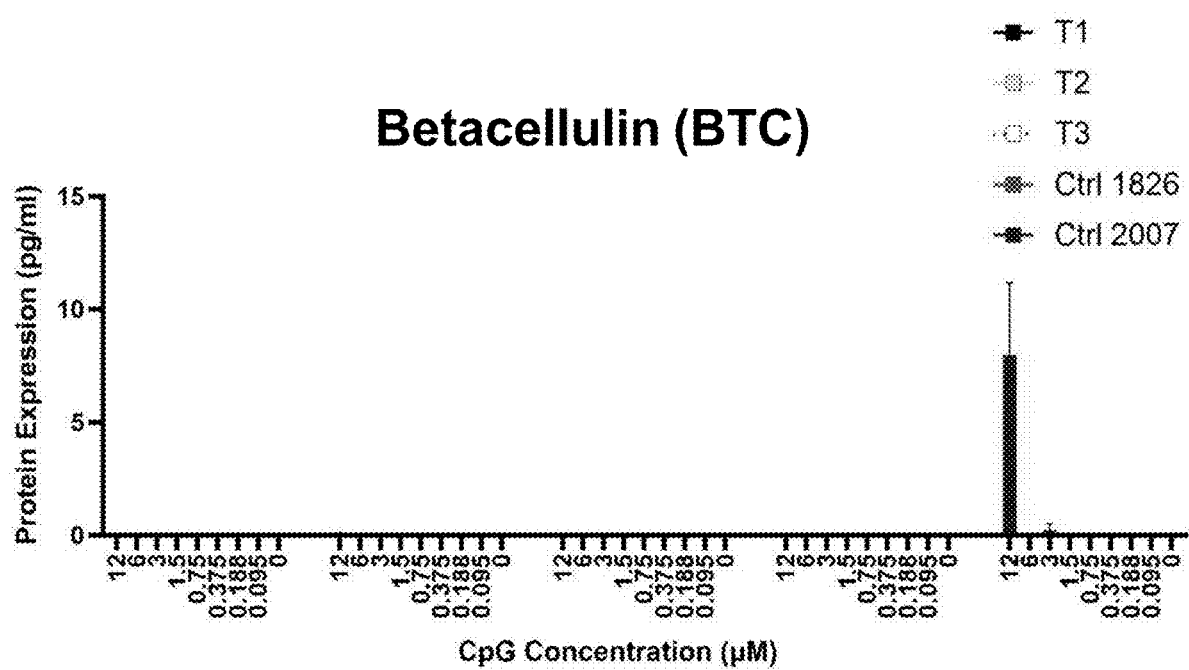
Figure 14C:
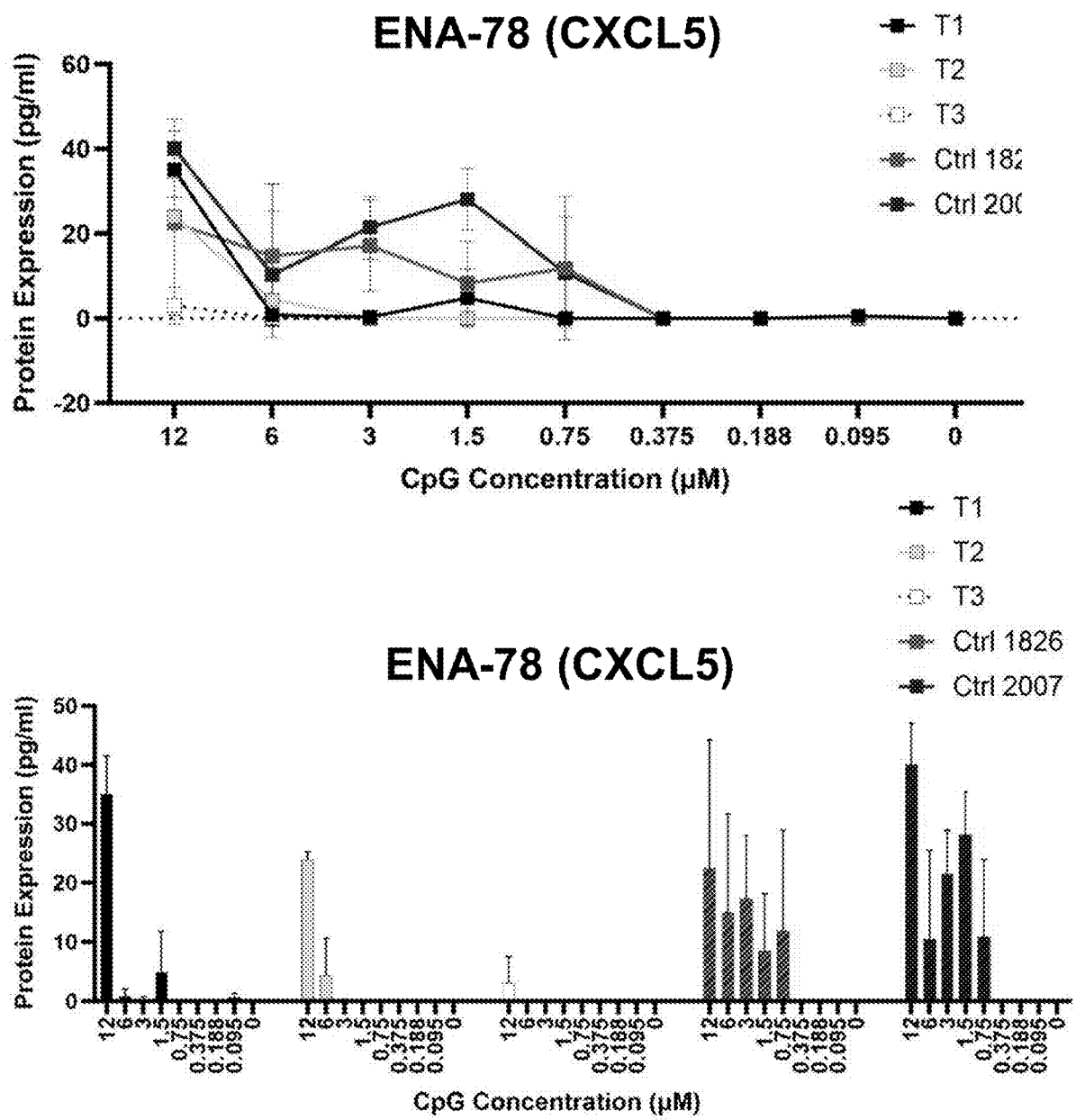
FIG. 14C depicts the protein target Epithelial Neutrophil-Activating Protein 78 Mouse (ENA-78) also known as C-X-C motif chemokine 5 (CXCL5).
Figure 14D:
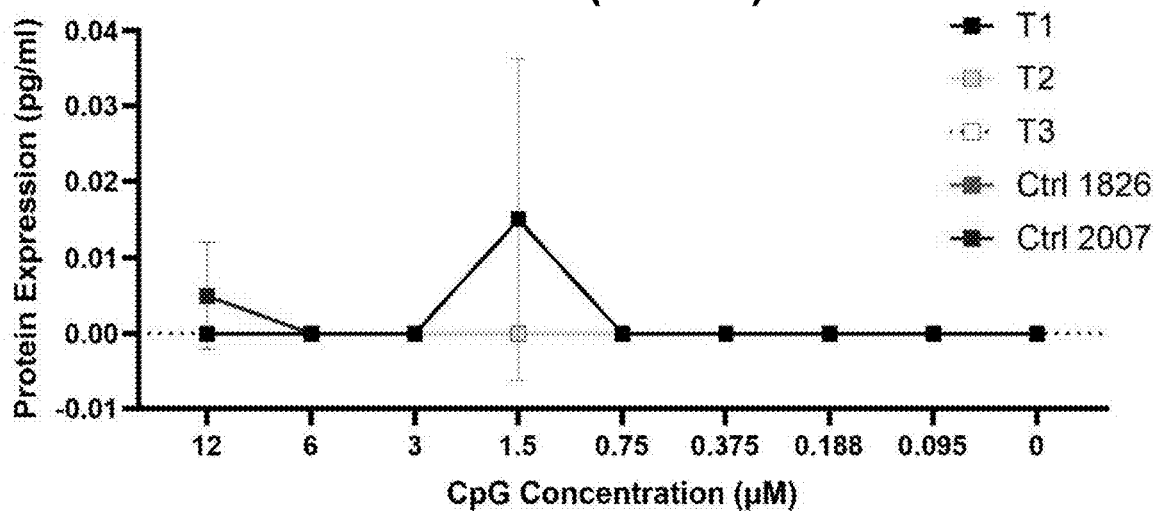
FIG. 14D depicts the protein target Eotaxin also known as C-C motif chemokine 11 (CCL11).
Figure 14D:
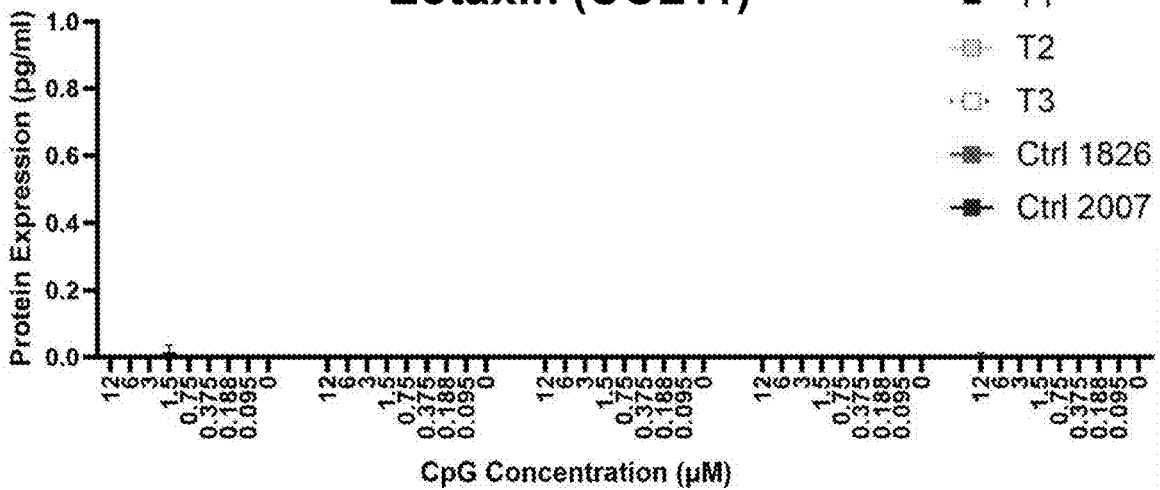
Figure 14E:
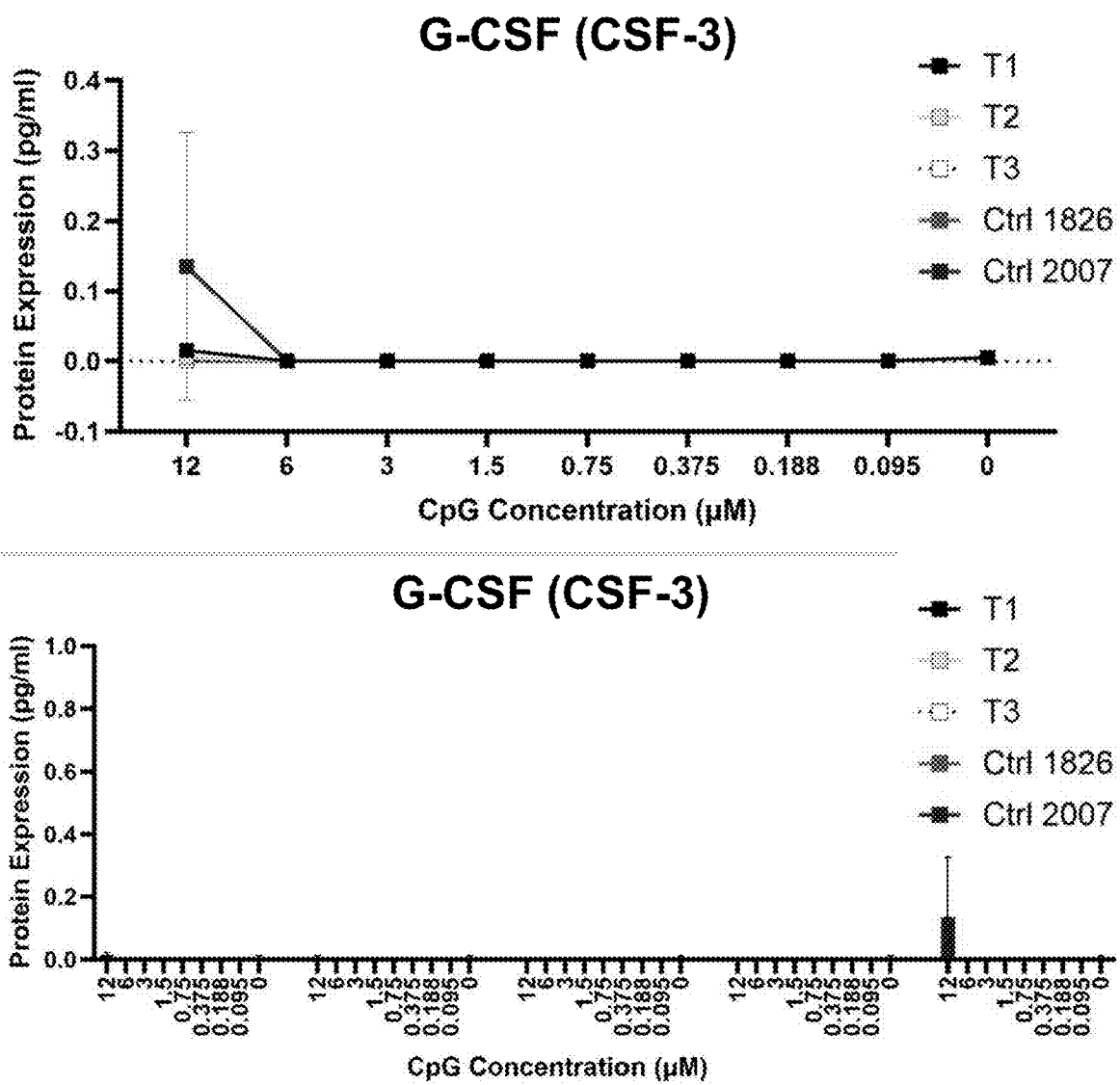
FIG. 14E depicts the protein target granulocyte colony-stimulating factor (G-CSF) also known as colony-stimulating factor 3 (CSF-3).
Figure 14F:
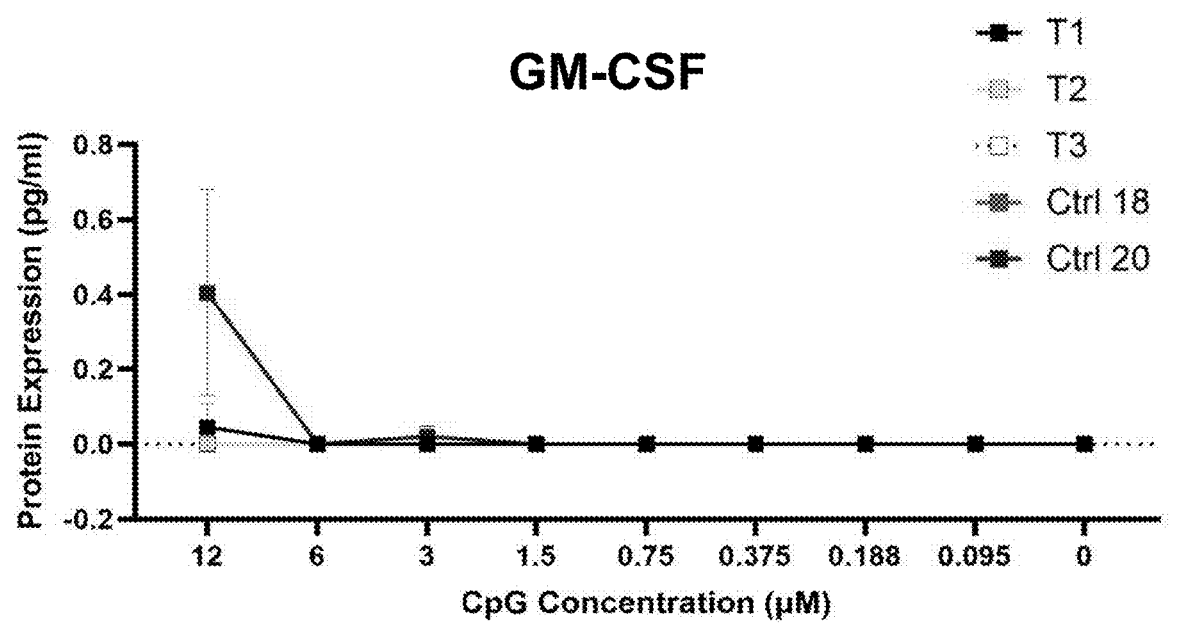
FIG. 14F depicts the protein target granulocyte-macrophage colony-stimulating factor (GM-CSF).
Figure 14F:
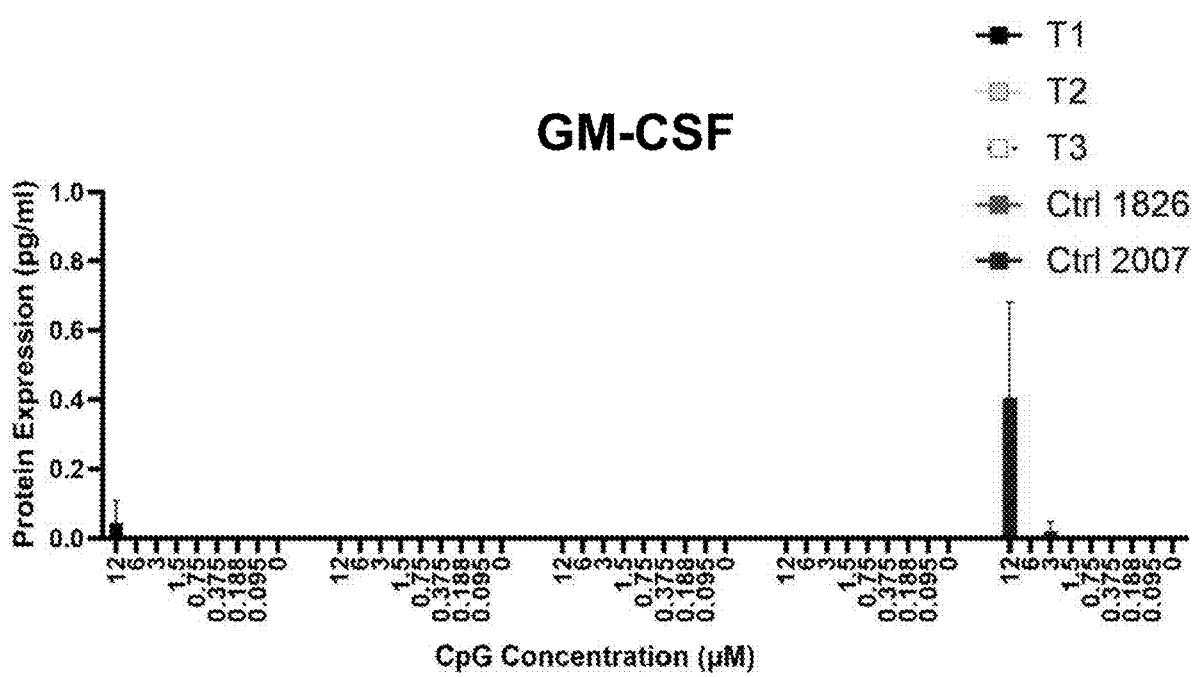
Figure 14G:
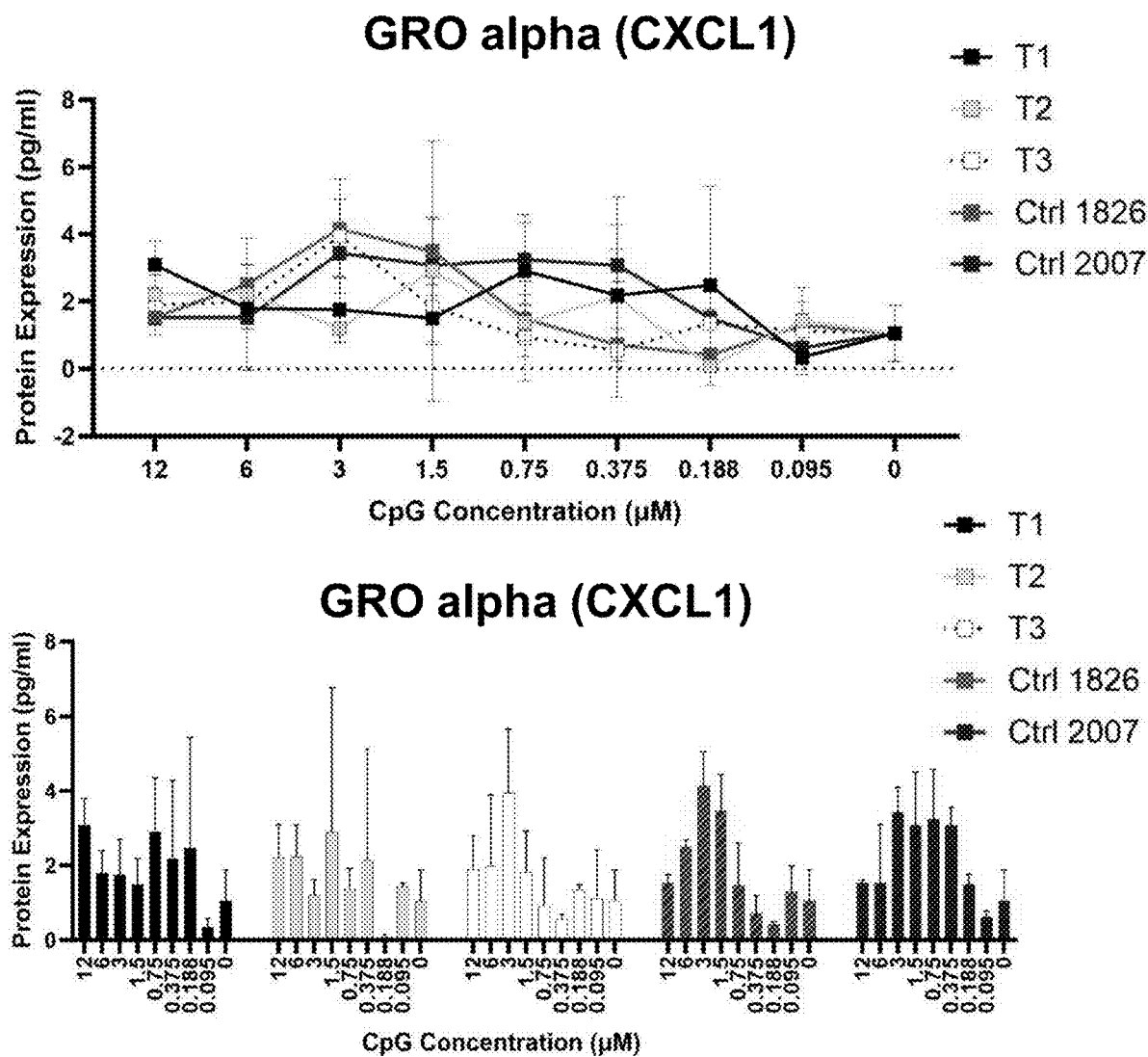
FIG. 14G depicts the protein target GRO alpha also known as chemokine (C-X-C motif) ligand 1 (CXCL1).
Figure 14H:
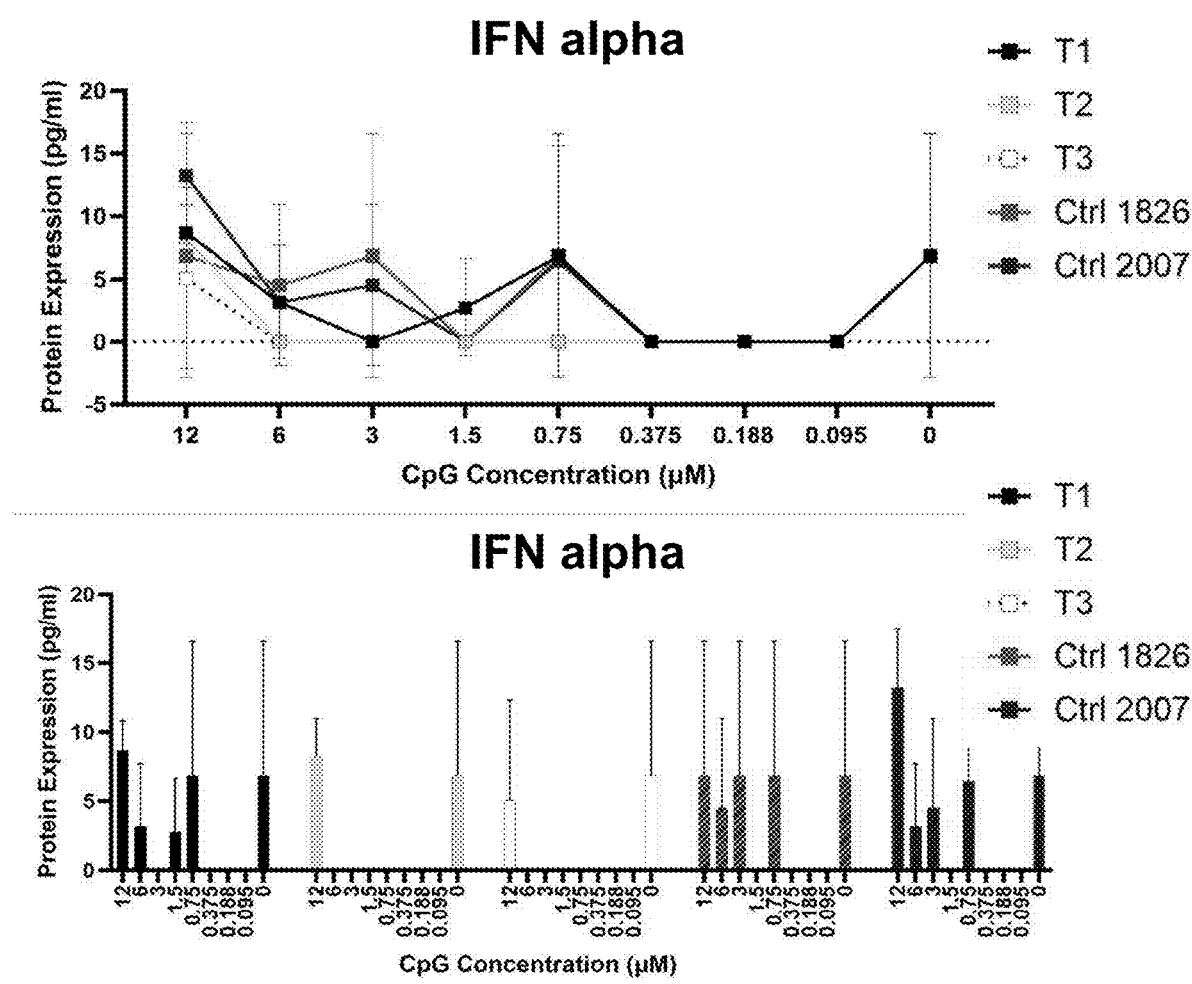
FIG. 14H depicts the protein target type-1 interferon (IFN) alpha.
Figure 14I:
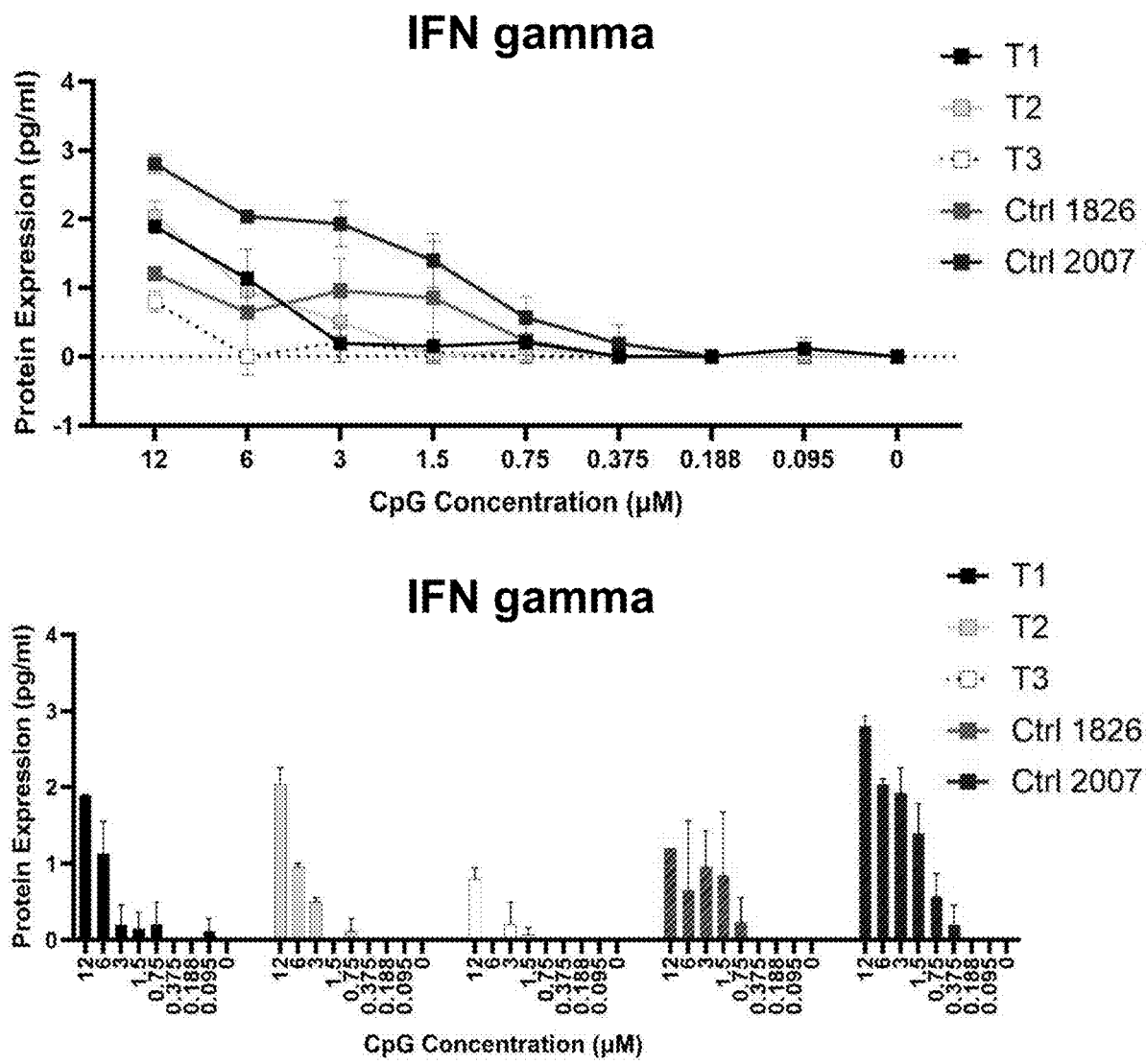
FIG. 14I depicts the protein target IFN gamma.
Figure 14J:
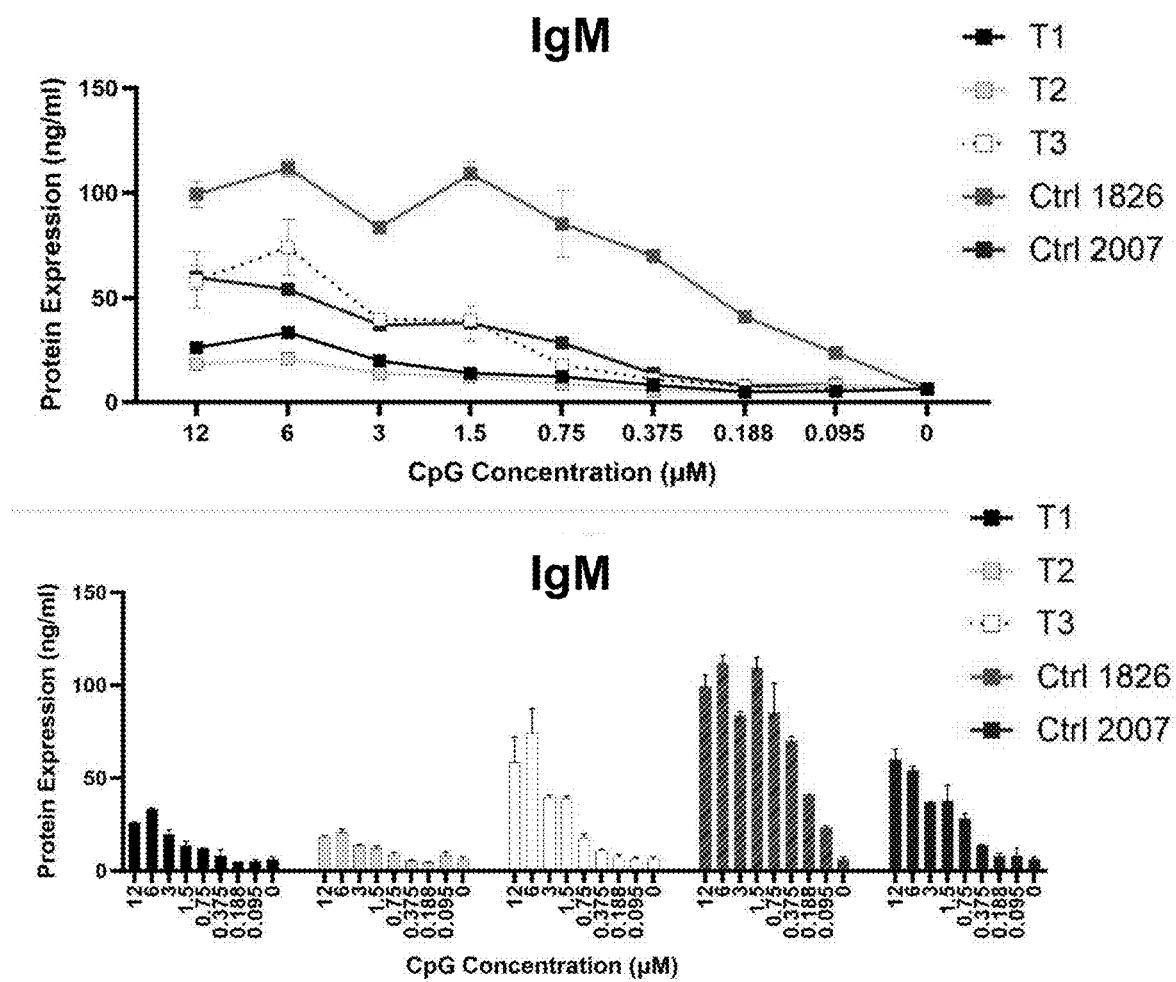
FIG. 14J depicts the protein target Immunoglobulin M (IgM).
Figure 14K:
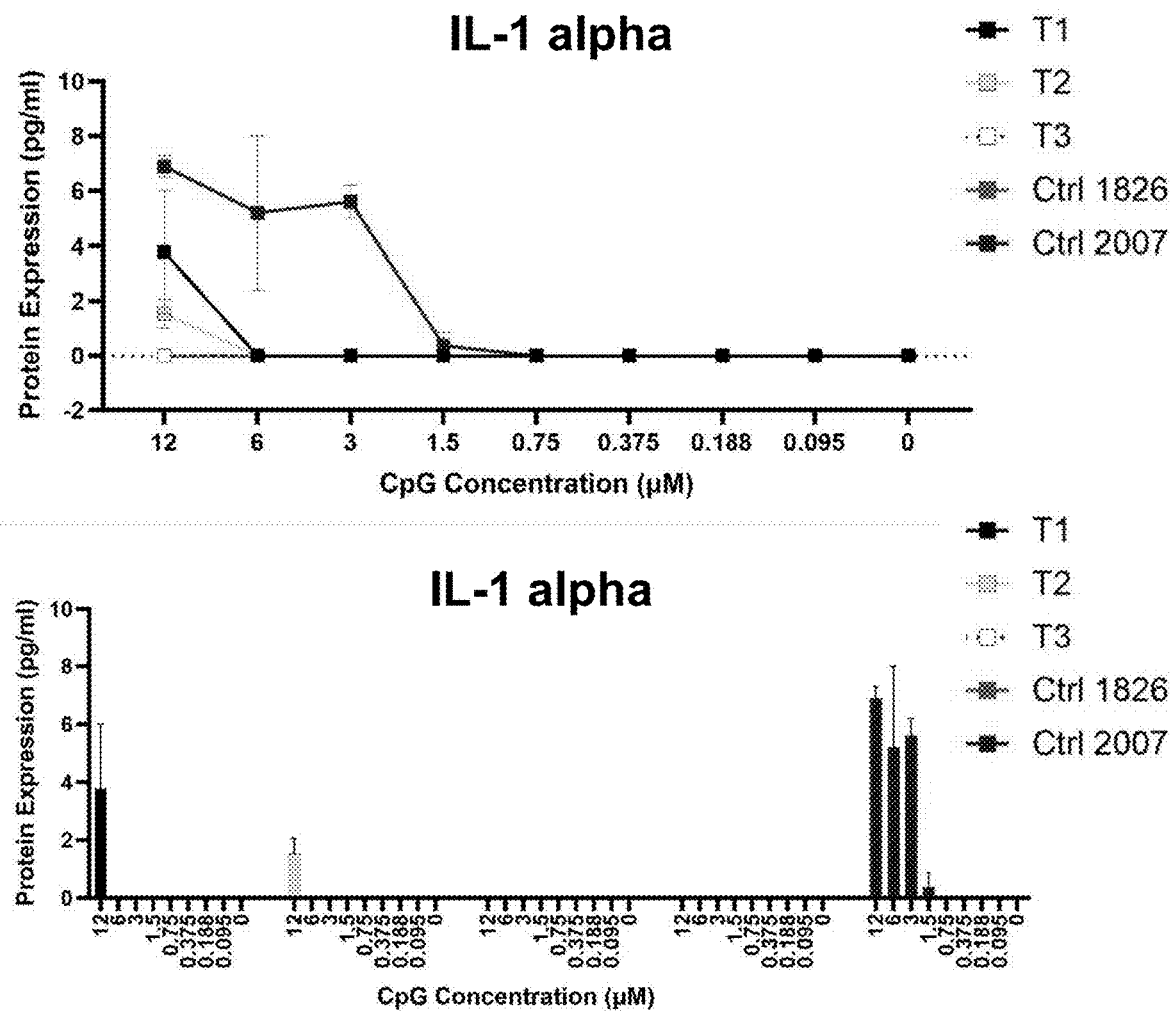
FIG. 14K depicts the protein target interleukin 1 (IL-1) alpha.
Figure 14L:
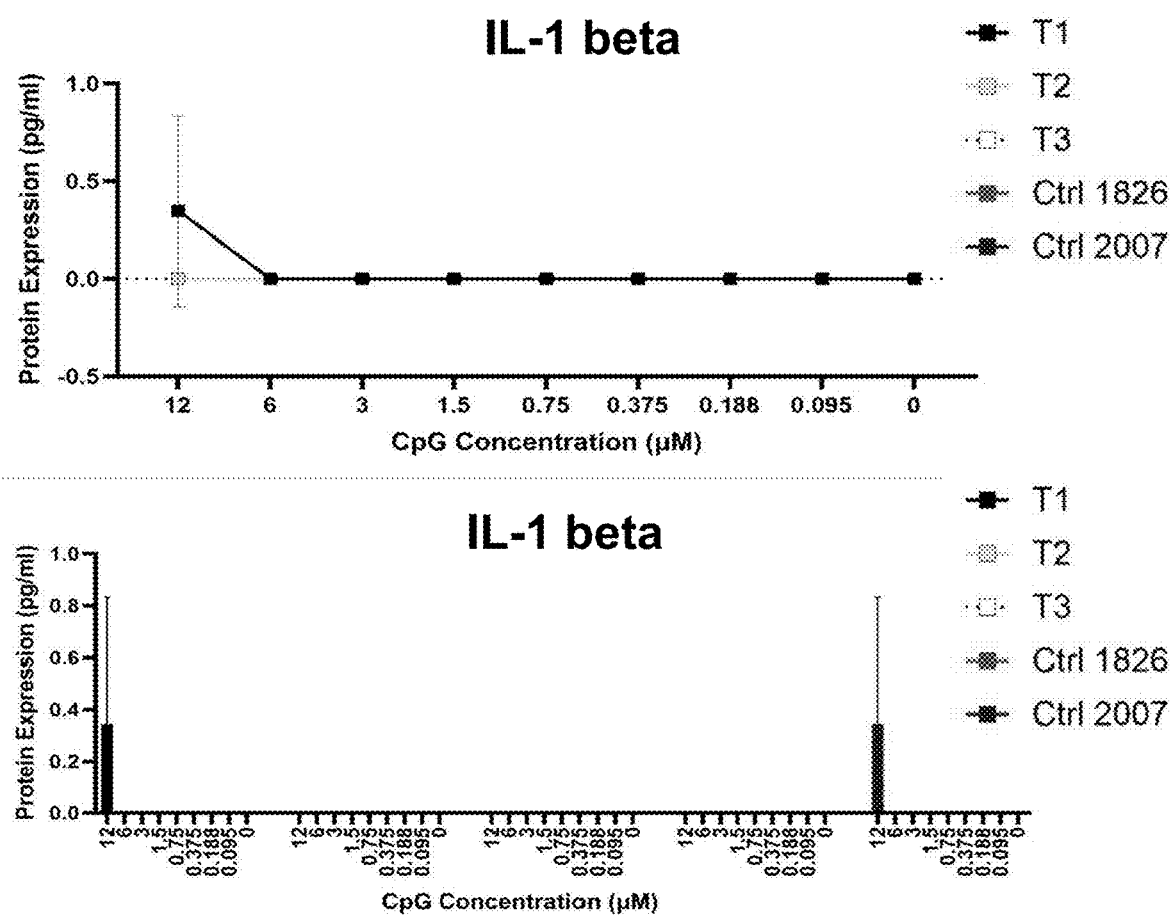
FIG. 14L depicts the protein target IL-1 beta.
Figure 14M:
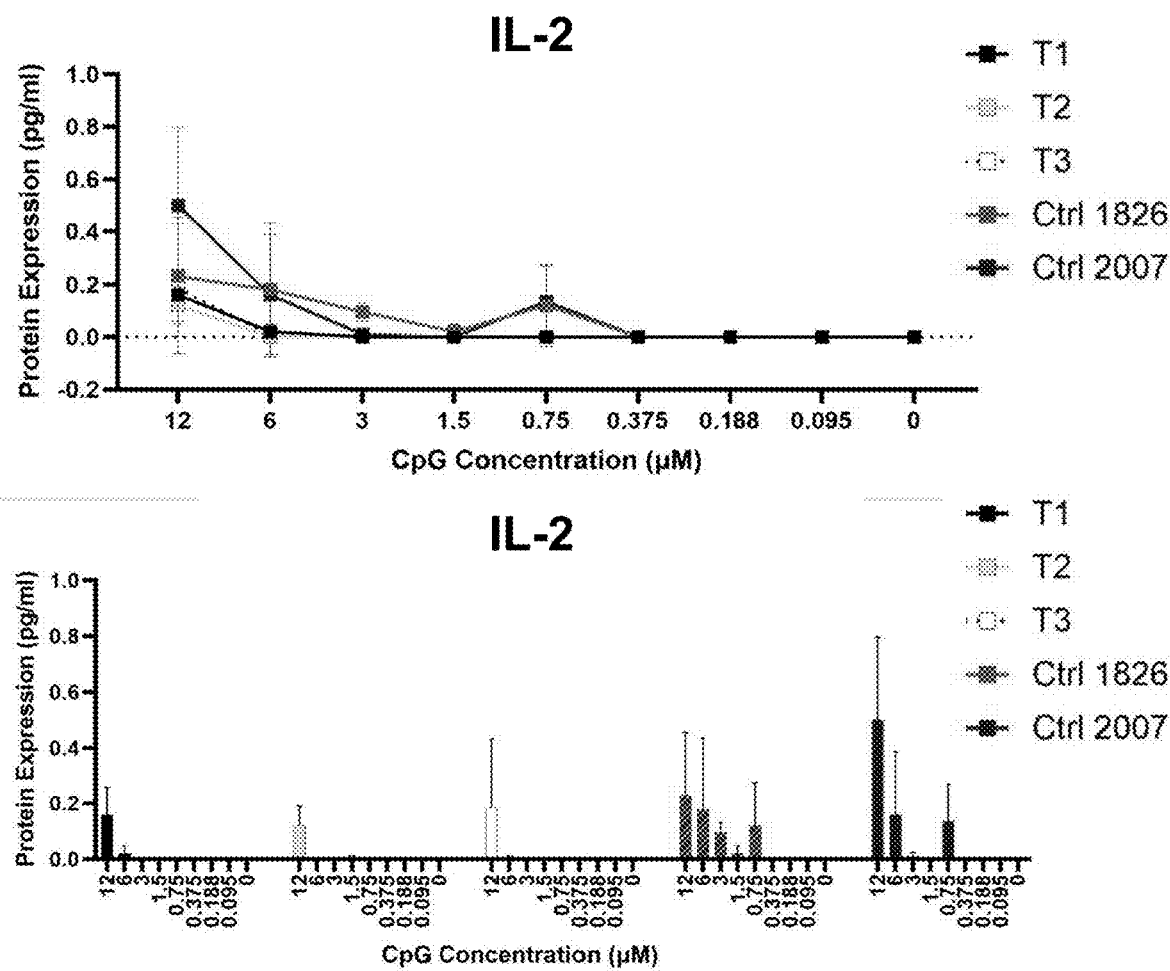
FIG. 14M depicts the protein target IL-2.
Figure 14N:
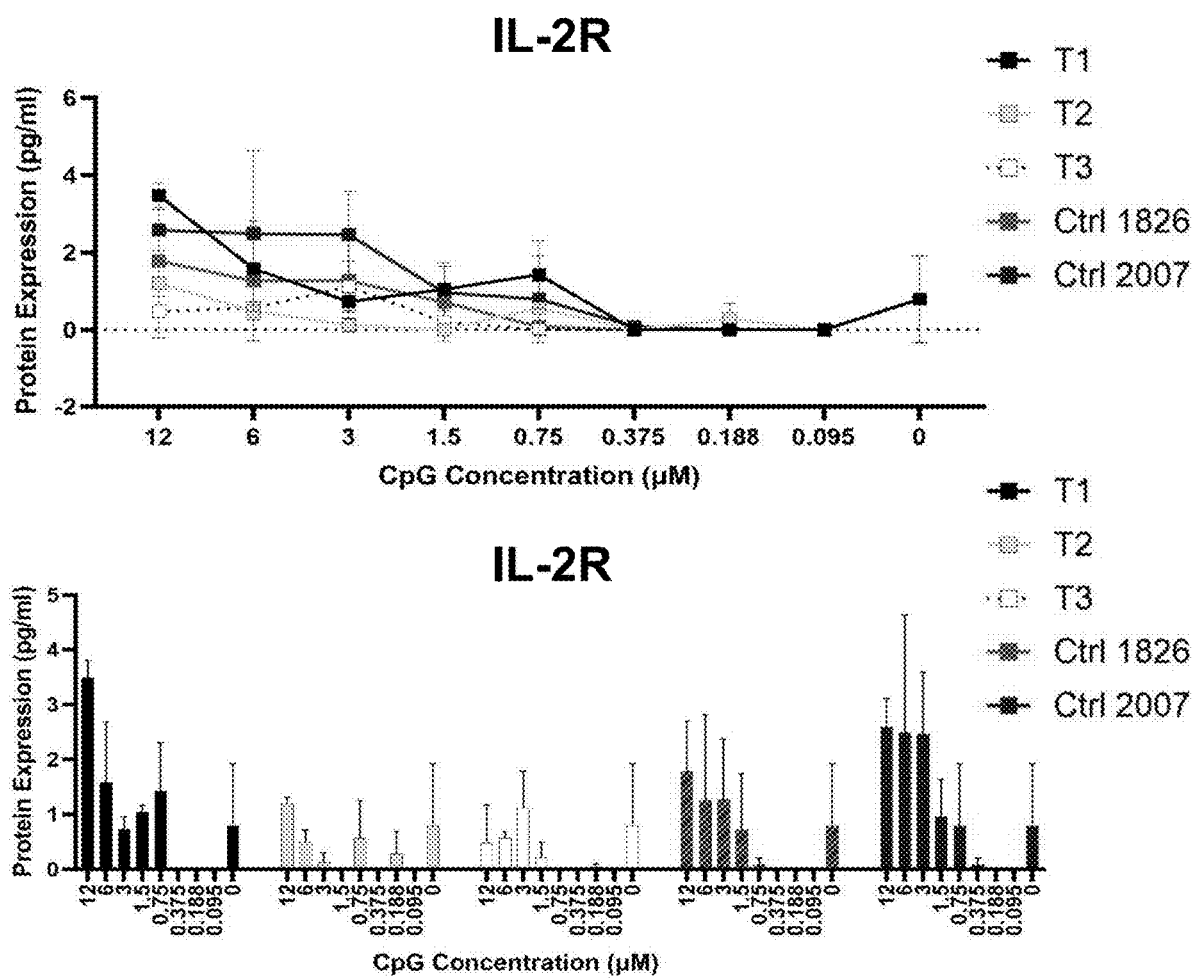
FIG. 14N depicts the protein target IL-2 receptor (IL-2R).
Figure 14O:
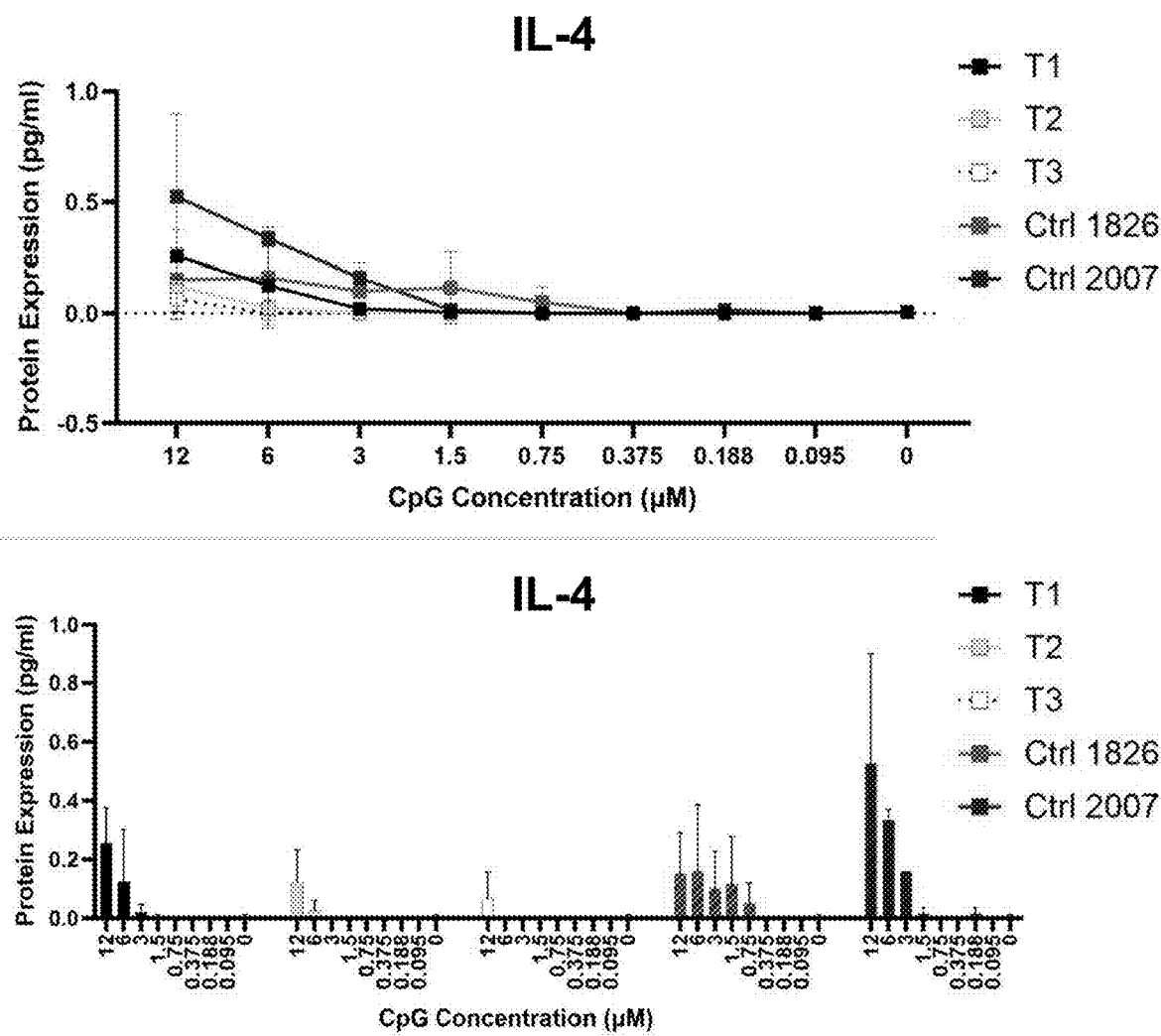
FIG. 14O depicts the protein target IL-4.
Figure 14P:
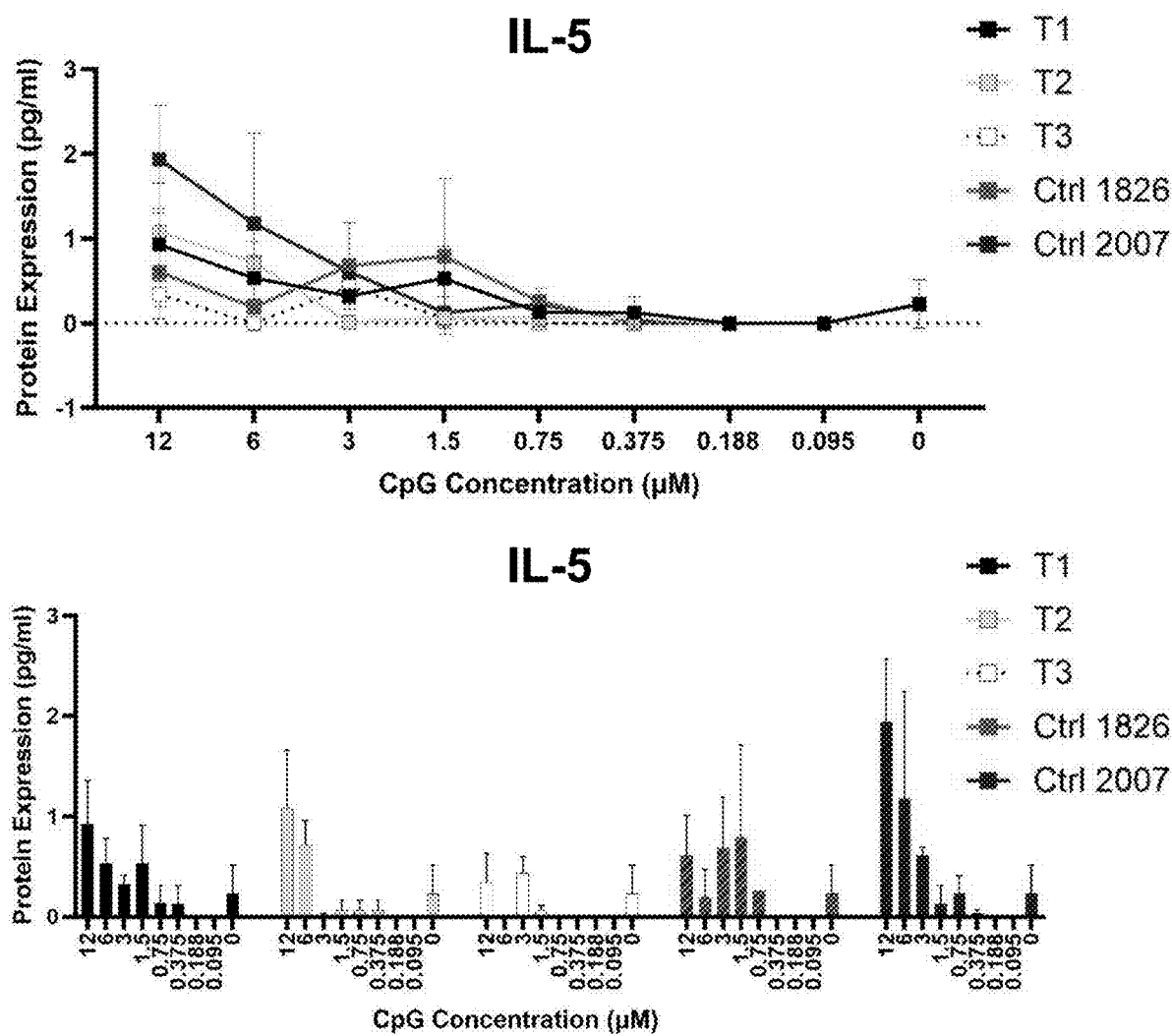
FIG. 14P depicts the protein target IL-5.
Figure 14Q:
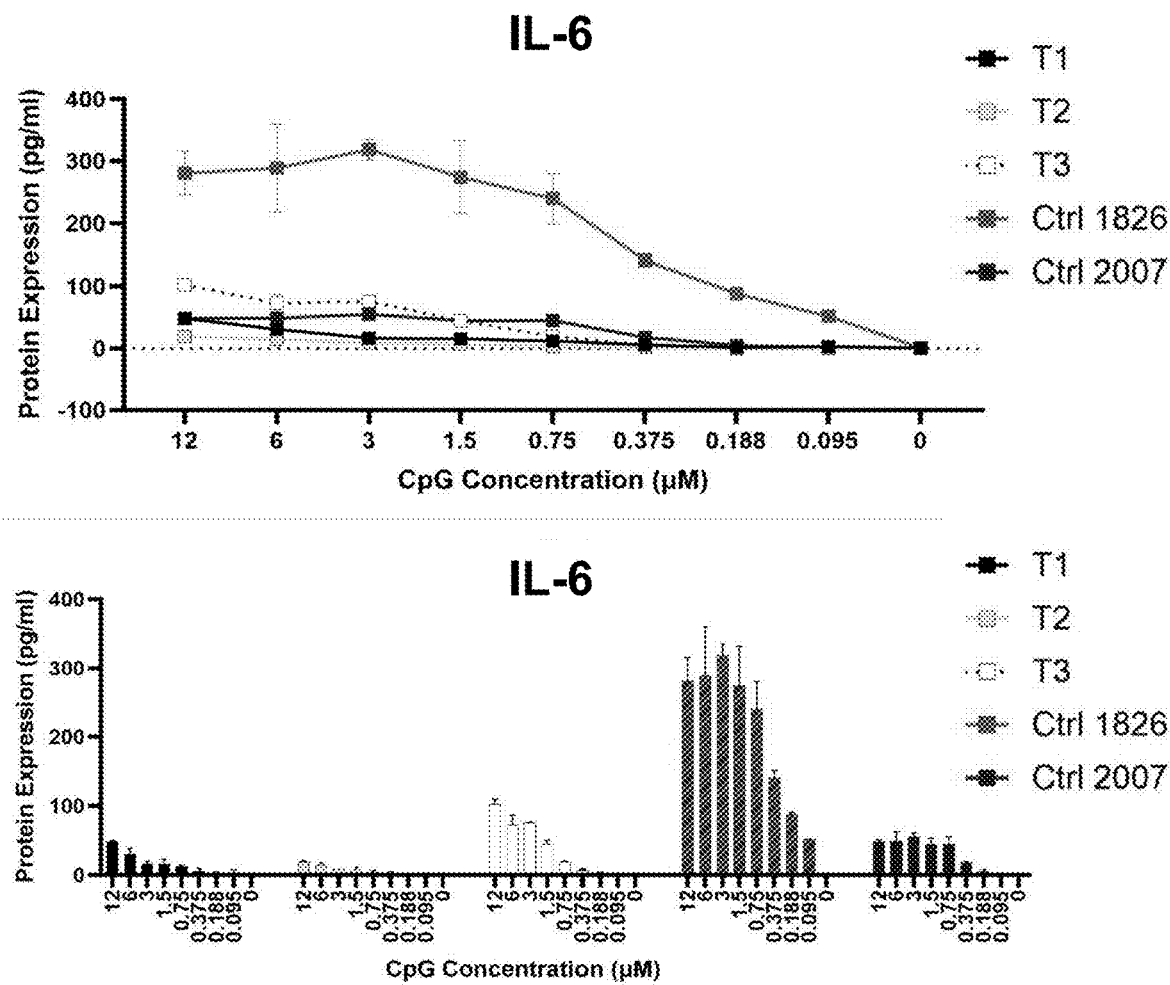
FIG. 14Q depicts the protein target IL-6.
Figure 14R:
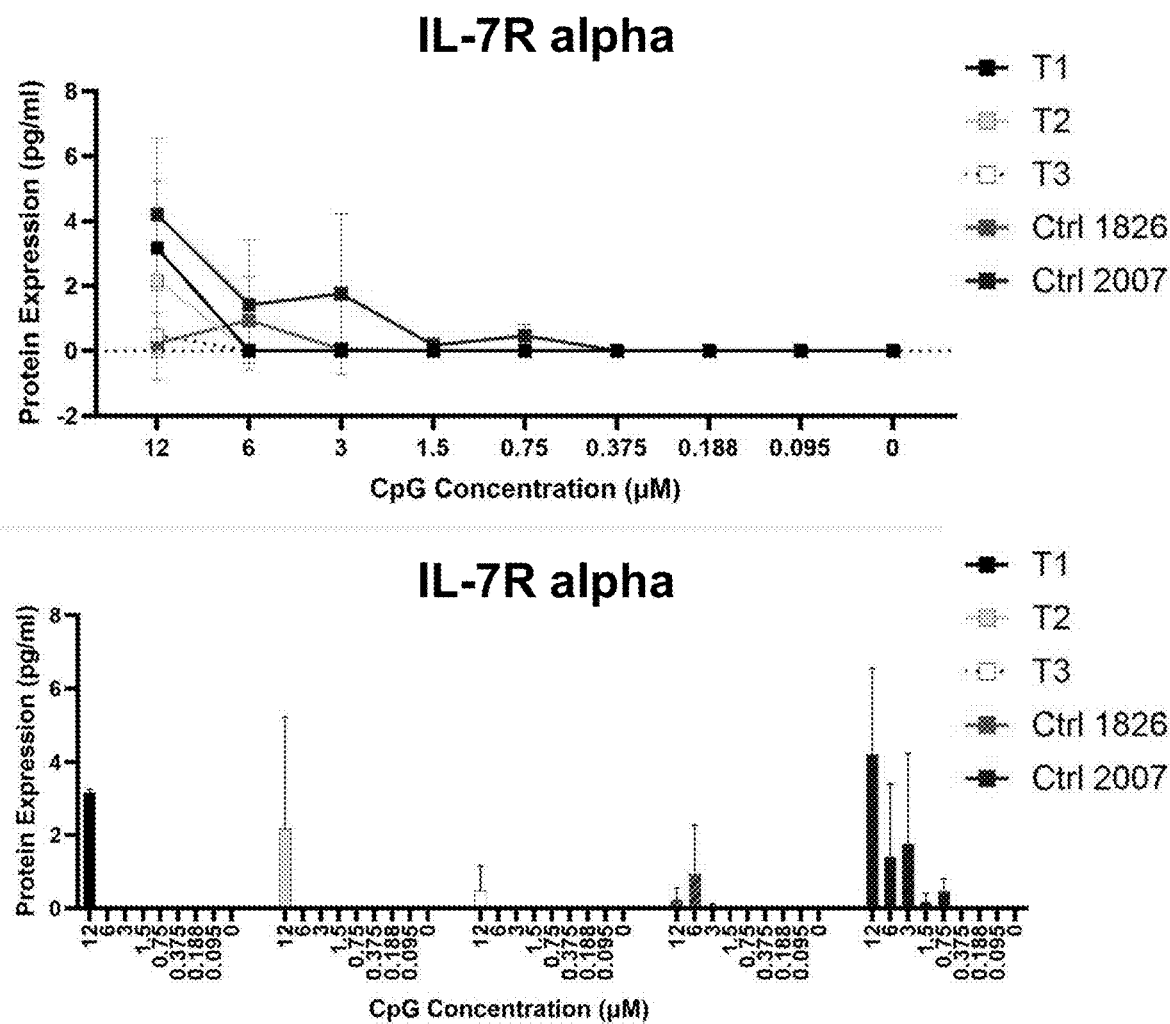
FIG. 14R depicts the protein target IL-7R alpha.
Figure 14S:
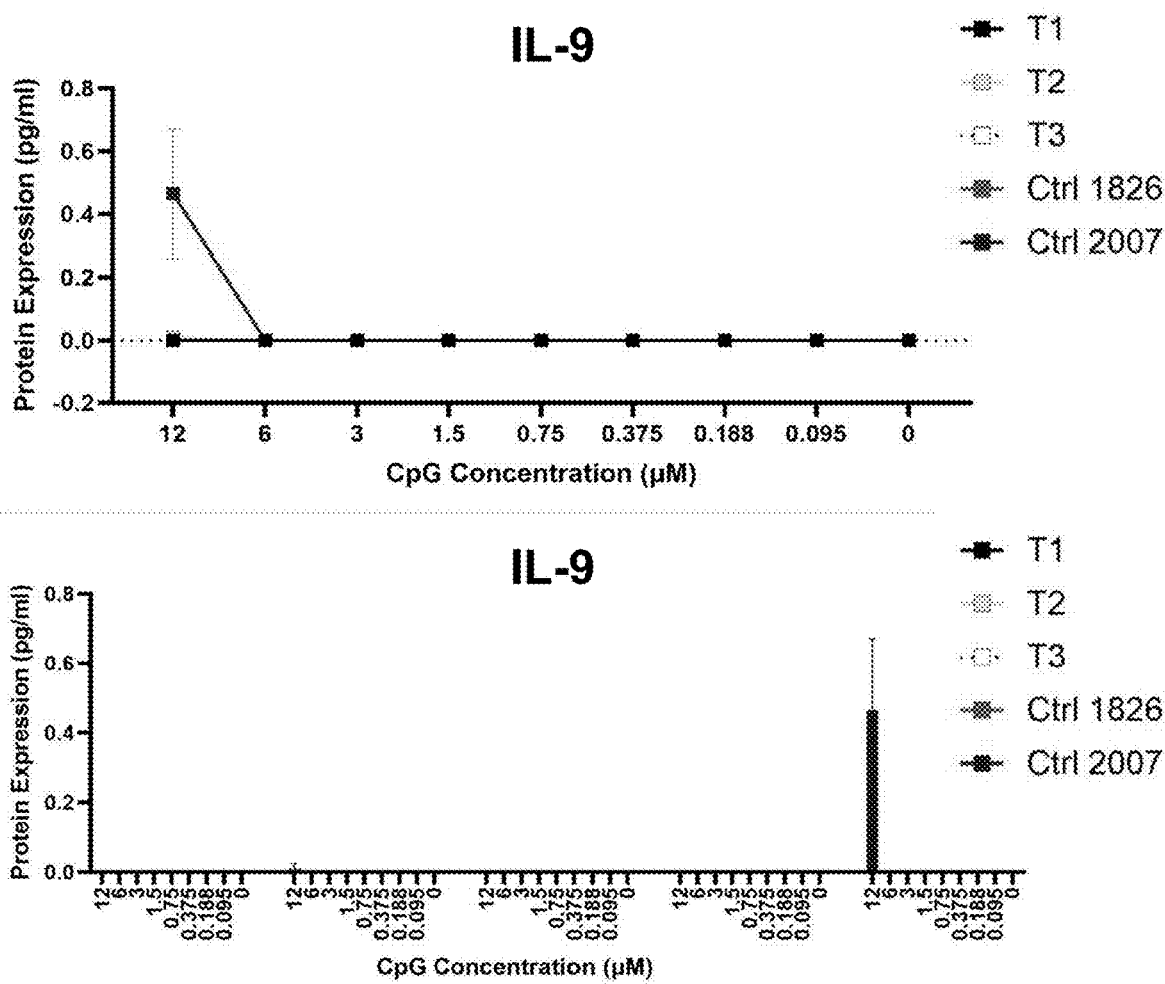
FIG. 14S depicts the protein target IL-9.
Figure 14T:
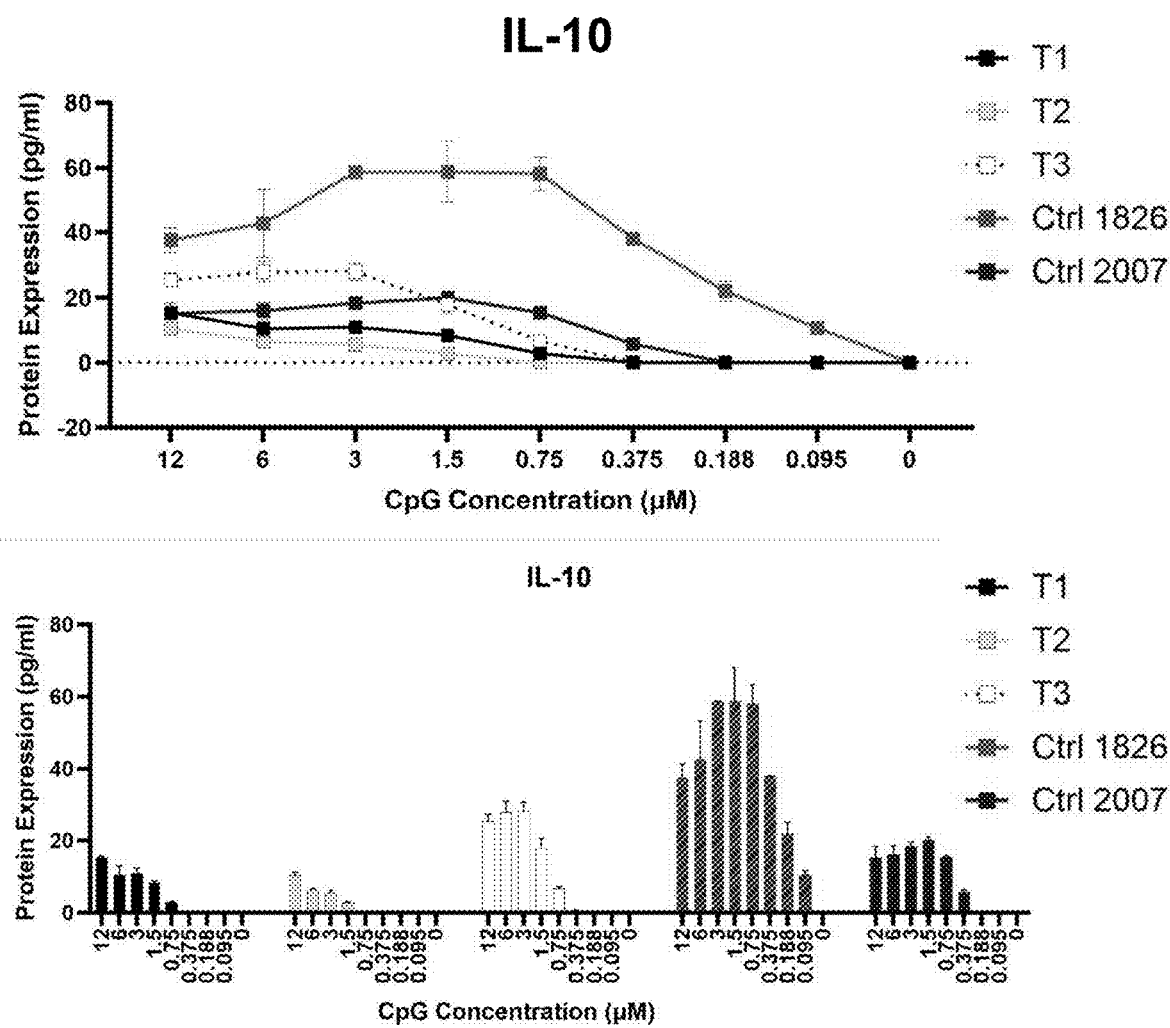
FIG. 14T depicts the protein target IL-10.
Figure 14U:
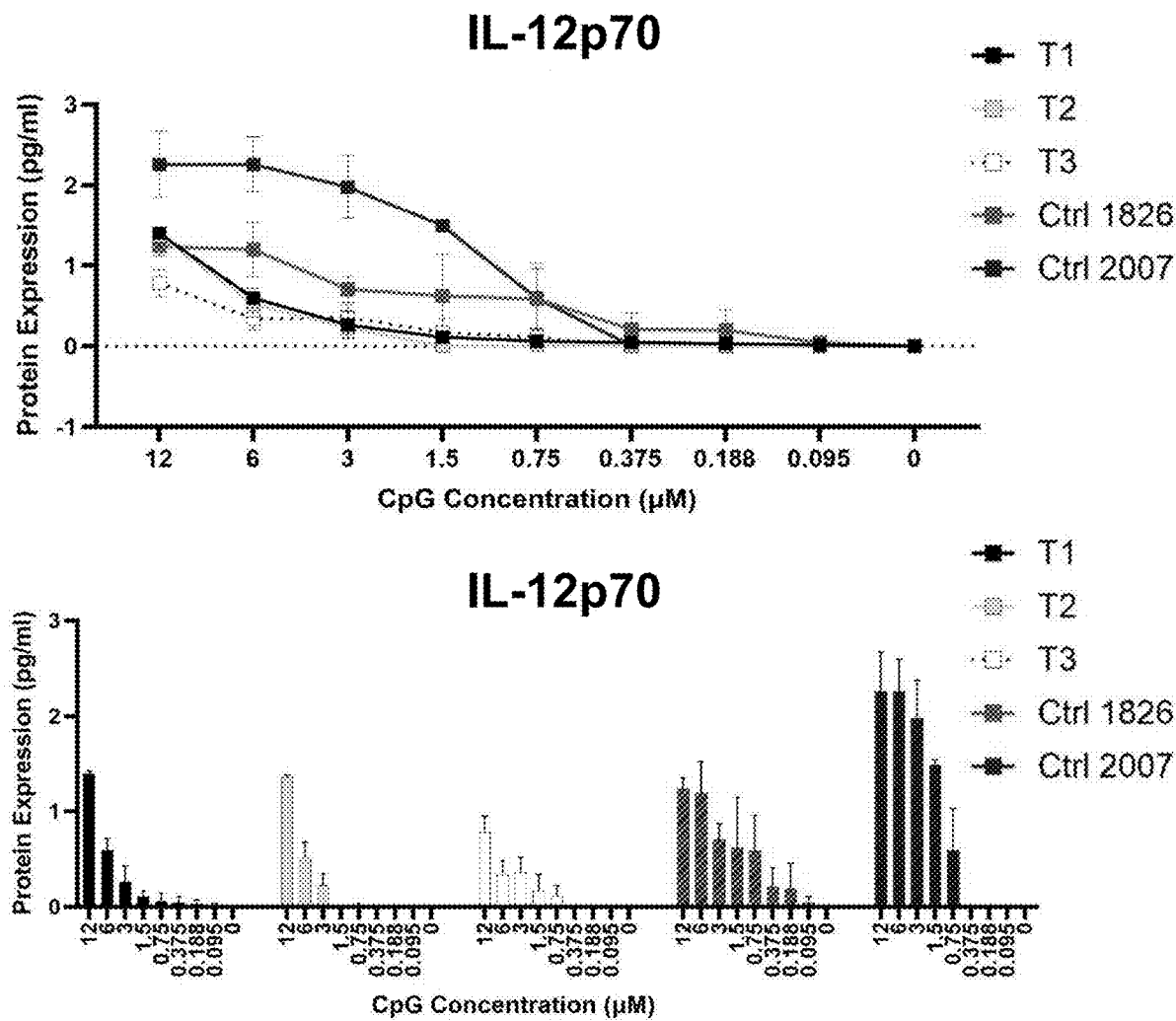
FIG. 14U depicts the protein target IL-12p70.
Figure 14V:
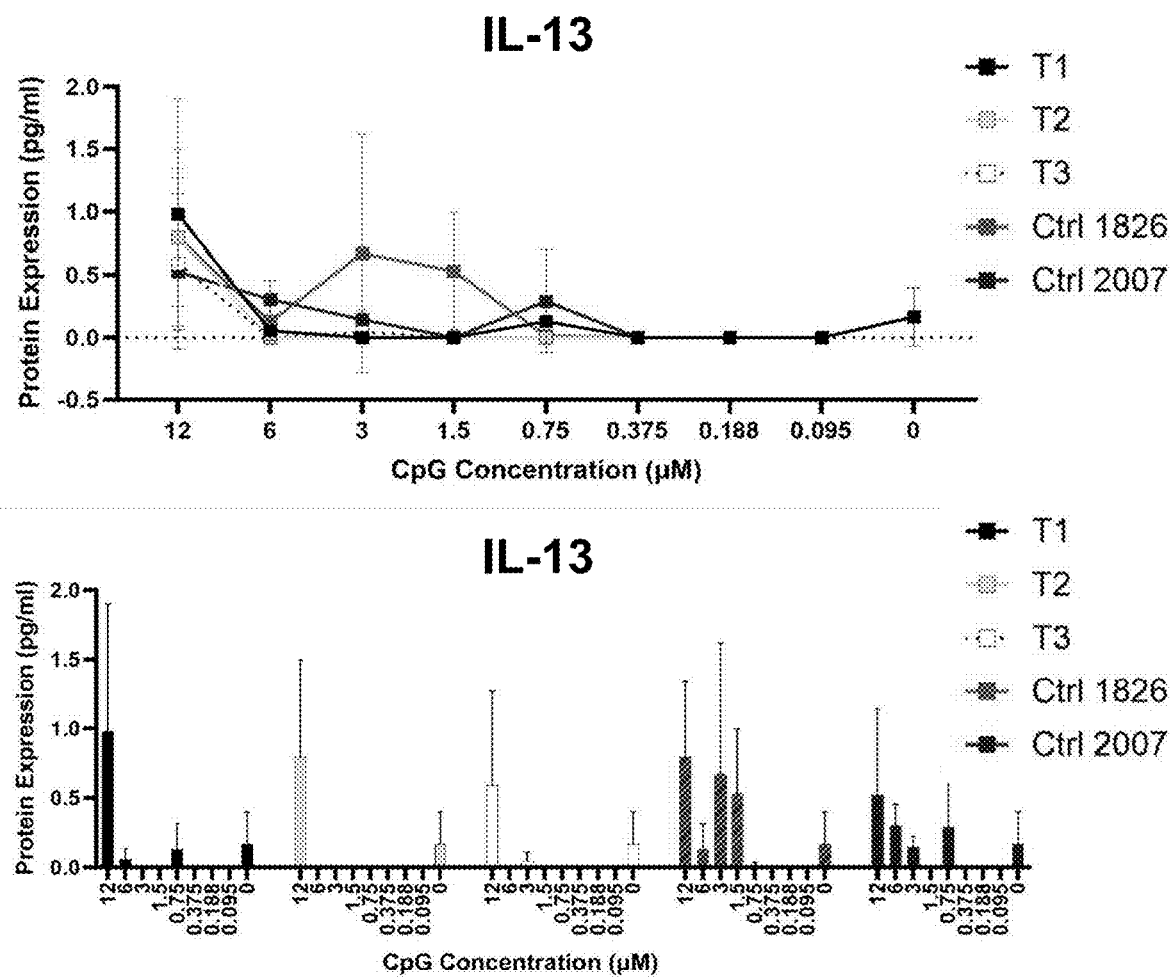
FIG. 14V depicts the protein target IL-13.
Figure 14W:
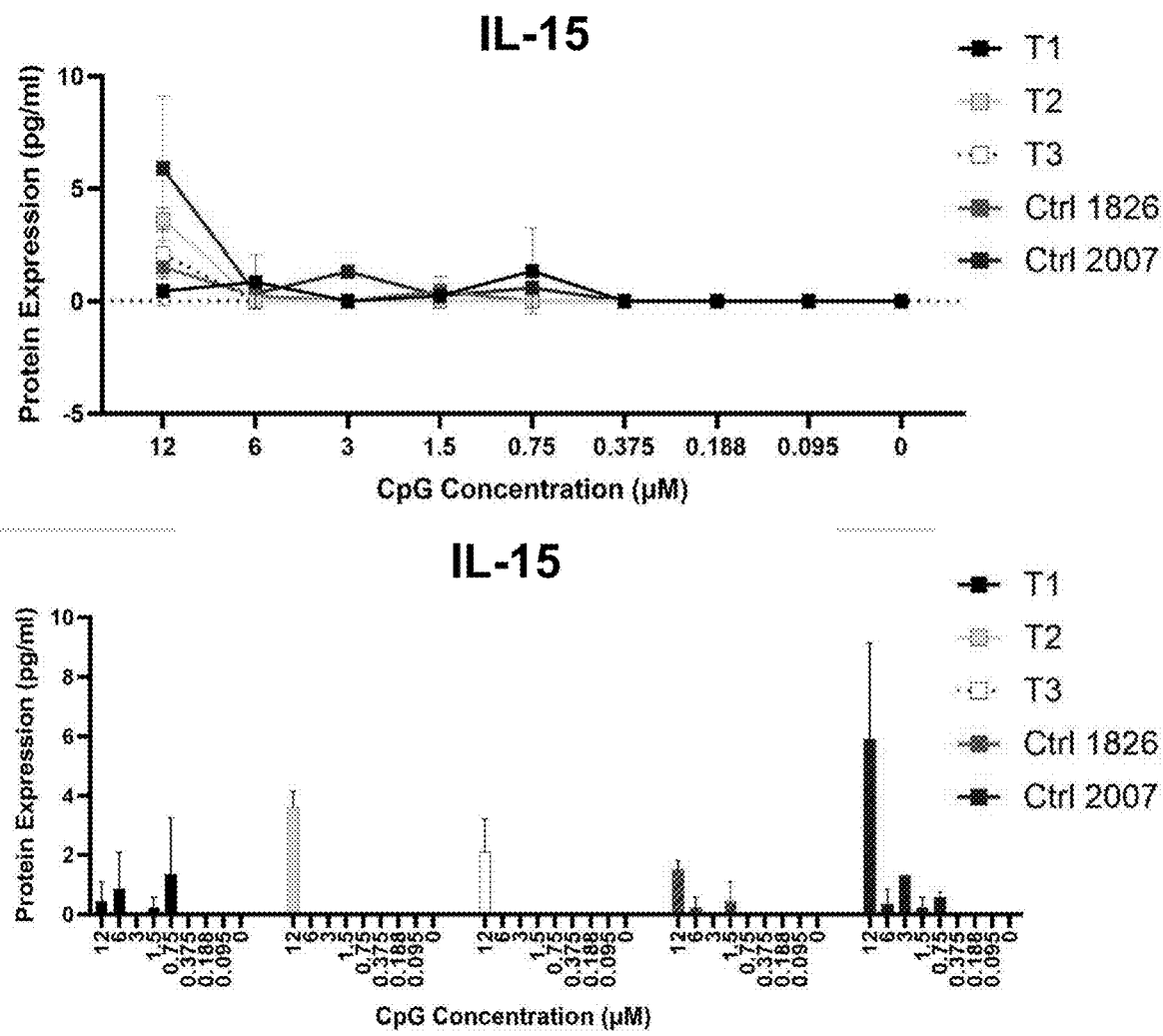
FIG. 14W depicts the protein target depicts the protein target IL-15.
Figure 14X:
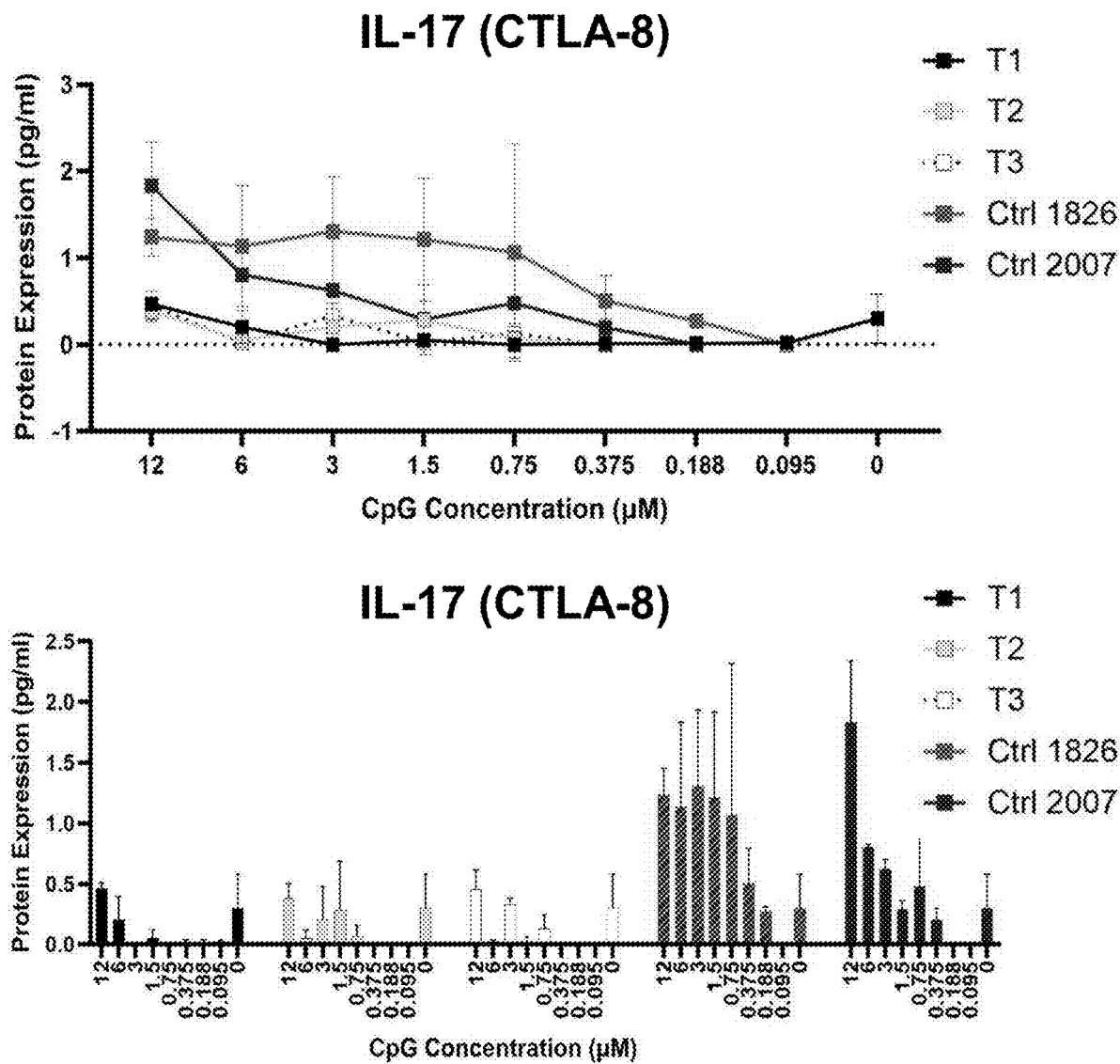
FIG. 14X depicts the protein target IL-17A also known as cytotoxic T-lymphocyte associated protein 8 (CTLA8).
Figure 14Y:
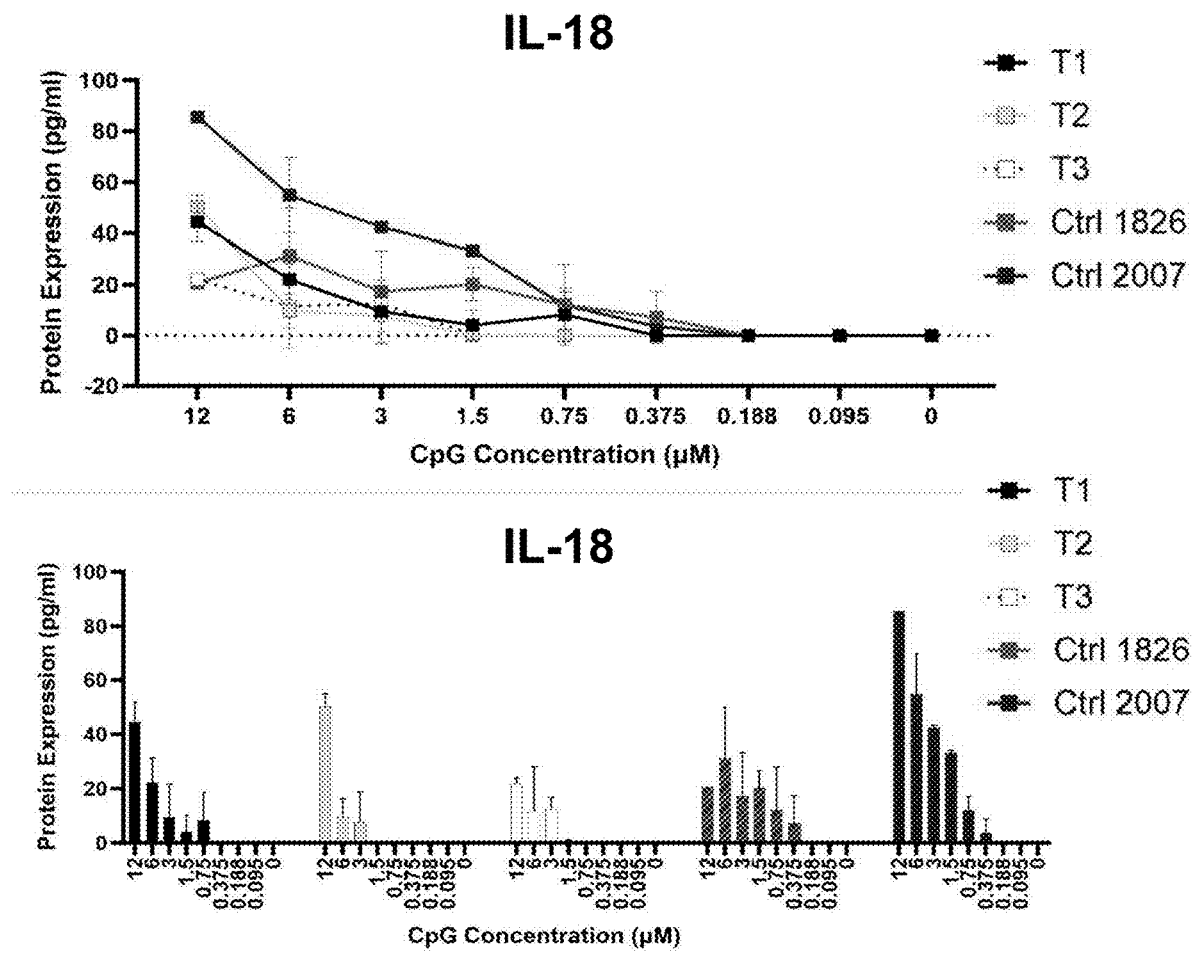
FIG. 14Y depicts the protein target IL-18.
Figure 14Z:
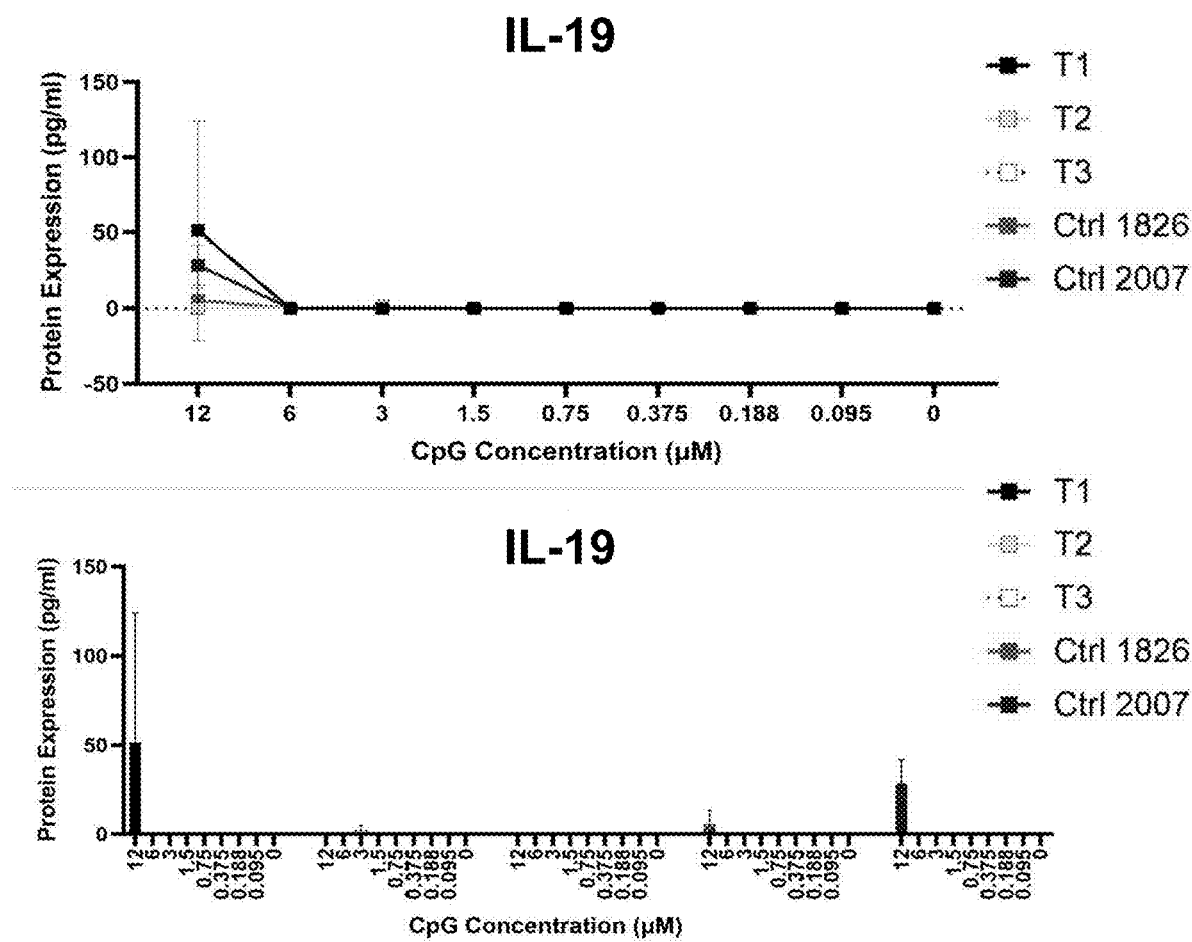
FIG. 14Z depicts the protein target IL-19.
Figure 14A:
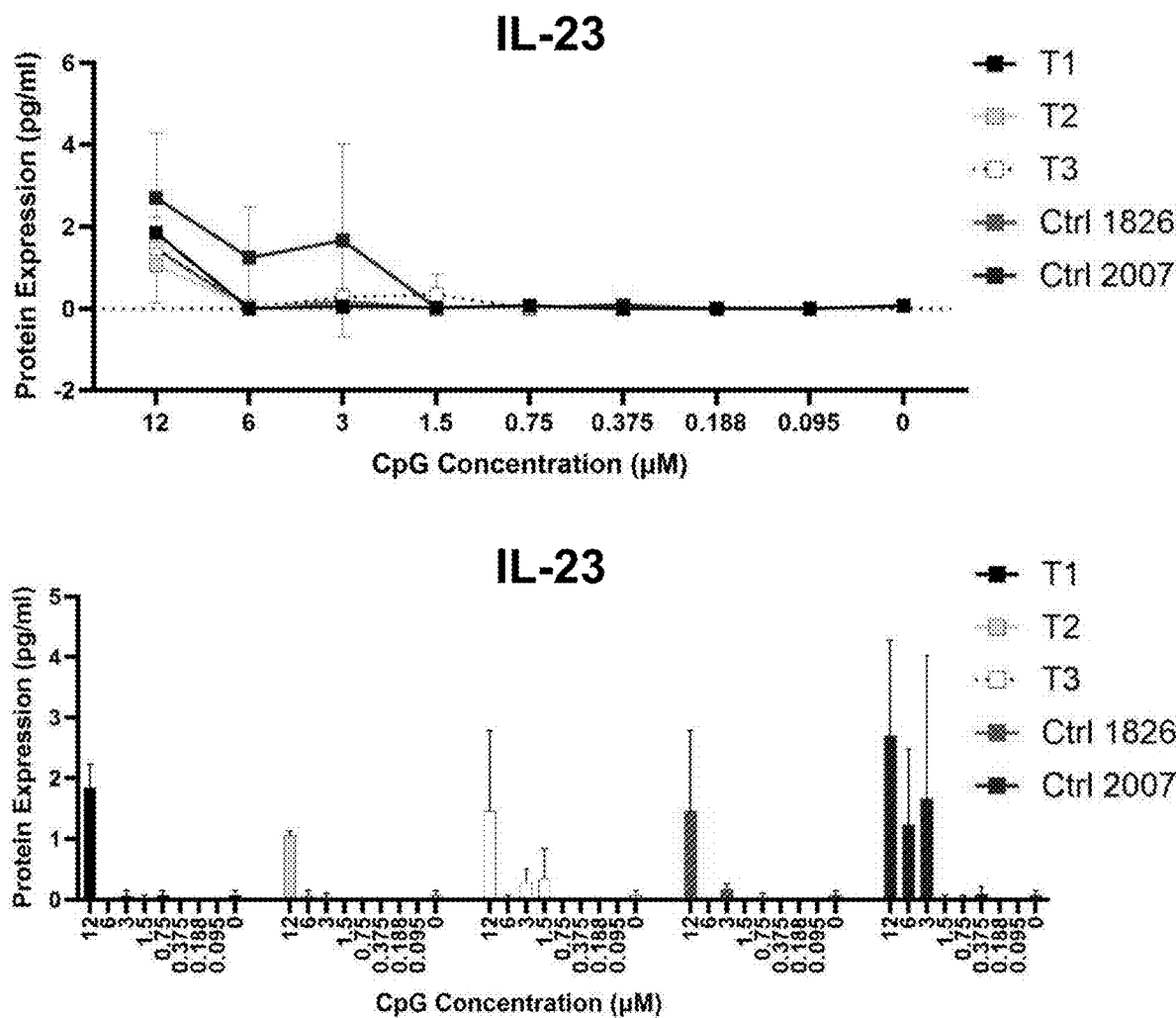
Figure 14A:
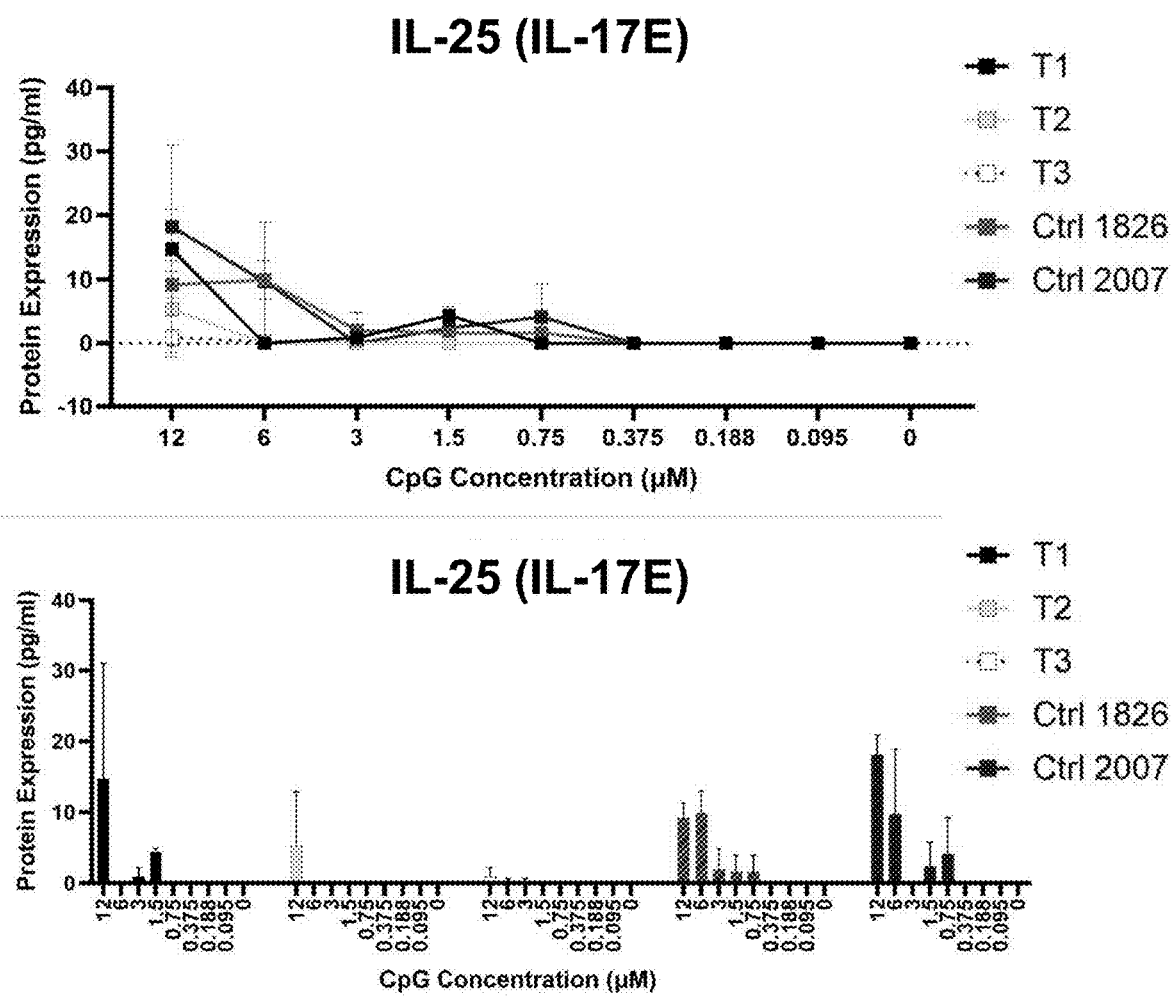
Figure 14A:
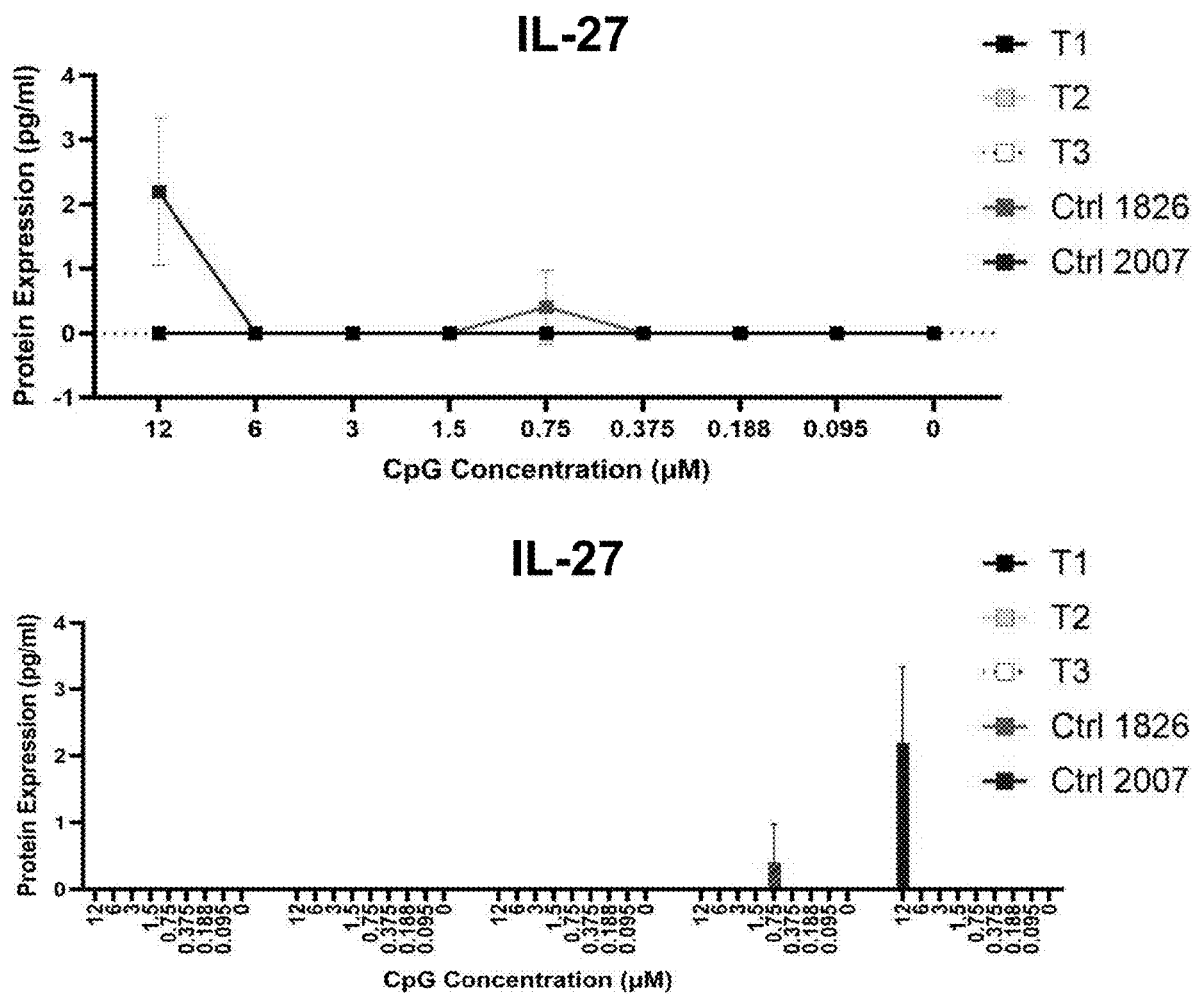
Figure 14A:
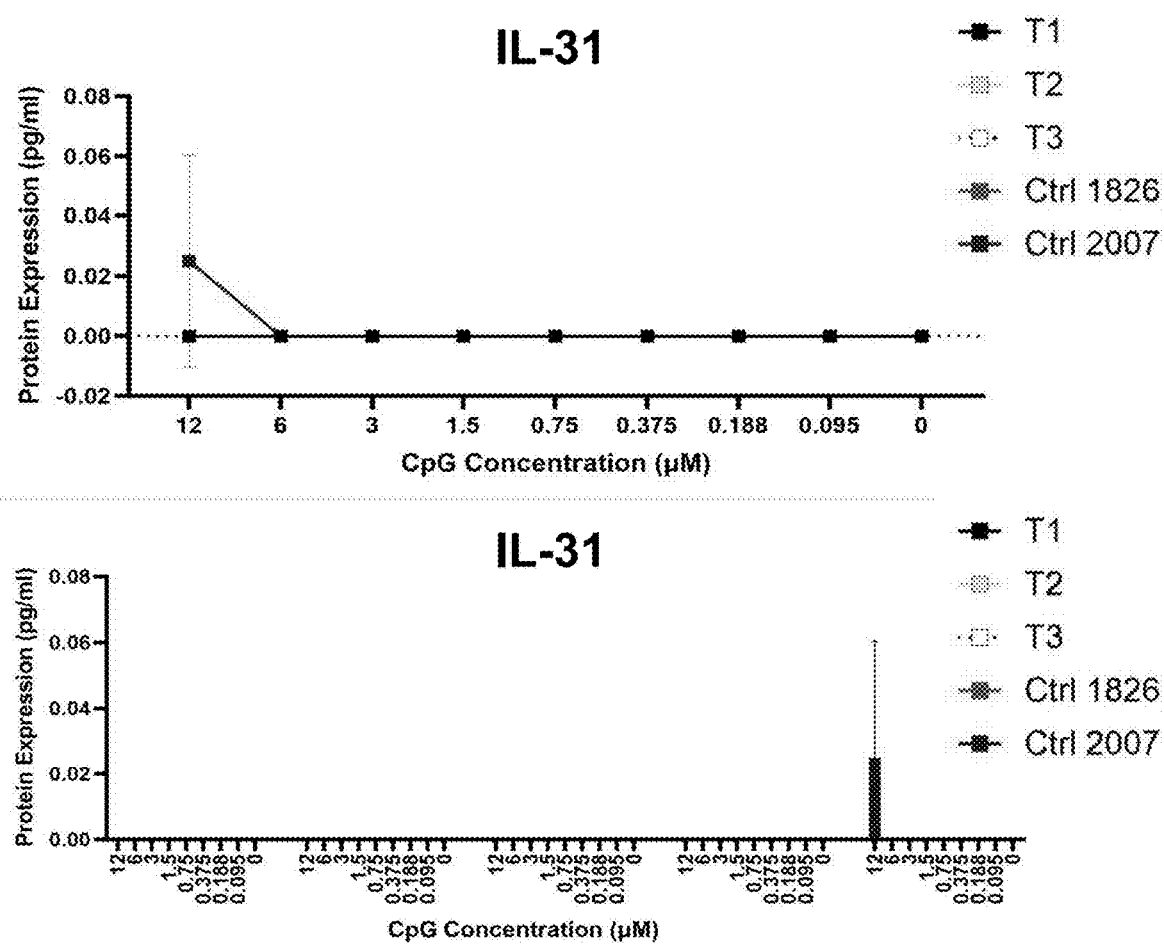
Figure 14A:
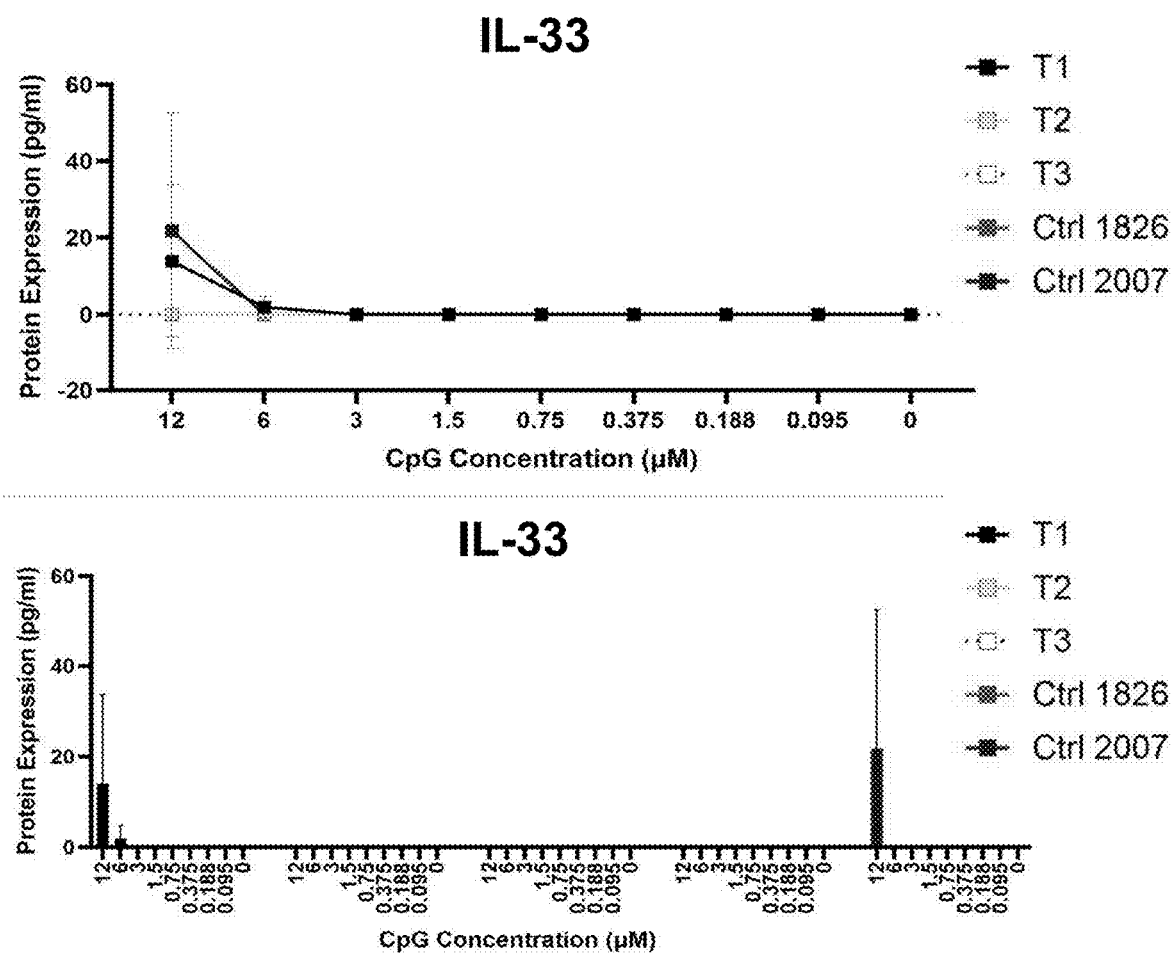
Figure 14A:
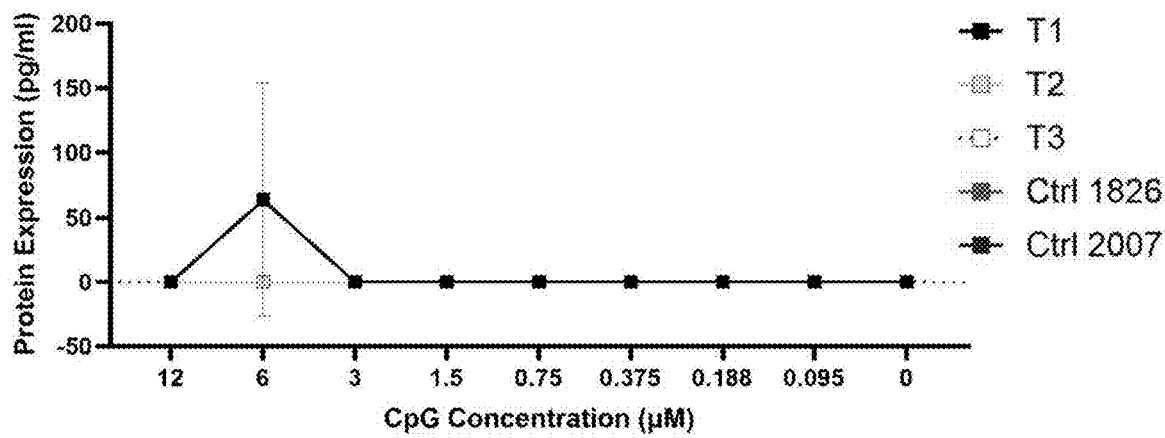
Figure 14A:
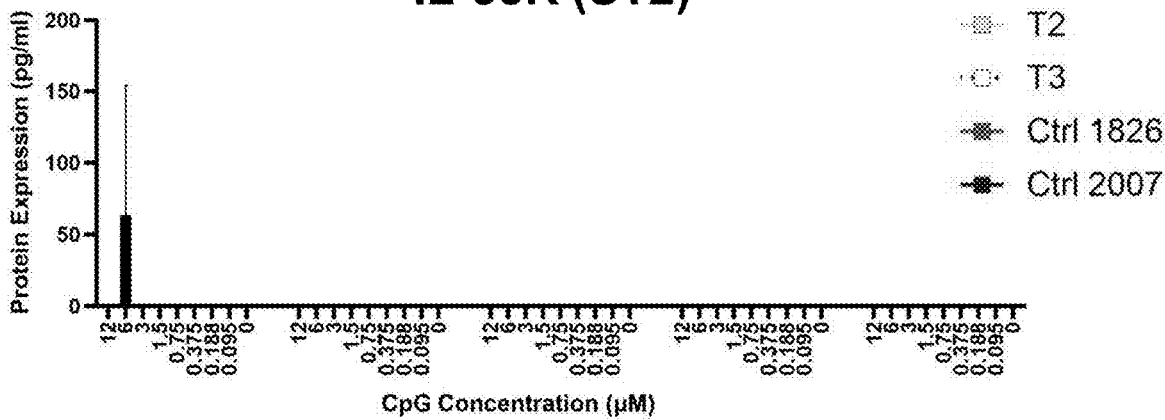
Figure 14A:
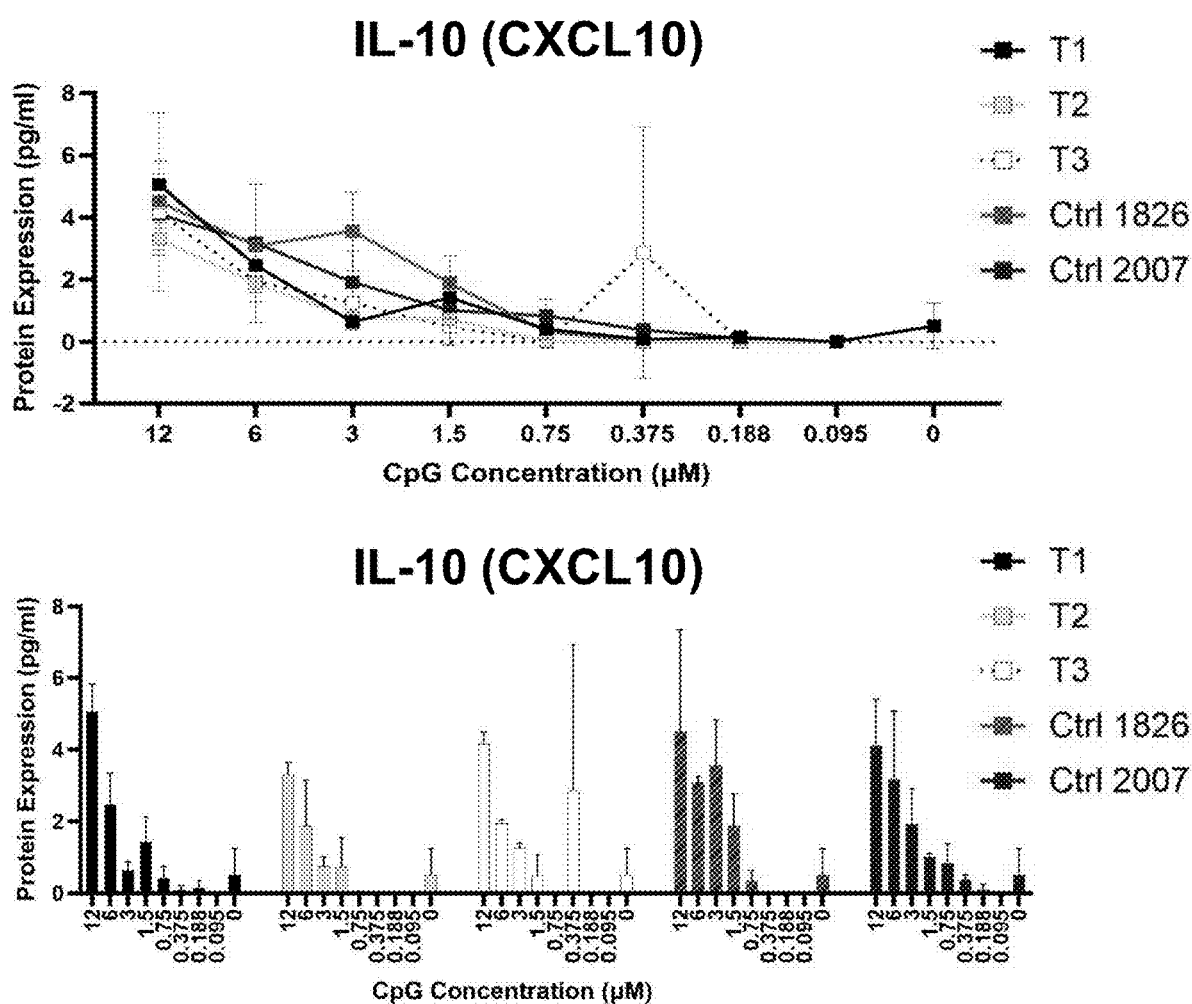
Figure 14A:
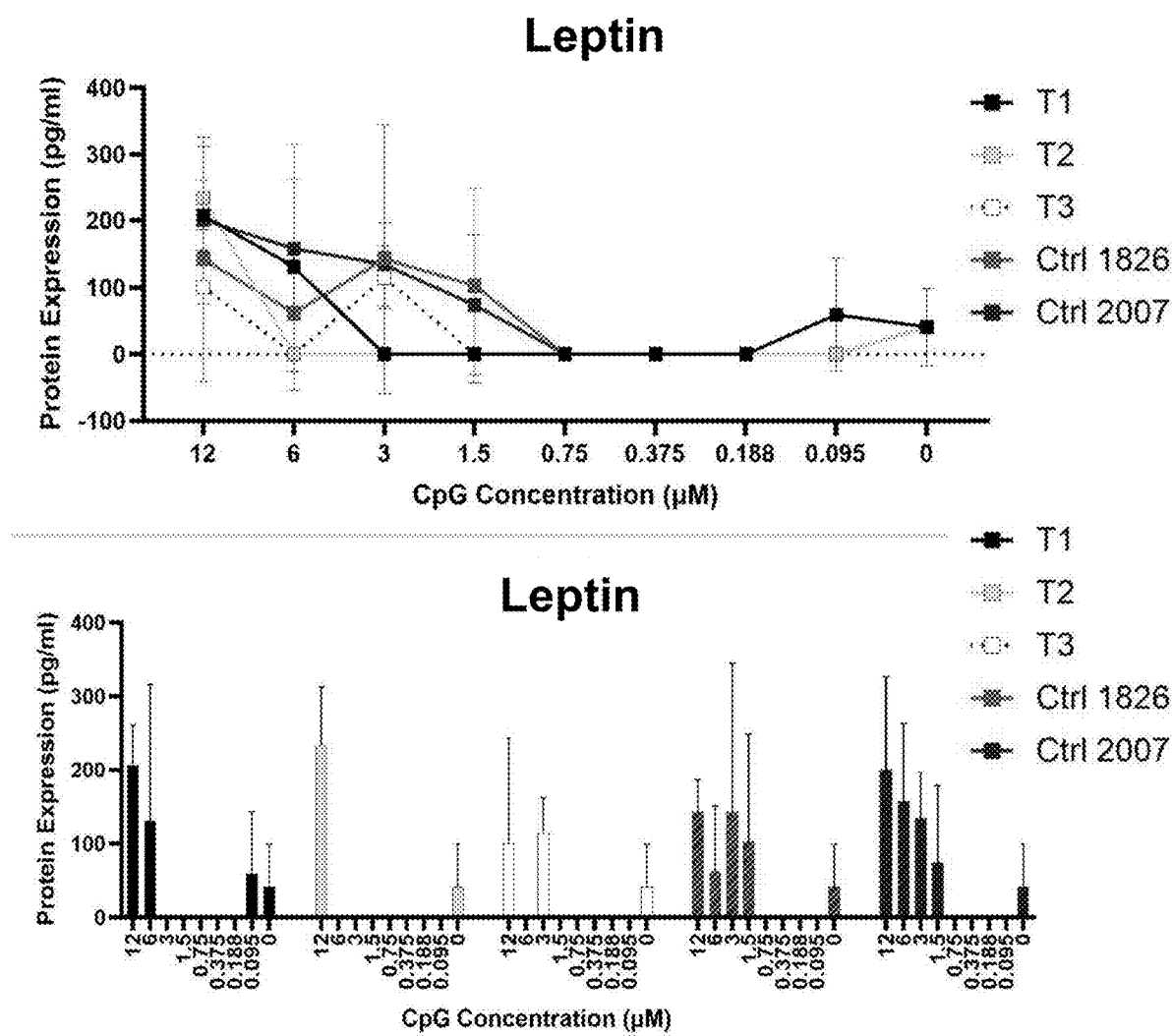
Figure 14A:
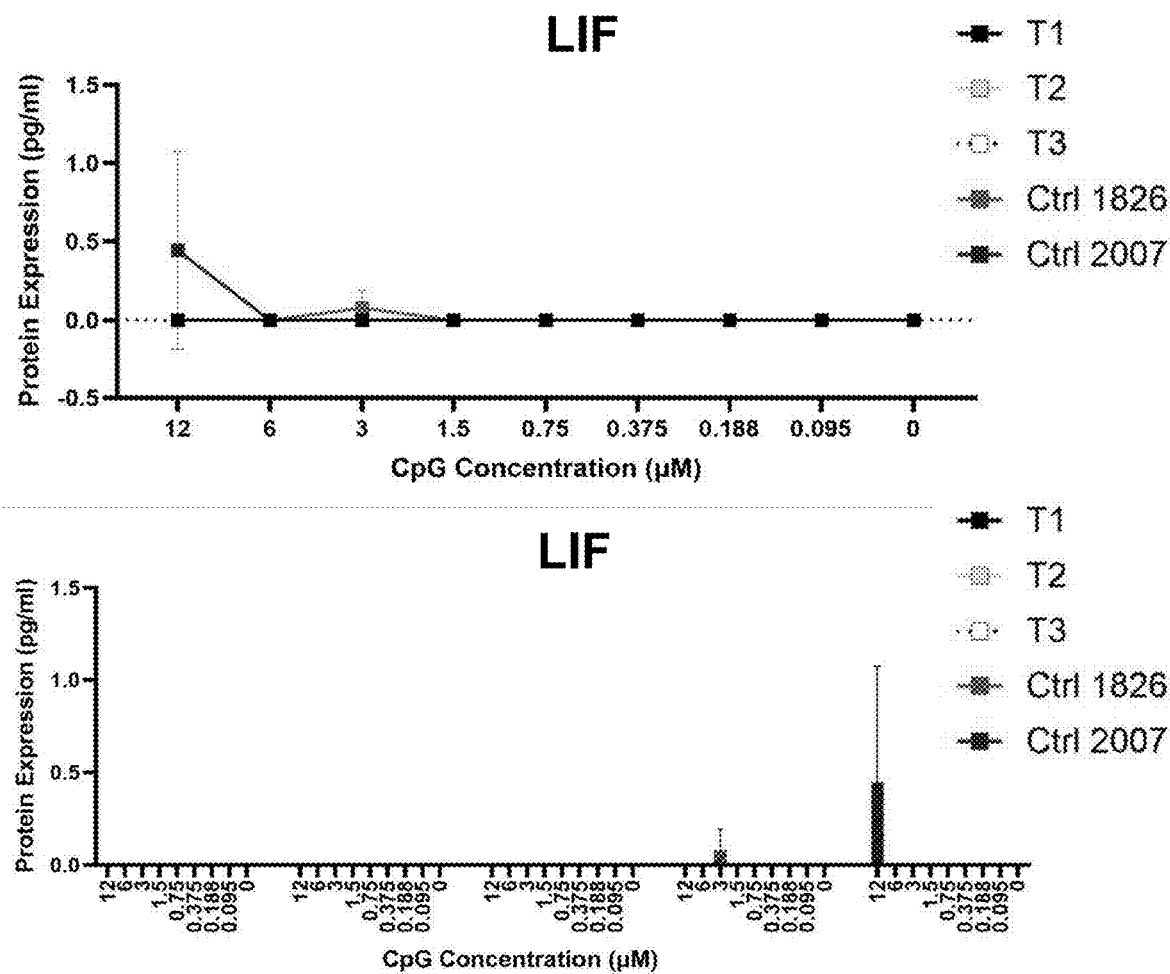
Figure 14A:
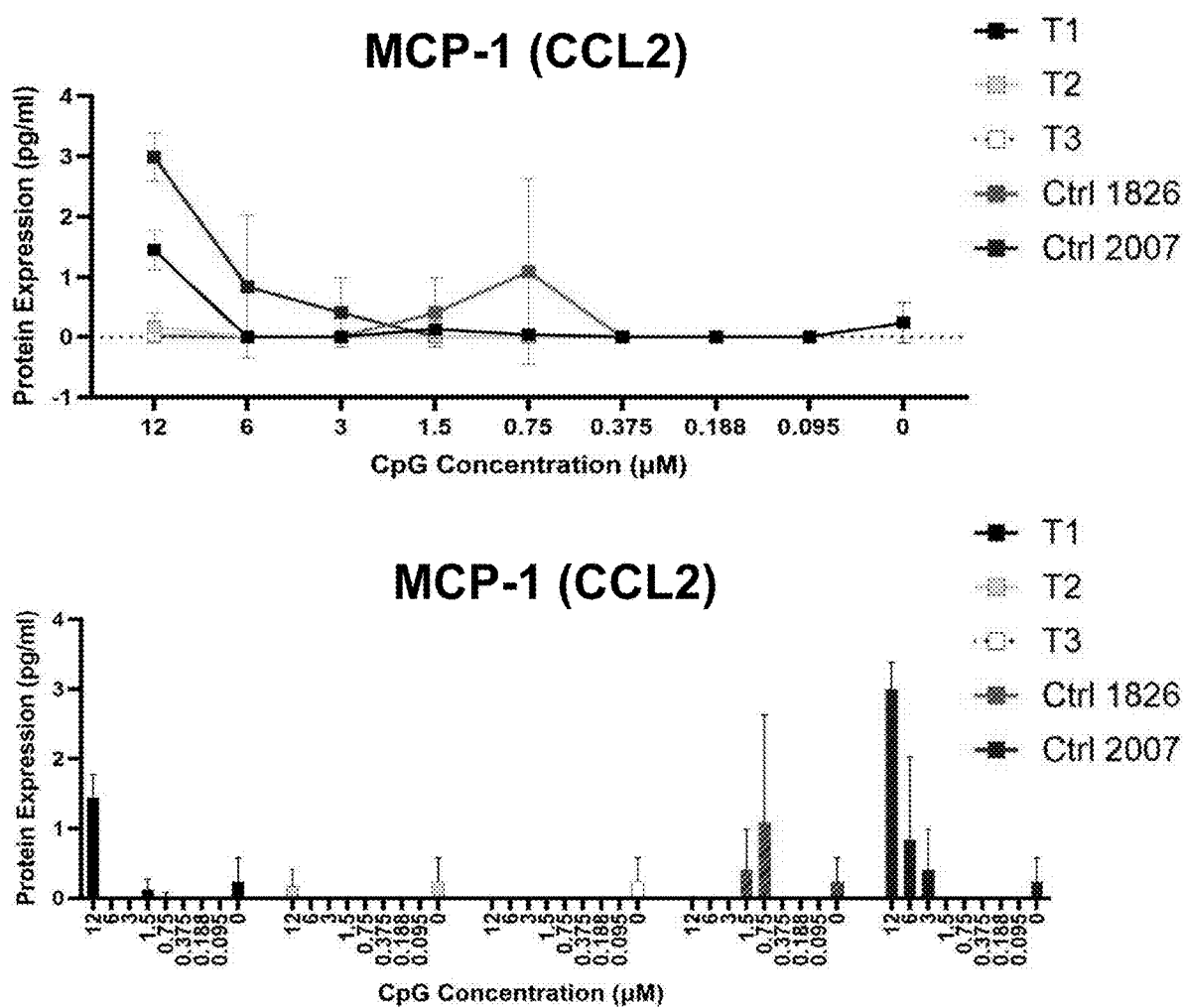
Figure 14A:
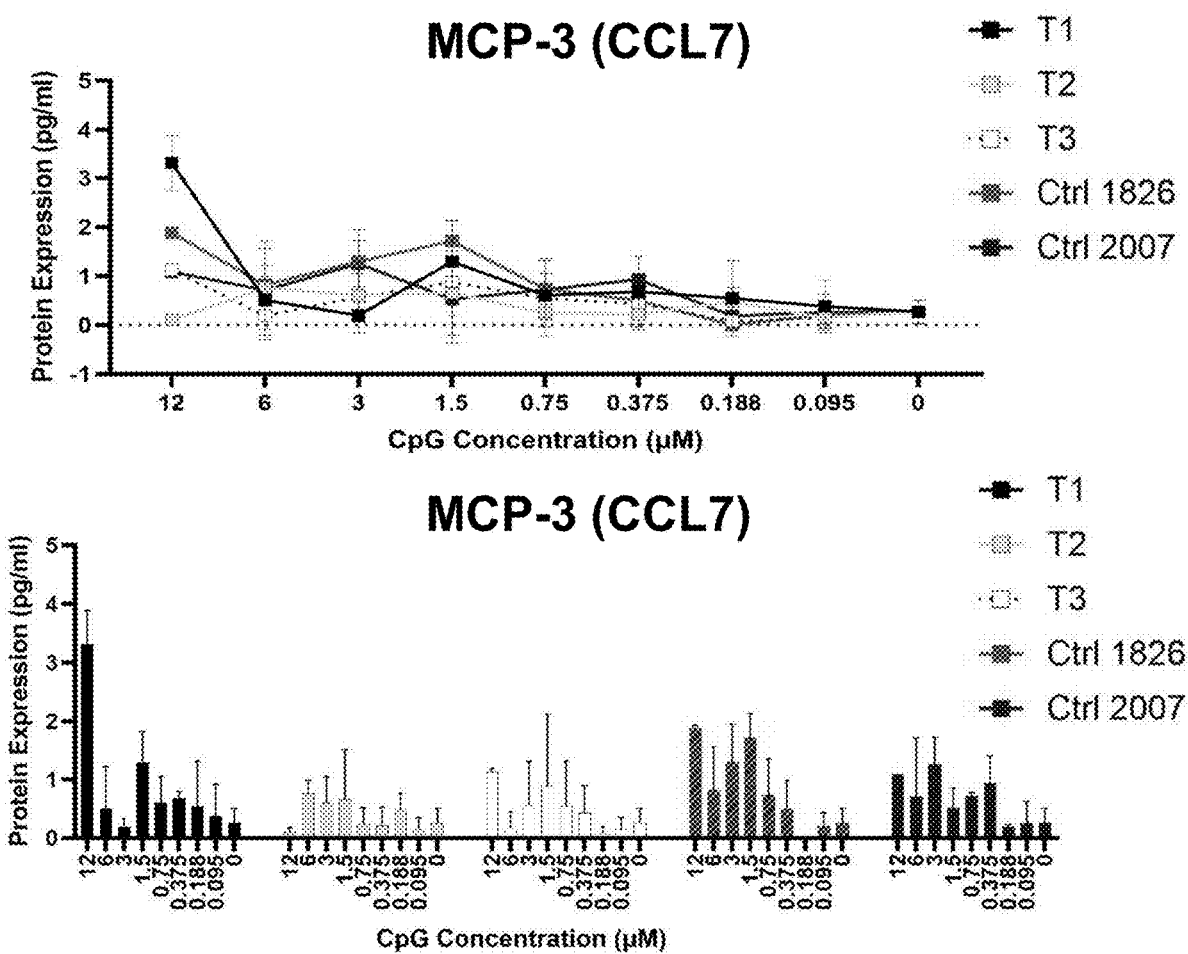
Figure 14A:
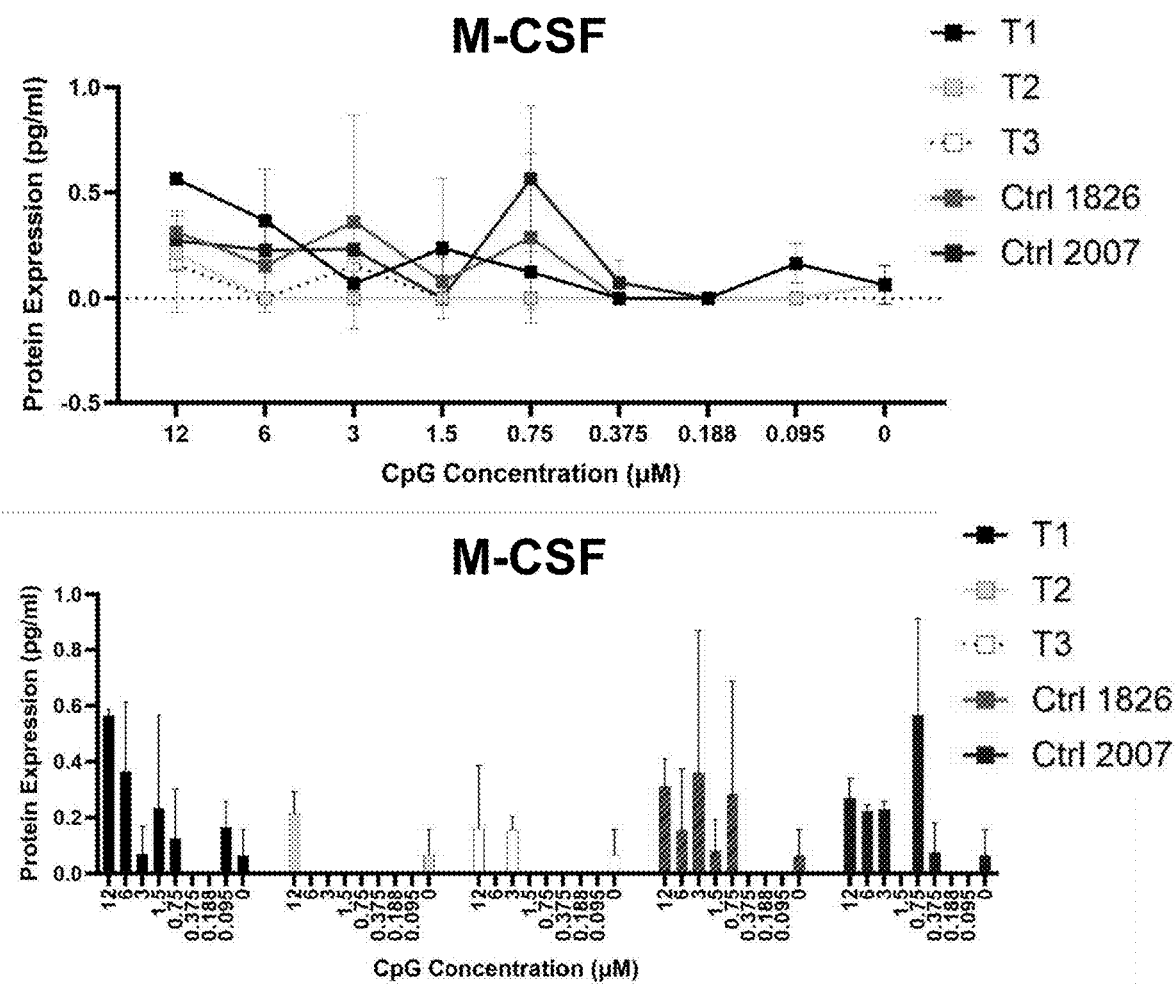
Figure 14A:
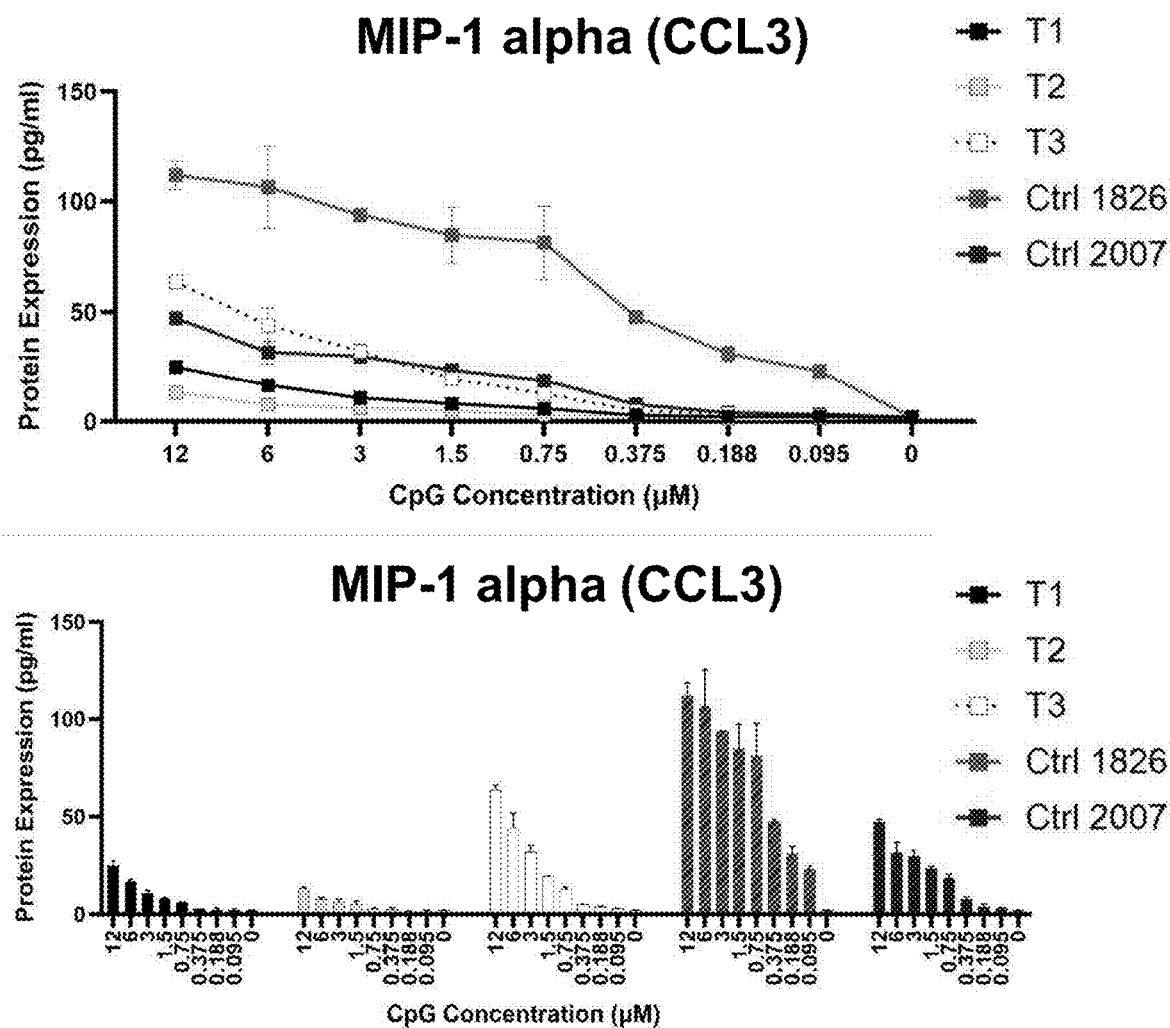
Figure 14A:
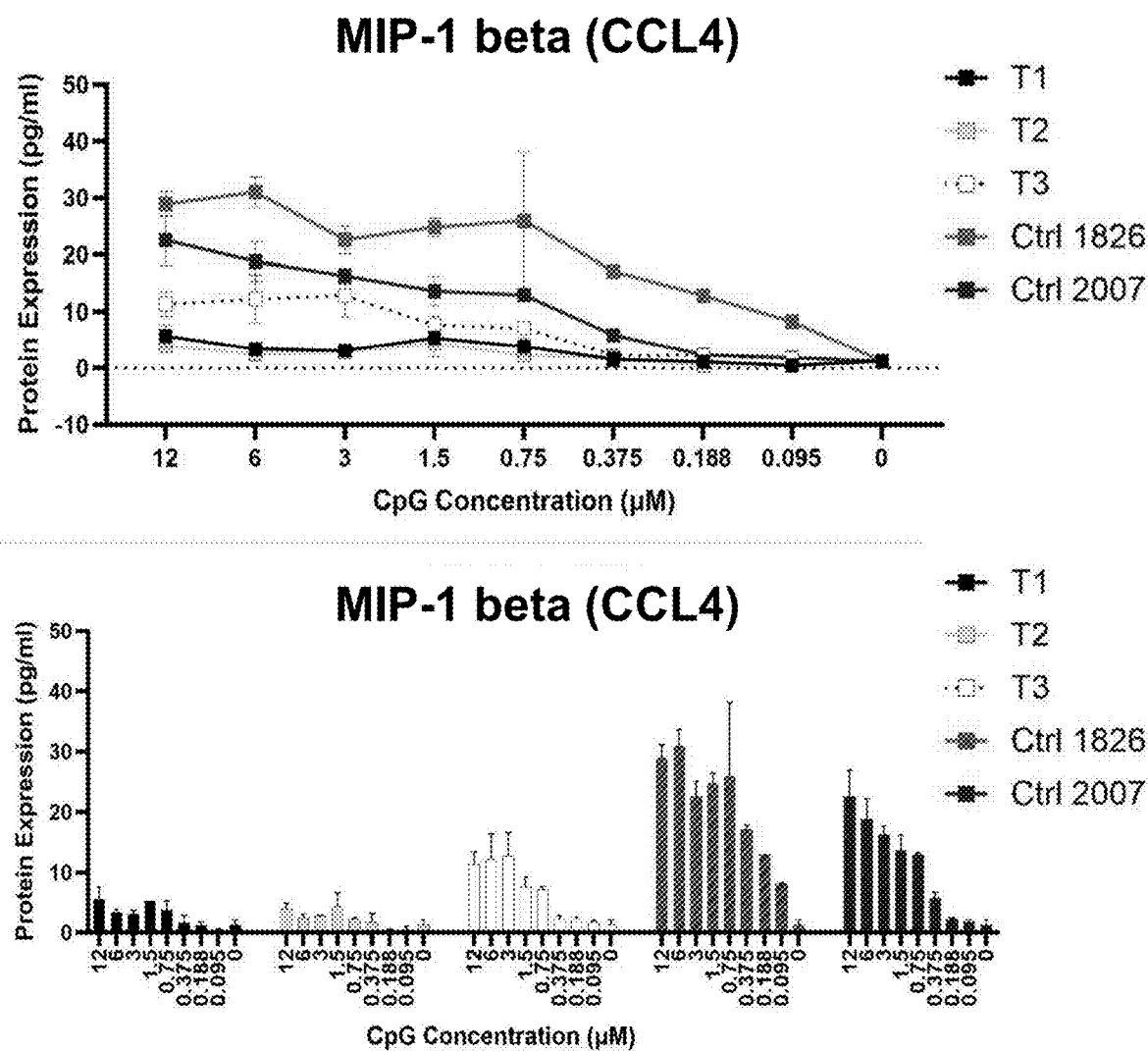
Figure 14A:
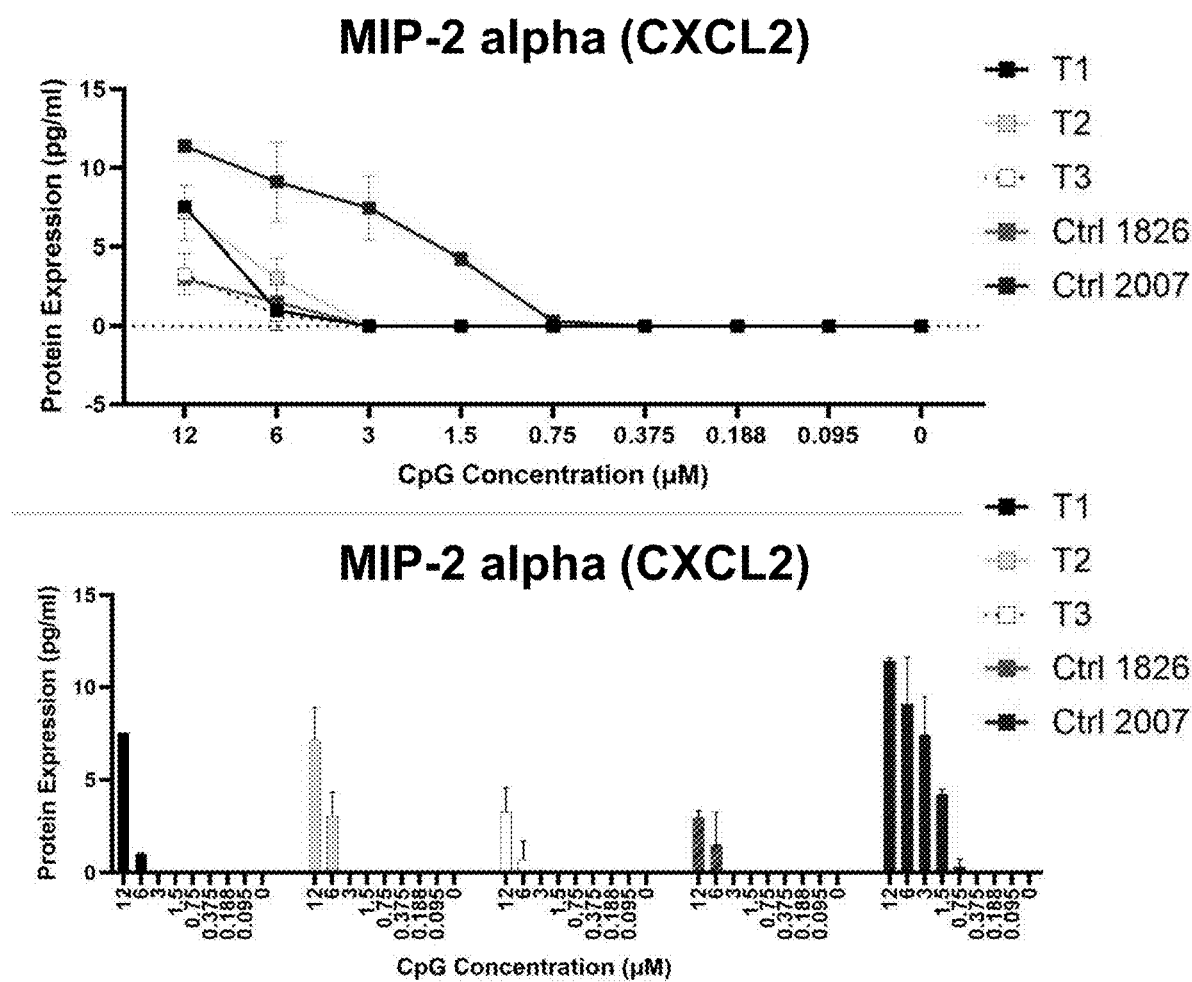
Figure 14A:
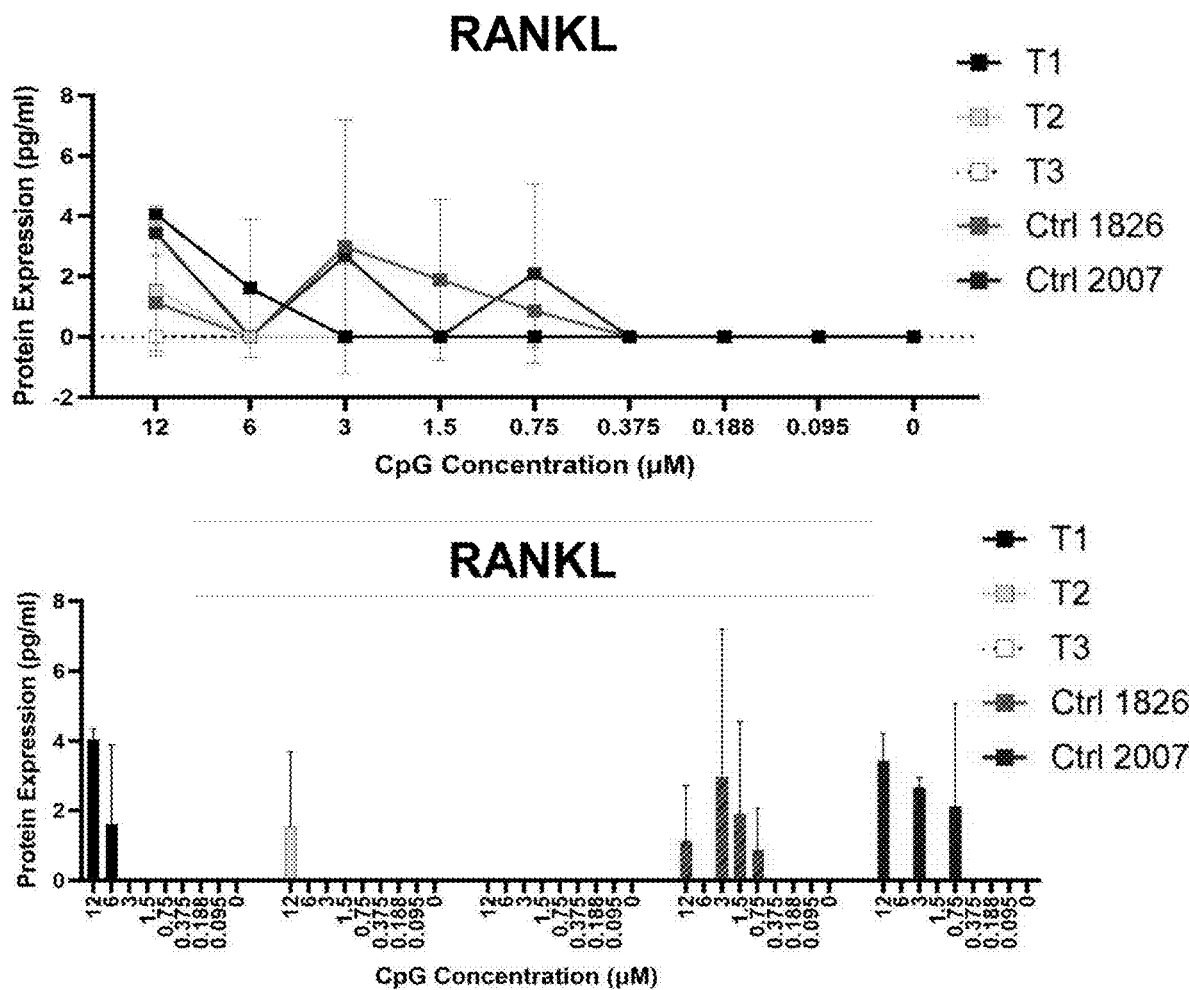
Figure 14A:
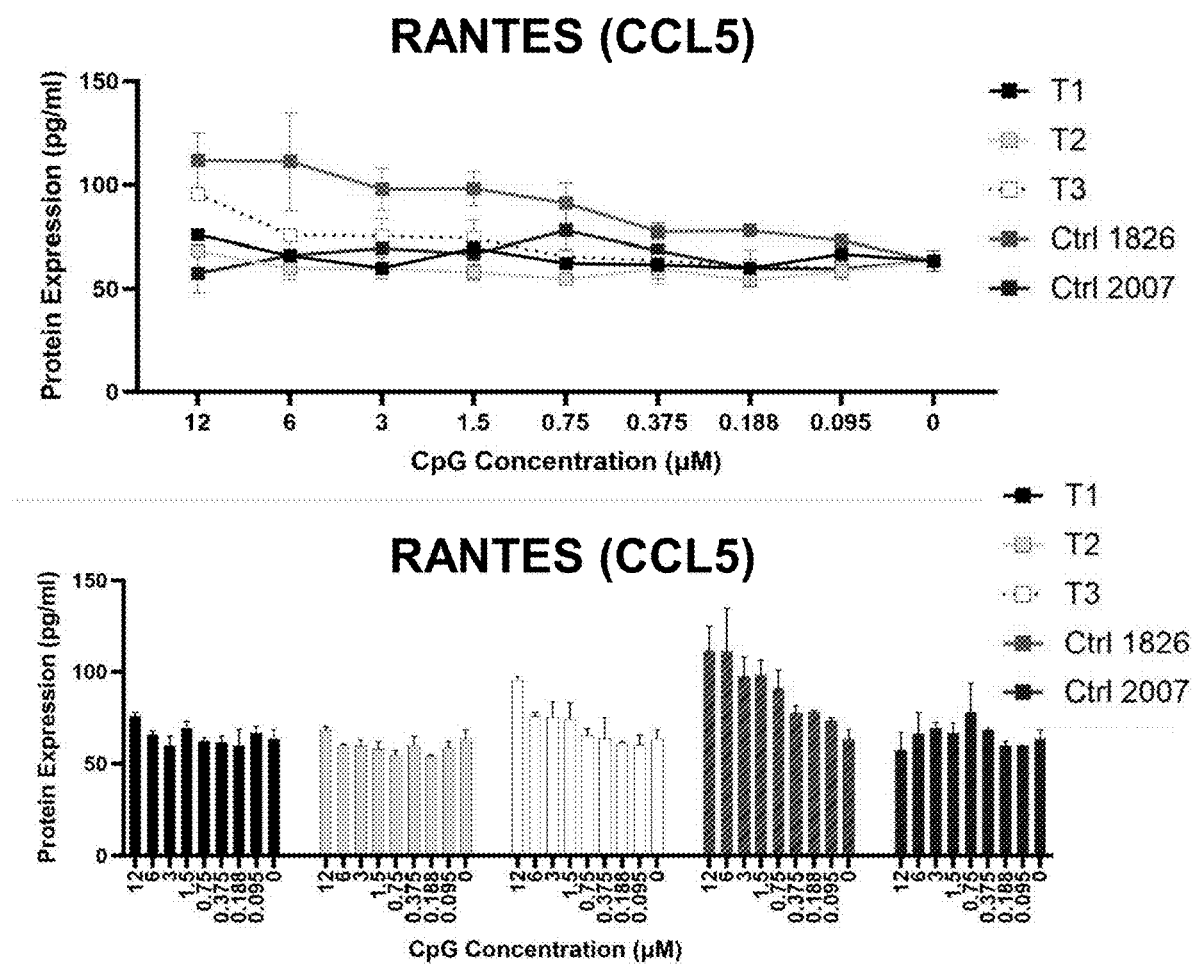
Figure 14A:
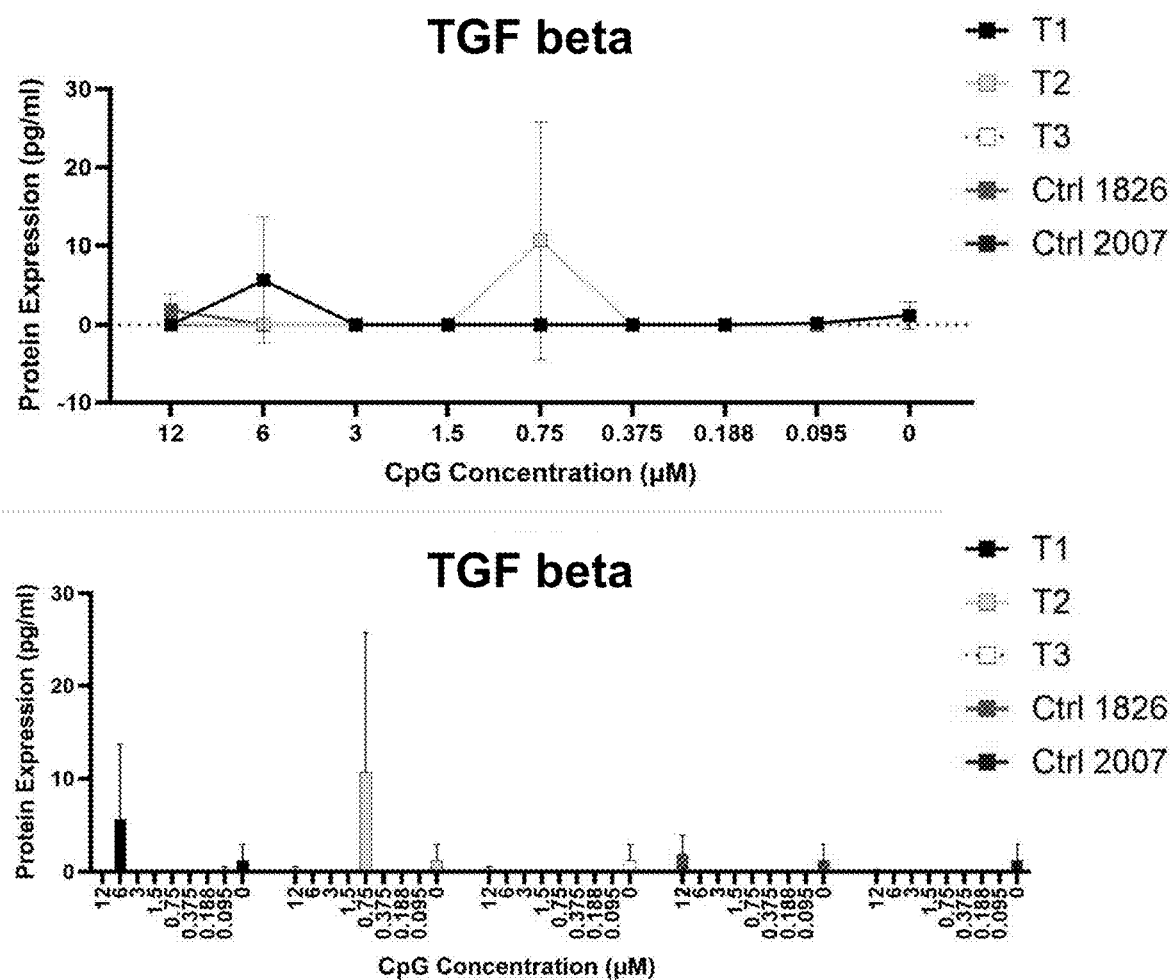
Figure 14A:
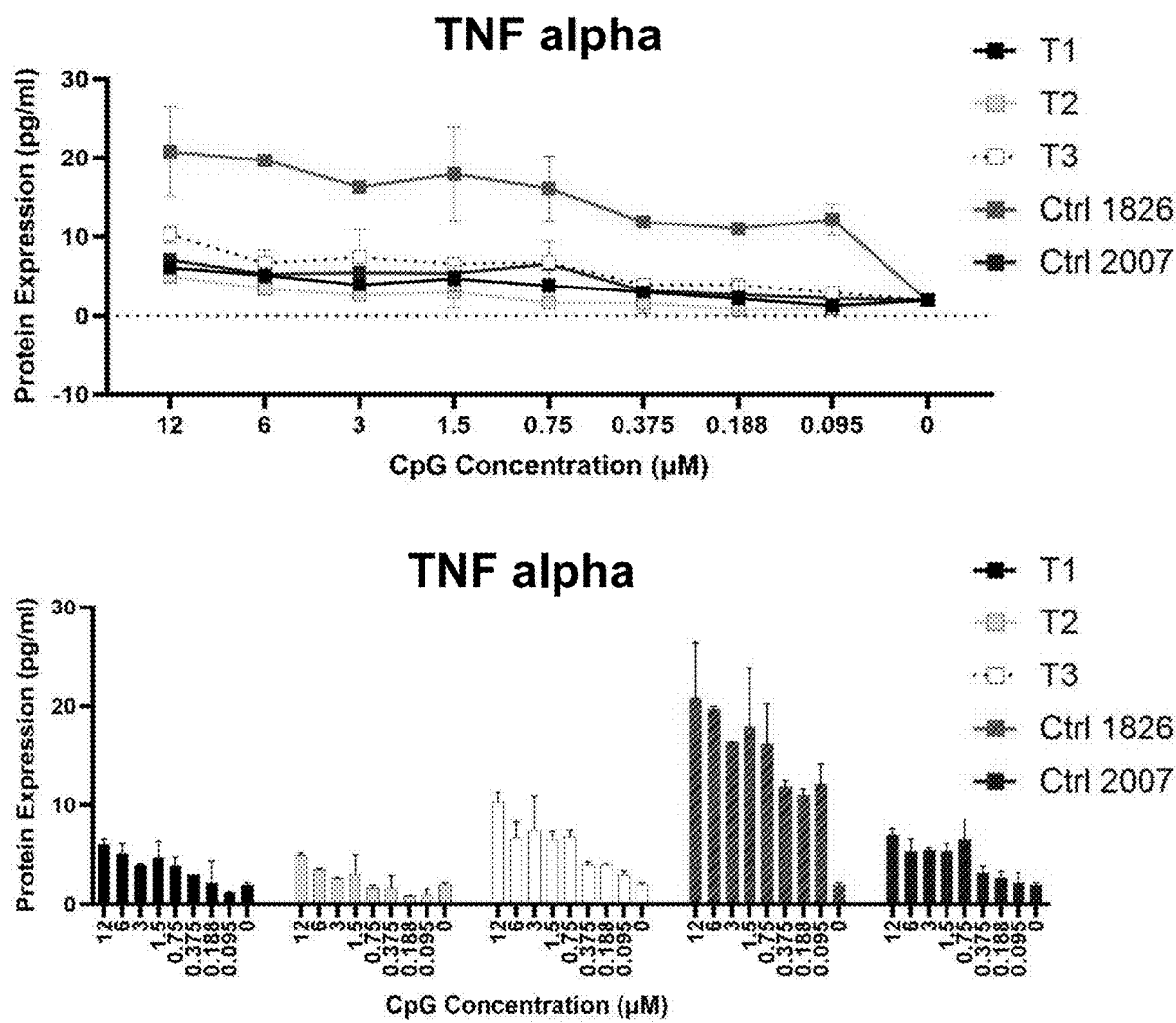
Figure 14A:
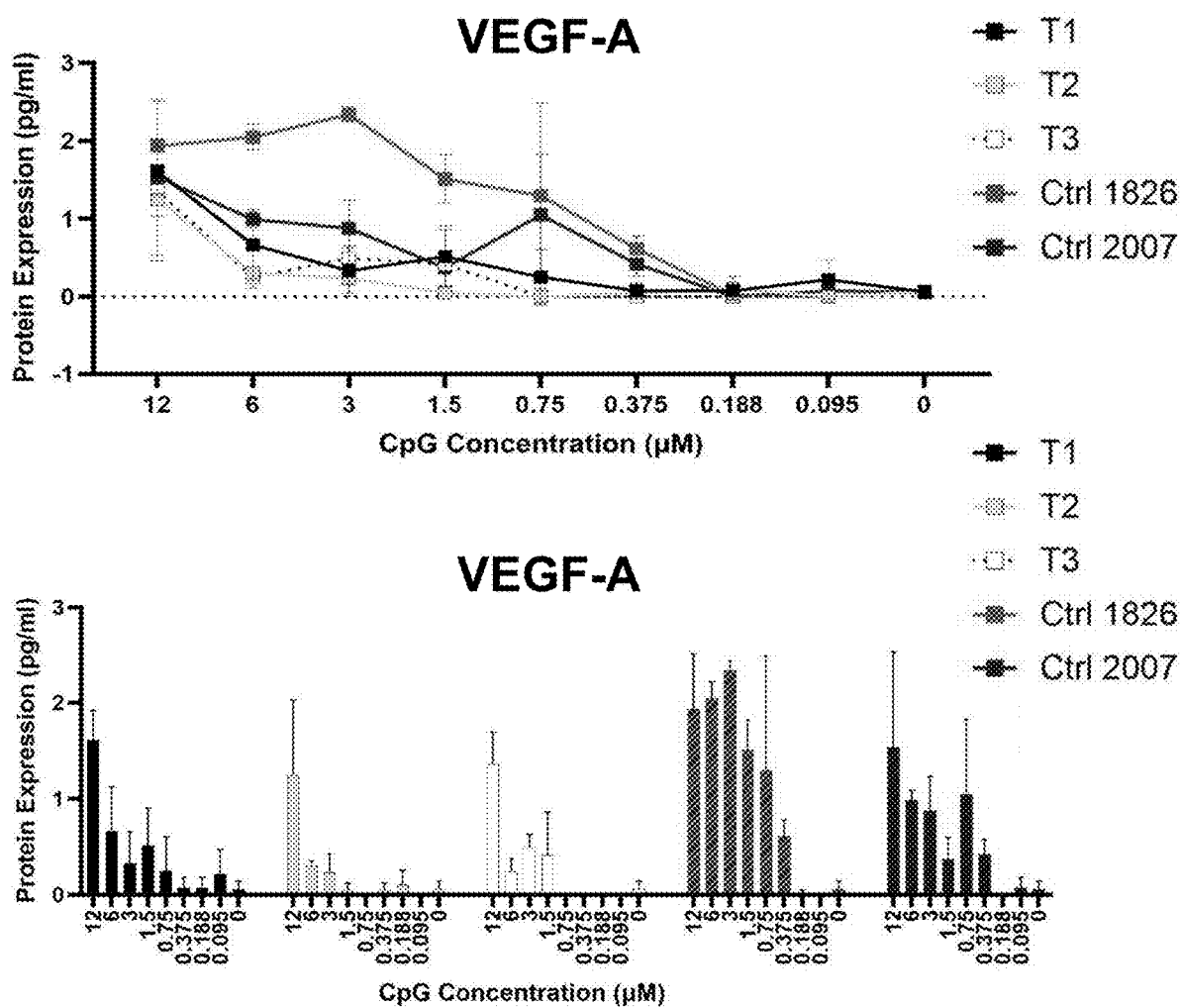
Figure 15A:
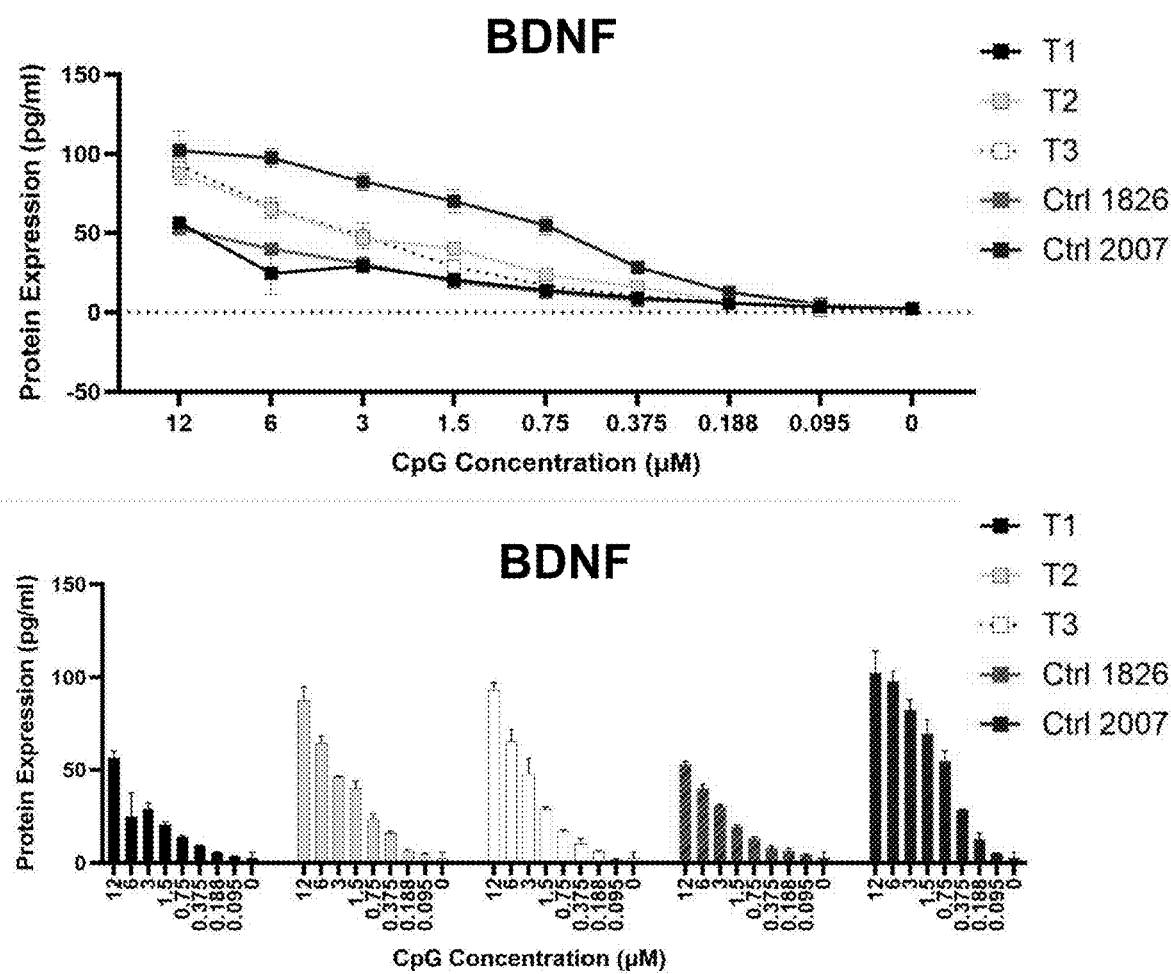
FIG. 15A-AQ shows line and bar graphs for each protein target in mouse peripheral blood mononuclear cells (PBMCs) after treatment with CpG oligonucleotides as disclosed herein (i.e., T1, T2 (SEQ ID NO: 17) and T3 (SEQ ID NO: 25)) and two controls with known stimulatory activity (i.e., CpG ODN 1826, CpG ODN 2007).
Figure 15B:
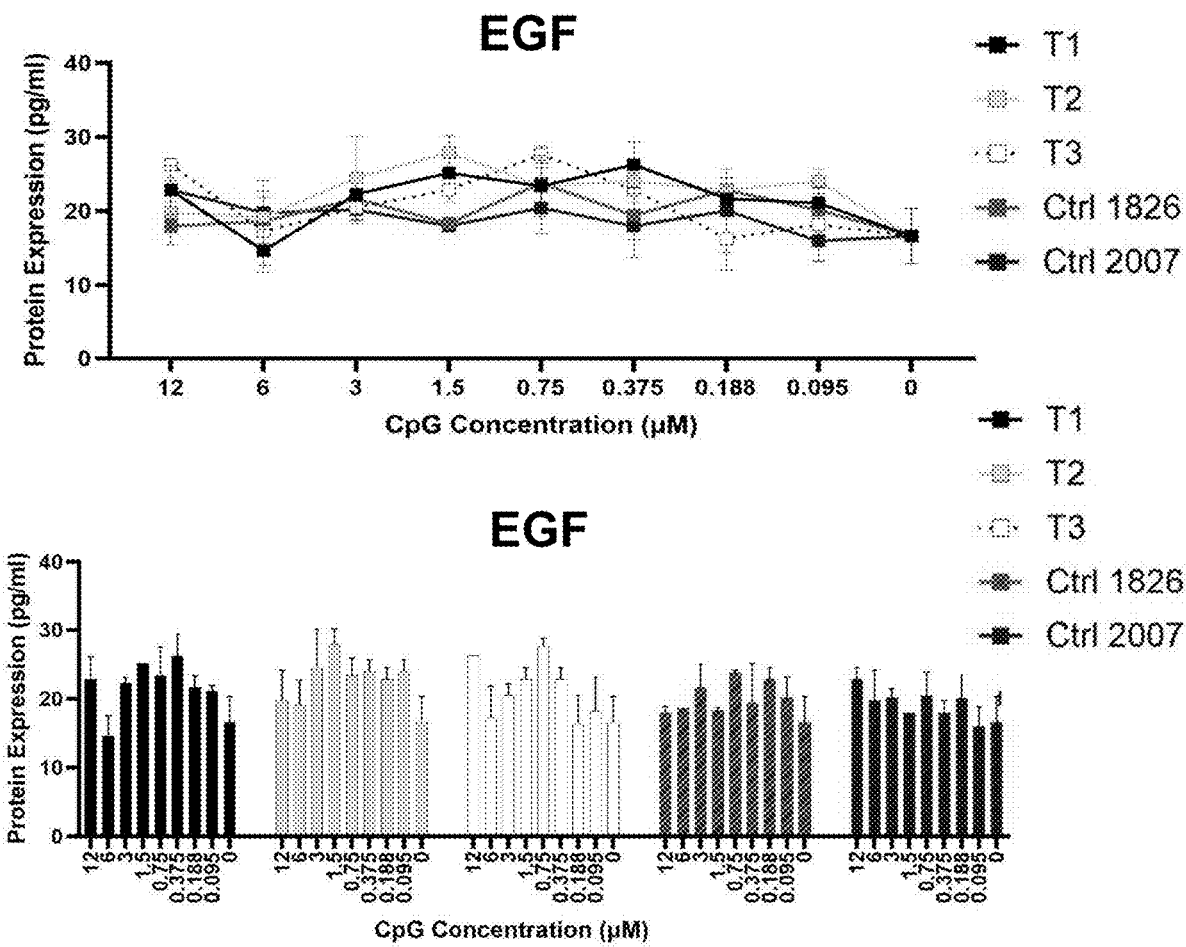
FIG. 15B depicts the protein target Epidermal growth factor (EGF).
Figure 15C:
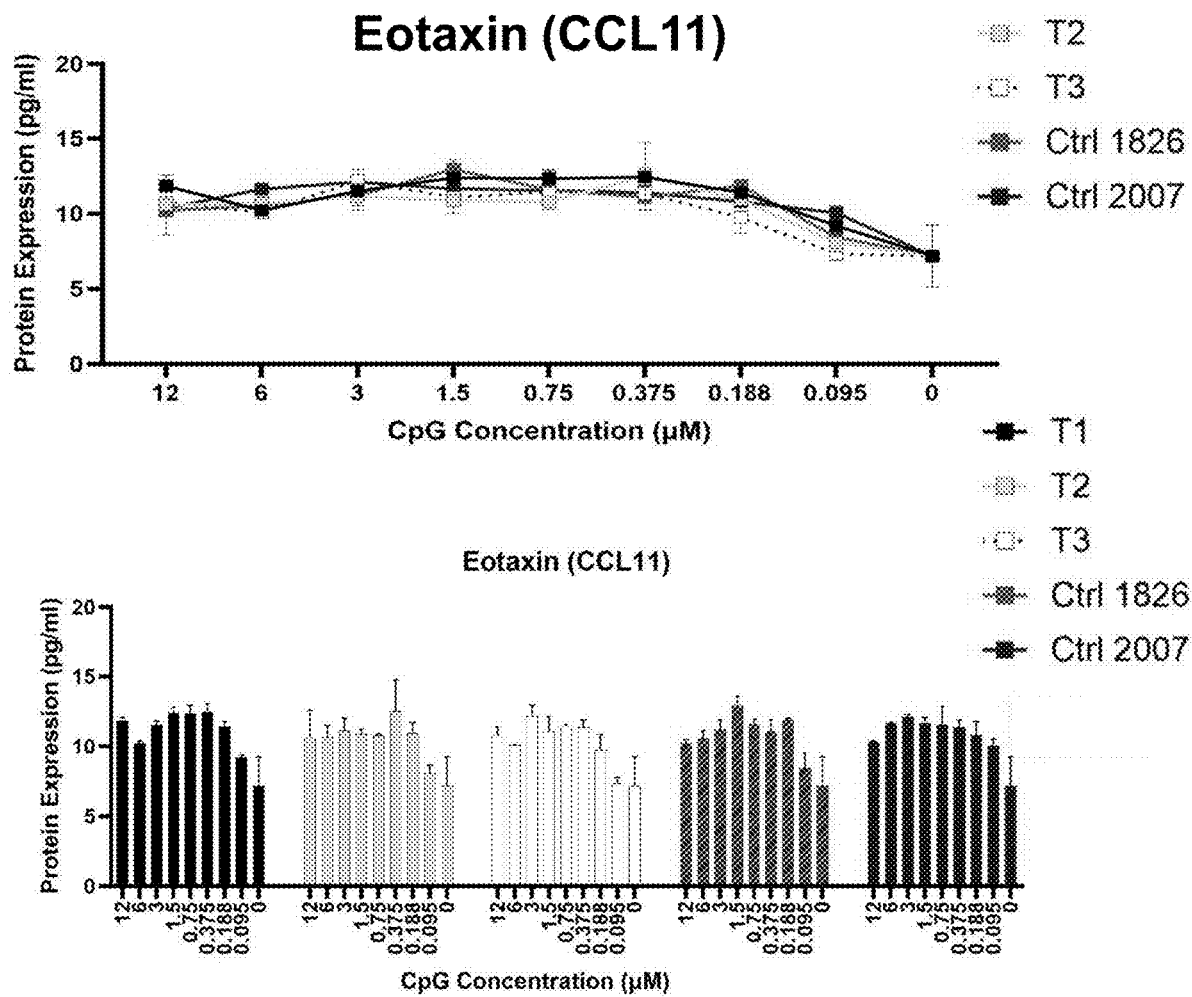
FIG. 15C depicts the protein target Eotaxin (CCL11).
Figure 15D:
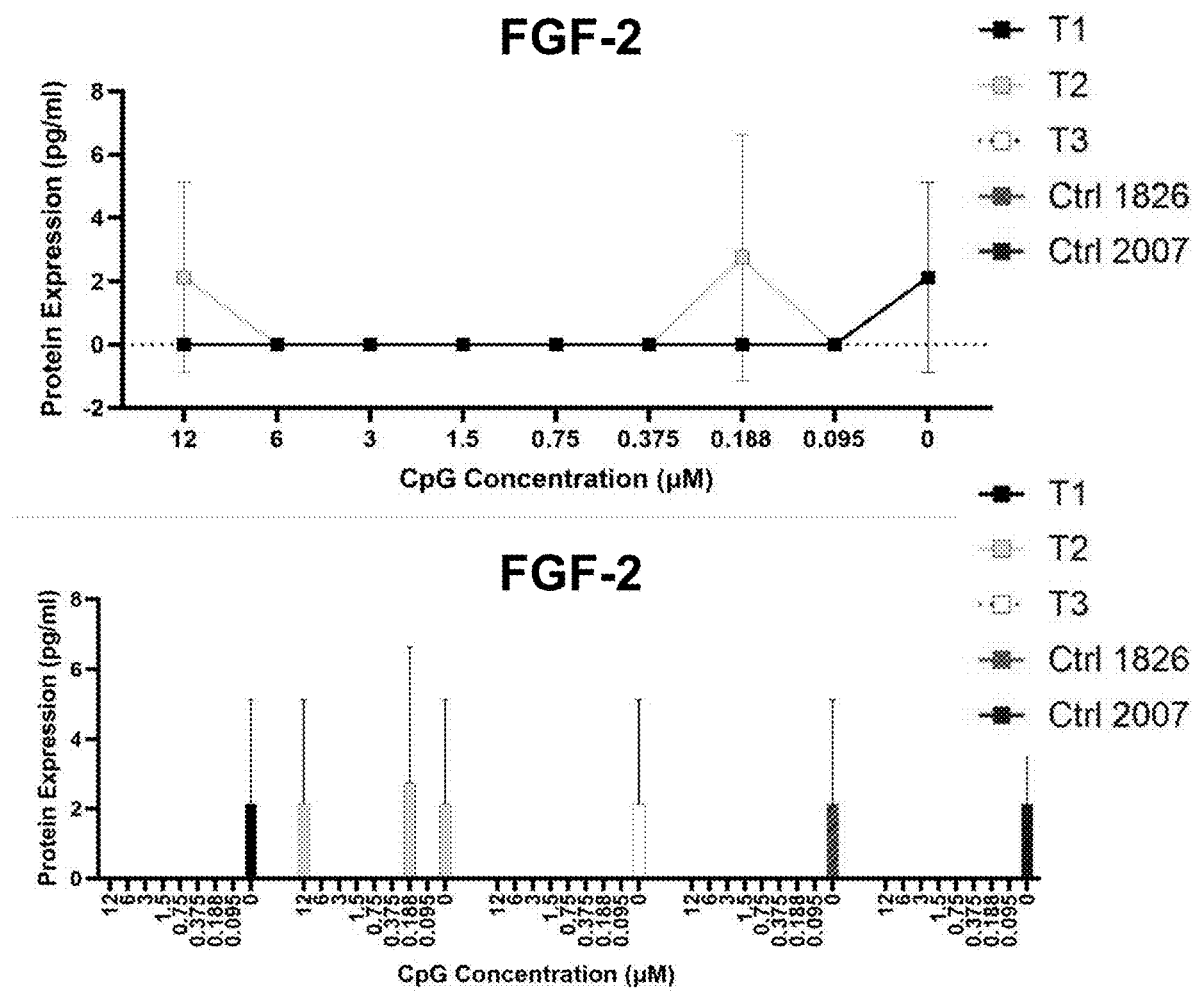
FIG. 15D depicts the protein target Fibroblast growth factor 2 (FGF-2).
Figure 15E:
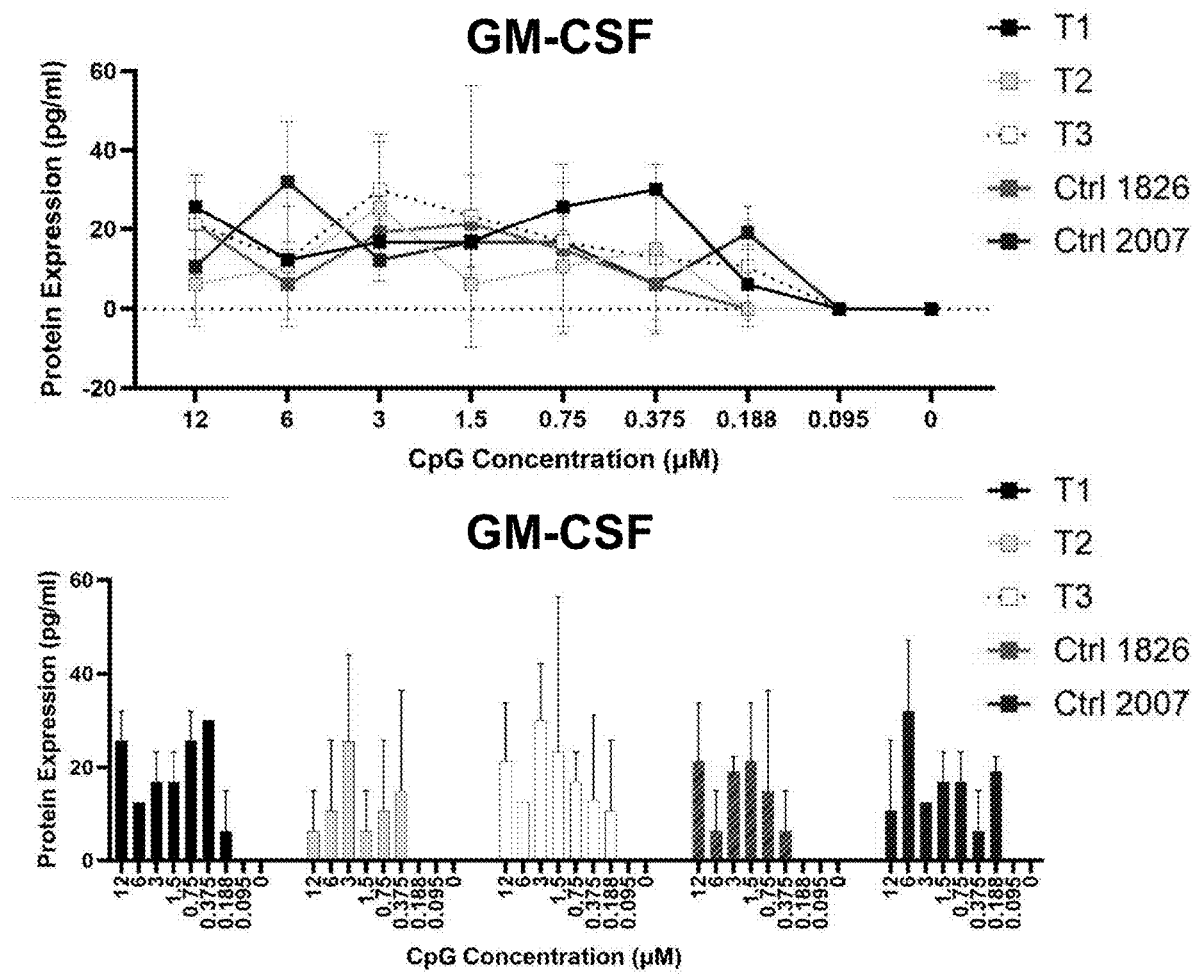
FIG. 15E depicts the protein target GM-CSF.
Figure 15F:
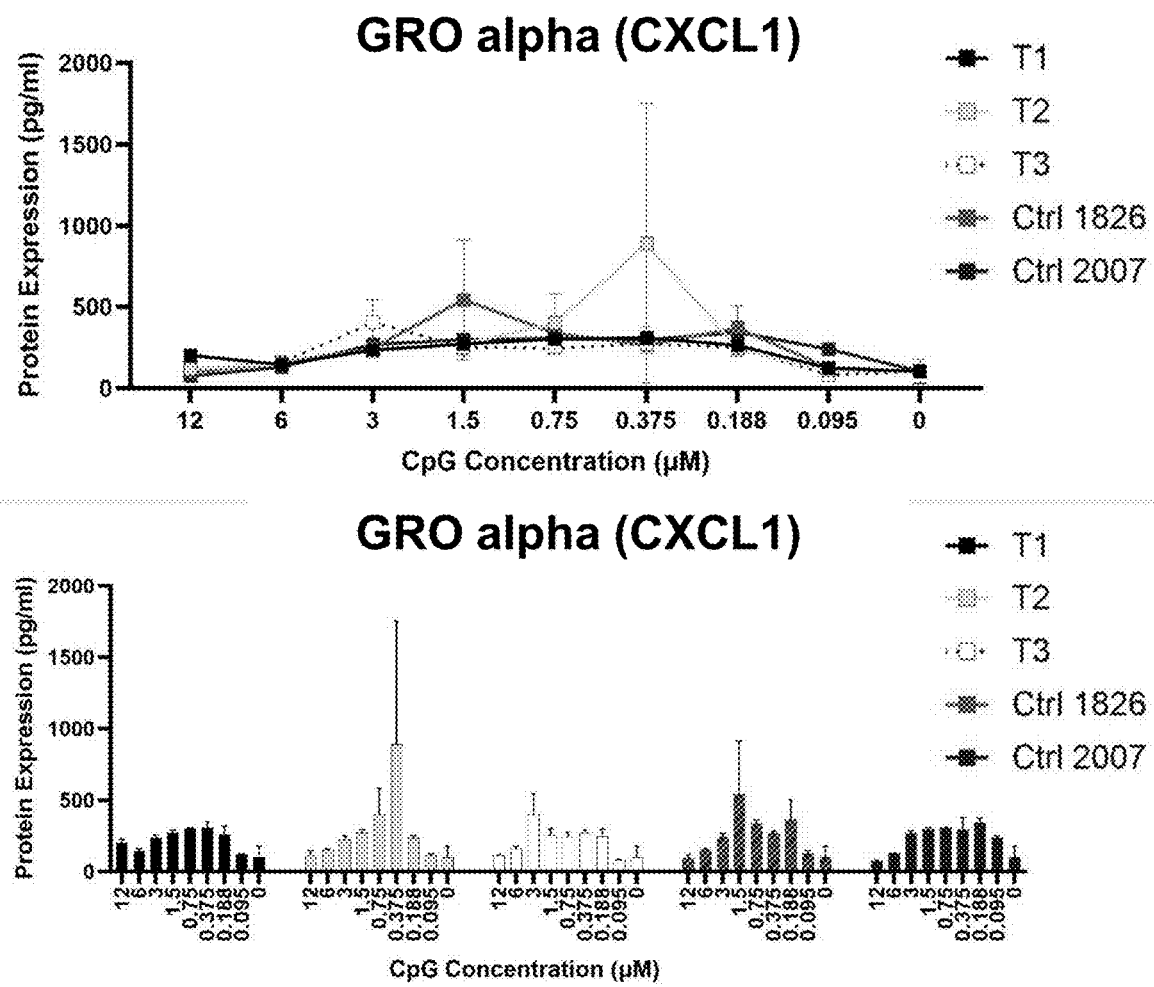
FIG. 15F depicts the protein target GRO alpha (CXCL1).
Figure 15G:
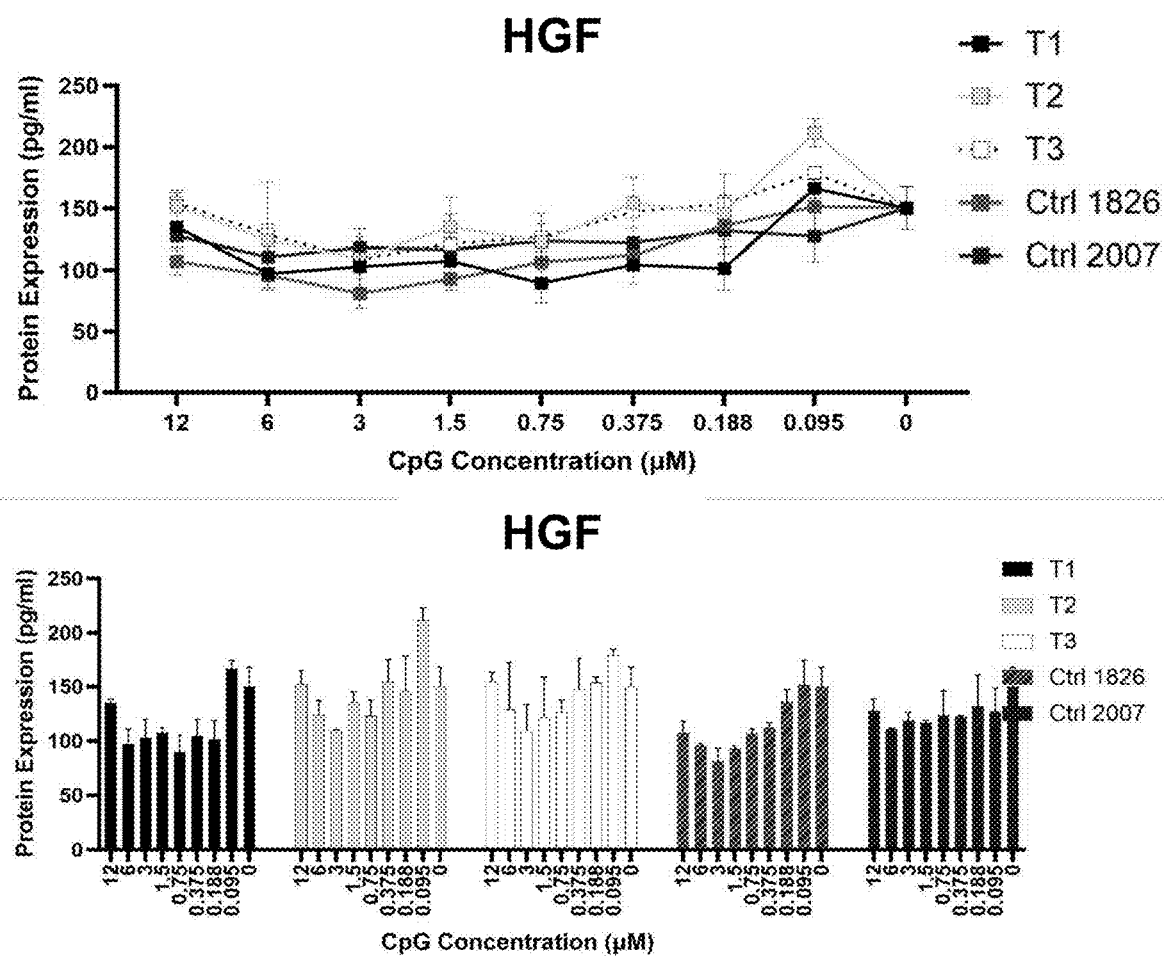
FIG. 15G depicts the protein target Hepatocyte growth factor (HGF).
Figure 15H:
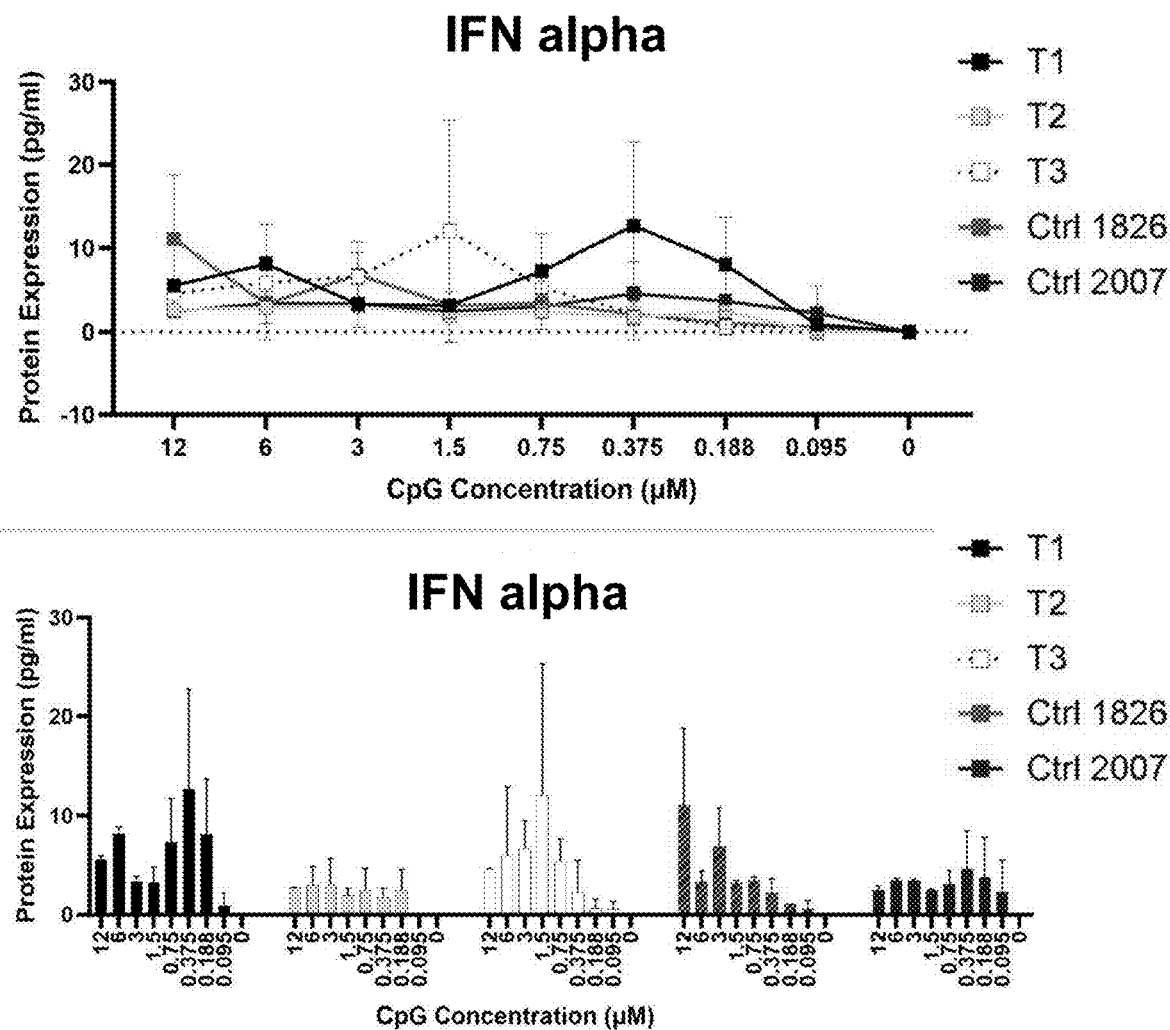
FIG. 15H depicts the protein target IFN alpha.
Figure 15I:
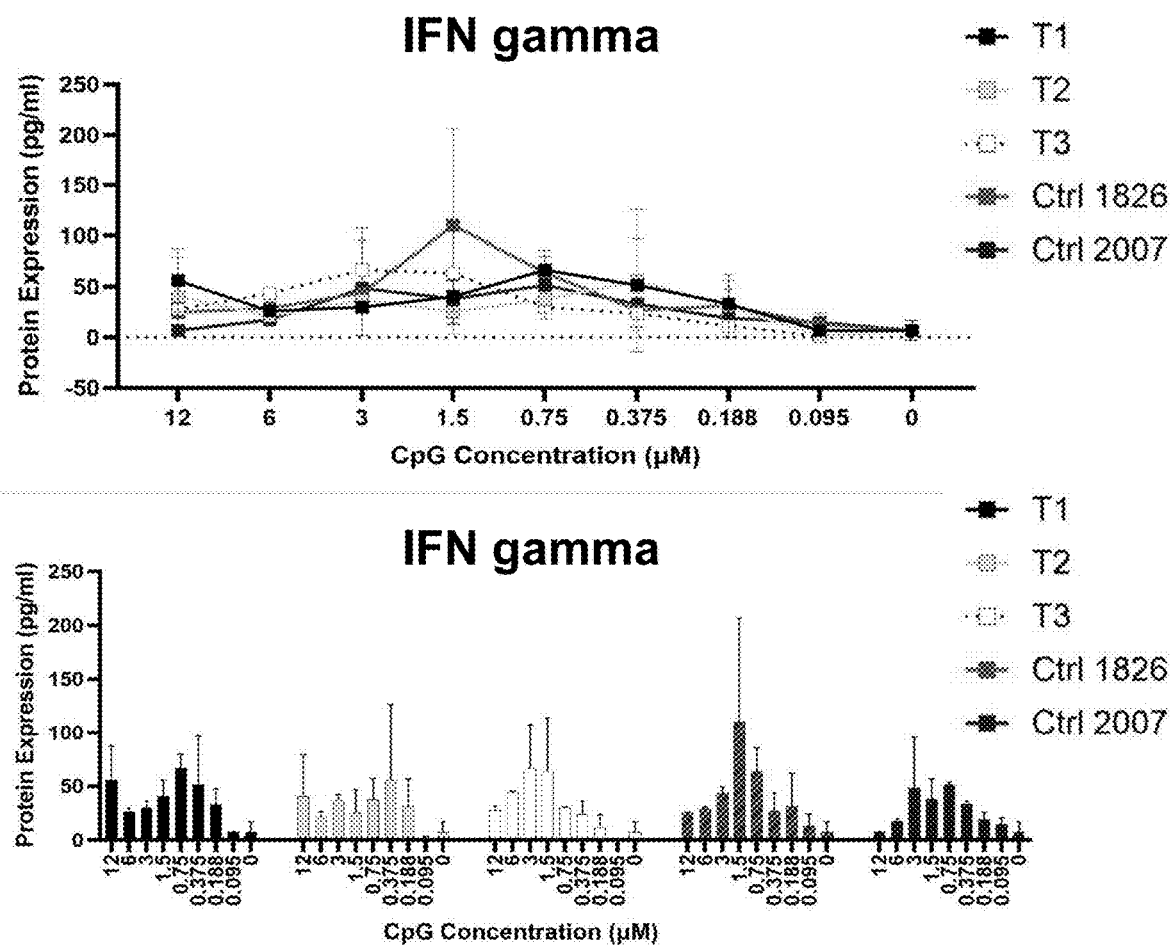
FIG. 15I depicts the protein target IFN gamma.
Figure 15J:
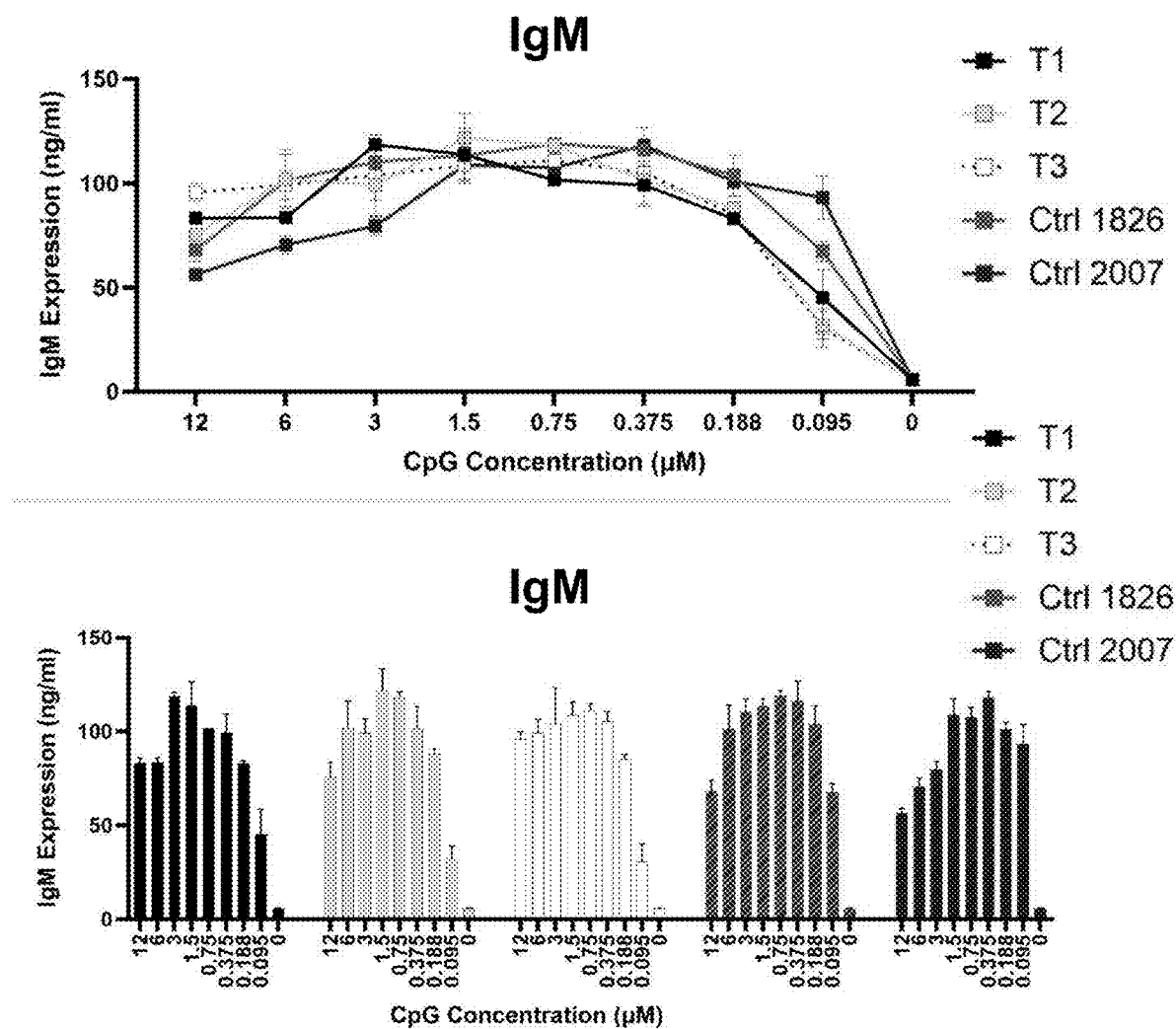
FIG. 15J depicts the protein target IgM.
Figure 15K:
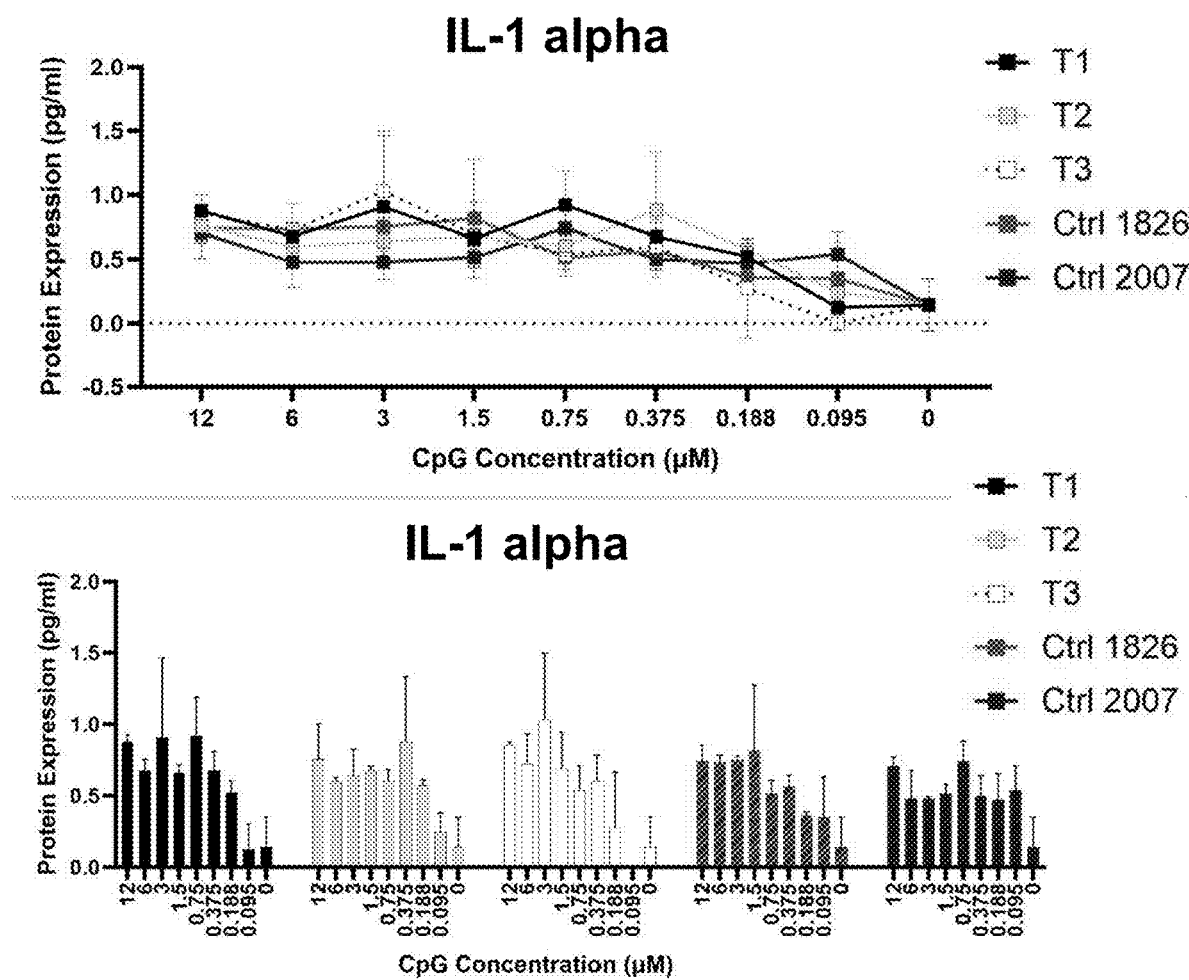
FIG. 15K depicts the protein target IL-1 alpha.
Figure 15L:
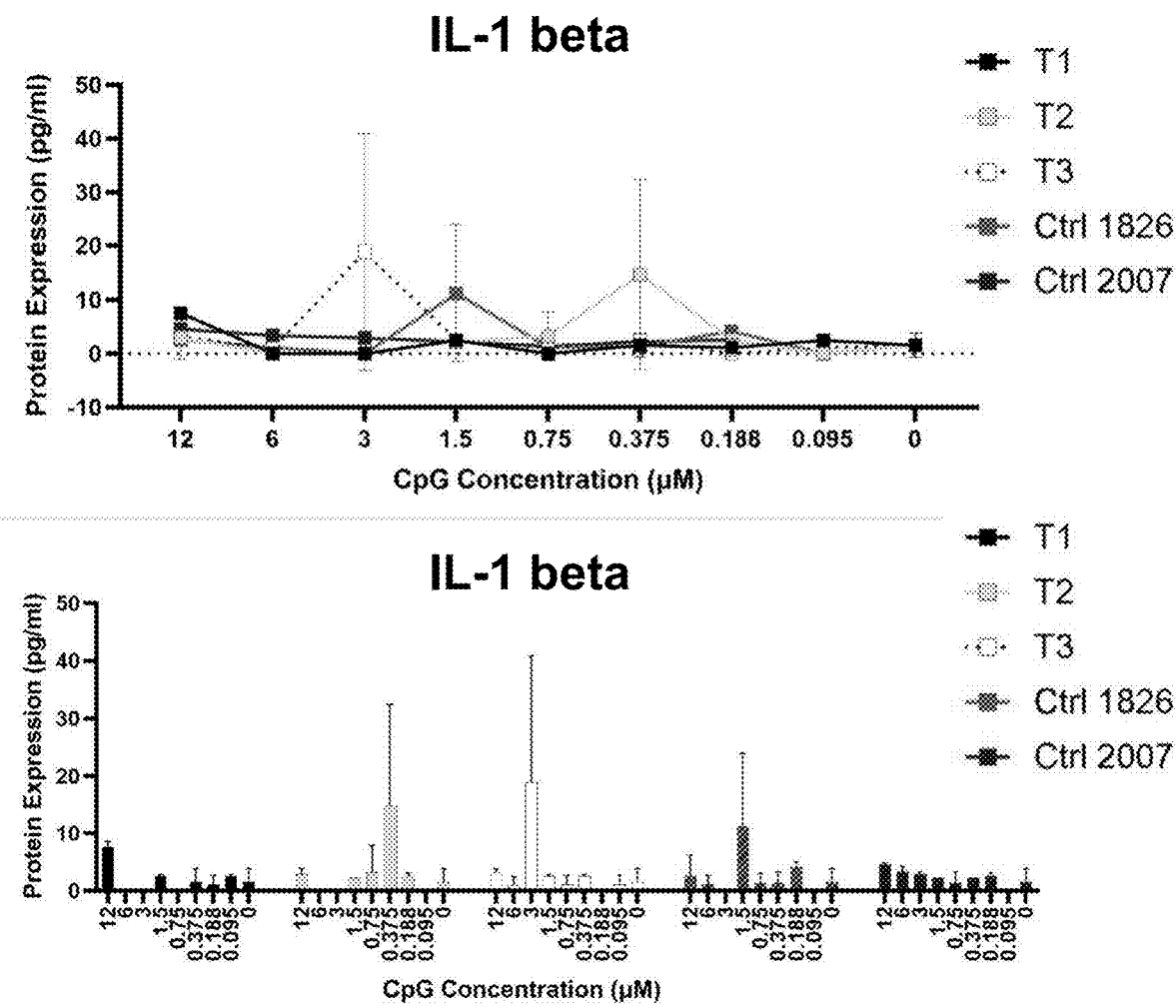
FIG. 15L depicts the protein target IL-1 beta.
Figure 15M:
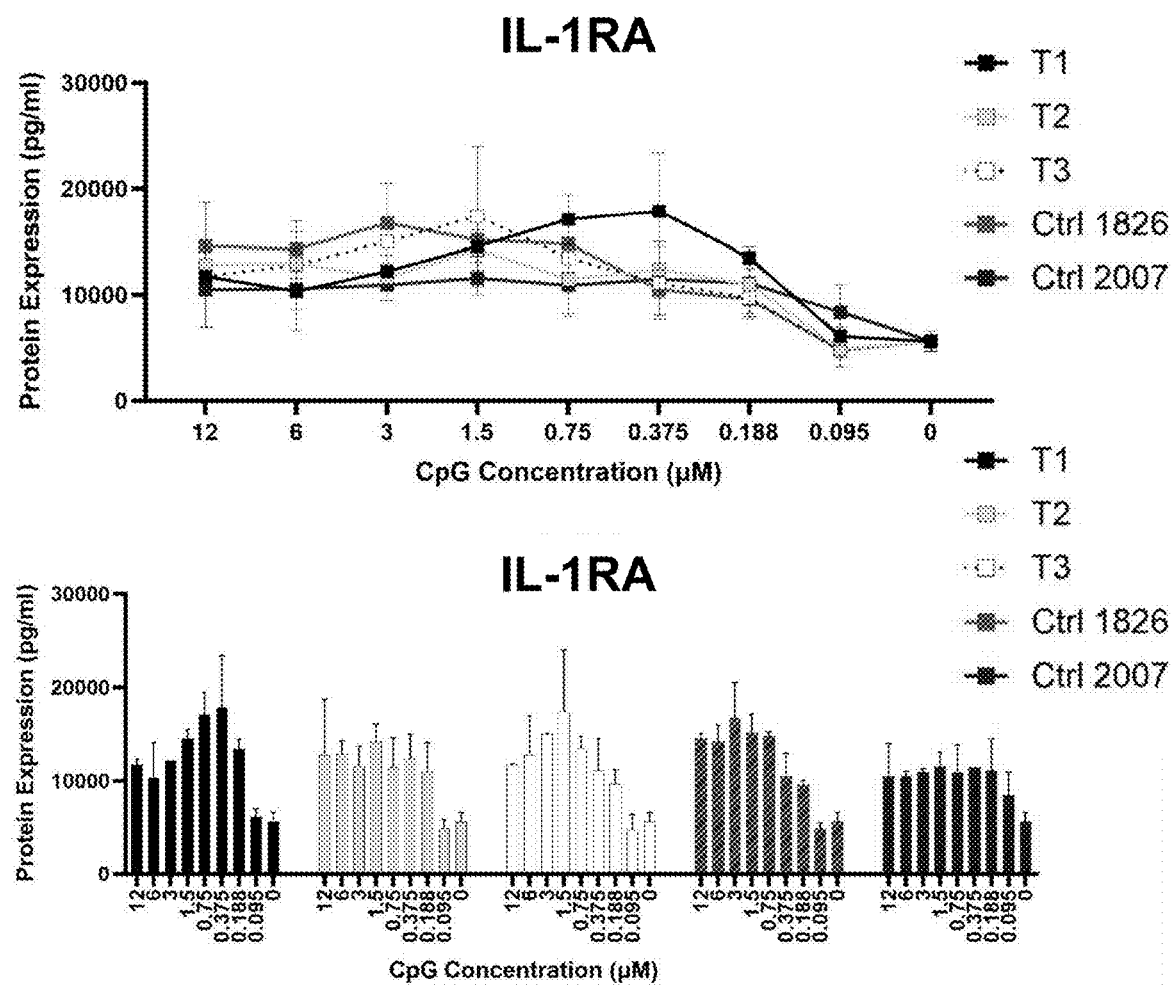
FIG. 15M depicts the protein target IL-1RA.
Figure 15N:
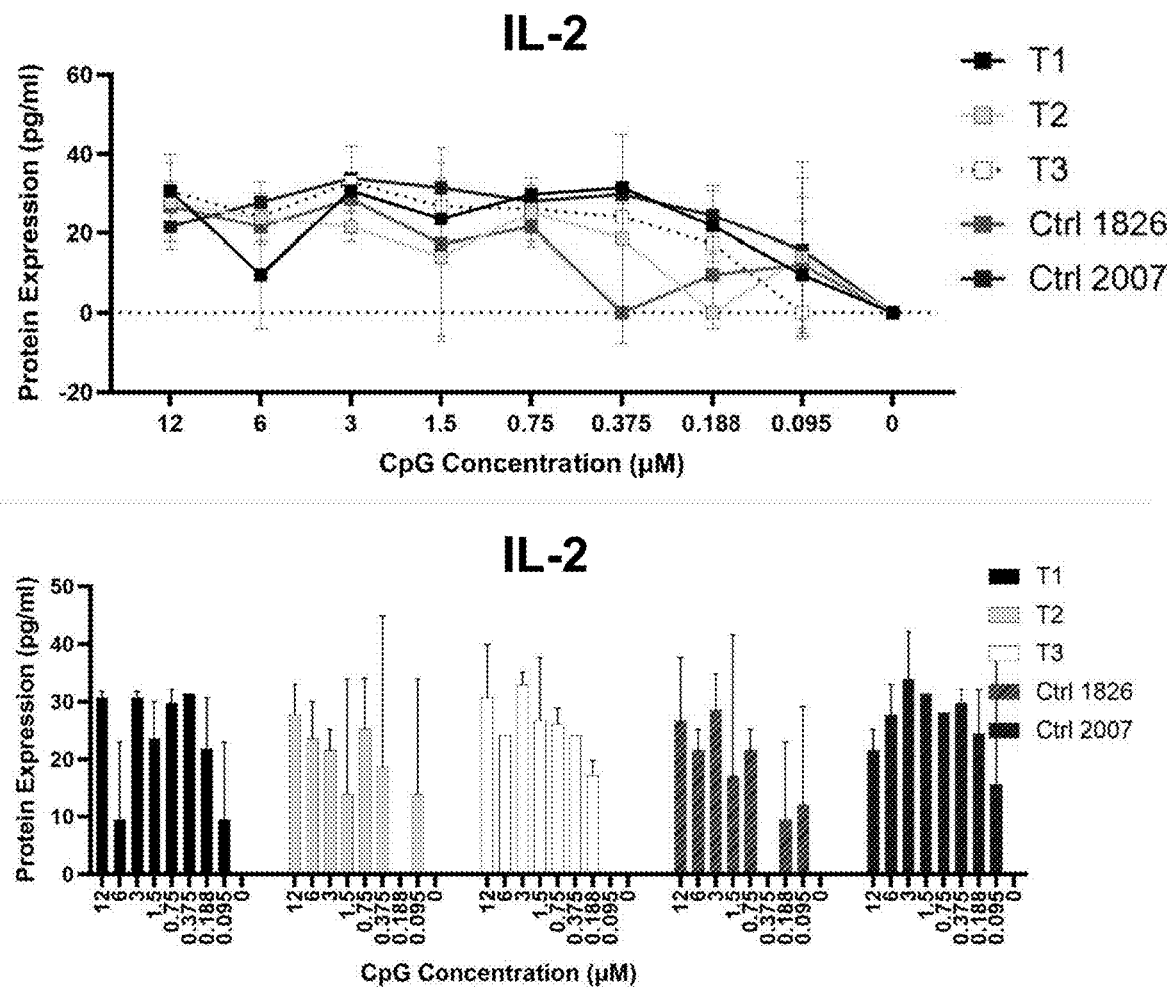
FIG. 15N depicts the protein target IL-2.
Figure 15O:
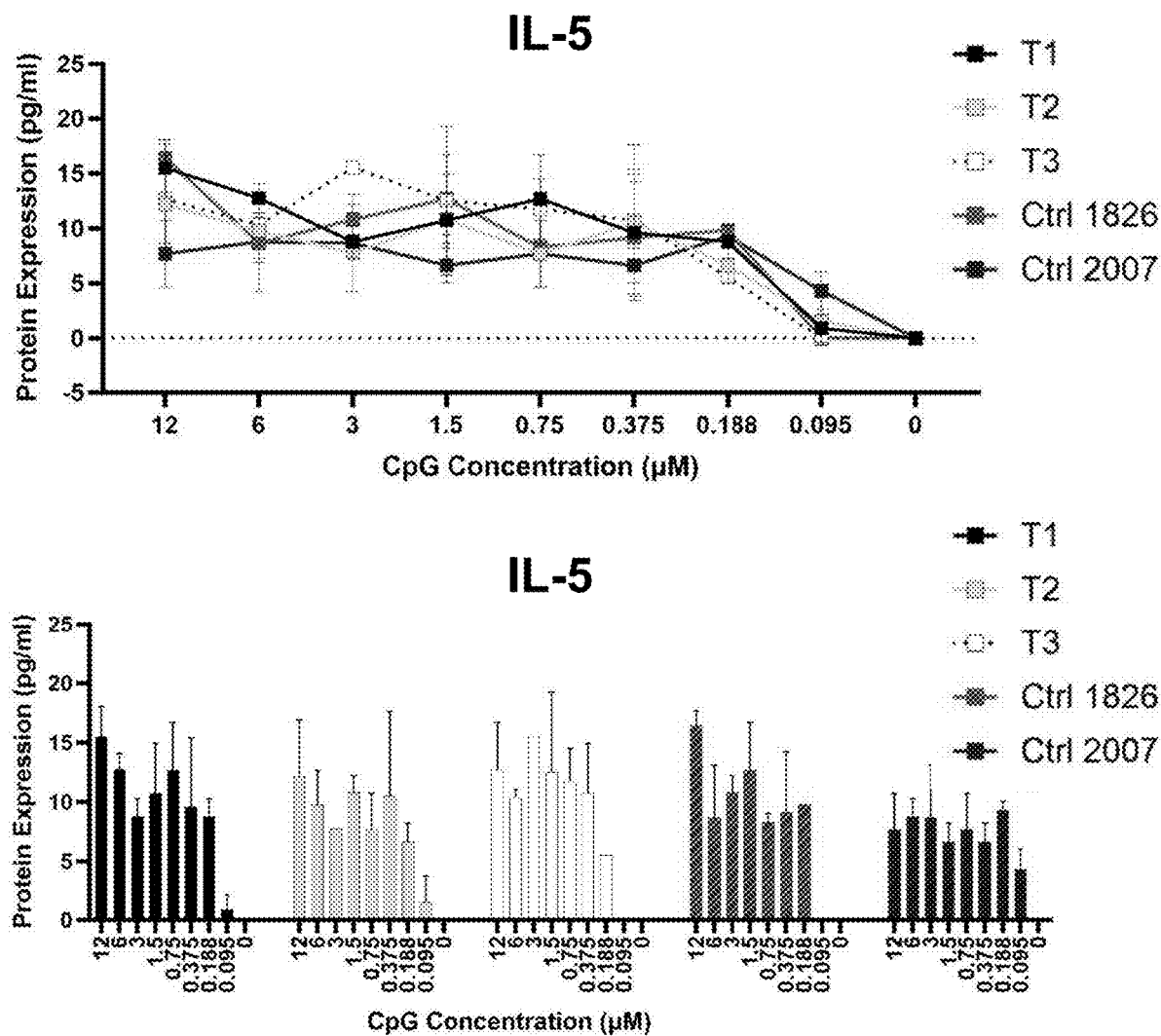
FIG. 15O depicts the protein target IL-5.
Figure 15P:
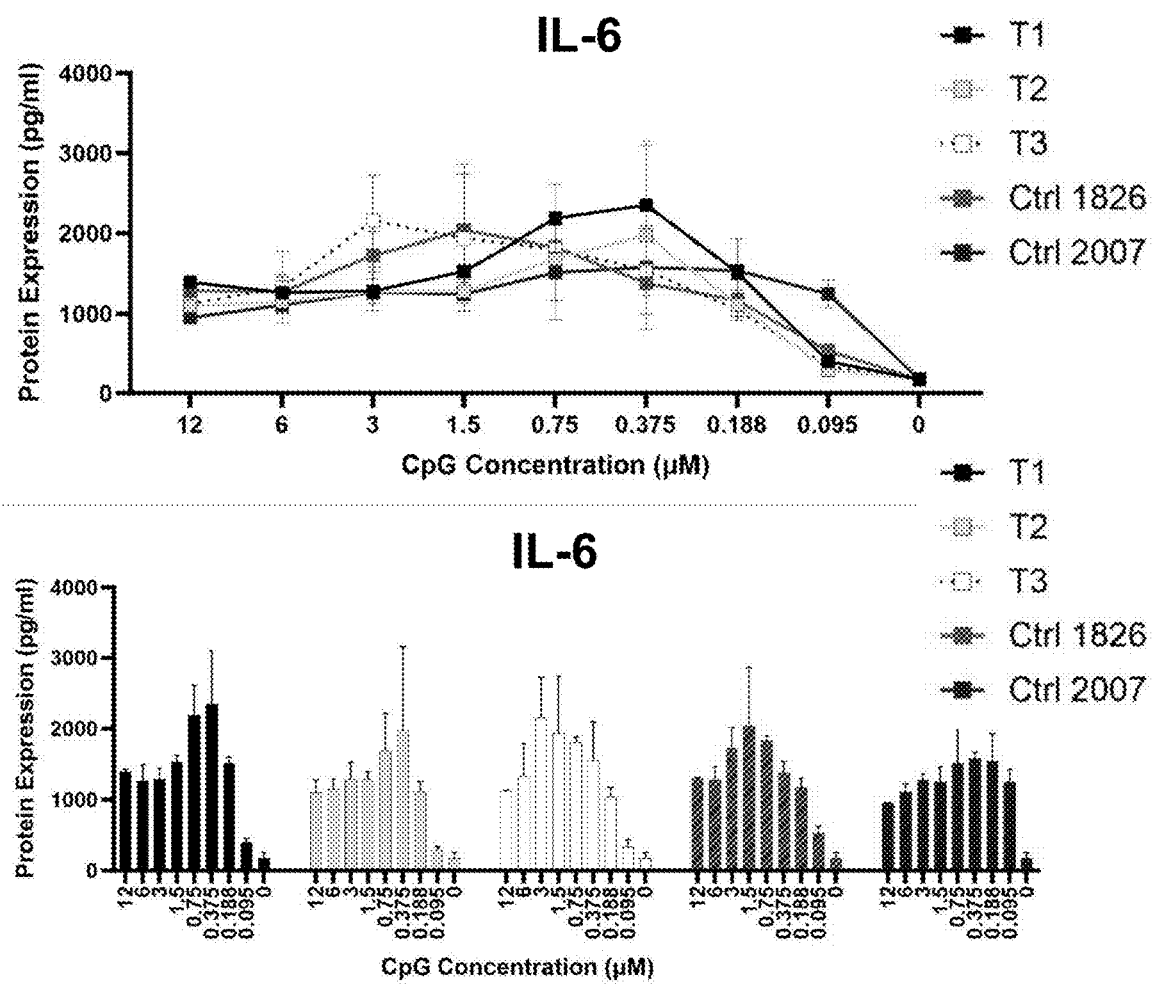
FIG. 15P depicts the protein target IL-6.
Figure 15Q:
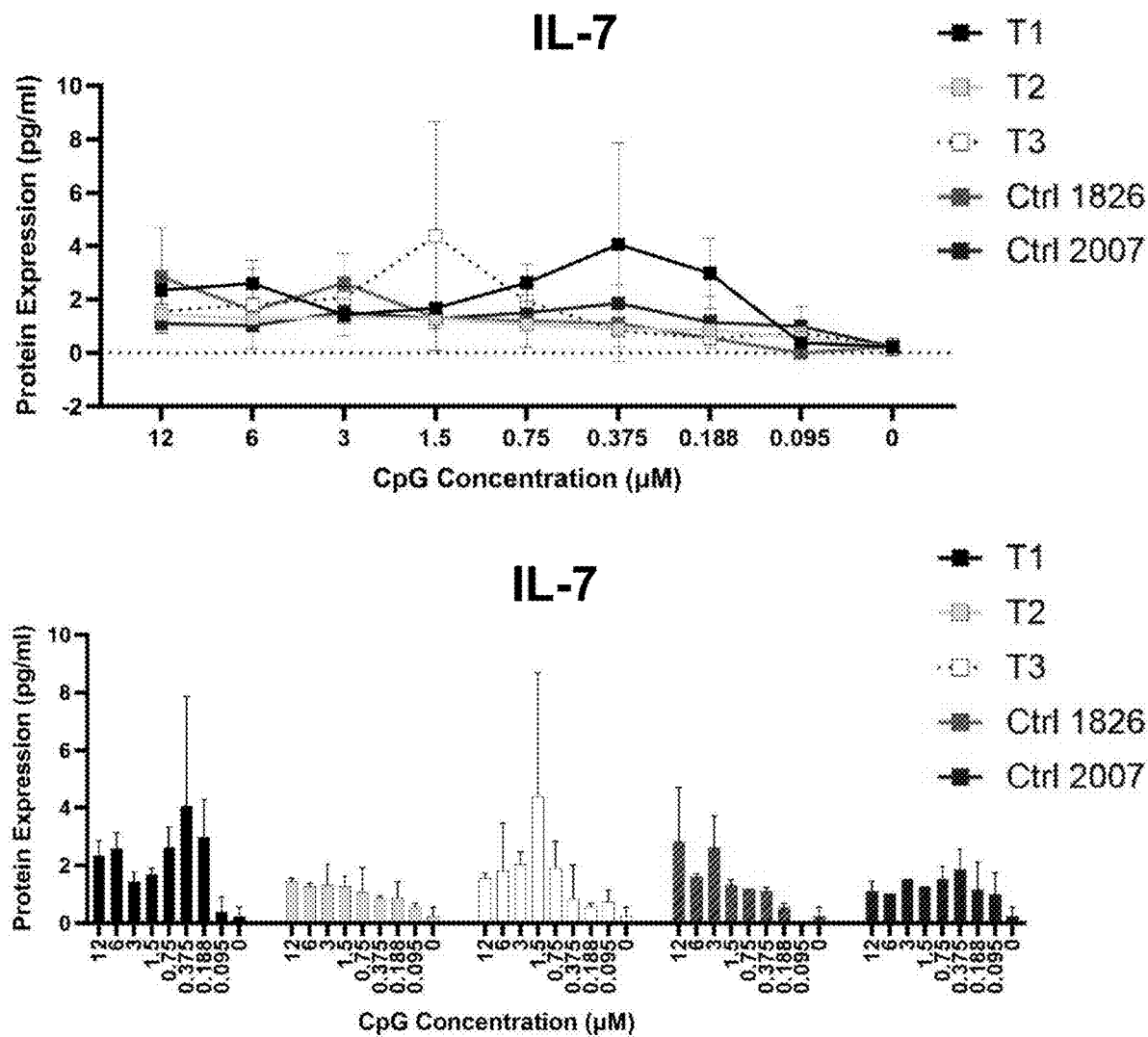
FIG. 15Q depicts the protein target IL-7.
Figure 15R:
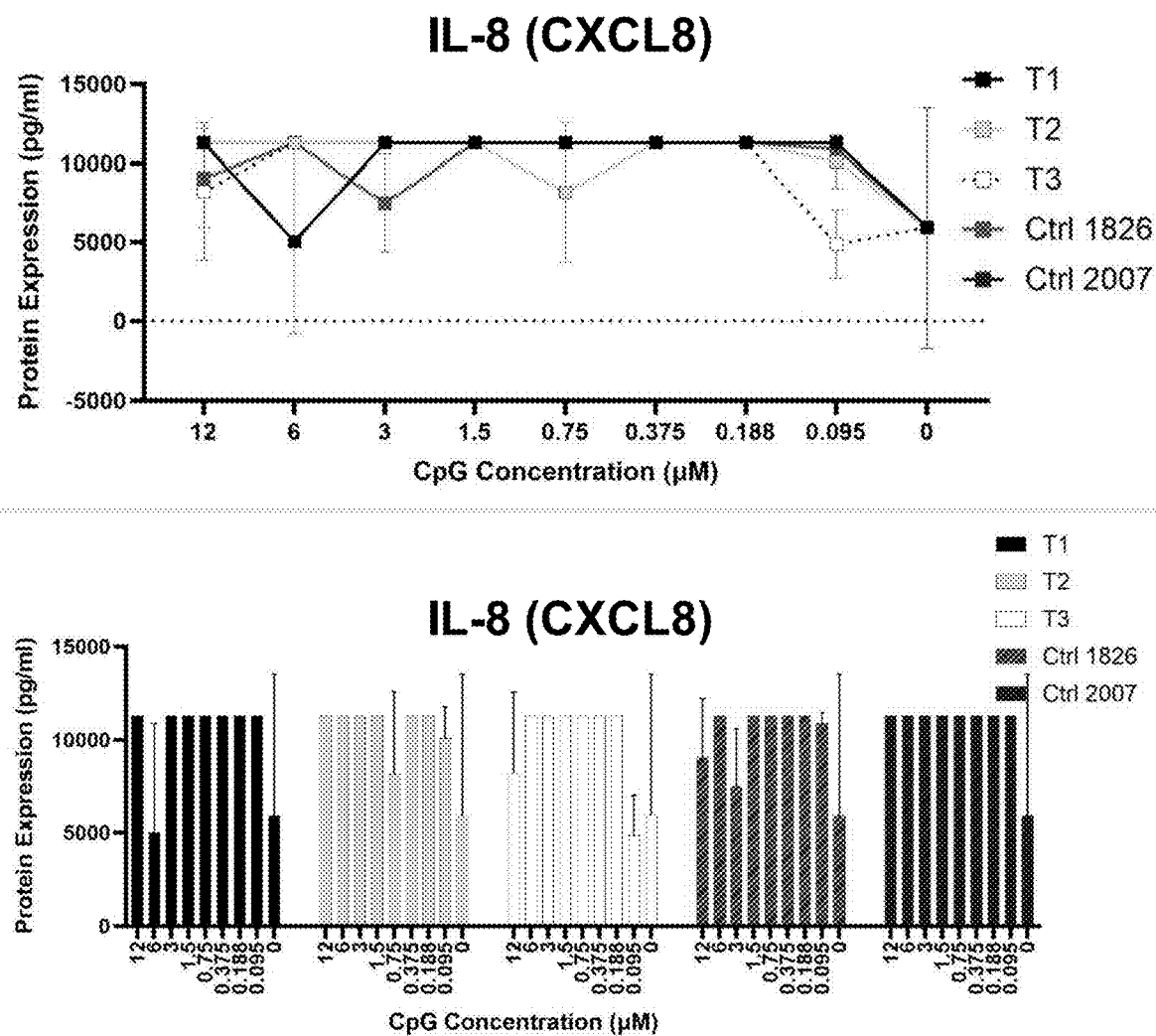
FIG. 15R depicts the protein target IL-8 (CXCL8).
Figure 15S:
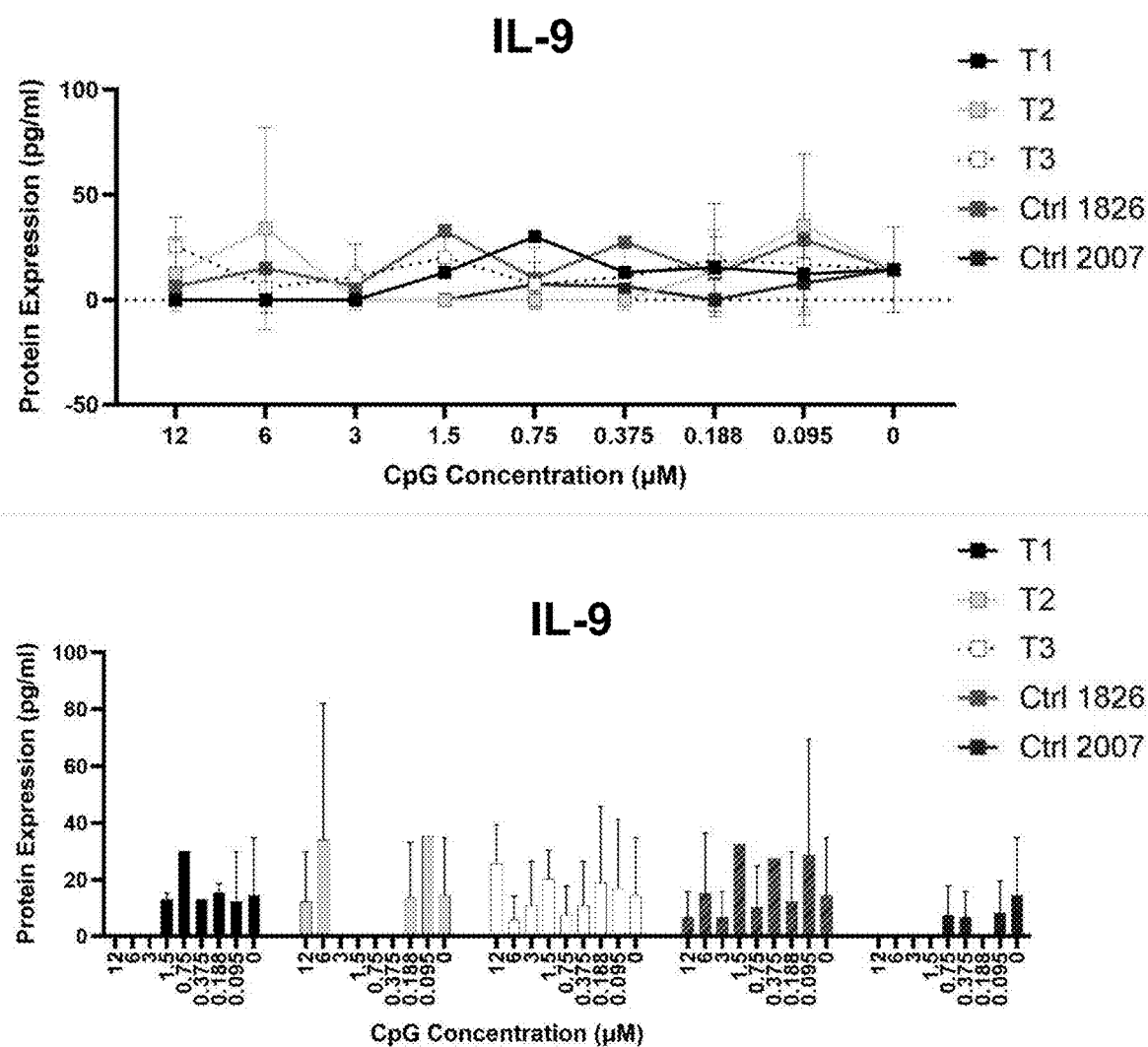
FIG. 15S depicts the protein target IL-9.
Figure 15T:
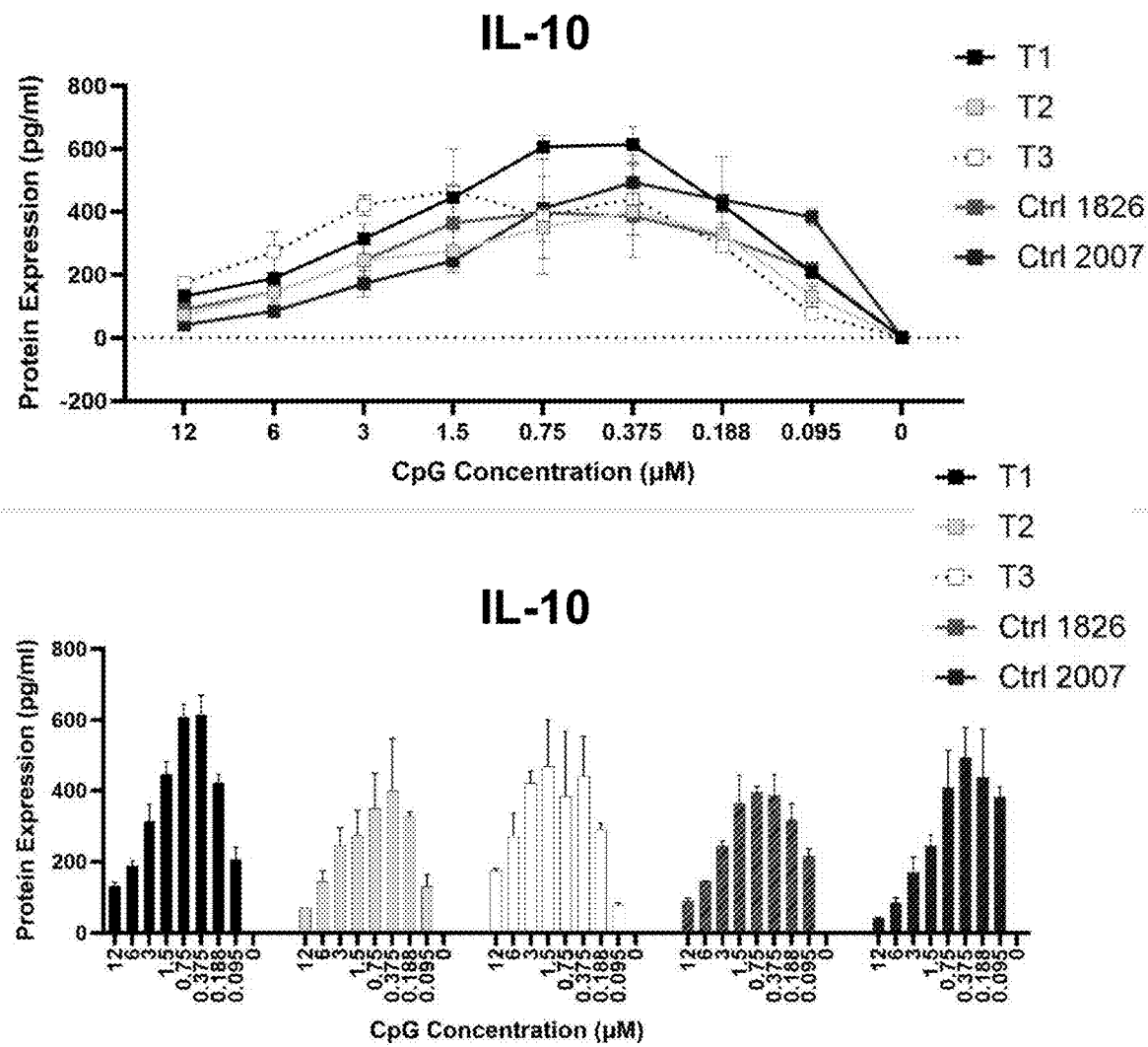
FIG. 15T depicts the protein target IL-10.
Figure 15U:
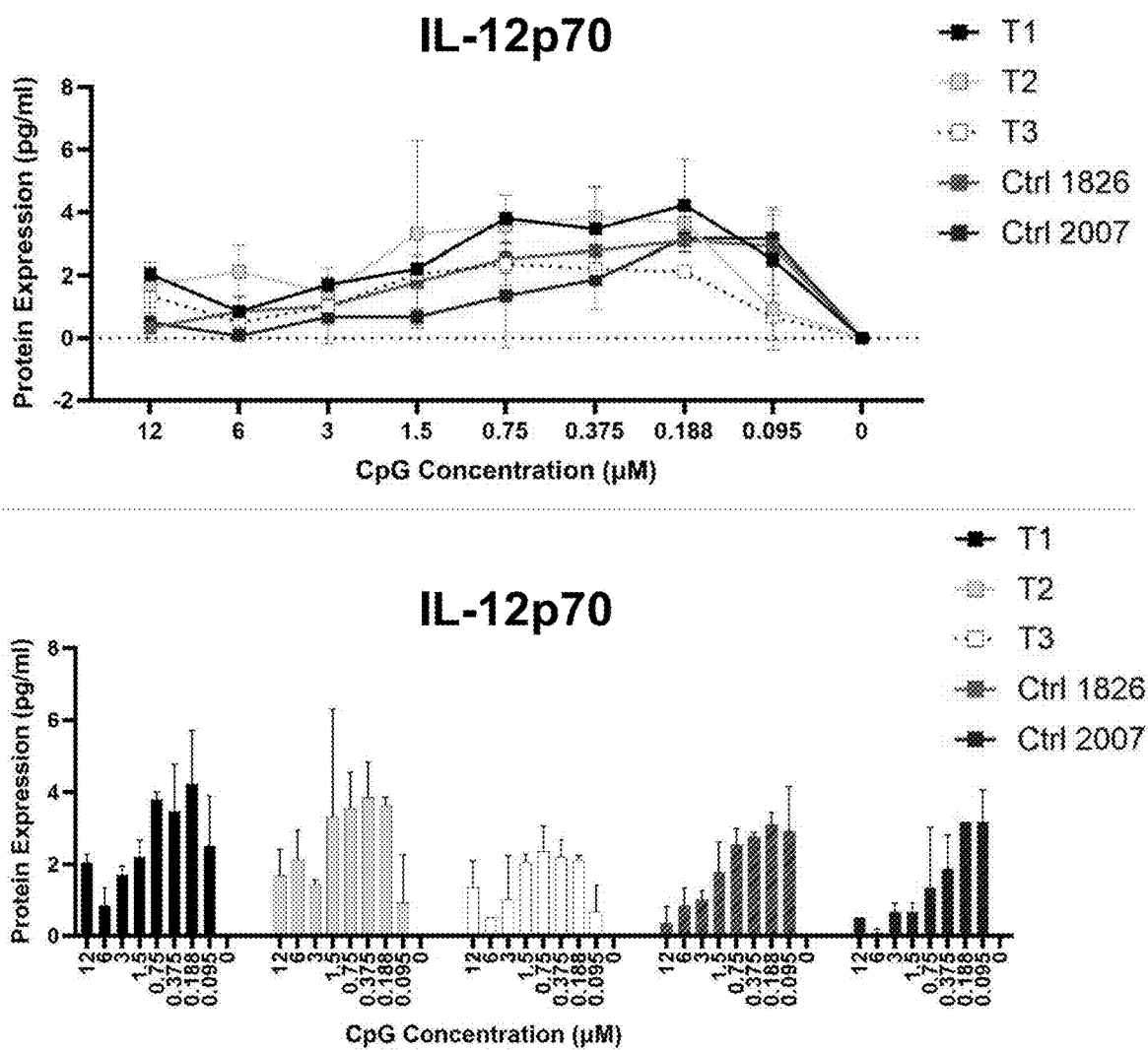
FIG. 15U depicts the protein target IL-12p70.
Figure 15V:
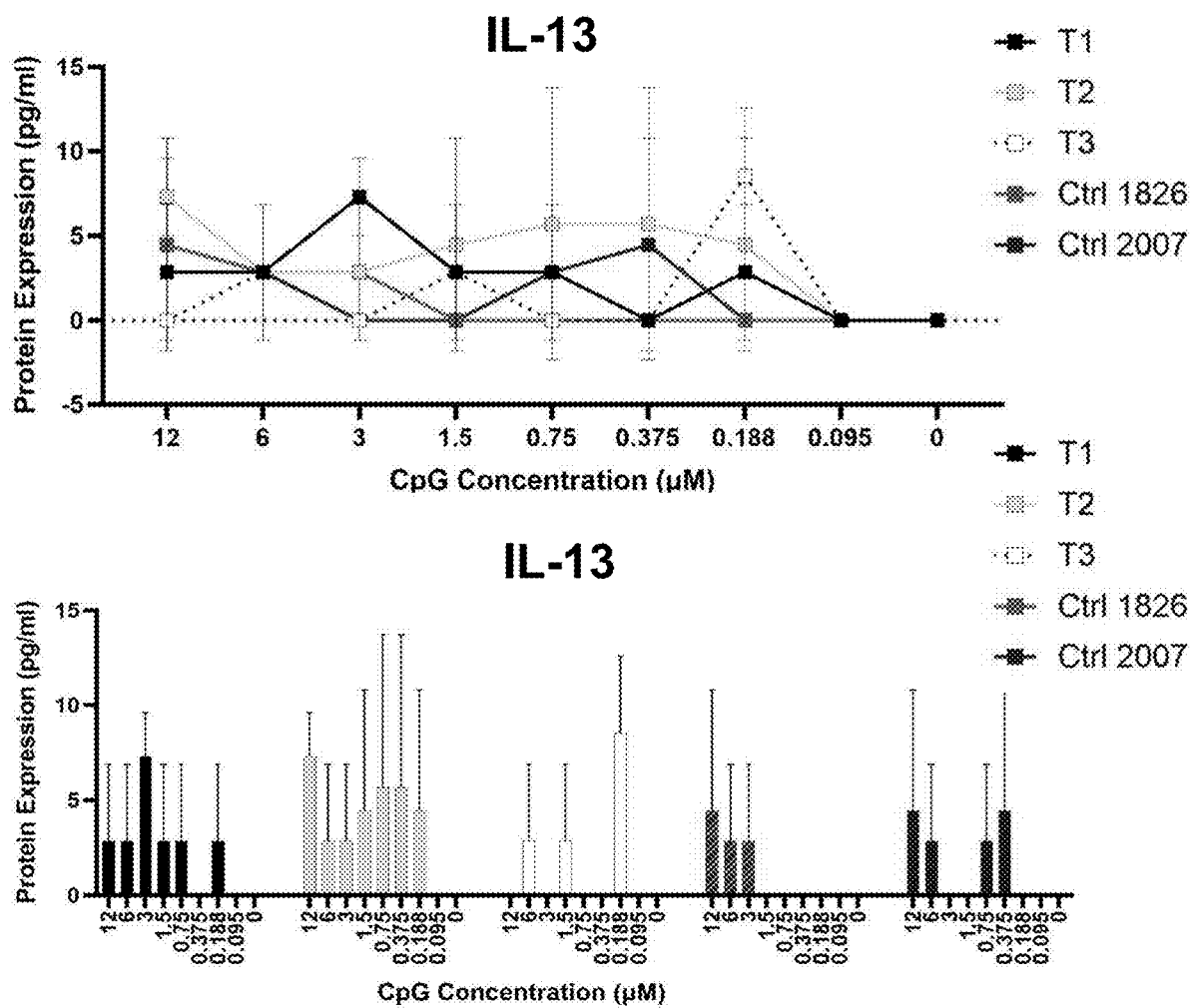
FIG. 15V depicts the protein target IL-13.
Figure 15W:
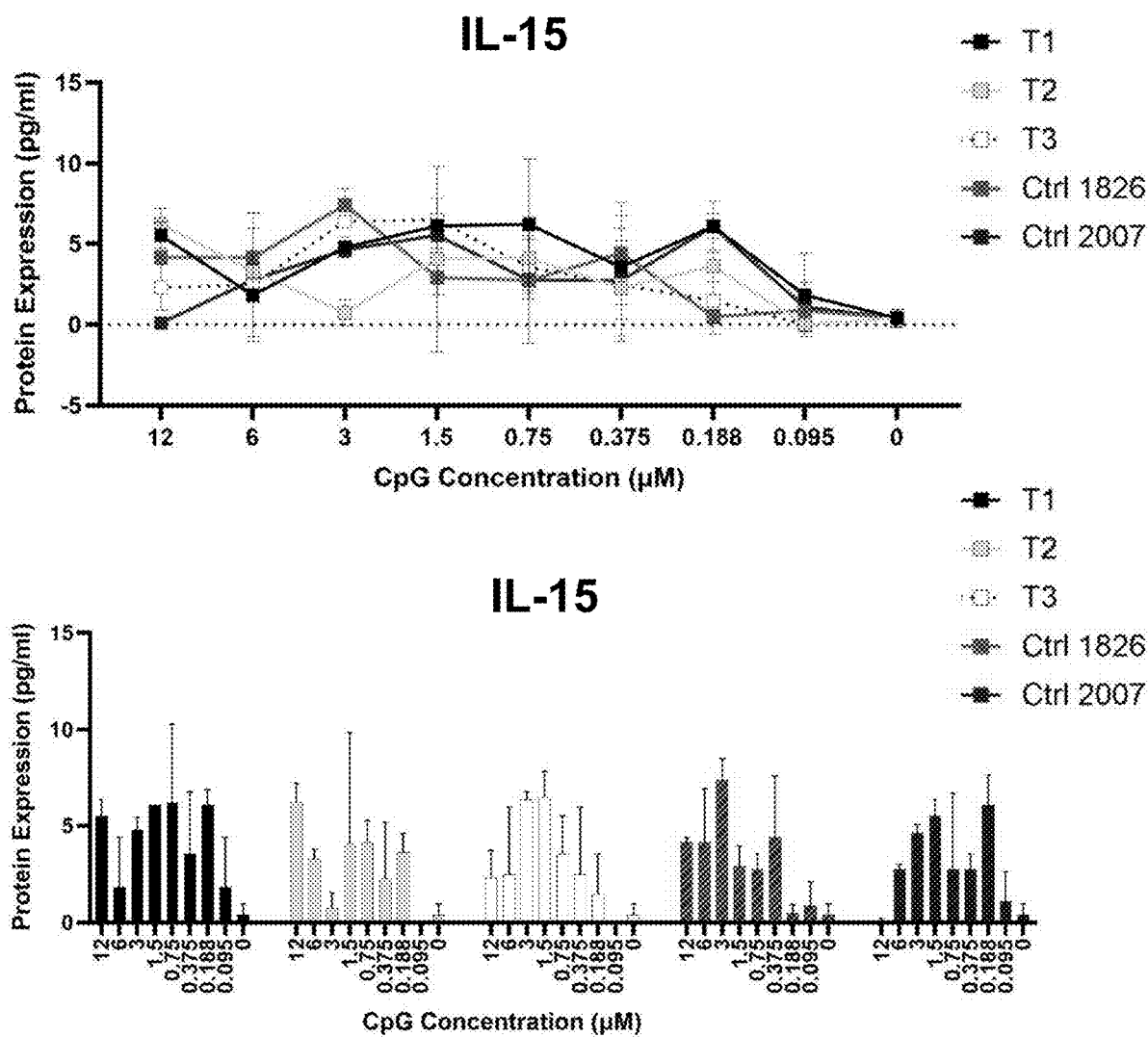
FIG. 15W depicts the protein target IL-15.
Figure 15X:
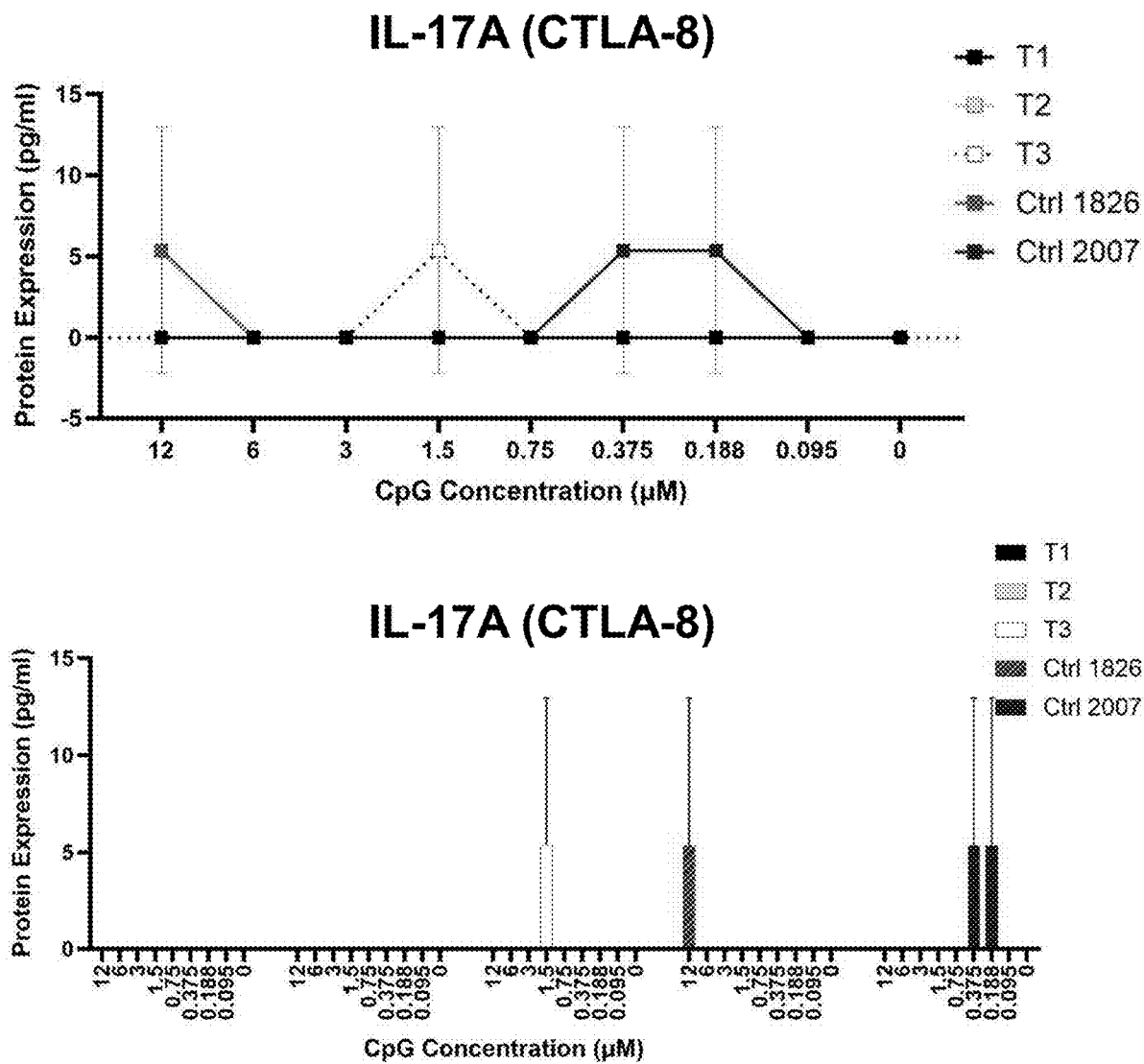
FIG. 15X depicts the protein target IL-17A (CTLA8).
Figure 15Y:
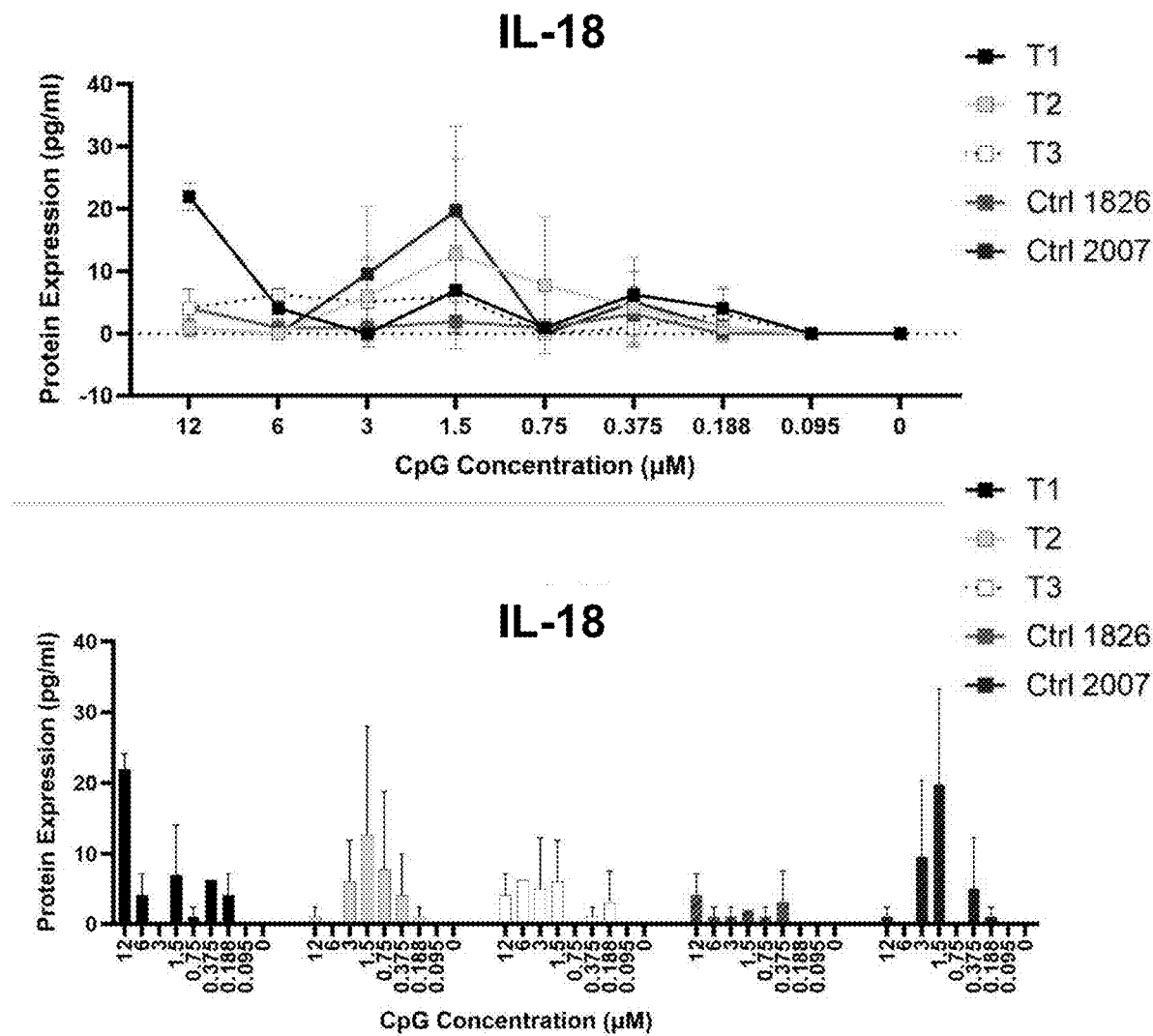
FIG. 15Y depicts the protein target IL-18.
Figure 15Z:
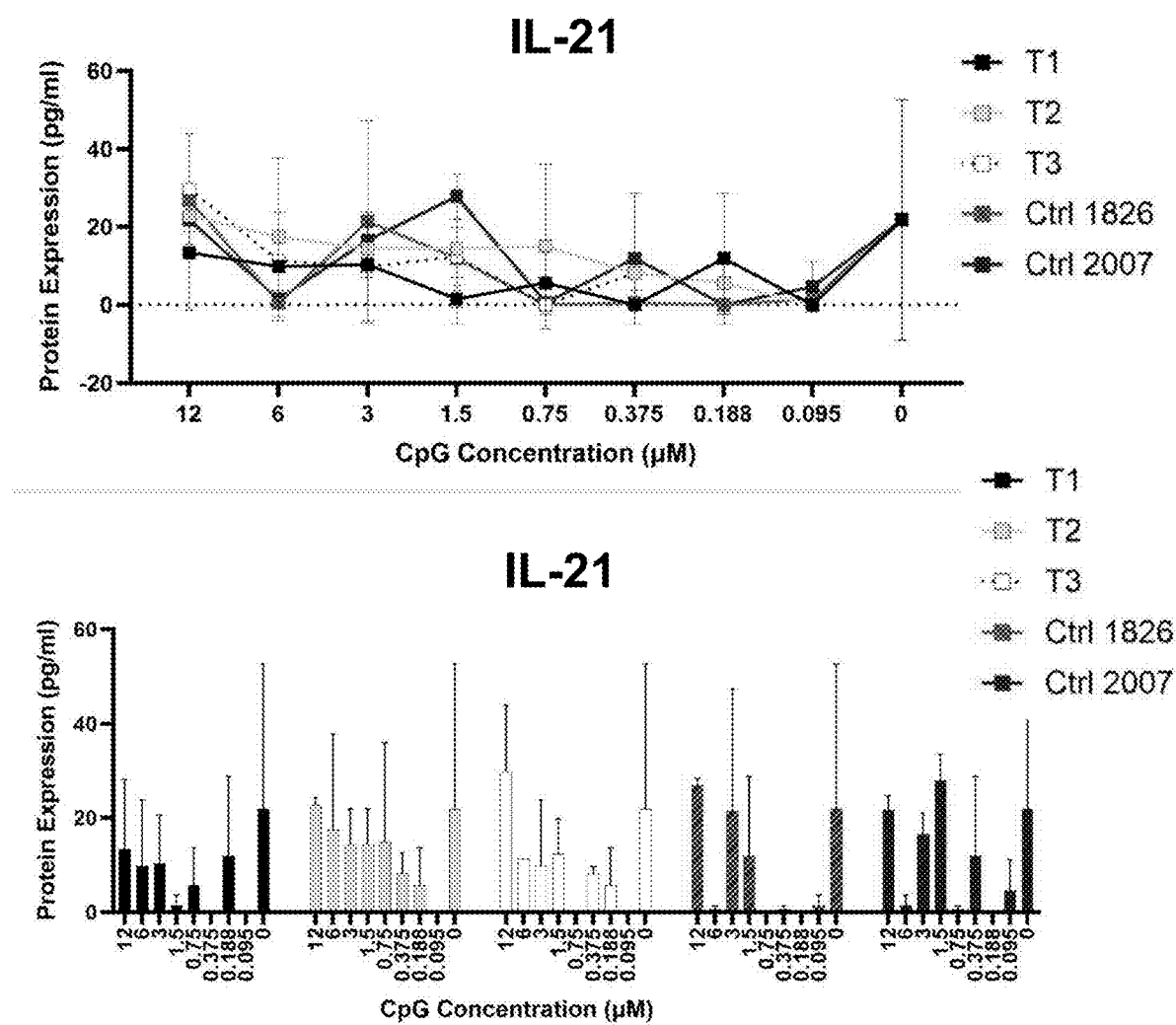
FIG. 15Z depicts the protein target IL-21.
Figure 15A:
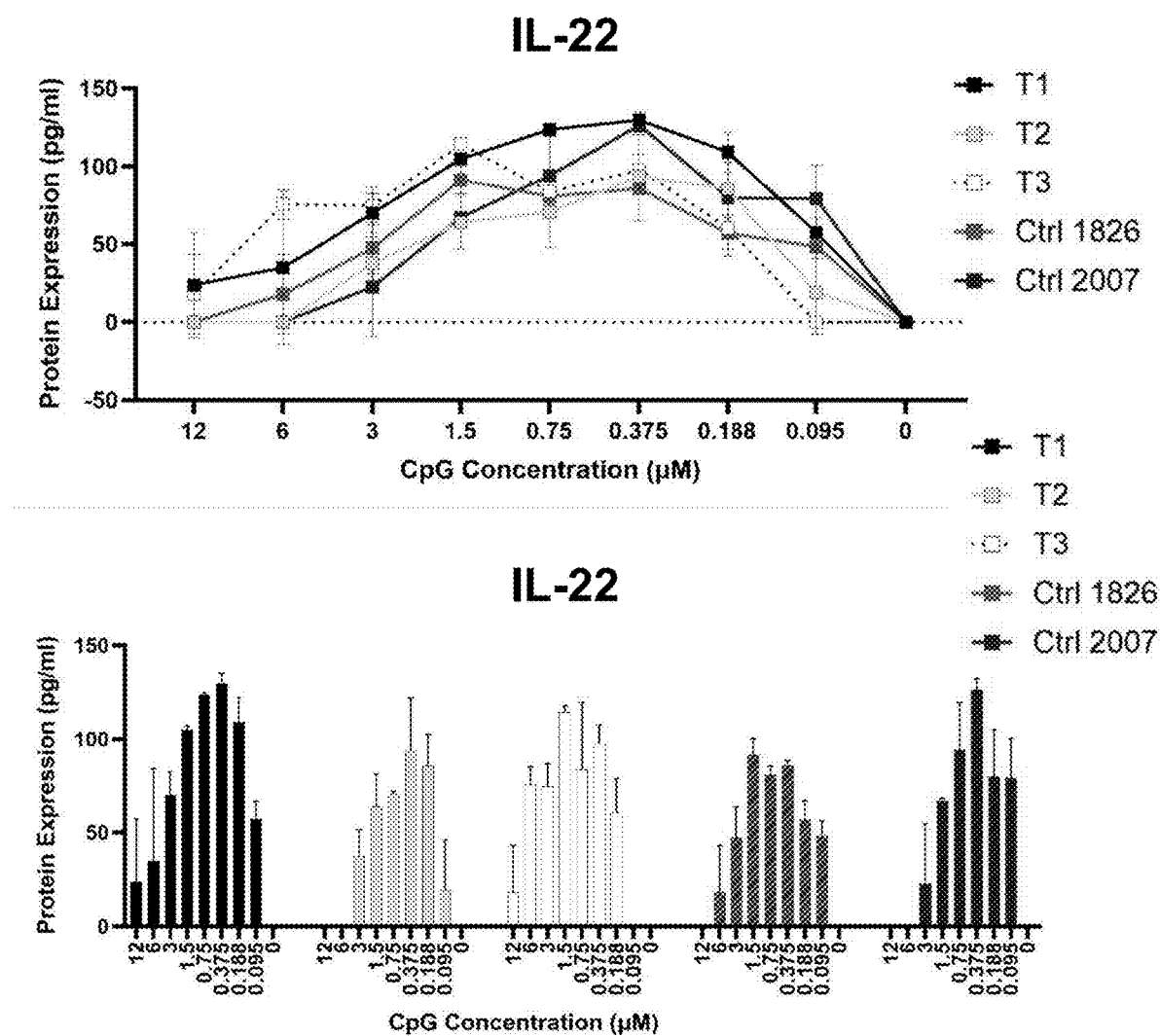
Figure 15A:
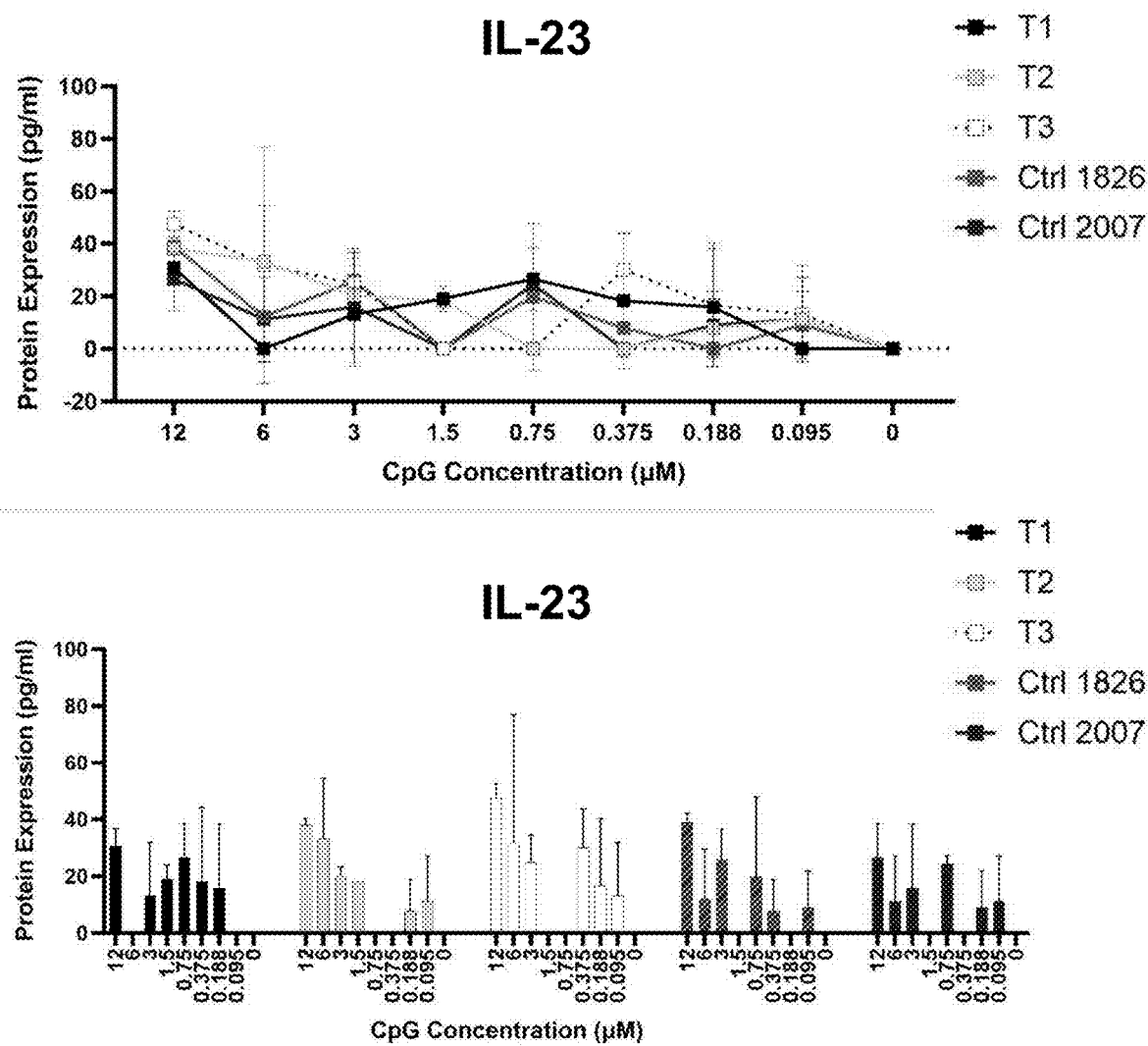
Figure 15A:
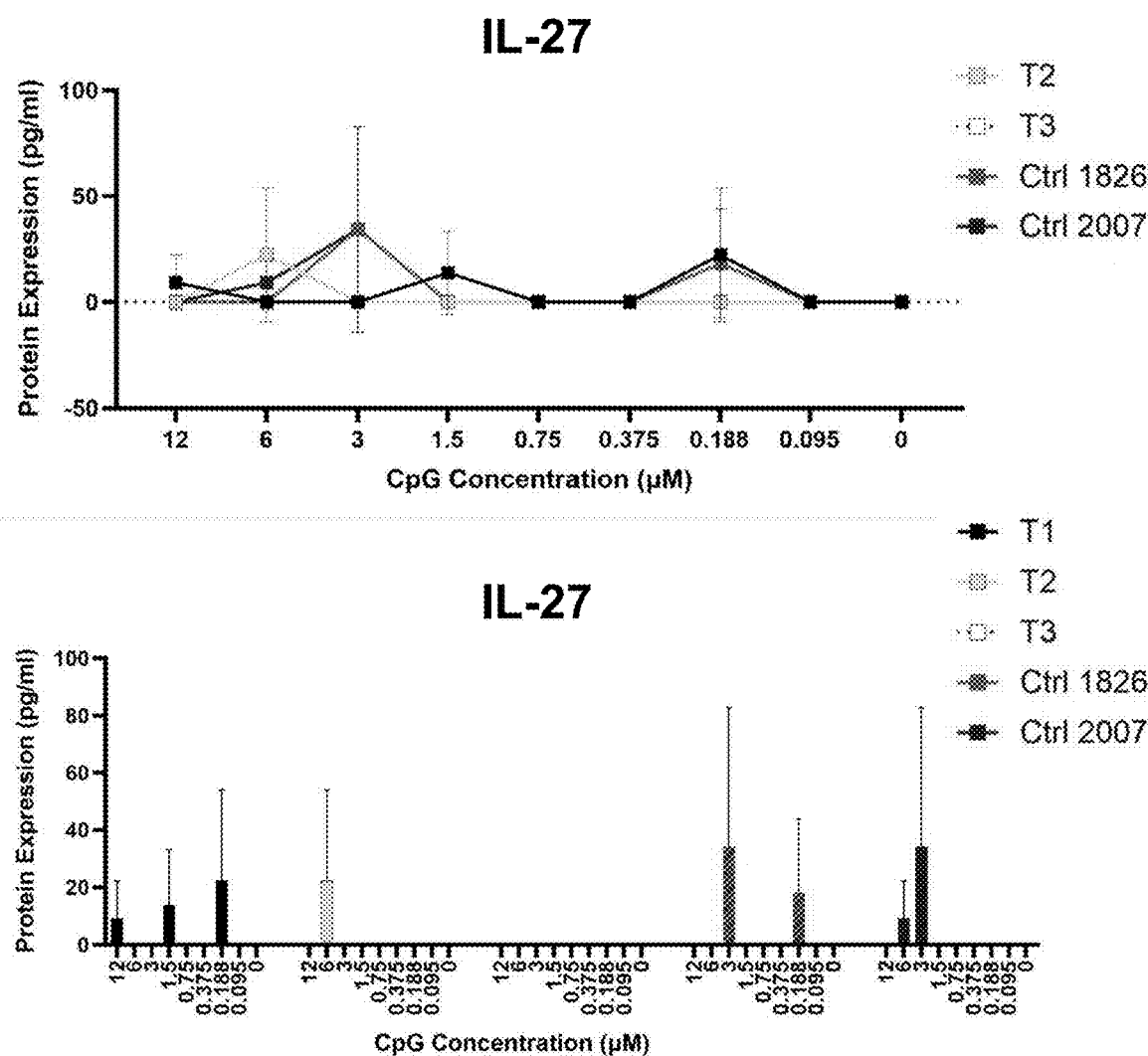
Figure 15A:
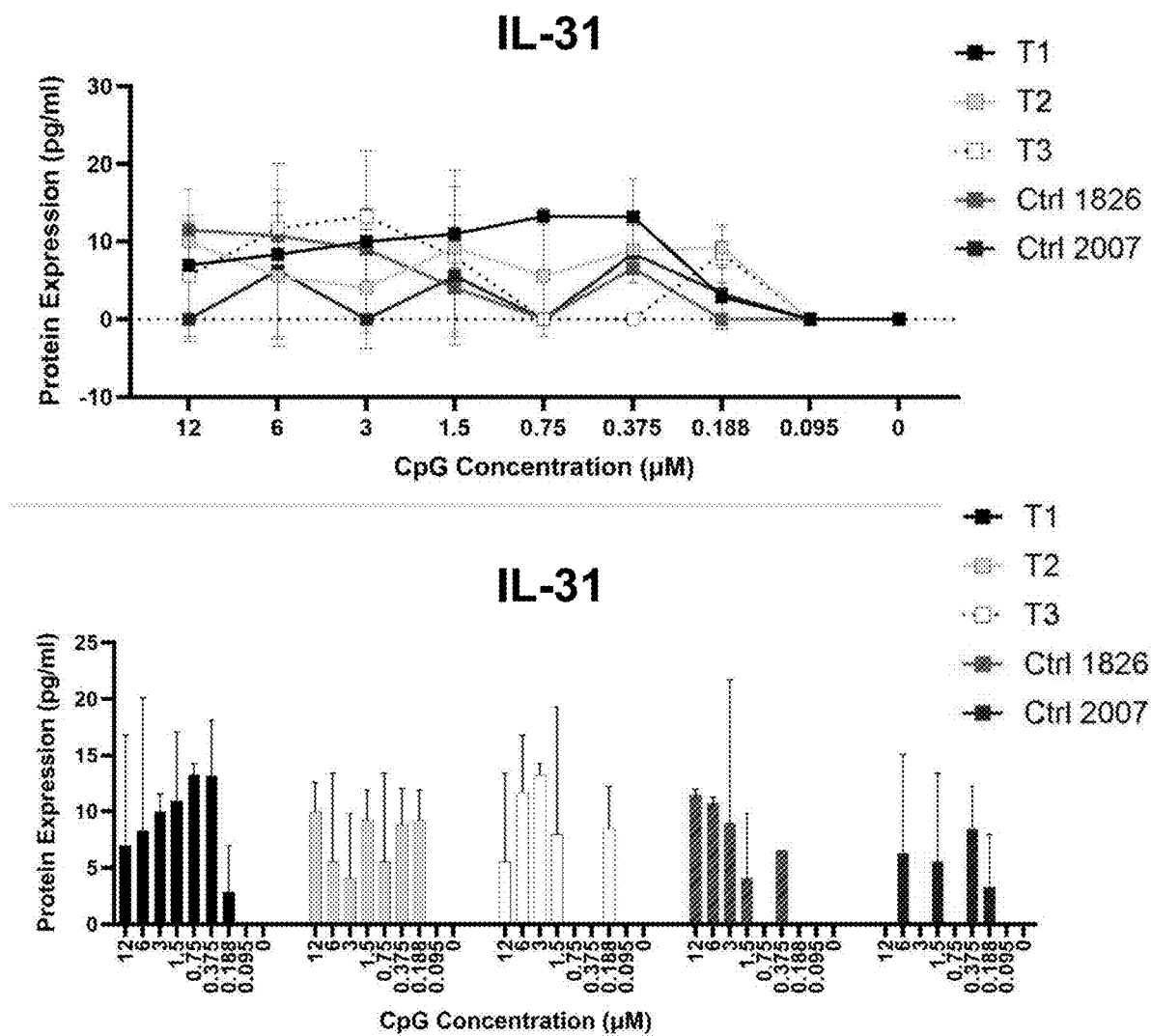
Figure 15A:
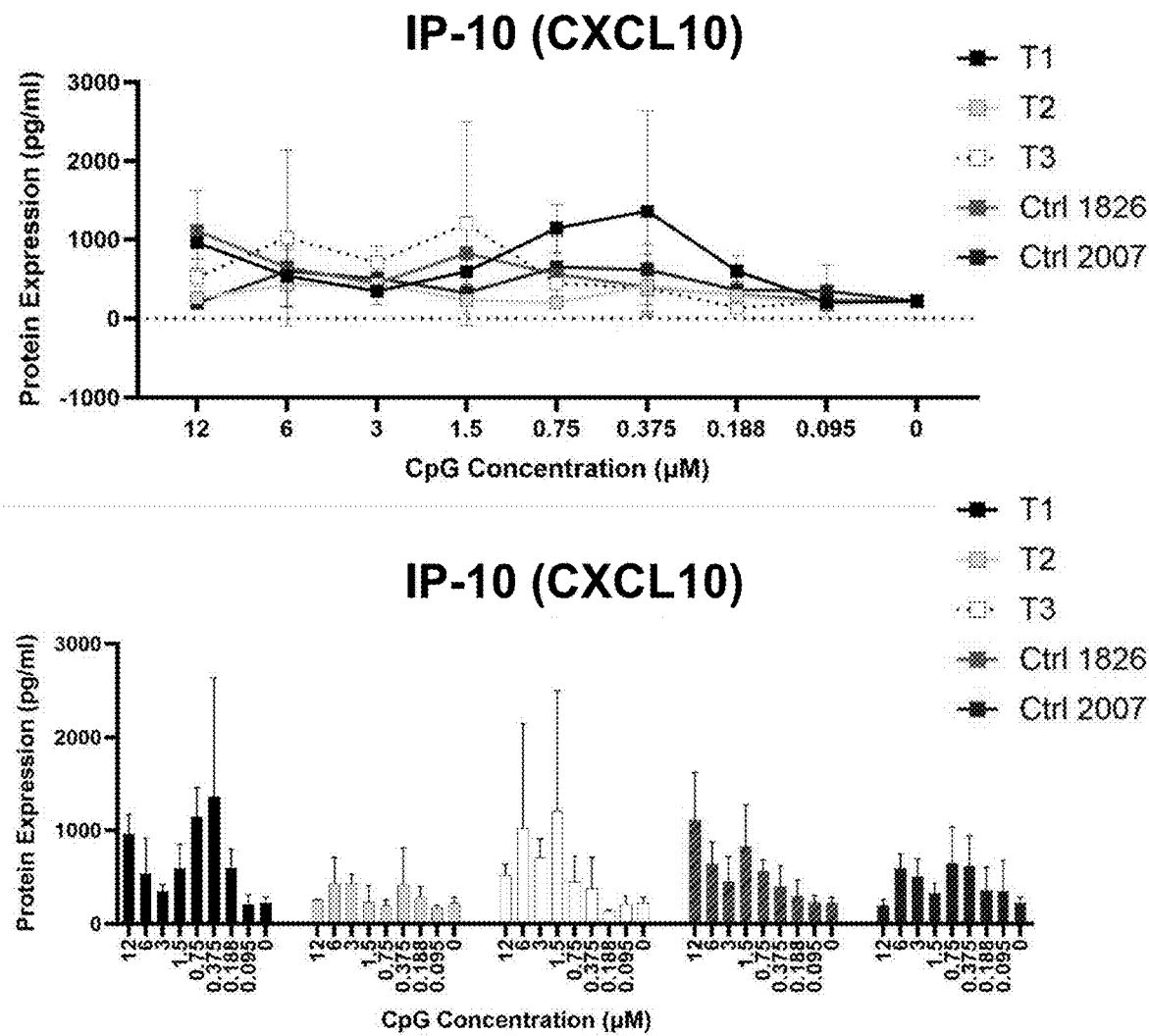
Figure 15A:
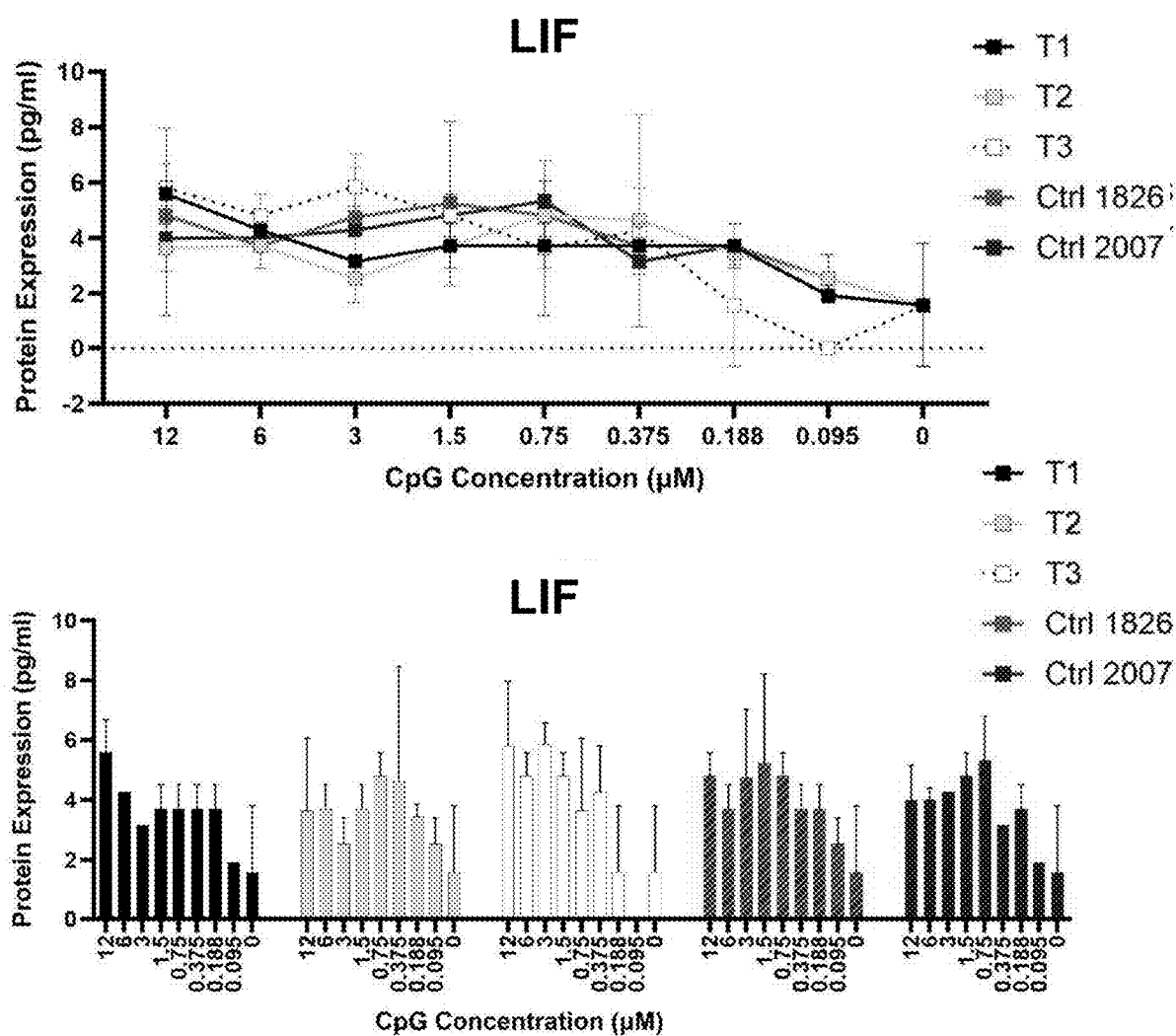
Figure 15A:
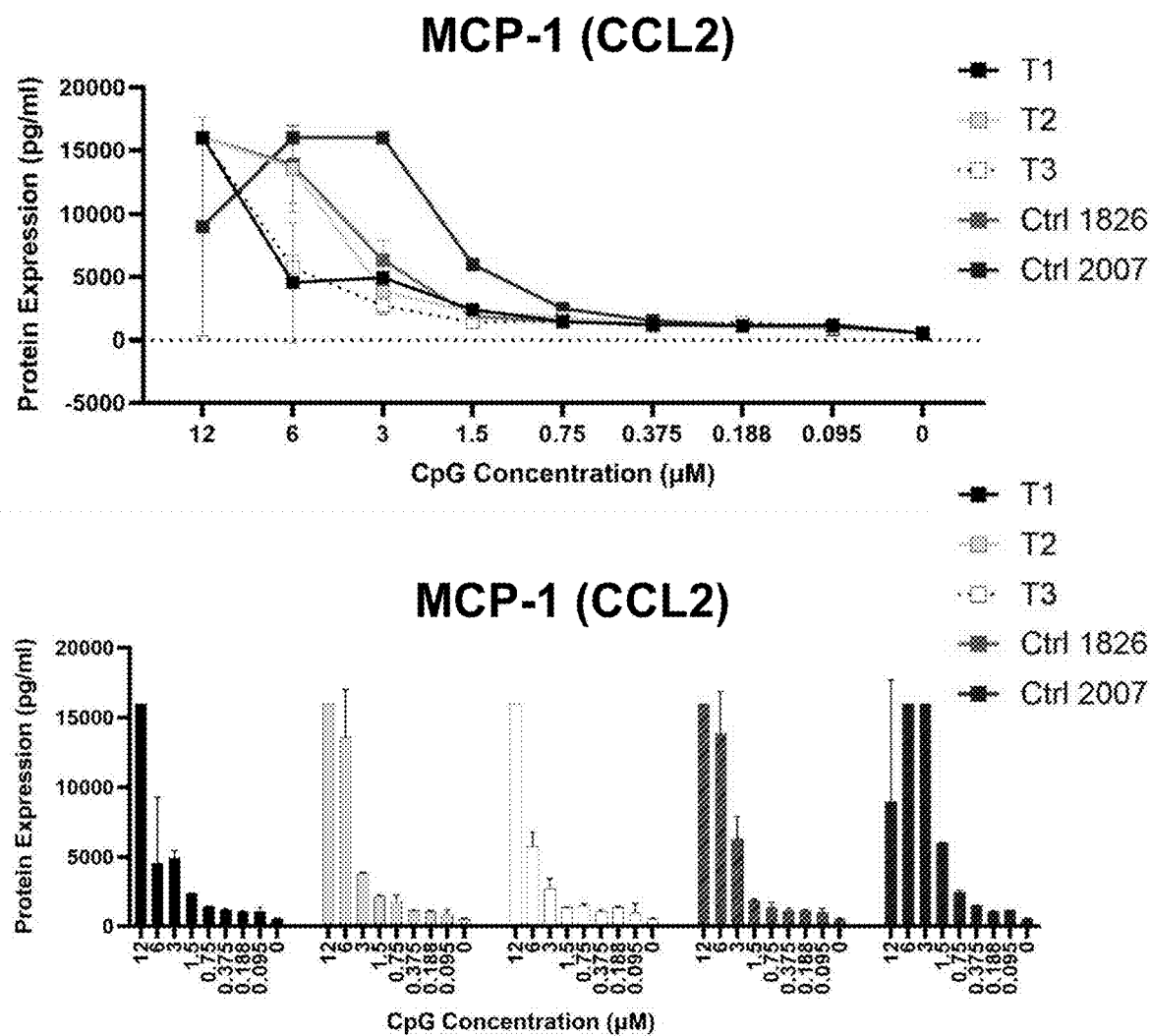
Figure 15A:
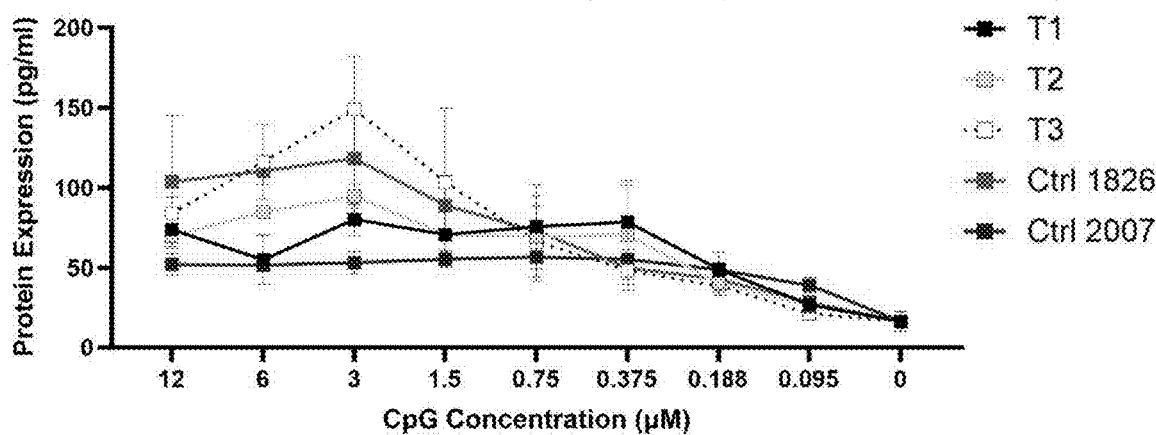
Figure 15A:
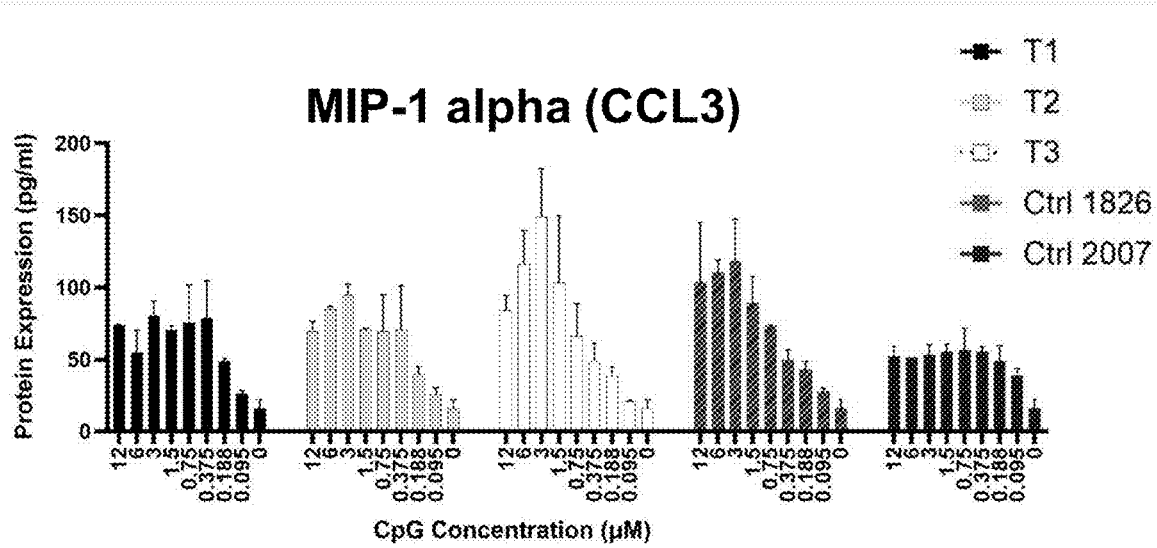
Figure 15A:
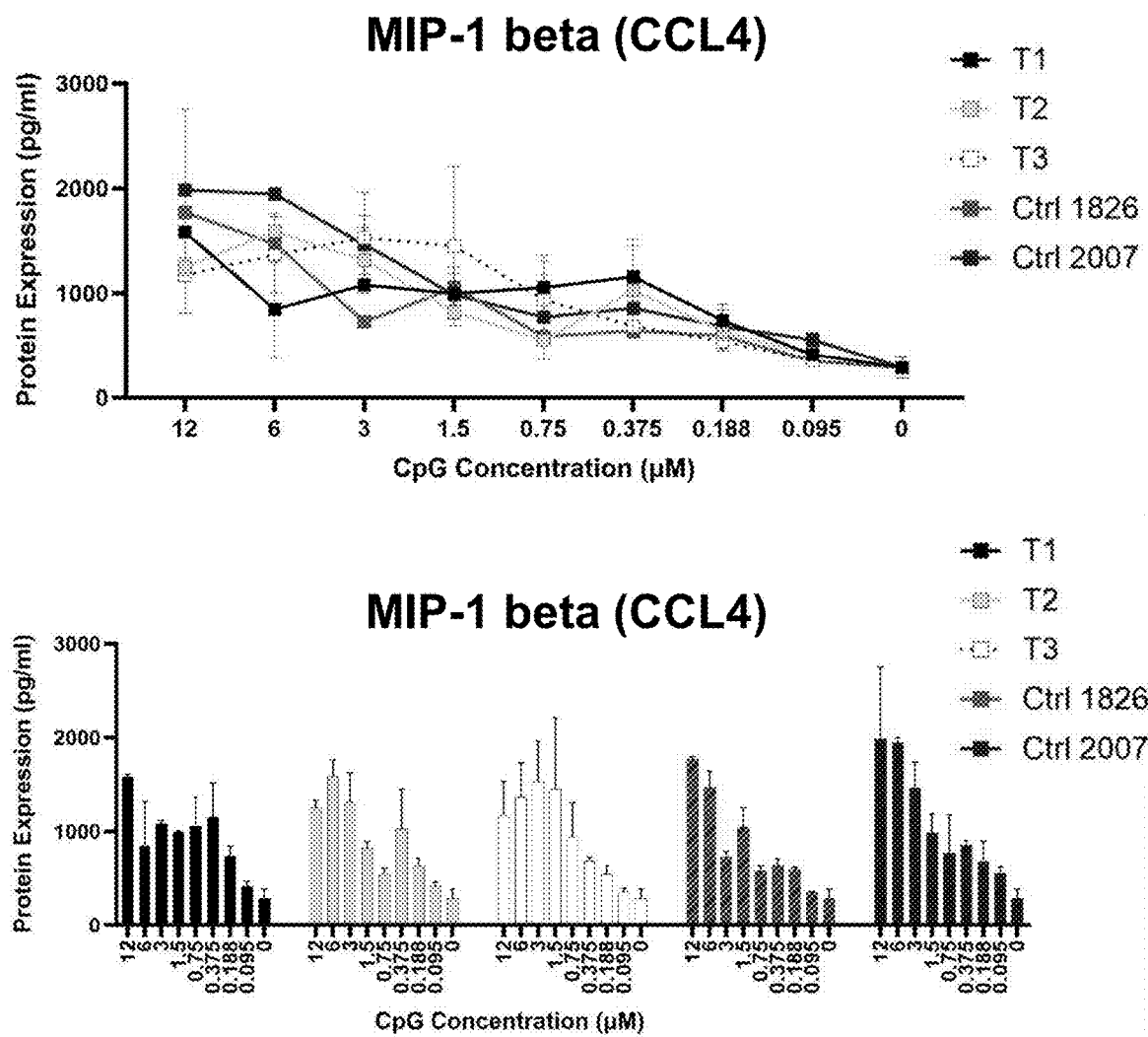
Figure 15A:
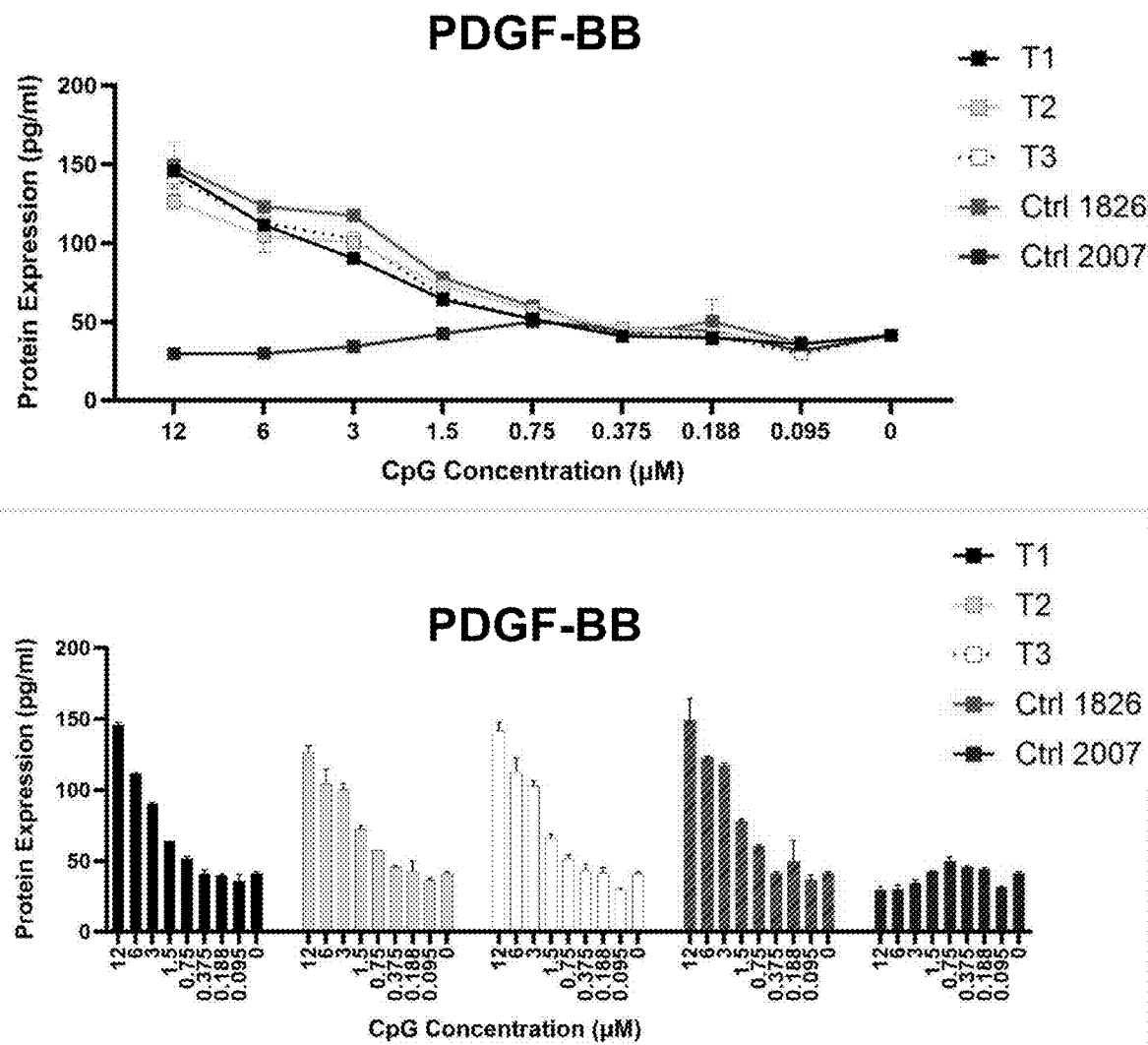
Figure 15A:
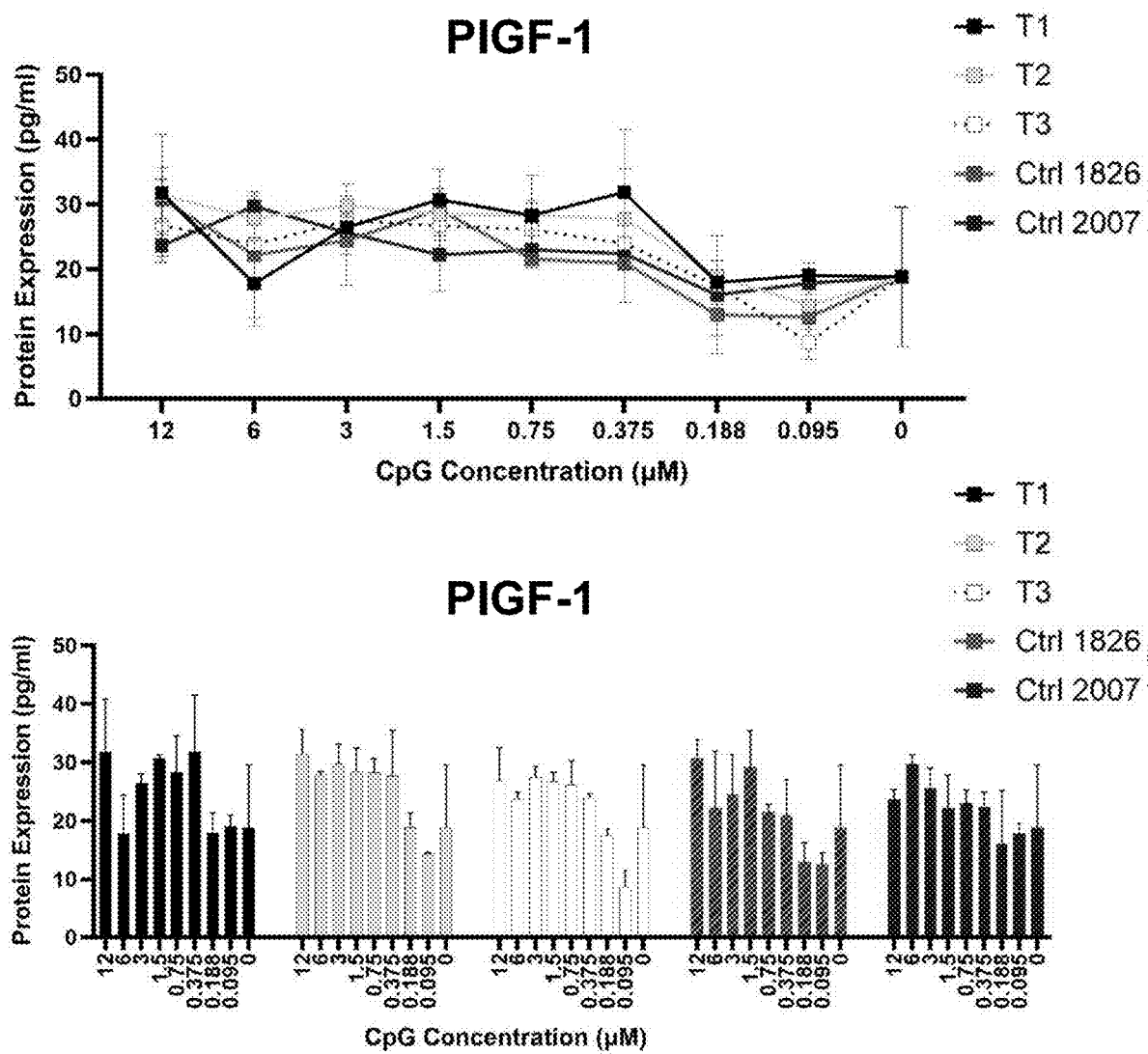
Figure 15A:
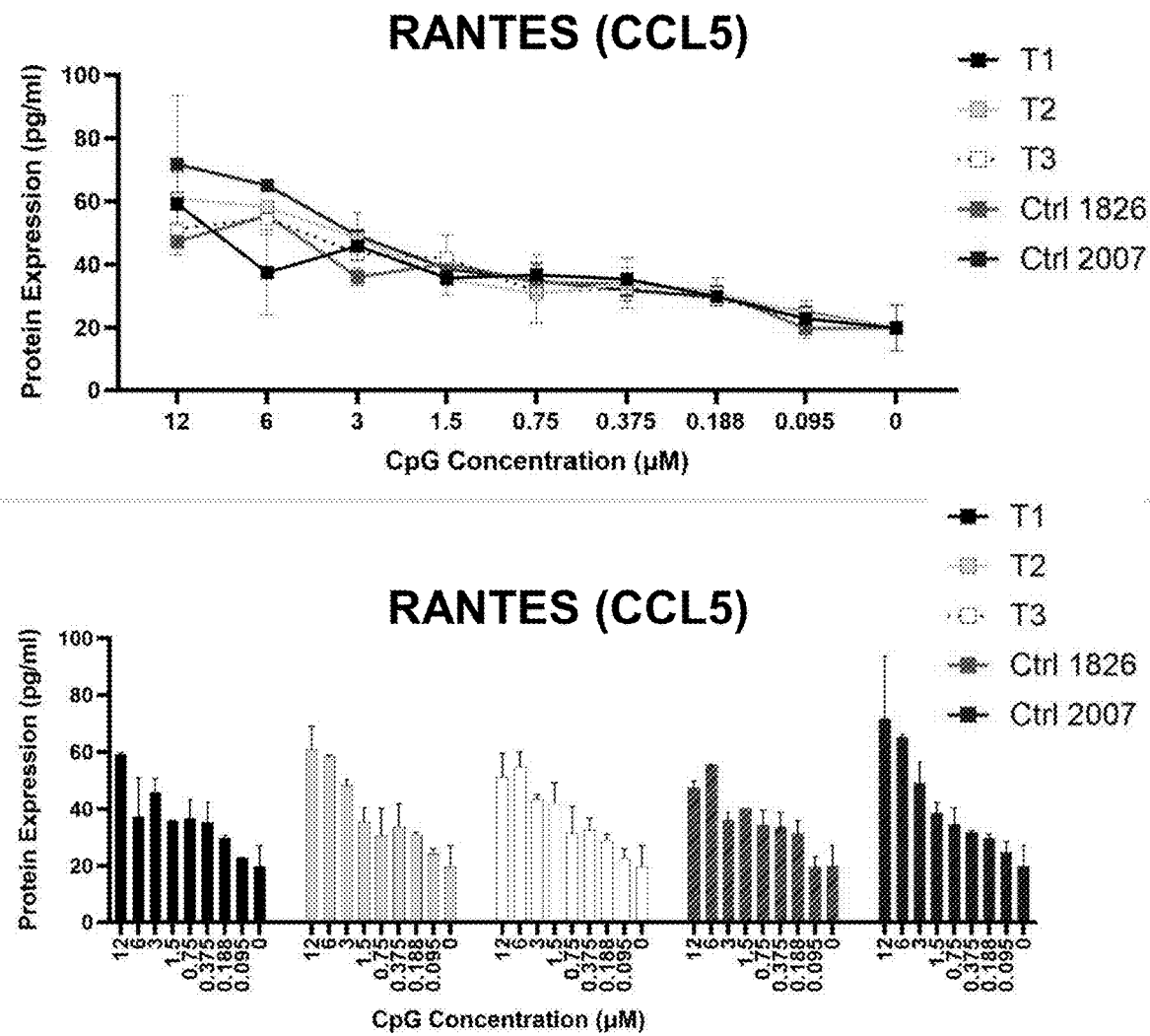
Figure 15A:
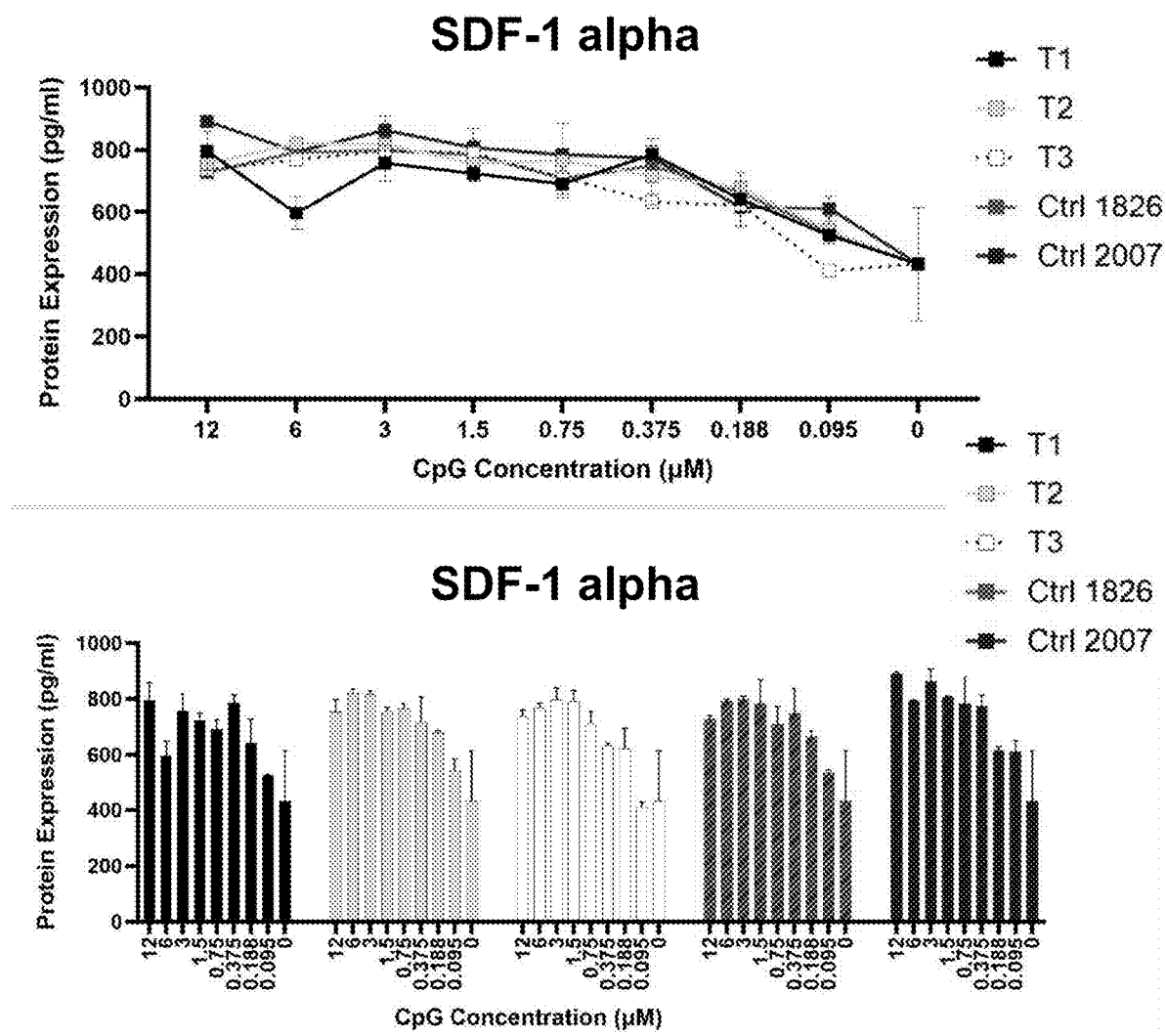
Figure 15A:
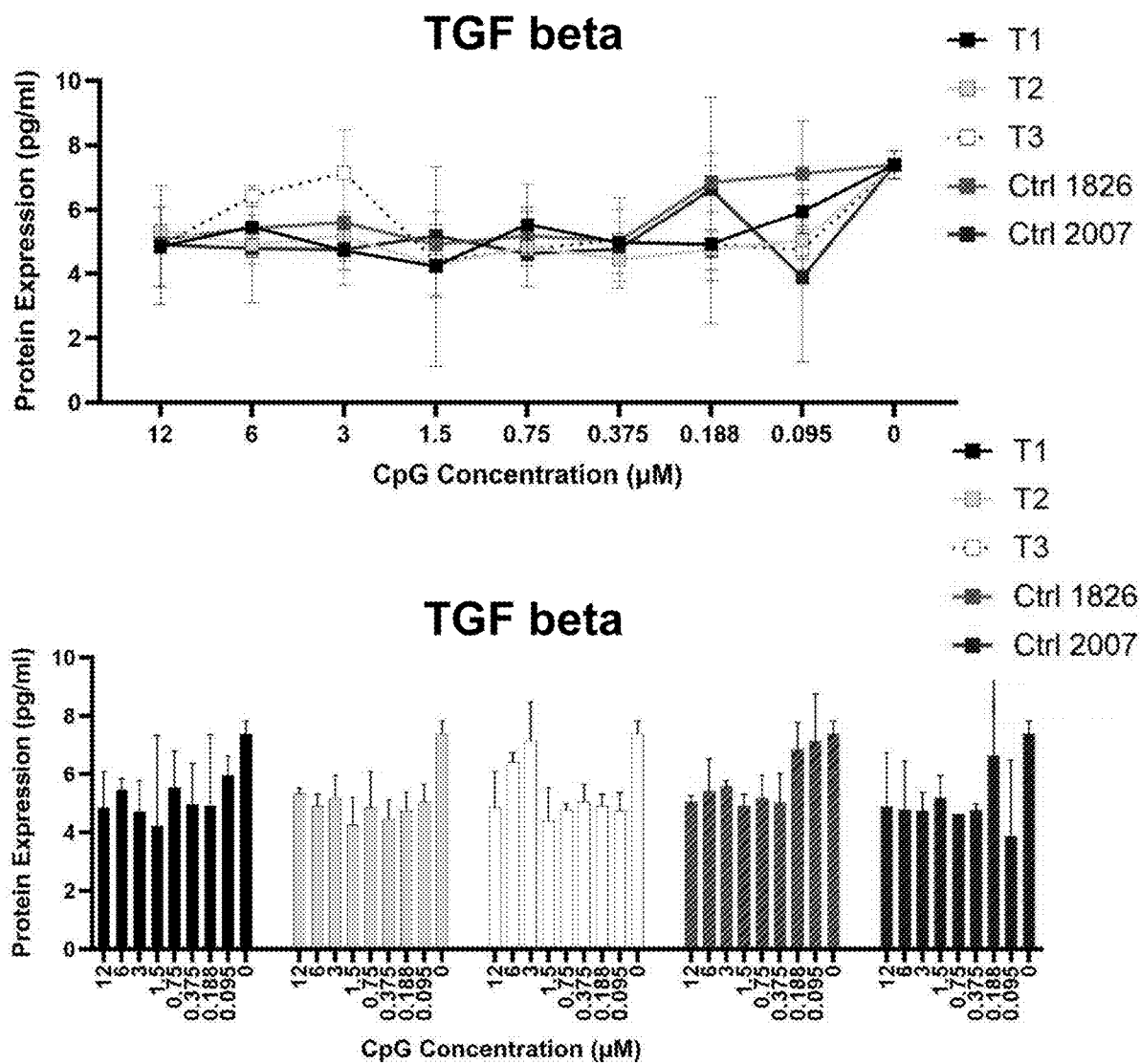
Figure 15A:
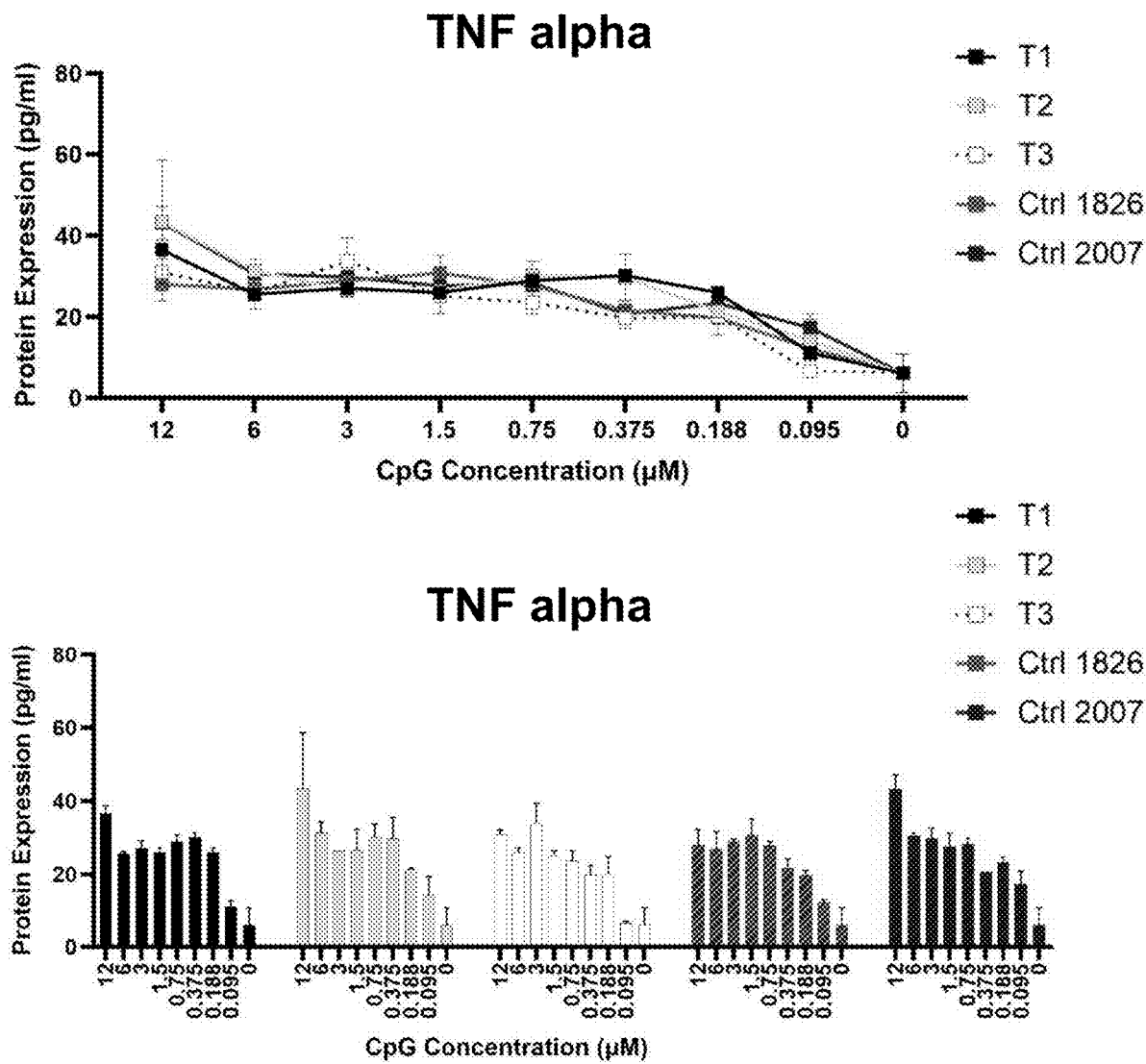
Figure 15A:
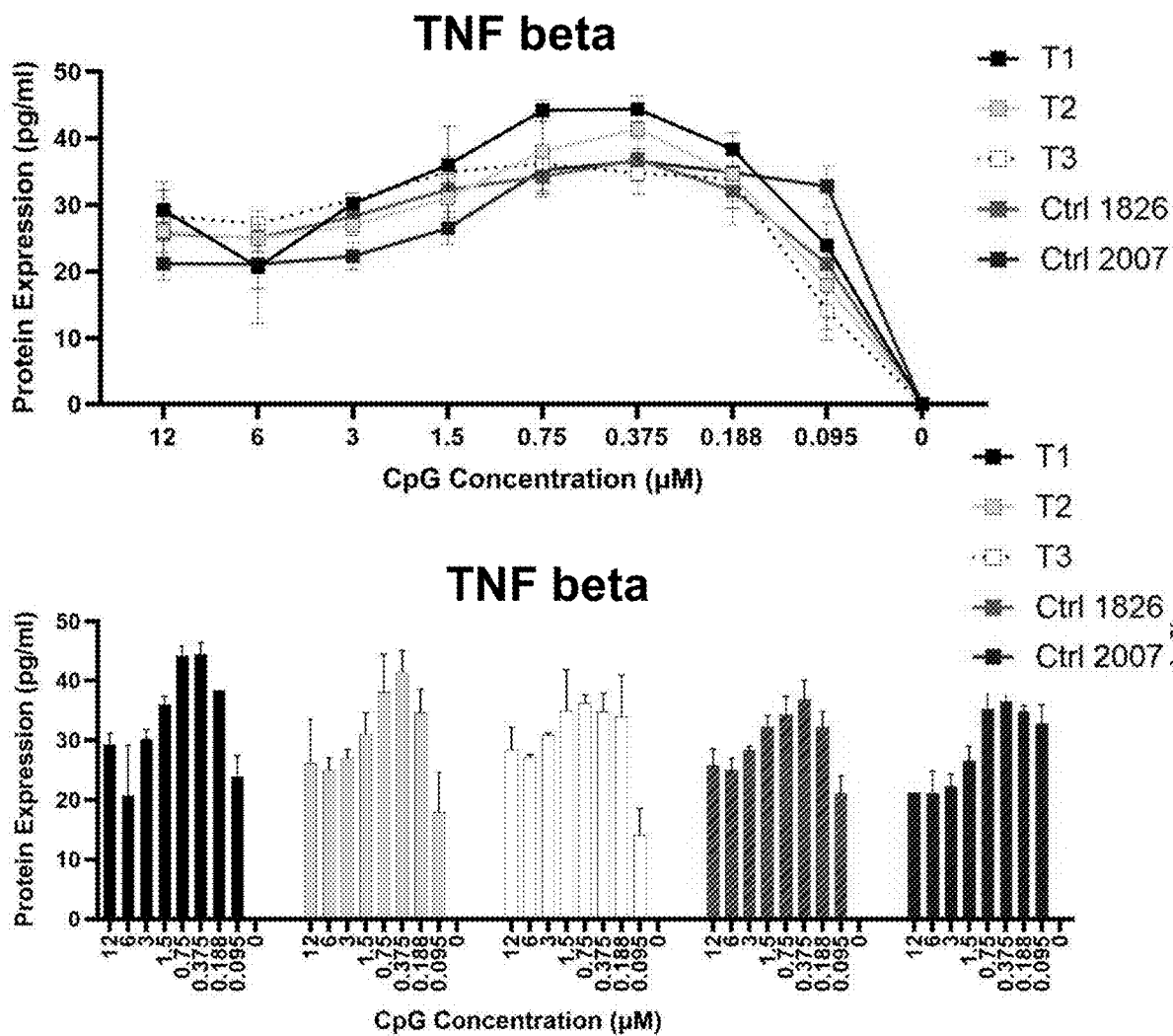
Figure 15A:
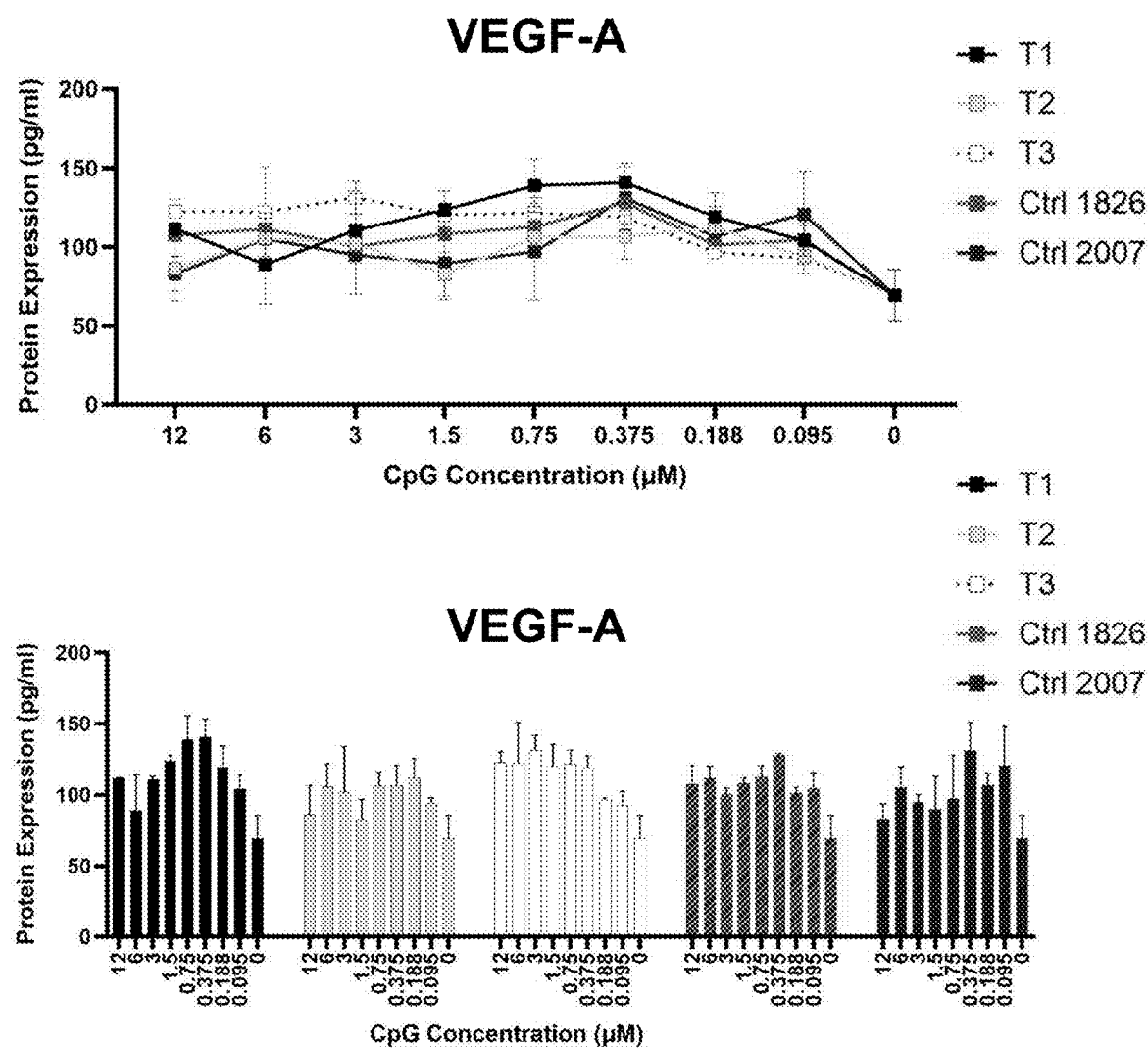

All synthetic CpG oligonucleotides tested resulted in significant changes in protein expression in human and mouse PBMCs after 48 hours of incubation in at least one protein target. Mouse protein targets include human B cell-activating factor (BAFF), betacellulin (BTC), Epithelial Neutrophil-Activating Protein 78 Mouse (ENA-78) also known as C-X-C motif chemokine 5 (CXCL5), Eotaxin also known as C-C motif chemokine 11 (CCL11), granulocyte colony-stimulating factor (G-CSF) also known as colony-stimulating factor 3 (CSF-3), granulocyte-macrophage colony-stimulating factor (GM-CSF), GRO alpha also known as chemokine (C-X-C motif) ligand 1 (CXCL1), type-1 interferon (IFN) alpha, IFN gamma, Immunoglobulin M (IgM), interleukin 1 (IL-1) alpha, IL-1 beta, IL-2, IL-2 receptor (IL-2R), IL-4, IL-5, IL-6, IL-7R alpha, IL-9, IL-10, IL-12p70, IL-13, IL-15, IL-17A also known as cytotoxic T-lymphocyte associated protein 8 (CTLA8), IL-18, IL-19, IL-23, IL-25 also known as IL-17E, IL-27, IL-31, IL-33, Interleukin 1 receptor-like 1 (IL1RL1), also known as IL-33R and ST2, Interferon gamma-induced protein 10 (IP-10) also known as CXCL10, Leptin, Leukemia inhibitory factor (LIF), monocyte chemoattractant protein 1 (MCP-1) also known as CCL2, MCP-3 also known as CCL7, macrophage colony-stimulating factor (M-CSF), macrophage inflammatory protein 1 (MIP-1) alpha also known as CCL3, MIP-1 beta also known as CCL4, MIP-2 alpha also known as CXCL2, Receptor activator of nuclear factor kappa-B ligand (RANKL), Regulated on activation, normal T cell expressed and secreted (RANTES) also known as CCL5, Transforming growth factor (TGF) beta, Tumor necrosis factor (TNF) alpha, and Vascular endothelial growth factor A (VEGF-A) (FIG. 14A-14AT). Human protein targets include Brain-derived neurotrophic factor (BDNF), Epidermal growth factor (EGF), Eotaxin (CCL11), Fibroblast growth factor 2 (FGF2), (GM-CSF), GRO alpha (CXCL1), Hepatocyte growth factor (HGF), IFN alpha, IFN gamma, IgM, IL-1 alpha, IL-1 beta, IL-1 RA, IL-2, IL-5, IL-6, IL-7, IL-8 (CXCL8), IL-9, IL-10, IL-12p70, IL-13, IL-15, IL-17A (CTLA-8), IL-18, IL-21, IL-22, IL-23, IL-27, IL-31, IP-10 (CXCL10), LIF, MCP-1 (CCL2), MIP-1 alpha (CCL3), MIP-1 beta (CCL4), Platelet-derived growth factor subunit B beta (PDGF-BB), Placenta growth factor 1 (PIGF-1), RANTES (CCL5), stromal cell-derived factor 1 (SDF-1) alpha, TGF beta, TNF alpha, TNF beta, VEGF-A (FIG. 15A-15AQ).

Protein expression varied by target protein, by PBMC species (mouse or human), and the type of synthetic CpG oligonucleotide and included no change in expression, increased expression, and decreased expression in various protein targets. Several proteins demonstrated a dose-dependent effect, which included increasing and decreasing protein expression with increasing CpG concentrations. For example, a significant dose-dependent increase in expression was observed in human PBMCs for the following protein targets: BDNF, HGF, IFN gamma, IgM, IL-1 alpha, IL-1 beta, IL-1RA, IL-2, IL-5, IL-6, IL-7, IL-10, IL-12p70, IL-18, IL-22, IL-23, IL-31, IP-10 (CXCL10), LIF, MCP-1 (CCL2), MIP-1 alpha (CCL3), MIP-1 beta (CCL4), PDGF-BB, RANTES, SDF-1 alpha, TNF alpha, TNF beta, and VEGF-A (p-values depicted in Table 6). The change in protein expression could be correlated with the relevance of the target protein on the intended biological effect of the synthetic CpG oligonucleotide.

TABLE 5

Protein expression p-value changes in mouse PBMC after treatment with CpG oligonucleotides

| Protein | Interaction between dose & type $F(32, 45)$ | Treatment dose $F(8, 45)$ | Treatment Type $F(4, 45)$ |
| --- | --- | --- | --- |
| BAFF | 0.9697 | <0.0001 | 0.0099 |
| Betacellulin (BTC) | <0.0001 | <0.0001 | <0.0001 |
| ENA-78 (CXCL5) | 0.0199 | <0.0001 | <0.0001 |
| Eotaxin (CCL11) | 0.4701 | 0.5053 | 0.5012 |
| G-CSF (CSF-3) | <0.0001 | 0.0002 | 0.0051 |
| GRO alpha (CXCL1) | 0.05356 | 0.0113 | 0.7464 |
| IFN alpha | 0.9999 | 0.0016 | 0.4764 |
| IFN gamma | <0.0001 | <0.0001 | <0.0001 |
| IgM | <0.0001 | <0.0001 | <0.0001 |
| IL-1 alpha | <0.0001 | <0.0001 | <0.0001 |
| IL-1 beta | 0.8015 | 0.0682 | 0.5632 |
| IL-2 | 0.7486 | <0.0001 | 0.0487 |
| IL-2R | 0.4180 | <0.0001 | 0.0051 |
| IL-4 | 0.1352 | <0.0001 | 0.0030 |
| IL-5 | 0.0752 | <0.0001 | 0.0212 |
| IL-6 | <0.0001 | <0.0001 | <0.0001 |
| IL-7R | 0.2490 | <0.0001 | 0.0212 |
| IL-9 | <0.0001 | <0.0001 | <0.0001 |
| IL-10 | <0.0001 | <0.0001 | <0.0001 |
| IL-12p70 | <0.0001 | <0.0001 | <0.0001 |
| IL-13 | 0.9905 | <0.0001 | 0.5131 |
| IL-15 | 0.0008 | <0.0001 | 0.0110 |
| IL-17A (CTLA-8) | 0.0878 | <0.0001 | <0.0001 |
| IL-18 | 0.0008 | <0.0001 | 0.0110 |
| IL-19 | 0.5876 | 0.0186 | 0.4775 |
| IL-23 | 0.8828 | <0.0001 | 0.0596 |
| IL-25 (IL-17E) | 0.1137 | <0.0001 | 0.0091 |
| IL-27 | <0.0001 | <0.0001 | 0.0010 |
| IL-31 | 0.4926 | 0.4494 | 0.4175 |
| IL-33 | 0.7816 | 0.0874 | 0.5166 |
| IL-33R (ST2) | 0.4926 | 0.4494 | 0.4175 |
| IP-10 (CXCL10) | 0.5466 | <0.0001 | 0.2381 |

TABLE 5-continued

Protein expression p-value changes in mouse PBMC after treatment with CpG oligonucleotides

| Protein | Interaction between dose & type $F(32, 45)$ | Treatment dose $F(8, 45)$ | Treatment Type $F(4, 45)$ |
| --- | --- | --- | --- |
| Leptin | 0.7636 | <0.0001 | 0.3754 |
| LIF | 0.4795 | 0.4814 | 0.4647 |
| MCP-1 (CCL2) | <0.0001 | <0.0001 | 0.0013 |
| MCP-3 (CCL7) | 0.0247 | <0.0001 | 0.0148 |
| M-CSF | 0.2984 | 0.0003 | 0.0080 |
| MIP-1 alpha (CCL3) | <0.0001 | <0.0001 | <0.0001 |
| MIP-1 beta (CCL4) | <0.0001 | <0.0001 | <0.0001 |
| MIP-2 alpha (CXCL2) | <0.0001 | <0.0001 | <0.0001 |
| RANKL | 0.1584 | 0.0005 | 0.0506 |
| RANTES (CCL5) | 0.0005 | <0.0001 | <0.0001 |
| TGF beta | 0.5016 | 0.5568 | 0.6059 |
| TNF alpha | 0.0006 | <0.0001 | <0.0001 |
| VEGF-A | 0.0111 | <0.0001 | <0.0001 |

TABLE 6

Protein expression p-value changes in human PBMC after treatment with CpG oligonucleotides

| Protein | Interaction between dose & type $F(32, 45)$ | Treatment dose $F(8, 45)$ | Treatment Type $F(4, 45)$ |
| --- | --- | --- | --- |
| BDNF | <0.0001 | <0.0001 | <0.0001 |
| EGF | 0.1038 | <0.0001 | 0.0147 |
| Eotaxin (CCL11) | 0.7018 | <0.0001 | 0.1138 |
| FGF-2 | 0.9996 | 0.0060 | 0.6056 |
| GM-CSF | 0.7198 | 0.0001 | 0.3054 |
| GRO alpha (CXCL1) | 0.3593 | <0.0001 | 0.6385 |
| HGF | 0.2528 | <0.0001 | <0.0001 |
| IFN alpha | 0.3111 | 0.0096 | 0.0427 |
| IFN gamma | 0.7598 | 0.0005 | 0.5918 |
| IgM | <0.0001 | <0.0001 | 0.0174 |
| IL-1 alpha | 0.5516 | <0.0001 | 0.6723 |
| IL-1 beta | 0.1865 | 0.4019 | 0.8624 |
| IL-1RA | 0.2800 | <0.0001 | 0.1409 |
| IL-2 | 0.6410 | <0.0001 | 0.0735 |
| IL-5 | 0.3964 | <0.0001 | 0.1164 |
| IL-6 | 0.1658 | <0.0001 | 0.3639 |
| IL-7 | 0.3970 | 0.0037 | 0.0470 |
| IL-8 (CXCL8) | 0.9277 | 0.0053 | 0.8661 |
| IL-9 | 0.7811 | 0.5772 | 0.1387 |
| IL-10 | 0.0003 | <0.0001 | <0.0001 |
| IL-12p70 | 0.2084 | <0.0001 | 0.0004 |
| IL-13 | 0.8170 | 0.2365 | 0.2296 |
| IL-15 | 0.0930 | <0.0001 | 0.2775 |
| IL-17A (CTLA-8) | 0.4739 | 0.7523 | 0.4864 |
| IL-18 | 0.0546 | 0.0007 | 0.2259 |
| IL-21 | 0.9989 | 0.0053 | 0.8280 |
| IL-22 | 0.0013 | <0.0001 | <0.0001 |
| IL-23 | 0.5160 | <0.0001 | 0.6010 |
| IL-27 | 0.7377 | 0.2715 | 0.6859 |
| IL-31 | 0.3815 | 0.0007 | 0.0926 |
| IP-10 (CXCL10) | 0.5878 | 0.0516 | 0.0733 |
| LIF | 0.8556 | <0.0001 | 0.8895 |
| MCP-1 (CCL2) | <0.0001 | <0.0001 | 0.0003 |
| MIP-1 alpha (CCL3) | 0.0055 | <0.0001 | 0.0003 |
| MIP-1 beta (CCL4) | 0.0351 | <0.0001 | 0.1153 |
| PDGF-BB | <0.0001 | <0.0001 | <0.0001 |
| PIGF-1 | 0.9311 | <0.0001 | 0.2029 |
| RANTES (CCL5) | 0.2415 | <0.0001 | 0.0997 |
| SDF-1 alpha | 0.7006 | <0.0001 | 0.0287 |
| TGF beta | 0.8790 | 0.0003 | 0.3990 |
| TNF alpha | 0.0780 | <0.0001 | 0.0088 |
| TNF beta | 0.0050 | <0.0001 | 0.0099 |
| VEGF-A | 0.1952 | <0.0001 | 0.0104 |

As one of skill in the art will readily appreciate, this disclosure has been presented for purposes of illustration and description. The disclosure above is not intended to limit the invention to the form or forms disclosed herein. Although the description of the disclosure has included description of one or more embodiments and certain variations and modifications, other variations and modifications are within the scope of the present disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

What is claimed is:

1. A composition comprising:
(i) a synthetic CpG oligonucleotide having the following sequence:
A*T*C*T*C*G*T*A*G*C*A*T*C*T*C*G*T*A*G*C (SEQ ID NO: 17);
A*T*C*T*C*G*G*A*G*C*A*T*C*T*C*G*G*A*G*C (SEQ ID NO: 19);
A*T*G*C*G*T*C*G*G*C*G*A*C*G*T*C*G*T*G*C (SEQ ID NO: 21);
T*A*G*C*G*T*C*G*A*C*G*A*C*G*T*C*G*A*T*G (SEQ ID NO: 22);
A*T*A*T*A*C*T*C*T*A*T*A*G*A*T*T*T*C*T*C (SEQ ID NO: 24),
A*T*C*T*CG*T*A*G*C*A*T*C*T*C*G*T*A*G*C (SEQ ID NO: 25);
A*T*C*T*CG*G*A*G*C*A*T*C*T*C*G*G*A*G*C (SEQ ID NO: 27);
A*T*G*C^G*T*C*G*G*C*G*A*C*G*T*C*G*T*G*C (SEQ ID NO: 29); or
T*A*G*C/G*T*C*G*A*C*G*A*C*G*T*C*G*A*T*G (SEQ ID NO: 30), wherein * indicates a phosphorothioate group and ^ indicates a phosphodiester group between a C and a G; and
(ii) an excipient, diluent, carrier, or any combination of these.

2. The composition of claim 1, wherein the synthetic CpG oligonucleotide in the composition is a TLR agonist.

3. The composition of claim 1, wherein the composition when contacted with a Ramos-Blue B lymphocyte cell, results in an increased concentration of secreted embryonic alkaline phosphatase (SEAP) from the Ramos-Blue B lymphocyte cell compared to an otherwise comparable Ramose-Blue B lymphocyte cell that is not contacted with the composition, in an in vitro assay.

4. The composition of claim 1, wherein the synthetic CpG oligonucleotide does not contain an epigenetic modification.

5. The composition of claim 1, wherein the synthetic CpG oligonucleotide comprises a chemical modification to a sugar of a nucleobase.

6. The composition of claim 1, wherein the composition is a pharmaceutical composition.

7. The composition of claim 6, wherein the pharmaceutical composition is in unit dose form.

8. The composition of claim 1, wherein the composition is formulated for topical administration.

9. The composition of claim 8, wherein the composition formulated for topical administration is in the form of a spray, a cream, a lotion, a powder, a gel, or is comprised on or in a pad, a bandage, or a dressing.

10. The composition of claim 1, wherein the synthetic CpG oligonucleotide is comprised in a vesicle, a liposome, a micelle, or a particle.

11. A method of accelerating a healing of a wound in a subject in need thereof, the method comprising contacting the wound of the subject with the composition of claim 1 to the subject in need thereof, in an amount effective to accelerate the healing of the wound in the subject, thereby accelerating the healing of the wound as compared to an otherwise comparable wound not contacted with the composition.

12. The method of claim 11, wherein the subject or the subject in need thereof is a human.

13. The method of claim 11, wherein the wound is a surgical wound, a scar, an unclean wound, a clean wound, a deep incisional wound, a superficial incisional wound, an ulcer, a diabetic ulcer, a diabetic foot ulcer, a radiation dermatitis, a burn, acne, a cancer, a skin cancer, a psoriasis, a combat wound, an infection, a viral infection, a bacterial infection, a fungal infection, a parasitic infection, a cutaneous infection, a subcutaneous infection, or any combination of these.

14. The method of claim 11, wherein the contacting comprises contacting a tissue in the subject in need thereof with the composition.

15. The method of claim 14, wherein the contacting is once, twice, three, four, five, six, seven, eight, nine, or ten times in a 24-hour period.

16. The method of claim 14, wherein the contacting occurs daily, every other day, every third day, every fourth day, every fifth day, every sixth day, weekly, every two weeks, every three weeks, once a month, once every three months, once every six months, once a year, or as needed.

17. The method of claim 11, wherein the synthetic CpG oligonucleotide is independently present in the composition in an amount ranging from about 1 ng to about 100 ng, about 100 ng to about 500 ng, about 500 ng to about 1 mg, or about 1 mg to about 100 mg, or about 1 ng to about 25,000 mg.

18. A composition formulated for topical administration comprising:
(i) a CpG oligonucleotide selected from the group consisting of:
A*T*C*T*C*G*T*A*G*C*A*T*C*T*C*G*T*A*G*C (SEQ ID NO: 17),
A*T*G*C*G*T*C*G*G*C*G*A*C*G*T*C*G*T*G*C (SEQ ID NO: 21),
A*T*C*T*C^G*T*A*G*C*A*T*C*T*C*G*T*A*G*C (SEQ ID NO: 25), and
A*T*G*CAG*T*C*G*G*C*G*A*C*G*T*C*G*T*G*C (SEQ ID NO: 29), wherein * indicates a phosphorothioate group and ^ indicates a phosphodiester group between a C and a G; and
(ii) an excipient,
in an effective amount to treat a wound in a subject in need thereof.

19. The composition of claim 18, wherein the CpG oligonucleotide is (SEQ ID NO: 17)
A*T*C*T*C*G*T*A*G*C*A*T*C*T*C*G*T*A*G*C.

20. The composition of claim 18, wherein the CpG oligonucleotide is (SEQ ID NO: 25)
A*T*C*T*C^G*T*A*G*C*A*T*C*T*C*G*T*A*G*C.

* * * * *

```
                               SEQUENCE LISTING

Sequence total quantity: 30
SEQ ID NO: 1            moltype = DNA  length = 40
FEATURE                 Location/Qualifiers
source                  1..40
                        mol_type = other DNA
                        organism = synthetic construct
misc_difference         1..9
                        note = Nucleotide with optional phosphorothioate linkage
misc_difference         12..14
                        note = Nucleotide with optional phosphorothioate linkage
misc_difference         17..19
                        note = Nucleotide with optional phosphorothioate linkage
misc_difference         22..24
                        note = Nucleotide with optional phosphorothioate linkage
misc_difference         27..29
                        note = Nucleotide with optional phosphorothioate linkage
misc_difference         32..40
                        note = Nucleotide with optional phosphorothioate linkage
misc_difference         1..3
                        note = This region may encompass 0-3 nucleotides
misc_difference         4..6
                        note = This region may encompass 0-3 nucleotides
misc_difference         7..9
                        note = This region may encompass 0-3 nucleotides
misc_difference         12..14
                        note = This region may encompass 0-3 nucleotides
misc_difference         17..19
                        note = This region may encompass 0-3 nucleotides
misc_difference         22..24
                        note = This region may encompass 0-3 nucleotides
misc_difference         27..29
                        note = This region may encompass 0-3 nucleotides
misc_difference         32..34
                        note = This region may encompass 0-3 nucleotides
misc_difference         35..37
                        note = This region may encompass 0-3 nucleotides
misc_difference         38..40
                        note = This region may encompass 0-3 nucleotides
SEQUENCE: 1
wwwwwgggc gtttcgaaac gaaacgtttc gwwwkkksss                               40

SEQ ID NO: 2            moltype = DNA  length = 40
FEATURE                 Location/Qualifiers
source                  1..40
                        mol_type = other DNA
                        organism = synthetic construct
misc_difference         1..9
                        note = a, t, g, c, or u with optional phosphorothioate
                          linkage
misc_difference         12..14
                        note = a, t, g, c, or u with optional phosphorothioate
                          linkage
misc_difference         17..19
                        note = a, t, g, c, or u with optional phosphorothioate
                          linkage
misc_difference         22..24
                        note = a, t, g, c, or u with optional phosphorothioate
                          linkage
misc_difference         27..29
                        note = a, t, g, c, or u with optional phosphorothioate
                          linkage
misc_difference         32..40
                        note = a, t, g, c, or u with optional phosphorothioate
                          linkage
misc_difference         1..3
                        note = This region may encompass 0-3 nucleotides
misc_difference         4..6
```

```
                        note = This region may encompass 0-3 nucleotides
misc_difference         7..9
                        note = This region may encompass 0-3 nucleotides
misc_difference         12..14
                        note = This region may encompass 0-3 nucleotides
misc_difference         17..19
                        note = This region may encompass 0-3 nucleotides
misc_difference         22..24
                        note = This region may encompass 0-3 nucleotides
misc_difference         27..29
                        note = This region may encompass 0-3 nucleotides
misc_difference         32..34
                        note = This region may encompass 0-3 nucleotides
misc_difference         35..37
                        note = This region may encompass 0-3 nucleotides
misc_difference         38..40
                        note = This region may encompass 0-3 nucleotides
SEQUENCE: 2
nnnnnnnnnc gnnncgnnnc gnnncgnnnc gnnnnnnnnn                                 40

SEQ ID NO: 3            moltype = DNA  length = 52
FEATURE                 Location/Qualifiers
source                  1..52
                        mol_type = other DNA
                        organism = synthetic construct
misc_difference         1..12
                        note = Nucleotide with optional phosphorothioate linkage
misc_difference         15..38
                        note = Nucleotide with optional phosphorothioate linkage
misc_difference         41..52
                        note = Nucleotide with optional phosphorothioate linkage
misc_difference         1..3
                        note = This region may encompass 0-3 nucleotides
misc_difference         4..6
                        note = This region may encompass 0-3 nucleotides
misc_difference         7..9
                        note = This region may encompass 0-3 nucleotides
misc_difference         10..12
                        note = This region may encompass 0-3 nucleotides
misc_difference         15..17
                        note = This region may encompass 0-3 nucleotides
misc_difference         18..20
                        note = This region may encompass 0-3 nucleotides
misc_difference         21..23
                        note = This region may encompass 0-3 nucleotides
misc_difference         24..26
                        note = This region may encompass 0-3 nucleotides
misc_difference         27..29
                        note = This region may encompass 0-3 nucleotides
misc_difference         30..32
                        note = This region may encompass 0-3 nucleotides
misc_difference         33..35
                        note = This region may encompass 0-3 nucleotides
misc_difference         36..38
                        note = This region may encompass 0-3 nucleotides
misc_difference         41..43
                        note = This region may encompass 0-3 nucleotides
misc_difference         44..46
                        note = This region may encompass 0-3 nucleotides
misc_difference         47..49
                        note = This region may encompass 0-3 nucleotides
misc_difference         50..52
                        note = This region may encompass 0-3 nucleotides
SEQUENCE: 3
aaatttccct ttcgkkkaaa gggcccaaat ttccctttcg wwwaaagggc cc                   52

SEQ ID NO: 4            moltype =  length =
SEQUENCE: 4
000

SEQ ID NO: 5            moltype = DNA  length = 20
FEATURE                 Location/Qualifiers
source                  1..20
                        mol_type = other DNA
                        organism = synthetic construct
misc_difference         1..19
                        note = Nucleotide with optional phosphorothioate linkage
SEQUENCE: 5
atcacgtagc atcacgtagc                                                       20
```

```
SEQ ID NO: 6                moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 6
atcacggagc atcacggagc                                                       20

SEQ ID NO: 7                moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 7
atctcgtagc atctcgtagc                                                       20

SEQ ID NO: 8                moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 8
atctcggagc atctcggagc                                                       20

SEQ ID NO: 9                moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 9
atcgcgtagc atcgcgtagc                                                       20

SEQ ID NO: 10               moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 10
atcgcggagc atcgcggagc                                                       20

SEQ ID NO: 11               moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 11
attcgtcggc gtcgacggtc                                                       20

SEQ ID NO: 12               moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 12
atgcgacgtc gacgtcggtc                                                       20

SEQ ID NO: 13               moltype = DNA  length = 20
FEATURE                     Location/Qualifiers
source                      1..20
                            mol_type = other DNA
                            organism = synthetic construct
misc_difference             1..19
                            note = Nucleotide with optional phosphorothioate linkage
SEQUENCE: 13
```

```
atacgacgtc gtcgtcgatc                                              20

SEQ ID NO: 14           moltype = DNA  length = 20
FEATURE                 Location/Qualifiers
source                  1..20
                        mol_type = other DNA
                        organism = synthetic construct
misc_difference         1..19
                        note = Nucleotide with optional phosphorothioate linkage
SEQUENCE: 14
atgcgtcggc gacgtcgtgc                                              20

SEQ ID NO: 15           moltype = DNA  length = 20
FEATURE                 Location/Qualifiers
source                  1..20
                        mol_type = other DNA
                        organism = synthetic construct
misc_difference         1..19
                        note = Nucleotide with optional phosphorothioate linkage
SEQUENCE: 15
gtacgacgtc gtcgacgtga                                              20

SEQ ID NO: 16           moltype = DNA  length = 20
FEATURE                 Location/Qualifiers
source                  1..20
                        mol_type = other DNA
                        organism = synthetic construct
misc_difference         1..19
                        note = Nucleotide with optional phosphorothioate linkage
SEQUENCE: 16
tagcgtcgac gacgtcgatg                                              20

SEQ ID NO: 17           moltype = DNA  length = 20
FEATURE                 Location/Qualifiers
source                  1..20
                        mol_type = other DNA
                        organism = synthetic construct
modified_base           1..19
                        mod_base = OTHER
                        note = Nucleotide with phosphorothioate linkage
SEQUENCE: 17
atctcgtagc atctcgtagc                                              20

SEQ ID NO: 18           moltype = DNA  length = 20
FEATURE                 Location/Qualifiers
source                  1..20
                        mol_type = other DNA
                        organism = synthetic construct
modified_base           1..19
                        mod_base = OTHER
                        note = Nucleotide with phosphorothioate linkage
SEQUENCE: 18
atctcgtagc atctcgtagc                                              20

SEQ ID NO: 19           moltype = DNA  length = 20
FEATURE                 Location/Qualifiers
source                  1..20
                        mol_type = other DNA
                        organism = synthetic construct
modified_base           1..19
                        mod_base = OTHER
                        note = Nucleotide with phosphorothioate linkage
SEQUENCE: 19
atctcggagc atctcggagc                                              20

SEQ ID NO: 20           moltype = DNA  length = 20
FEATURE                 Location/Qualifiers
source                  1..20
                        mol_type = other DNA
                        organism = synthetic construct
modified_base           1..19
                        mod_base = OTHER
                        note = Nucleotide with phosphorothioate linkage
SEQUENCE: 20
atctcggagc atctcggagc                                              20

SEQ ID NO: 21           moltype = DNA  length = 20
FEATURE                 Location/Qualifiers
source                  1..20
```

```
                            mol_type = other DNA
                            organism = synthetic construct
modified_base               1..19
                            mod_base = OTHER
                            note = Nucleotide with phosphorothioate linkage
SEQUENCE: 21
atgcgtcggc gacgtcgtgc                                               20

SEQ ID NO: 22               moltype = DNA  length = 20
FEATURE                     Location/Qualifiers
source                      1..20
                            mol_type = other DNA
                            organism = synthetic construct
modified_base               1..19
                            mod_base = OTHER
                            note = Nucleotide with phosphorothioate linkage
SEQUENCE: 22
tagcgtcgac gacgtcgatg                                               20

SEQ ID NO: 23               moltype = DNA  length = 20
FEATURE                     Location/Qualifiers
source                      1..20
                            mol_type = other DNA
                            organism = synthetic construct
modified_base               1..19
                            mod_base = OTHER
                            note = Nucleotide with phosphorothioate linkage
SEQUENCE: 23
atgcactctg caggcttctc                                               20

SEQ ID NO: 24               moltype = DNA  length = 20
FEATURE                     Location/Qualifiers
source                      1..20
                            mol_type = other DNA
                            organism = synthetic construct
modified_base               1..19
                            mod_base = OTHER
                            note = Nucleotide with phosphorothioate linkage
SEQUENCE: 24
atatactcta tagatttctc                                               20

SEQ ID NO: 25               moltype = DNA  length = 20
FEATURE                     Location/Qualifiers
source                      1..20
                            mol_type = other DNA
                            organism = synthetic construct
modified_base               1..4
                            mod_base = OTHER
                            note = Nucleotide with phosphorothioate linkage
modified_base               6..19
                            mod_base = OTHER
                            note = Nucleotide with phosphorothioate linkage
SEQUENCE: 25
atctcgtagc atctcgtagc                                               20

SEQ ID NO: 26               moltype = DNA  length = 20
FEATURE                     Location/Qualifiers
source                      1..20
                            mol_type = other DNA
                            organism = synthetic construct
modified_base               1..4
                            mod_base = OTHER
                            note = Nucleotide with phosphorothioate linkage
modified_base               6..19
                            mod_base = OTHER
                            note = Nucleotide with phosphorothioate linkage
SEQUENCE: 26
atctcgtagc atctcgtagc                                               20

SEQ ID NO: 27               moltype = DNA  length = 20
FEATURE                     Location/Qualifiers
source                      1..20
                            mol_type = other DNA
                            organism = synthetic construct
modified_base               1..4
                            mod_base = OTHER
                            note = Nucleotide with phosphorothioate linkage
modified_base               6..19
                            mod_base = OTHER
```

```
                         note = Nucleotide with phosphorothioate linkage
SEQUENCE: 27
atctcggagc atctcggagc                                              20

SEQ ID NO: 28            moltype = DNA  length = 20
FEATURE                  Location/Qualifiers
source                   1..20
                         mol_type = other DNA
                         organism = synthetic construct
modified_base            1..4
                         mod_base = OTHER
                         note = Nucleotide with phosphorothioate linkage
modified_base            6..19
                         mod_base = OTHER
                         note = Nucleotide with phosphorothioate linkage
SEQUENCE: 28
atctcggagc atctcggagc                                              20

SEQ ID NO: 29            moltype = DNA  length = 20
FEATURE                  Location/Qualifiers
source                   1..20
                         mol_type = other DNA
                         organism = synthetic construct
modified_base            1..3
                         mod_base = OTHER
                         note = Nucleotide with phosphorothioate linkage
modified_base            5..19
                         mod_base = OTHER
                         note = Nucleotide with phosphorothioate linkage
SEQUENCE: 29
atgcgtcggc gacgtcgtgc                                              20

SEQ ID NO: 30            moltype = DNA  length = 20
FEATURE                  Location/Qualifiers
source                   1..20
                         mol_type = other DNA
                         organism = synthetic construct
modified_base            1..3
                         mod_base = OTHER
                         note = Nucleotide with phosphorothioate linkage
modified_base            5..19
                         mod_base = OTHER
                         note = Nucleotide with phosphorothioate linkage
SEQUENCE: 30
tagcgtcgac gacgtcgatg                                              20
```